US012540188B2

(12) United States Patent
Kastelein et al.

(10) Patent No.: US 12,540,188 B2
(45) Date of Patent: Feb. 3, 2026

(54) IL10Rα/IL2Rγ SYNTHETIC CYTOKINES

(71) Applicant: Synthekine, Inc., Menlo Park, CA (US)

(72) Inventors: Robert Kastelein, Menlo Park, CA (US); Deepti Rokkam, Menlo Park, CA (US); Patrick J. Lupardus, Menlo Park, CA (US); Mahalakshmi Ramadass, Menlo Park, CA (US); Sandro Vivona, Menlo Park, CA (US)

(73) Assignee: SYNTHEKINE, INC., Menlo Park, CA (US)

( * ) Notice: Subject to any disclaimer, the term of this patent is extended or adjusted under 35 U.S.C. 154(b) by 0 days.

(21) Appl. No.: 18/017,838

(22) PCT Filed: Aug. 6, 2021

(86) PCT No.: PCT/US2021/044858

§ 371 (c)(1),
(2) Date: Jan. 24, 2023

(87) PCT Pub. No.: WO2022/032045

PCT Pub. Date: Feb. 10, 2022

(65) Prior Publication Data

US 2023/0272095 A1 Aug. 31, 2023

Related U.S. Application Data

(60) Provisional application No. 63/135,884, filed on Jan. 11, 2021, provisional application No. 63/136,098, filed on Jan. 11, 2021, provisional application No. 63/078,745, filed on Sep. 15, 2020, provisional application No. 63/061,562, filed on Aug. 5, 2020.

(51) Int. Cl.

*C07K 16/28* (2006.01)
*A61K 45/06* (2006.01)
*C12N 15/63* (2006.01)

(52) U.S. Cl.

CPC .......... *C07K 16/2866* (2013.01); *A61K 45/06* (2013.01); *C12N 15/63* (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/92* (2013.01)

(58) Field of Classification Search

None
See application file for complete search history.

(56) References Cited

U.S. PATENT DOCUMENTS 7,553,932 B1 6/2009 Von Herrath et al.
8,258,268 B2 9/2012 Wu et al.
8,420,784 B2 4/2013 Kato et al.
8,921,528 B2 12/2014 Holt et al.
8,975,382 B2 3/2015 Revets et al.
9,028,830 B2 5/2015 Tso et al.
9,334,331 B2 5/2016 Igawa et al.
10,167,338 B2 1/2019 Wang et al.
10,246,512 B2 4/2019 Wang et al.
10,421,807 B2 9/2019 Gonzales et al.
10,927,186 B2 2/2021 Roobrouck et al.
12,077,594 B2 * 9/2024 Kastelein ........... C07K 16/2866
12,297,281 B2 5/2025 Kastelein et al.
2006/0002935 A1 1/2006 Brewis et al.
2006/0024295 A1 2/2006 Brunetta
2007/0110713 A1 5/2007 Paul
2009/0155275 A1 6/2009 Wu et al.
2009/0220511 A1 9/2009 Kotenko et al.
2010/0233173 A1 9/2010 Wu
2010/0297127 A1 11/2010 Ghilardi et al.
2011/0028695 A1 2/2011 Revets et al.
2011/0053865 A1 3/2011 Saunders et al.
2011/0142831 A1 6/2011 Cua et al.
2011/0177081 A1 7/2011 Thiry et al.
2011/0250213 A1 10/2011 Tso et al.
2012/0201746 A1 8/2012 Liu et al.
2012/0225081 A1 9/2012 Gschwind et al.
2012/0316324 A1 12/2012 Adams et al.
2013/0189262 A1 7/2013 Wong et al.
2014/0065142 A1 3/2014 Roschke et al.
2014/0154256 A1 6/2014 Wu et al.
2014/0170154 A1 6/2014 Presta
2014/0302038 A1 10/2014 Dimasi et al.
2014/0348839 A1 11/2014 Chowdhury et al.
2014/0363426 A1 * 12/2014 Moore .................. C07K 16/22
435/69.6

(Continued)

FOREIGN PATENT DOCUMENTS

CN 101952312 A 1/2011
CN 103396482 A 11/2013

(Continued)

OTHER PUBLICATIONS

International Search Report in PCT/US2021/044858, mailed Dec. 20, 2021, (three pages).
Delgoffe et al., "Interpreting mixed signals: the cell's cytokine conundrum," Current Opinion in Immunology, vol. 23(5), pp. 632-638, Retrieved from the internet, URL: https://www.ncbi.nlm.nih.gov/pmc/articles/PMC3190023/pdf/nihms315192.pdf, (Oct. 2011).
Almagro et al., "Humanization of Antibodies", Frontiers in Bioscience, vol. 13, No. 5, Jan. 1, 2008, pp. 1619-1633.
Apantaku , "Breast Cancer Diagnosis and Screening", American Family Physician, vol. 62, No. 3, Aug. 1, 2000, pp. 596-602.
Crepaldi et al., "Up-Regulation of IL-10R1 Expression is Required to Render Human Neutrophils Fully Responsive to IL-10", The Journal of Immunology, vol. 167, No. 4, Aug. 15, 2001, pp. 2312-2322.

(Continued)

*Primary Examiner* — Marianne P Allen
(74) *Attorney, Agent, or Firm* — Kilpatrick Townsend & Stockton LLP

(57) ABSTRACT

Provided herein are IL10Rα/IL2Rγ binding molecules that bind to IL10Rα and IL2Rγ and comprise an anti-IL2Rγ sdAb and an anti-IL2Rγ $V_H$H antibody.

14 Claims, 4 Drawing Sheets

Specification includes a Sequence Listing.

(56) References Cited

U.S. PATENT DOCUMENTS

| | | | | |
|---|---|---|---|---|
| 2015/0079088 | A1 | 3/2015 | Lowman et al. | |
| 2016/0017387 | A1 | 1/2016 | Hsieh et al. | |
| 2016/0046730 | A1 | 2/2016 | Ghayur et al. | |
| 2016/0244499 | A1 | 8/2016 | Garcia et al. | |
| 2016/0251440 | A1 | 9/2016 | Roobrouck et al. | |
| 2017/0088631 | A1 | 3/2017 | Ast et al. | |
| 2017/0106051 | A1 | 4/2017 | Oh et al. | |
| 2017/0298149 | A1 | 10/2017 | Baeuerle et al. | |
| 2018/0362655 | A1 | 12/2018 | Wang et al. | |
| 2019/0315864 | A1 | 10/2019 | Xu et al. | |
| 2019/0352404 | A1 | 11/2019 | Xu et al. | |
| 2019/0382500 | A1 | 12/2019 | Abujoub et al. | |
| 2020/0055946 | A1 | 2/2020 | Timmer et al. | |
| 2020/0071716 | A1 | 3/2020 | Raab et al. | |
| 2020/0087624 | A1 | 3/2020 | Wood et al. | |
| 2020/0148772 | A1 | 5/2020 | Ting et al. | |
| 2020/0157237 | A1 | 5/2020 | Regev et al. | |
| 2020/0399382 | A1 | 12/2020 | Blanchetot et al. | |
| 2021/0260162 | A1 | 8/2021 | Gonzalez et al. | |
| 2022/0032045 | A1 | 2/2022 | Vivona et al. | |
| 2023/0272090 | A1 | 8/2023 | Kastelein et al. | |
| 2023/0272091 | A1 * | 8/2023 | Kastelein | C07K 16/2866 530/387.3 |
| 2023/0272094 | A1 | 8/2023 | Kastelein et al. | |
| 2023/0272095 | A1 | 8/2023 | Kastelein et al. | |
| 2023/0322936 | A1 * | 10/2023 | Kastelein | C12N 15/63 424/134.1 |
| 2024/0181009 | A1 | 6/2024 | Gonzalez et al. | |
| 2025/0163162 | A1 | 5/2025 | Kastelein et al. | |

FOREIGN PATENT DOCUMENTS

| | | | |
|---|---|---|---|
| CN | 104011221 | A | 8/2014 |
| CN | 104619334 | A | 5/2015 |
| CN | 111018985 | A | 4/2020 |
| CN | 111040035 | A | 4/2020 |
| EP | 2213735 | A1 | 8/2010 |
| JP | 07223968 | A | 8/1995 |
| JP | 2004505641 | A | 2/2004 |
| JP | 2006504401 | A | 2/2006 |
| JP | 2011502163 | A | 1/2011 |
| WO | 2002012345 | A2 | 2/2002 |
| WO | 2003089603 | A2 | 10/2003 |
| WO | 2006036878 | A2 | 4/2006 |
| WO | 2008011081 | A2 | 1/2008 |
| WO | 2009058888 | A1 | 5/2009 |
| WO | 2009068631 | A1 | 6/2009 |
| WO | 2010142551 | A2 | 12/2010 |
| WO | 2011051327 | A2 | 5/2011 |
| WO | 2011095604 | A1 | 8/2011 |
| WO | 2013006544 | A1 | 1/2013 |
| WO | 2013059299 | A1 | 4/2013 |
| WO | 2015044386 | A1 | 4/2015 |
| WO | 2015142675 | A2 | 9/2015 |
| WO | 2016097313 | A1 | 6/2016 |
| WO | 2017198212 | A1 | 11/2017 |
| WO | 2018182935 | A1 | 10/2018 |
| WO | 2018233624 | A1 | 12/2018 |
| WO | 2019129221 | A1 | 7/2019 |
| WO | 20200052543 | A1 | 3/2020 |
| WO | 2020094834 | A1 | 5/2020 |
| WO | 2020094836 | A1 | 5/2020 |
| WO | 2020113164 | A1 | 6/2020 |
| WO | 2020135559 | A1 | 7/2020 |
| WO | 2020144164 | A1 | 7/2020 |
| WO | 2020187711 | A1 | 9/2020 |
| WO | 2022032006 | A2 | 2/2022 |
| WO | 2022032040 | A1 | 2/2022 |
| WO | 2022032045 | A1 | 2/2022 |
| WO | WO 2022/031884 | * | 2/2022 |
| WO | WO 2022/031885 | * | 2/2022 |
| WO | WO 2022/032022 | * | 2/2022 |
| WO | WO 2022/055641 | * | 3/2022 |
| WO | 2022150791 | A2 | 7/2022 |
| WO | WO 2022/150788 | * | 7/2022 |

OTHER PUBLICATIONS

De Genst et al., "Antibody Repertoire Development in Camelids", Developmental and Comparative Immunology, vol. 30, Nos. 1-2, 2006, pp. 187-198.

Donnelly et al., "The Expanded Family of Class II Cytokines that Share the IL-10 Receptor-2 (IL-10R2) Chain", Journal of Leukocyte Biology, vol. 76, No. 2, Aug. 2004, pp. 314-321.

Fenton et al., "Rheostat Positions: A New Classification of Protein Positions Relevant to Pharmacogenomics", Medicinal Chemistry Research, vol. 29, Jun. 7, 2020, pp. 1133-1146.

Fu et al., "Camelus Bactrianus Clone VHH-BC-17 Immunoglobulin Heavy Chain Variable Region mRNA, Rartial Cds", Genbank Entry (online) National Center for Biotechnology Information, Available online at: www.ncbi.nlm.nih.gov/nucleotide/KF179376.1, Sep. 21, 2013, 1 page.

Fu et al., "Comparison of Camelus Bactrianus VHH Sequences from Conventional and Heavy Chain Antibodies", National Center for Biotechnology Information, Available Online at: https://www.ncbi.nlm.nih.gov/nucleotide/KF179376.1, GenBank: KF179376.1, Sep. 21, 2013, 1 page.

Jiang et al., "Regulation of Interleukin-10 Receptor Ubiquitination and Stability by Beta-TrCP-Containing Ubiquitin E3 Ligase", PLoS ONE, vol. 6, No. 11, Nov. 8, 2011, pp. 1-14.

Khan et al., "Adjustable Locks and Flexible Keys: Plasticity of Epitope-Paratope Interactions in Germline Antibodies", The Journal of Immunology, vol. 192, Issue 11, 2014, pp. 5398-5405.

Lundin et al., "Production and Partial Characterization of Mouse Monoclonal Antibodies Recognizing Common Cytokine Receptor Gamma Chain (γc) of Human, Mouse and Primate Origin", Acta Pathologica, Microbiologica, et Immunologica Scandinavica, vol. 109, No. 10, Oct. 2001, pp. 647-655.

Martin et al., "Genetic and Hormonal Risk Factors in Breast Cancer", Journal of the National Cancer Institute, vol. 92, No. 14, Jul. 19, 2000, pp. 1126-1135.

Application No. PCT/US2021/044602 , International Preliminary Report on Patentability, Mailed On Feb. 16, 2023, 10 pages.

Application No. PCT/US2021/044602 , International Search Report and Written Opinion, Mailed On Feb. 2, 2022, 13 pages.

Application No. PCT/US2021/044603 , International Preliminary Report on Patentability, Mailed On Feb. 16, 2023, 9 pages.

Application No. PCT/US2021/044803 , International Preliminary Report on Patentability, Mailed On Feb. 16, 2023, 7 pages.

Application No. PCT/US2021/044803 , International Search Report and Written Opinion, Mailed On Jan. 26, 2022, 11 pages.

Application No. PCT/US2021/044834 , International Preliminary Report on Patentability, Mailed On Feb. 16, 2023, 11 pages.

Application No. PCT/US2021/044834 , International Search Report and Written Opinion, Mailed On Feb. 2, 2022, 15 pages.

Application No. PCT/US2021/044853 , International Preliminary Report on Patentability, Mailed On Feb. 16, 2023, 7 pages.

Application No. PCT/US2021/044853 , International Search Report and Written Opinion, Mailed On Dec. 17, 2021, 10 pages.

Application No. PCT/US2021/044858 , International Preliminary Report on Patentability, Mailed On Feb. 16, 2023, 7 pages.

Application No. PCT/US2022/012049 , International Preliminary Report on Patentability, Mailed On Jul. 20, 2023, 10 pages.

Application No. PCT/US2022/012049 , International Search Report and Written Opinion, Mailed On Jun. 21, 2022, 14 pages.

Application No. PCT/US2022/012055 , International Preliminary Report on Patentability, Mailed On Jul. 20, 2023, 12 pages.

Application No. PCT/US2022/012055 , International Search Report and the Written Opinion, Mailed On Jun. 29, 2022, 18 pages.

Pingwara et al., "IFN-λ Modulates the Migratory Capacity of Canine Mammary Tumor Cells via Regulation of the Expression of Matrix Metalloproteinases and Their Inhibitors", Cells, vol. 10, No. 5, Apr. 23, 2021, pp. 1-15.

(56) References Cited

OTHER PUBLICATIONS

Shouval et al., "Interleukin 10 Receptor Signaling: Master Regulator of Intestinal Mucosal Homeostasis in Mice and Humans", Advances in Immunology, vol. 122, 2014, pp. 1-29.
Yoshinaga et al., "Ig L-Chain Shuffling for Affinity Maturation of Phage Library-Derived Human Anti-Human MCP-1 Antibody Blocking its Chemotactic Activity", The Journal of Biochemistry, vol. 143, No. 5, May 2008, pp. 593-601.
U.S. Appl. No. 18/260,709, filed Jan. 11, 2022, Synthekine, Inc.
Franke et al. "Human and Murine Interleukin 23 Receptors are Novel Substrates for a Disintegrin and Metalloproteases ADAM10 and ADAM17", The Journal of Biological Chemistry, vol. 291, No. 20, May 13, 2016, pp. 10551-10561.
Application No. PCT/US2021/044603 , International Search Report and Written Opinion, Mailed On Feb. 2, 2022, 12 pages.
Watzka et al., "Guided Selection of Antibody Fragments Specific for Human Interferon Gamma Receptor 1 from a Human VH- and VL-Gene Repertoire", Immunotechnology, vol. 3, No. 4, Jan. 1998, pp. 279-291.
Weidle et al., "The Intriguing Options of Multispecific Antibody Formats for Treatment of Cancer", Cancer Genomics & Proteomics, vol. 10, No. 1, Jan.-Feb. 2013, pp. 1-18.
Wilton et al., "sdAb-DB: The Single Domain Antibody Database", American Chemical Society Synthetic Biology, vol. 7, No. 11, Nov. 16, 2018, pp. 2480-2484.
EP21853105.1 , "Partial Supplementary European Search Report", dated Apr. 4, 2025, 16 pages.
EP21853257.0 , Extended European Search Report, dated Mar. 28, 2025, 7 pages.
EP21853681.1 , "Partial Supplementary European Search Report", dated Apr. 2, 2025, 14 pages.
EP21854022.7 , "Partial Supplementary European Search Report", dated Aug. 21, 2024, 13 pages.
Gorby et al., "Engineered IL-10 Variants Elicit Potent Immuno-Modulatory Activities at Therapeutic Low Ligand Doses", Science Signaling, vol. 13, No. 649, Sep. 15, 2020, pp. 1-46.
Harris et al., "A Bispecific Antibody Agonist of the Il-2 Heterodimeric Receptor Preferentially Promotes in Vivo Expansion of CD8 and NK Cells", Scientific Reports, vol. 11, No. 1, May 19, 2021, 15 pages.
Hechinger et al., "Therapeutic Activity of Multiple Common γ-Chain Cytokine Inhibition in Acute and Chronic GVHD", Blood, vol. 125, No. 3, Jan. 15, 2015, pp. 570-580.
Le Floc'h et al., "Blockade of Common Gamma Chain Cytokines with REGN7257, An Interleukin 2 Receptor Gamma (IL2RG) Monoclonal Antibody, Protected Mice from Graft-Versus-Host Disease", Transplantation and Cellular Therapy, vol. 27, No. 3, Jan. 31, 2021, pp. s250-s251.
Rudikoff et al., "Single amino acid substitution altering antigen-binding specificity," PNAS, 79(6), Mar. 1, 1982, pp. 1979-1983.
Victoria et al., "Activation of Toll-Like Receptor 2 Increases Macrophage Resistance to HIV-1 Infection", Immunobiology, vol. 218, No. 12, Dec. 2013, pp. 1529-1536.
Winkler et al., "Changing The Antigen Binding Specificity By Single Point Mutations of An Anti-p24 (HIV-1) Antibody", The Journal of Immunology, vol. 165, No. 8, Oct. 15, 2000, pp. 4505-4514.
Zadka et al., "The Expression of IL10RA in Colorectal Cancer and its Correlation with the Proliferation Index and the Clinical Stage of the Disease", Cytokine, vol. 110, Oct. 2018, pp. 116-125.
U.S. Appl. No. 19/180,030, filed Apr. 15, 2025, Kastelein et al.
Aagaard et al., "RNAi Therapeutics: Principles, Prospects and Challenges", Advanced Drug Delivery Reviews, vol. 59, Issues 2-3, Mar. 30, 2007, pp. 75-86.
Bork, Genome Research, vol. 10, 2000, pp. 398-400.
Brown et al., J Immunol., 156(9), May 1996, pp. 3285-3291.
Burgess et al., J. Cell Biol., vol. 111, 1990, pp. 2129-2138.
Clark et al., "Discovery and Development of Janus Kinase (JAK) Inhibitors for Inflammatory Diseases", Journal of Medicinal Chemistry, vol. 57, No. 12, Jan. 13, 2014, pp. 5023-5038.
Difalco et al., "The Improved Survival of Hematopoietic Cells Cultured with a Fusion Protein of Insulin-Like Growth Factor II (IGF-II) and Interleukin 3 (IL-3) is Associated with Increases in Bcl-XI and Phosphatidylinositol-3 Kinase Activity", Journal of Leukocyte Biology, vol. 73, No. 2, Feb. 2003, pp. 297-305.
Duarte et al., "La Vía JAK-STAT De Señalización Intracelular Y Su Repercusión En Oncogénesis, Inmunomodulación Y Desarrollo", Medicina Clínica (Barc), vol. 114, 2000, pp. 227-234.
Edwards et al., Mol. Biol., vol. 334(1), Nov. 14, 2003, pp. 103-118.
Application No. EP18774902.3, Extended European Search Report, dated Nov. 26, 2020, 11 pages.
Application No. EP18774902.3 , Office Action, Mailed On Nov. 28, 2023, 4 pages.
Gillies et al., "Bi-Functional Cytokine Fusion Proteins for Gene Therapy and Antibody-Targeted Treatment of Cancer", Cancer Immunology, Immunotherapy, vol. 51, No. 8, Oct. 2002, pp. 449-460.
Goel et al., J. Immunol., vol. 173(2), Dec. 15, 2004, pp. 7358-7367.
Gorby et al., "Mapping Determinants of Cytokine Signaling via Protein Engineering", Frontiers in Immunology, vol. 9, Article 2143, Sep. 2018, pp. 1-9.
Guido et al., "Virtual Screening and Its Integration With Modern Drug Design Technologies", Current Medicinal Chemistry, vol. 15, No. 1, Feb. 2008, pp. 37-46.
Jahn et al., "An Il12-Il2-Antibody Fusion Protein Targeting Hodgkin's Lymphoma Cells Potentiates Activation Of Nk And T Cells For An Anti-Tumor Attack", PLoS ONE, vol. 7, No. 9, Sep. 18, 2012, pp. 1-13.
Kawahara et al., "Replacing Factor-dependency With That For Lysozyme: Affordable Culture of Il-6-dependent Hybridoma by Transfecting Artificial Cell Surface Receptor", Biotechnology and Bioengineering, vol. 74, No. 5, Sep. 5, 2001, pp. 416-423.
Kermer et al., "Combining Antibody-Directed Presentation of IL-15 and 4-1 BBL in a Trifunctional Fusion Protein for Cancer Immunotherapy", Molecular Cancer Therapeutics, vol. 13, No. 1, Jan. 2014, pp. 112-121.
Kontermann, "Dual Targeting Strategies with Bispecific Antibodies", Monoclonal Antibodies (mABs), vol. 4, No. 2, Mar. 1, 2012, pp. 182-197.
Kulmanov et al., Bioinformatics, vol. 34(4), 2018, pp. 660-668.
Lazar et al., Mol. Cell., vol. 8, 1988, pp. 1247-1252.
Lorenzen et al., "The Structure of the Interleukin-15 Receptor and Its Implications for Ligand Binding", Journal of Biological Chemistry, vol. 281, No. 10, Apr. 2006, pp. 6642-6647.
McKeague et al., "Challenges and Opportunities for Small Molecule Aptamer Development", Journal of Nucleic Acids, vol. 2012, Article 748913, Oct. 2012, 20 pages.
Miosge, Proc Nat'l Acad Sci USA, 112(37), Sep. 15, 2015, pp. E5189-E5198.
Application No. PCT/US2018/021301, International Search Report and Written Opinion, dated Jun. 19, 2018, 12 pages.
Rudikoff et al., "Single amino acid substitution altering antigen-binding specificity," Proceeding of the National Academy of Sciences (PNAS), vol. 79, No. 6, Mar. 1, 1982, pp. 1979-1983.
Skolnick et al., Trends Biotechnol., 18(1), Jan. 2000, pp. 34-39.
Terai et al., "Human interleukin 10 receptor 1/lgG1-Fc fusion proteins: immunoadhesins for human IL-10 with therapeutic potential," Cancer Immunol Immunother, 2009, vol. 58, No. 8, pp. 1307-1317.
Vajdos et al., J Mol Biol, 320(2), Jul. 5, 2002, pp. 415-428.
Warzocha et al., "Antisense Strategy: Biological Utility and Prospects in the Treatment of Hematological Malignancies", Leukemia & Lymphoma, vol. 24, Issue 3-4, 1997, pp. 267-281.
Zou et al., "Structure-Function Analysis of the p35 Subunit of Mouse Interleukin 12", The Journal of Biological Chemistry, vol. 270, No. 11, Mar. 17, 1995, pp. 5864-5871.

* cited by examiner

A

B

IL10Rα/IL2Rγ SYNTHETIC CYTOKINES

CROSS-REFERENCES TO RELATED APPLICATIONS

This application is a U.S. National Stage of International Application No. PCT/US2021/044858, filed on Aug. 6, 2021, which claims priority to U.S. Provisional Application No. 63/061,562, filed Aug. 5, 2020, U.S. Provisional Application No. 63/078,745, filed Sep. 15, 2020, U.S. Provisional Application No. 63/135,884, filed Jan. 11, 2021, and U.S. Provisional Application No. 63/136,098, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Sep. 15, 2021, is named 106249-1258357-004110PC_SL.txt and is 255,549 bytes in size.

BACKGROUND OF THE DISCLOSURE

The anti-inflammatory cytokine interleukin-10 (IL-10), also known as human cytokine synthesis inhibitory factor (CSIF), is classified as a type (class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29). Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds. The IL-10 receptor, a type II cytokine receptor, consists of alpha (IL10Ra) and beta (IL10Rb) subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

IL-10 exhibits pleiotropic effects in immunoregulation and inflammation through actions on T cells, B cells, macrophages, and antigen presenting cells (APC). IL-10 is produced by mast cells, counteracting the inflammatory effect that these cells have at the site of an allergic reaction. Although IL-10 is predominantly expressed in macrophages, expression has also been detected in activated T cells, B cells, mast cells, and monocytes. IL-10 can suppress immune responses by inhibiting expression of IL-1α, IL-1β, IL-6, IL8, TNFα, GM-CSF and G-CSF in activated monocytes and activated macrophages, and it also suppresses IFN-γ production by NK cells. IL10 can block NF-κB activity and is involved in the regulation of the JAK-STAT signaling pathway.

IL2 is a pluripotent cytokine which is produced by antigen activated T cells. IL2 exerts a wide spectrum of effects on the immune system and plays important roles in regulating both immune activation, suppression and homeostasis. IL2 promotes the proliferation and expansion of activated T lymphocytes, induces proliferation and activation of naïve T cells, potentiates B cell growth, and promotes the proliferation and expansion of NK cells. Human interleukin 2 (IL2) is a 4 alpha-helix bundle cytokine of 133 amino acids. IL2 is a member of the IL2 family of cytokines which includes IL2, IL-4, IL-7, IL 9, IL-15 and IL21.

IL2 exerts its effect on mammalian immune cells through interaction with three different cell surface proteins: (1) CD25 (also referred to as the IL2 receptor alpha, IL2Rα, p55), CD122 (also referred to as the interleukin-2 receptor beta, IL2Rβ, IL15Rβ and p70-75), and CD132 (also referred to as the interleukin 2 receptor gamma, IL2Rγ; or common gamma chain as it is a component of other multimeric receptors in the IL2 receptor family). In addition to the "low affinity" CD25 IL2 receptor, two additional IL2 receptor complexes have been characterized: (a) an "intermediate affinity" dimeric IL2 receptor comprising CD122 and CD132 (also referred to as "IL2Rβγ"), and (b) a "high affinity" trimeric IL2 receptor complex comprising the CD25, CD122 and CD132 proteins (also referred to as "IL2Rαβγ"). hIL2 possesses a Kd of approximately $10^{-9}$M with respect to the intermediate affinity CD122/CD132 (IL2βγ) receptor complex. hIL2 possesses a Kd of approximately $10^{-11}$M with respect to the high IL2 affinity receptor complex.

In addition to forming a subunit of the high affinity IL2 receptor, CD132 is a type 1 cytokine receptor and is shared by the receptor complexes for IL-4, IL-7, IL-9, IL-15, and IL21, hence it being referred to in the literature as the "common" gamma chain. Human CD132 (hCD132) is expressed as a 369 amino acid pre-protein comprising a 22 amino acid N-terminal signal sequence. Amino acids 23-262 (amino acids 1-240 of the mature protein) correspond to the extracellular domain, amino acids 263-283 (amino acids 241-262 of the mature protein) correspond to the 21 amino acid transmembrane domain, and amino acids 284-369 (amino acids 262-347 of the mature protein) correspond to the intracellular domain. hCD132 is referenced at UniProtKB database as entry P31785. Human CD132 nucleic acid and protein sequences may be found as Genbank accession numbers: NM_000206 and NP_000197 respectively.

IL10Ra

IL10Ra binding molecules of the present disclosure specifically bind to the extracellular domain of the IL10Ra.

Human IL10Ra

In one embodiment, the IL10Ra is the human IL10Ra. The canonical full length IL10Ra is a polypeptide possessing the amino acid sequence:

```
                                         (SEQ ID NO: 1)
MLPCLVVLLAALLSLRLGSDAHGTELPSPPSVWFEAEFFHHILHWTPIP

NQSESTCYEVALLRYGIESWNSISNCSQTLSYDLTAVTLDLYHSNGYRA

RVRAVDGSRHSNWTVTNTRFSVDEVTLTVGSVNLEIHNGFILGKIQLPR

PKMAPANDTYESIFSHFREYEIAIRKVPGNFTFTHKKVKHENFSLLTSG

EVGEFCVQVKPSVASRSNKGMWSKEECISLTRQYFTVTNVIIFFAFVLL

LSGALAYCLALQLYVRRRKKLPSVLLFKKPSPFIFISQRPSPETQDTIH

PLDEEAFLKVSPELKNLDLHGSTDSGFGSTKPSLQTEEPQFLLPDPHPQ

ADRTLGNREPPVLGDSCSSGSSNSTDSGICLQEPSLSPSTGPTWEQQVG

SNSRGQDDSGIDLVQNSEGRAGDTQGGSALGHHSPPEPEVPGEEDPAAV

AFQGYLRQTRCAEEKATKTGCLEEESPLTDGLGPKFGRCLVDEAGLHPP

ALAKGYLKQDPLEMTLASSGAPTGQWNQPTEEWSLLALSSCSDLGISDW

SFAHDLAPLGCVAAPGGLLGSFNSDLVTLPLISSLOSSE
```

For purposes of the present disclosure, the numbering of amino acid residues of the human IL10Ra polypeptides as described herein is made in accordance with the numbering of this canonical sequence UniProg Database Reference No. Q13651. Amino acids 1-21 of SEQ ID NO: 1 are identified as the signal peptide of the IL10Ra, amino acids 22-235 of SEQ ID NO:1 are identified as the extracellular domain, amino acids 236-256 of SEQ ID NO: 1 are identified as the transmembrane domain, and amino acids 257-578 of SEQ ID NO: 1 are identified as the intracellular domain.

To generate sdAbs against the human IL2Rb, the extracellular domain of the hIL2Rb protein may be used an immunogen. The extracellular domain of the mature (lacking the signal sequence) hIL2Rb possesses the amino acid sequence (amino acids 22-235 of SEQ ID NO: 1) has the amino acid sequence (SEQ ID NO: 2)

```
HGTELPSPPSVWFEAEFFHHILHWTPIPNQSESTCYEVALLRYGIESWN
SISNCSQTLSYDLTAVTLDLYHSNGYRARVRAVDGSRHSNWTVTNTRFS
VDEVTLTVGSVNLEIHNGFILGKIQLPRPKMAPANDTYESIFSHFREYE
IAIRKVPGNFTFTHKKVKHENFSLLTSGEVGEFCVQVKPSVASRSNKGM
WSKEECISLTRQYFTVTN
```

IL2Rg

The IL2Rg binding molecules of the present disclosure specifically bind to the extracellular domain of the IL2Rg.

Human IL2Rg

The IL2Rg binding molecules of the present disclosure specifically bind to the extracellular domain of the IL2Rg (CD132). In one embodiment, the IL2Rg is the human IL2Rg. The canonical full length IL2Rg (including the signal peptide) is a polypeptide possessing the amino acid sequence:

(SEQ ID No: 3)

```
MLKPSLPFTSLLFLQLPLLGVGLNTTILTPNGNEDTTADFFLTTMPTDS
LSVSTLPLPEVQCFVFNVEYMNCTWNSSSEPQPTNLTLHYWYKNSDNDK
VQKCSHYLFSEEITSGCQLQKKEIHLYQTFVVQLQDPREPRRQATQMLK
LQNLVIPWAPENLTLHKLSESQLELNWNNRFLNHCLEHLVQYRTDWDHS
WTEQSVDYRHKFSLPSVDGQKRYTFRVRSRFNPLCGSAQHWSEWSHPIH
WGSNTSKENPFLFALEAVVISVGSMGLIISLLCVYFWLERTMPRIPTLK
NLEDLVTEYHGNFSAWSGVSKGLAESLQPDYSERLCLVSEIPPKGGALG
EGPGASPCNQHSPYWAPPCYTLKPET.
```

To generate sdAbs against the human IL2Rg, the extracellular domain of the hIL2Rg protein was used as an immunogen. The extracellular domain of the mature (lacking the signal sequence) hIL2Rg possesses the amino acid sequence:

(SEQ ID NO: 4)

```
LNTTILTPNGNEDTTADFFLTTMPTDSLSVSTLPLPEVQCFVFNVEYMN
CTWNSSSEPQPTNLTLHYWYKNSDNDKVQKCSHYLFSEEITSGCQLQKK
EIHLYQTFVVQLQDPREPRRQATQMLKLQNLVIPWAPENLTLHKLSESQ
LELNWNNRFLNHCLEHLVQYRTDWDHSWTEQSVDYRHKFSLPSVDGQKR
YTFRVRSRFNPLCGSAQHWSEWSHPIHWGSNTSKENPFLFALEA
```

For purposes of the present disclosure, the numbering of amino acid residues of the human IL2Rg (hIL2Rg) polypeptides as described herein is made in accordance with the numbering of this canonical sequence (UniProt ID: 31785; SEQ ID NO:3). Amino acids 1-22 of SEQ ID NO: 3 are identified as the signal peptide of hIL2Rg, amino acids 23-262 of SEQ ID NO: 3 are identified as the extracellular domain, amino acids 263-283 SEQ ID NO: 3 are identified as the transmembrane domain, and amino acids 284-269 of SEQ ID NO: 3 are identified as the intracellular domain.

Murine IL2Rg

In one embodiment, the IL2Rg is the murine IL2Rg. The murine CD132 (mCD132) is expressed as a 369 amino acid precursor, the first 22 amino acids comprising a signal sequence which is post-translationally cleaved to provide the mature 353 amino acid protein. Amino acids 23-263 (amino acids 1-214 of the mature protein) correspond to the extracellular domain, amino acids 264-284 (amino acids 242-266 of the mature protein) correspond to the transmembrane domain and amino acids 285-369 (amino acids 263-347 of the mature protein) correspond to the intracellular domain. The canonical full length mIL2Rg precursor protein including the signal sequence is a polypeptide of the amino acid sequence:

(SEQ ID NO: 5)

```
MLKLLLSPRSFLVLQLLLLRAGWSSKVLMSSANEDIKADLILTSTAPEH
LSAPTLPLPEVQCFVFNIEYMNCTWNSSSEPQATNLTLHYRYKVSDNNT
FQECSHYLFSKEITSGCQIQKEDIQLYQTFVVQLQDPQKPQRRAVQKLN
LQNLVIPRAPENLTLSNLSESQLELRWKSRHIKERCLQYLVQYRSNRDR
SWTELIVNHEPRFSLPSVDELKRYTFRVRSRYNPICGSSQQWSKWSQPV
HWGSHTVEENPSLFALEAVLIPVGTMGLIITLIFVYCWLERMPPIPPIK
NLEDLVTEYQGNFSAWSGVSKGLTESLQPDYSERFCHVSEIPPKGGALG
EGPGGSPCSLHSPYWPPPCYSLKPEA
```

To generate sdAbs against mIL2Rg, the extracellular domain of the mIL2Rg protein was used as an immunogen. The extracellular domain of the mature (lacking the signal sequence) hIL2Rg possesses the amino acid sequence (amino acids 23-263):

(SEQ ID NO: 6)

```
WSSKVLMSSANEDIKADLILTSTAPEHLSAPTLPLPEVQCFVFNIEYMN
CTWNSSSEPQATNLTLHYRYKVSDNNTFQECSHYLFSKEITSGCQIQKE
DIQLYQTFVVQLQDPQKPQRRAVQKLNLQNLVIPRAPENLTLSNLSESQ
LELRWKSRHIKERCLQYLVQYRSNRDRSWTELIVNHEPRFSLPSVDELK
RYTFRVRSRYNPICGSSQQWSKWSQPVHWGSHTVEENPSLFALEA
```

For purposes of the present disclosure, the numbering of amino acid residues of the murine IL2Rg polypeptides as described herein is made in accordance with the numbering of this canonical sequence (UniProt ID: P34902). Amino acids 1-22 of SEQ ID NO: 5 are identified as the signal peptide of the IL2Rg, amino acids 23-263 of SEQ ID NO: 5 are identified as the extracellular domain, amino acids 264-284 of SEQ ID NO: 5 are identified as the transmembrane domain, and amino acids 285-369 of SEQ ID NO: 5 are identified as the intracellular domain.

SUMMARY OF THE DISCLOSURE

The present disclosure provides compositions useful in the pairing of cellular receptors to generate desirable effects useful in treatment of disease in mammalian subjects.

The present disclosure provides binding molecules that comprise a first domain that binds to IL10Rα of the IL10Rα/IL2Rγ receptor and a second domain that binds to IL2Rγ of the IL10Rα/IL2Rγ receptor, such that upon contacting with a cell expressing IL10Rα and IL2Rγ, the IL10Rα/IL2Rγ binding molecule causes the functional association of IL10Rα and IL2Rγ, thereby resulting in functional dimerization of the receptors and downstream signaling.

The present disclosure provides compositions useful in the pairing of cellular receptors to generate desirable effects useful in treatment of diseases. In general, binding proteins are provided that comprise a first domain that binds to IL10Rα (also referred to as IL10R1) and a second domain that binds to IL2Rγ, such that upon contacting with a cell expressing IL10Rα and IL2Rγ, the binding protein causes the functional association of IL10Rα and IL2Rγ, thereby resulting in functional dimerization of the receptors and downstream signaling.

Several advantages flow from the binding proteins described herein. Unlike IL10R's natural ligand, IL10, which can trigger both immunosuppressive and immunostimulatory effects on various cell types, the binding proteins described herein can decouple the immunosuppressive and immunostimulatory effects and selectively provide only the desired effect on the desired cell type(s). When IL10 is used as a therapeutic in mammalian, particularly human, subjects, it may also trigger a number of adverse and undesirable effects by a variety of mechanisms including the presence of IL10R on different cell types and the binding to IL10R on the different cell types may result in undesirable effects and/or undesired signaling on cells expressing the IL10 receptor. The present disclosure is directed to methods and compositions that modulate the multiple effects of IL10R binding so that desired therapeutic signaling occurs, particularly in a desired cellular or tissue subtype, while also minimizing undesired activity and/or intracellular signaling.

For example, it is known that IL10 has activities on macrophages (e.g., monocytes) and T cells (e.g., $CD4^+$ T cells and $CD8^+$ T cells). Macrophages is a cell type that expresses both IL10Rα and IL10Rβ receptors but when activated significantly can result in the phagocytosis of aging red blood cells and resulting in side effects such as anemia in patients receiving IL10 therapy. In some embodiments, the method provided herein uses a binding protein of the present disclosure that binds to IL10Rα and IL2Rγ resulting in the selective activation of T cells relative to activation of macrophages. The selective activation of T cells relative to macrophages is beneficial because IL10-activated macrophages and its associated side effect of anemia can be avoided. Binding proteins as described herein that provide for the selective substantial activation of T cells while providing a minimal activation of macrophages resulting in a molecule which retains the beneficial properties of an native IL10 ligand but results in diminished undesirable side effects relative to the native IL10 ligand.

In some embodiments, the binding molecule that specifically binds to IL10Rα and IL2Rγ has a reduced $E_{max}$ compared to the $E_{max}$ of IL10. $E_{max}$ reflects the maximum response level in a cell type that can be obtained by a ligand (e.g., a binding protein described herein or the native cytokine (e.g., IL10)). In some embodiments, the binding protein that specifically binds to IL10Rα and IL2Rγ described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IL10. In some embodiments, by varying the linker length of the binding protein that specifically binds to IL10Rα and IL2Rγ, the $E_{max}$ of the binding protein can be changed. The binding protein can cause $E_{max}$ in the most desired cell types, for example, $CD8^+$ T cells. In some embodiments, the $E_{max}$ in $CD8^+$ T cells caused by a binding protein that specifically binds to IL10Rα and IL2Rγ is between 1% and 100% (e.g., between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ in other T cells caused by the binding protein. In other embodiments, the $E_{max}$ of the binding protein that specifically binds to IL10Rα and IL2Rγ is greater (e.g., at least 1%, 5%, 10%, 15%, 20%, 25%, 30%, 35%, 40%, 45%, or 50% greater) than the $E_{max}$ of the natural ligand.

In some embodiments, the binding proteins described herein are designed such that the binding proteins provide the maximal desired IL10 intracellular signaling from binding to IL10Rα and IL2Rγ on the desired cell types, while providing significantly less IL10 signaling in other undesired cell types. This can be achieved, for example, by selection of binding proteins having differing affinities or causing different $E_{max}$ for IL10Rα and IL2Rγ as compared to the affinity of IL10 for IL10R. Because different cell types respond to the binding of ligands to its cognate receptor with different sensitivity, by modulating the affinity of the dimeric ligand (or its individual binding moieties) for the IL10 receptor relative to wild-type IL10 binding facilitates the stimulation of desired activities while reducing undesired activities on non-target cells. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signaling caused by the binding protein, can also be measured.

In some embodiments, the IL10Rα/IL2Rγ binding molecules described herein are partial agonists. In some embodiments, the binding molecules described herein are designed such that the binding molecules are full agonists. In some embodiments, the binding molecules described herein are designed such that the binding molecules are super agonists.

The present disclosure provides disclosure provides bivalent binding molecules that are agonists of the IL10Rα/IL2Rγ receptor, the bivalent binding molecule comprising:

- a first single domain antibody (sdAb) that specifically binds to the extracellular domain of IL10Rα of the IL10Rα/IL2Rγ (an "anti-IL10Rα sdAb"), and
- a second single domain antibody that specifically binds to extracellular domain IL2Rγ of the IL10Rα/IL2Rγ ((an "anti-IL2Rγ sdAb"), wherein the anti-IL10Rα sdAb and anti-IL2Rγ sdAb are stably associated, and wherein contacting a cell expressing IL10Rα and IL2Rγ with an effective amount of the bivalent binding molecule results in the dimerization of IL10Rα and IL2Rγ and results in intraceullar signaling. In some embodiments, one or both of the sdAbs is a an scFv. In some embodiments, one or both of the sdAbs is a VHH.

In some embodiments, one sdAb of the bivalent binding molecule is an scFv and the other sdAb is a VHH.

In some embodiments, the first and second sdAbs are covalently bound via a chemical linkage.

In some embodiments, the first and second sdAbs are provided as single continuous polypeptide.

In some embodiments, the first and second sdAbs are provided as single continuous polypeptide optionally comprising an intervening polypeptide linker between the amino acid sequences of the first and second sdAbs.

In some embodiments the bivalent binding molecule optionally comprising a linker, is optionally expressed as a fusion protein with an additional amino acid sequence. In some embodiments, the additional amino acid sequence is a purification handle such as a chelating peptide or an additional protein such as a subunit of an Fc molecule.

The disclosure also provides an expression vector comprising a nucleic acid encoding the bispecific binding molecule operably linked to one or more expression control sequences. The disclosure also provides an isolated host cell comprising the expression vector expression vector comprising a nucleic acid encoding the bispecific binding molecule operably linked to one or more expression control sequences functional in the host cell.

In another aspect, the disclosure provides a pharmaceutical composition comprising the IL10Rα/IL2Rγ binding molecule described herein and a pharmaceutically acceptable carrier.

In another aspect, the disclosure provides a method of treating an autoimmune or inflammatory disease, disorder, or condition or a viral infection in a subject in need thereof, comprising administering to the subject a therapeutically effective amount of an IL10Rα/IL2Rγ binding molecule described herein or a pharmaceutical composition described herein.

BRIEF DESCRIPTION OF THE FIGURES

FIG. 4, Panel B provides a schematic representations of a bivalent binding molecule the binding domains are single domain antibodies associated via transition metal coordinate covalent complex. As illustrated, the bivalent binding molecules comprises two polypeptide subunits: the first subunit comprising a first single domain antibody (1) is attached via a first linker (15) to a first chelating peptide (17) and second subunit comprising a second single domain antibody (3) is attached via a second linker (16) to a second chelating peptide (18), wherein the first chelating peptide (17) and second chelating peptide (18) form a coordinate covalent complex with a single transition metal ion ("M"). The transition metal ion may be in a kinetically labile or kinetically inert oxidation state.

DETAILED DESCRIPTION OF THE INVENTION

Figure 1:
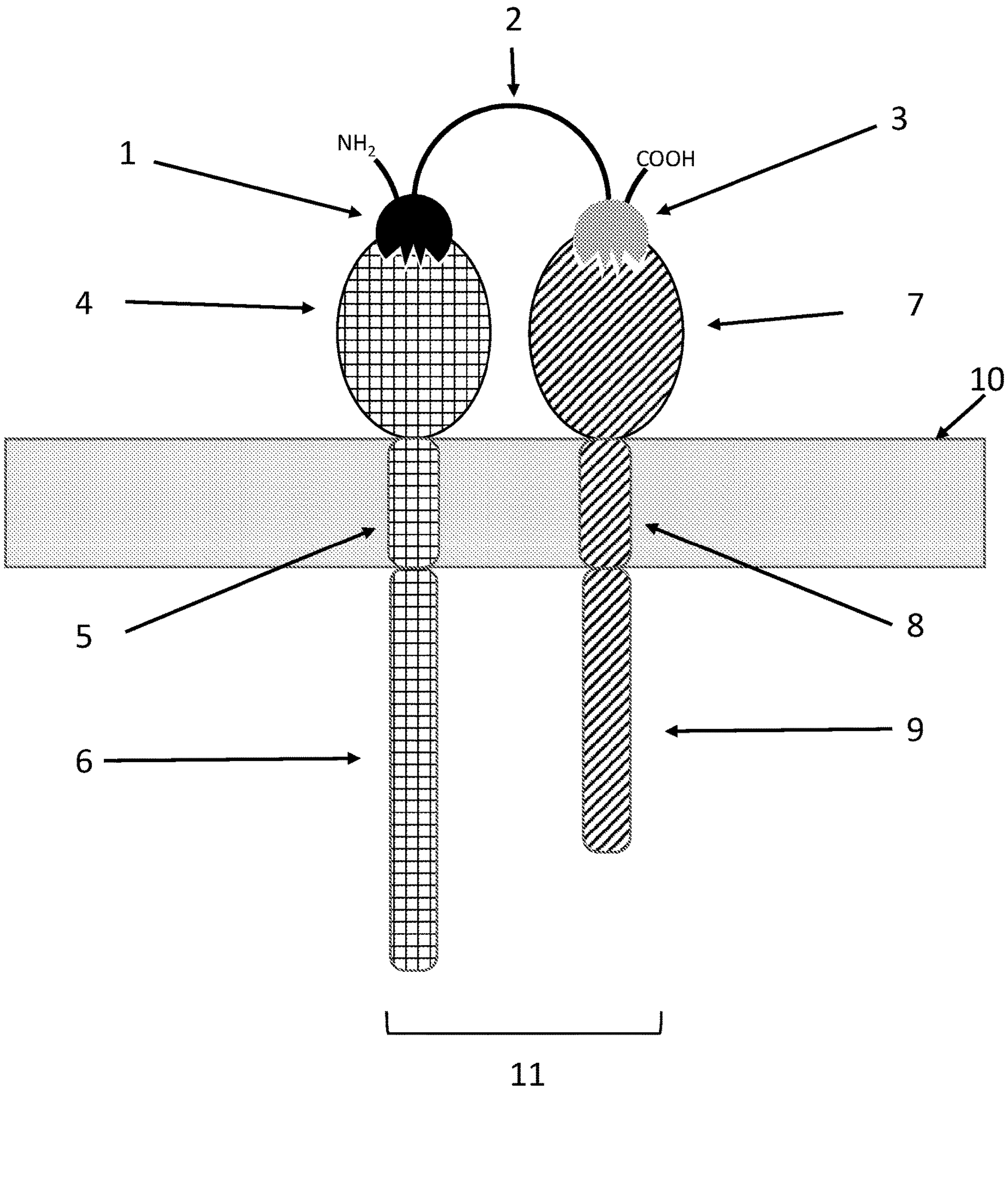
FIG. 1 of the attached drawings provides a schematic representation of one embodiment of the bivalent binding molecule of the present disclosure comprising a first single domain antibody (1) and a second single domain antibody (3) and a linker (2) depicted as interacting with a cell membrane (10) associated heterodimeric receptor comprising a first receptor subunit comprising an extracellular domain (4), and transmembrane domain (5) and an intracellular domain (6) interaction of a bivalent binding molecule and a second first receptor subunit comprising an extracellular domain (7), and transmembrane domain (8) and an intracellular domain (9) wherein the intracellular domain of the first receptor (6) and the intracellular domain of the second receptor (9) on of a bivalent binding molecule are within a proximal distance (11).
Figure 2:
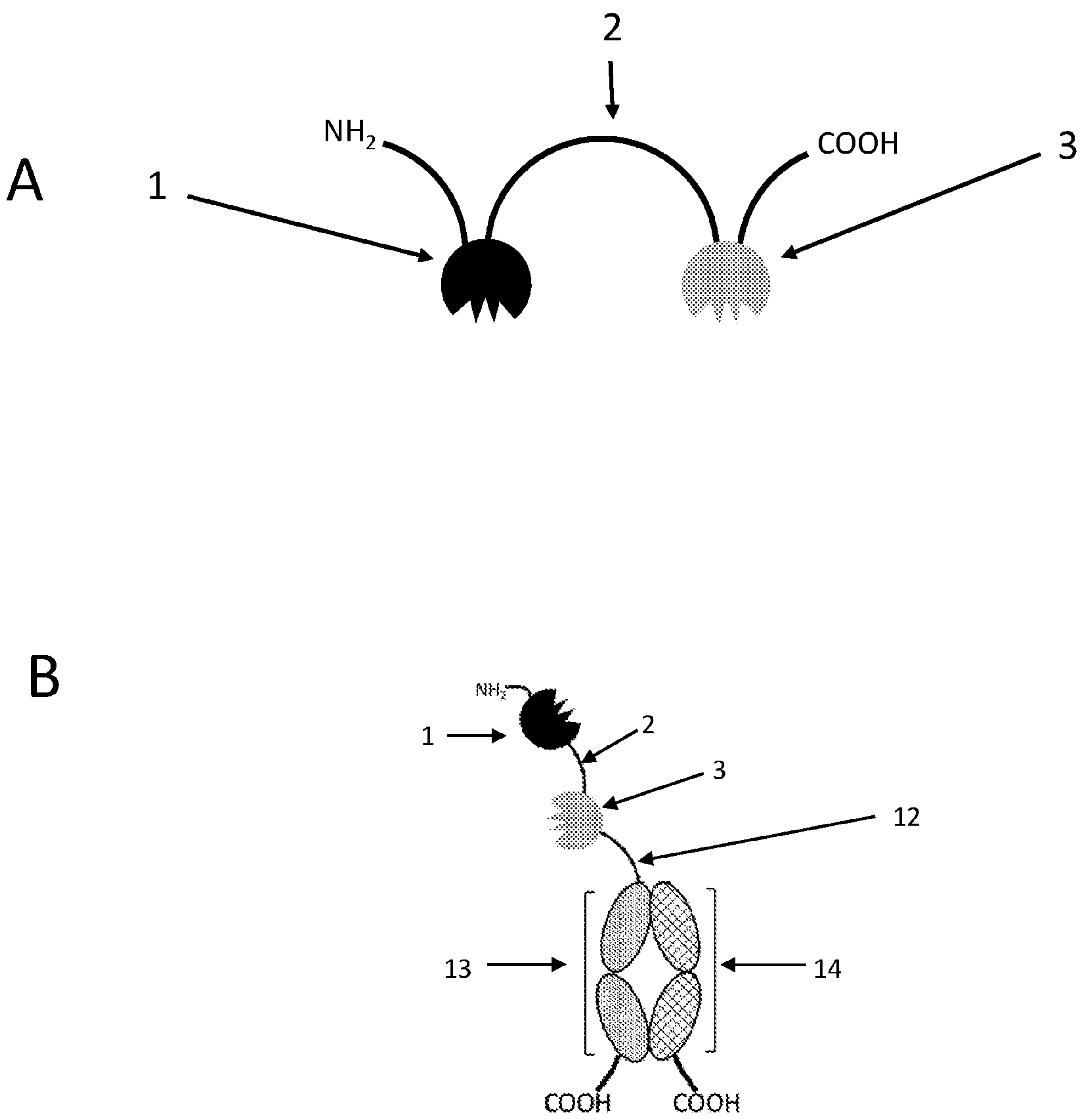
FIG. 2 of the attached drawings provides a schematic representation of two illustrative configurations of bivalent binding molecules of the present disclosure. Panel A provides a schematic representation of an illustrative single polypeptide chain bivalent binding molecule comprising, from amino to carboxy, a first single domain antibody (1) and a second single domain antibody (3) and a linker (2). Panel B provides a schematic representation of a bivalent binding molecule comprising a first single domain antibody (1) and a second single domain antibody (3) and a linker (2) and a knob-into-hole Fc domain comprising a first subunit which is a Fc knob (13) and a second subunit which is a Fc hole (14) wherein the single domain antibody is stably associated with the Fc domain via a IgG hinge sequence (12).

To facilitate the understanding of present disclosure, certain terms and phrases are defined below as well as throughout the specification. The definitions provided herein are non-limiting and should be read in view of the knowledge of one of skill in the art would know.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); AA or aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=once weekly; QM=once monthly; HPLC=high performance liquid chromatography; BW=body weight; U=unit; ns=not statistically significant; PBS=phosphate-buffered saline; PCR=polymerase chain reaction; HSA=human serum albumin; MSA=mouse serum albumin; DMEM=Dulbeco’s Modification of Eagle’s Medium; EDTA=ethylenediaminetetraacetic acid.

It will be appreciated that throughout this disclosure reference is made to amino acids according to the single letter or three letter codes. For the reader’s convenience, the single and three letter amino acid codes are provided in Table 1 below:

TABLE 1

| Amino Acid Abbreviations | | |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term “activate” is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term “activity” is used with respect to a molecule to describe a property of the molecule with respect to a test system (e.g. an assay) or biological or chemical property (e.g. the degree of binding of the molecule to another molecule) or of a physical property of a material or cell (e.g. modification of cell membrane potential). Examples of such biological functions include but are not limited to catalytic activity of a biological agent, the ability to stimulate intracellular signaling, gene expression, cell proliferation, the ability to modulate immunological activity such as inflammatory response. “Activity” is typically expressed as a level of a biological activity per unit of agent tested such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc. As used herein, the term “proliferative activity” refers to an activity that promotes cell proliferation and replication.

Administer/Administration: The terms “administration” and “administer” are used interchangeably herein to refer the act of contacting a subject, including contacting a cell, tissue, organ, or biological fluid of the subject in vitro, in vivo or ex vivo with an agent (e.g. an ortholog, an IL2 ortholog, an engineered cell expressing an orthogonal receptor, an engineered cell expressing an orthogonal IL2 receptor, a CAR-T cell expressing an orthogonal IL2 receptor, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, inhalation and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the binding kinetics expressed as $K_d$, a ratio of the dissociation constant between the molecule and its target ($K_{off}$) and the association constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state, resulting in a biological response. The response mimics the effect of the endogenous activator of the receptor. The term "agonist" includes partial agonists, full agonists and superagonists. An agonist may be described as a "full agonist" when such agonist which leads to a substantially full biological response (i.e., the response associated with the naturally occurring ligand/receptor binding interaction) induced by receptor under study, or a partial agonist. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway, or cell.

Antibody: As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4)delta$C_H$2, F(ab')2, Fab, ScFv, $V_H$, $V_L$, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, and camelids antibodies (e.g., human antibodies). The term "antibody" encompasses antibodies isolatable from natural sources or from animals following immunization with an antigen and as well as engineered antibodies including monoclonal antibodies, bispecific antibodies, trispecific, chimeric antibodies, humanized antibodies, human antibodies, CDR-grafted, veneered, or deimmunized (e.g., to remove T-cell epitopes) antibodies. The term "human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries.

Binding molecule: As used herein, the term "binding molecule" refers to a bivalent molecule that can bind to the extracellular domain of two cell surface receptors. In some embodiments, a binding molecule specifically binds to two different receptors (or domains or subunits thereof) such that the receptors (or domains or subunits) are maintained in proximity to each other such that the receptors (or domains or subunits), including domains thereof (e.g., intracellular domains) interact with each other and result in downstream signaling.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chem.* 252:6609-6616 (1977); Kabat et al., U.S. Dept. of Health and Human Services, "Sequences of proteins of immunological interest" (1991) (also referred to herein as Kabat 1991); by Chothia et al., *J Mol. Biol.* 196:901-917 (1987) (also referred to herein as Chothia 1987); and MacCallum et al., *J. Mol. Biol.* 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein.

In the context of the present disclosure, the numbering of the CDR positions is provided according to Kabat numbering conventions.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Effective Concentration (EC): As used herein, the terms "effective concentration" or its abbreviation "EC" are used interchangeably to refer to the concentration of an agent (e.g., an hIL2 mutein) in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect. The EC of a particular effective concentration of a test agent may be abbreviated with respect to the with respect to particular parameter and test system.

Extracellular Domain: As used herein the term "extracellular domain" or its abbreviation "ECD" refers to the portion of a cell surface protein (e.g. a cell surface receptor) which is outside of the plasma membrane of a cell. The term "ECD" may include the extra-cytoplasmic portion of a transmembrane protein or the extra-cytoplasmic portion of a cell surface (or membrane associated protein).

Identity: As used herein, the term "percent (%) sequence identity" or "substantially identical" used in the context of nucleic acids or polypeptides, refers to a sequence that has at least 50% sequence identity with a reference sequence. Alternatively, percent sequence identity can be any integer from 50% to 100%. In some embodiments, a sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined with BLAST using standard parameters, as described below. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned. Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)). The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about $10^{-20}$.

Intracellular Signaling: As used herein, the terms "intracellular signaling" and "downstream signaling" are used interchangeably to refer to the to the cellular signaling process that is caused by the interaction of the intracellular domains (ICDs) of two or more cell surface receptors that are in proximity of each other. In receptor complexes via the JAK/STAT pathway, the association of the ICDS of the receptor subunits brings the JAK domains of the ICDs into proximity which initiates a phosphorylation cascade in which STAT molecules are phosphorylated and translocate to the nucleus associating with particular nucleic acid sequences resulting in the activation and expression of particular genes in the cell. In some embodiments, the binding molecules of the present disclosure provide intraceullar signaling. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signaling caused by the binding molecule, can also be measured.

Ligand: As used herein, the term "ligand" refers to a molecule that exhibits specific binding to a receptor and results in a change in the biological activity of the receptor so as to effect a change in the activity of the receptor to which it binds. In one embodiment, the term "ligand" refers to a molecule, or complex thereof, that can act as an agonist or antagonist of a receptor. As used herein, the term "ligand" encompasses natural and synthetic ligands. "Ligand" also encompasses small molecules, e.g., peptide mimetics of cytokines and peptide mimetics of antibodies. The complex of a ligand and receptor is termed a "ligand-receptor complex."

As used herein, the term "linker" refers to a linkage between two elements, e.g., protein domains. A linker can be a covalent bond or a peptide linker. The term "bond" refers to a chemical bond, e.g., an amide bond or a disulfide bond, or any kind of bond created from a chemical reaction, e.g., chemical conjugation. The term "peptide linker" refers to an amino acid or polypeptide that may be employed to link two protein domains to provide space and/or flexibility between the two protein domains.

Modulate: As used herein, the terms "modulate", "modulation" and the like refer to the ability of a test agent to affect a response, either positive or negative or directly or indirectly, in a system, including a biological system or biochemical pathway.

Multimerization: As used herein, the term "multimerization" refers to two or more cell surface receptors, or domains or subunits thereof, being brought in close proximity to each other such that the receptors, or domains or subunits thereof, can interact with each other and cause intracellular signaling.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. The terms "immediately N-terminal" or "immediately C-terminal" are used to refers to a position of a first amino acid residue relative to a second amino acid residue where the first and second amino acid residues are covalently bound to provide a contiguous amino acid sequence.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the Operably Linked: The term "operably linked" is used herein to refer to the relationship between nucleic acid sequences encoding differing functions when combined into a single nucleic acid sequence that, when introduced into a cell, provides a nucleic acid which is capable of effecting the transcription and/or translation of a particular nucleic acid sequence in a cell. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, certain genetic elements such as enhancers need not be contiguous with respect to the sequence to which they provide their effect.

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. In some embodiments, by varying the linker length of the IL10Rα/IL2Rγ binding molecule, the $E_{max}$ of the IL10Rα/IL2Rγ binding molecule can be changed. The IL10Rα/IL2Rγ binding molecule can cause $E_{max}$ in the most desired cell types, and a reduced $E_{max}$ in other cell types.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; fusion proteins of immunologically active proteins (e.g. antigenic diphtheria or tetanus toxin fragments) and the like.

As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Proximity: As used herein, the term "proximity" refers to the spatial proximity or physical distance between two cell surface receptors, or domains or subunits thereof, after a binding molecule described herein binds to the two cell surface receptors, or domains or subunits thereof. In some embodiments, after the binding molecule binds to the cell surface receptors, or domains or subunits thereof, the spatial proximity between the cell surface receptors, or domains or subunits thereof, can be, e.g., less than about 500 angstroms, such as e.g., a distance of about 5 angstroms to about 500 angstroms. In some embodiments, the spatial proximity amounts to less than about 5 angstroms, less than about 20 angstroms, less than about 50 angstroms, less than about 75 angstroms, less than about 100 angstroms, less than about 150 angstroms, less than about 250 angstroms, less than about 300 angstroms, less than about 350 angstroms, less than about 400 angstroms, less than about 450 angstroms, or less than about 500 angstroms. In some embodiments, the spatial proximity amounts to less than about 100 angstroms. In some embodiments, the spatial proximity amounts to less than about 50 angstroms. In some embodiments, the spatial proximity amounts to less than about 20 angstroms. In some embodiments, the spatial proximity amounts to less than about 10 angstroms. In some embodiments, the spatial proximity ranges from about 10 to 100 angstroms, from about 50 to 150 angstroms, from about 100 to 200 angstroms, from about 150 to 250 angstroms, from about 200 to 300 angstroms, from about 250 to 350 angstroms, from about 300 to 400 angstroms, from about 350 to 450 angstroms, or about 400 to 500 angstroms. In some embodiments, the spatial proximity amounts to less than about 250 angstroms, alternatively less than about 200 angstroms, alternatively less than about 150 angstroms, alternatively less than about 120 angstroms, alternatively less than about 100 angstroms, alternatively less than about 80 angstroms, alternatively less than about 70 angstroms, or alternatively less than about 50 angstroms.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. In some embodiments, the receptor is a cell surface receptor that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface molecule having not associated with any intracellular signaling alone but upon ligand binding facilitates the formation of a multimeric complex that results in intracellular signaling.

Recombinant: As used herein, the term "recombinant" is used as an adjective to refer to the method by a polypeptide, nucleic acid, or cell that was modified using recombinant DNA technology. A recombinant protein is a protein produced using recombinant DNA technology and may be designated as such using the abbreviation of a lower case "r" (e.g., rhIL2) to denote the method by which the protein was produced. Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors. In contrast, the terms "inhibition", "down-regulation" and the like refer to the opposite effects.

Single Domain Antibody (sdAb): The term "single-domain antibody" or "sdAbs," refers to an antibody having a single (only one) monomeric variable antibody domain. A sdAb is able to bind selectively to a specific antigen. A $V_HH$ antibody, further defined below, is an example of a sdAb.

Specifically Binds: As used herein, the term "specifically bind" refers to the degree of selectivity or affinity for which one molecule binds to another. In the context of binding pairs (e.g., a binding molecule described herein/receptor, a ligand/receptor, antibody/antigen, antibody/ligand, antibody/receptor binding pairs), a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample.

Stably Associated: As used herein, the term "stably associated" or "in stable association with" are used to refer to the various means by which one molecule (e.g., a polypeptide) may be associated with another molecule over an extended period of time. The stable association of one molecule to another may be effected by a variety of means, including covalent bonding and non-covalent interactions. In some embodiments, stable association of two molecules may be effected by covalent bonds such as peptide bonds. In other embodiments, stable association of two molecules may be effected b non-covalent interactions. Examples of non-covalent interactions which may provide a stable association between two molecules include electrostatic interactions (e.g., hydrogen bonding, ionic bonding, halogen binding, dipole-dipole interactions, Van der Waals forces and π-effects including cation-π interactions, anion-π interactions and π-π interactions) and hydrophobilic/hydrophilic interactions. In some embodiments, the stable association of sdAbs of the bivalent binding molecules of the present disclosure may be effected by non-covalent interactions. In one embodiment, the non-covalent stable association of the sdAbs of the bivalent binding molecules may be achieved by conjugation of the sdAbs to "knob-into-hole" modified Fc monomers. An Fc "knob" monomer stably associates non-covalently with an Fc "hole" monomer. Conjugation of a first sdAb which specifically binds to the extracellular domain of a first subunit of a heterodimeric receptor to an "Fc knob" monomer and conjugation of an second sdAb which specifically binds to the extracellular domain of a second subunit of a heterodimeric receptor to an "Fc hole" monomer provides stable association of the first and second sdAbs.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially: As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher of a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g., blood count), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

Therapeutically Effective Amount: As used herein, the term The phrase "therapeutically effective amount" is used in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, modification of biomarker levels, increase in duration of survival, extended duration of progression free survival, extension of the time to progression, increased time to treatment failure, extended duration of event free survival, extension of time to next treatment, improvement objective response rate, improvement in the duration of response, and the like that that are relied upon by clinicians in the field for the assessment of an improvement in the condition of the subject in response to administration of an agent.

Treat: The terms "treat", "treating", treatment" and the like refer to a course of action (such as administering a binding molecule described herein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

VHH: As used herein, the term "$V_H$H" is a type of sdAb that has a single monomeric heavy chain variable antibody domain. Such antibodies can be found in or produced from Camelid mammals (e.g., camels, llamas) which are naturally devoid of light chains $V_H$Hs can be obtained from immunization of camelids (including camels, llamas, and alpacas (see, e.g., Hamers-Casterman, et al. (1993) Nature 363:446-448) or by screening libraries (e.g., phage libraries) constructed in $V_H$H frameworks. Antibodies having a given specificity may also be derived from non-mammalian sources such as $V_H$Hs obtained from immunization of cartilaginous fishes including, but not limited to, sharks. In a particular embodiment, a $V_H$H in a bispecific $V_H$H$^2$ binding molecule described herein binds to a receptor (e.g., the first receptor or the second receptor of the natural or non-natural receptor pairs) if the equilibrium dissociation constant between the $V_H$H and the receptor is greater than about $10^6$ M, alternatively greater than about $10^8$ M, alternatively greater than about $10^{10}$ M, alternatively greater than about $10^{11}$ M, alternatively greater than about $10^{10}$ M, greater than about $10^{12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in Methods in Molecular Biology, Walker, J. editor (Humana Press, Totowa NJ). Specific binding may be assessed using techniques known in the art including but not limited to competition ELISA, BIACORE® assays and/or KINEXA® assays. In some embodiments, a $V_H$H described herein can be humanized to contain human framework regions. Examples of human germlines that could be used to create humanized $V_H$Hs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

$V_H$H$^2$: As used herein, the term "$V_H$H$^2$" and "bispecific $V_H$H$^2$" and "VHH dimer" refers to are used interchangeably to refer to a subtype of the binding molecules of the present disclosure wherein the first and second sdAbs are both VHHs and first $V_H$H binding to a first receptor, or domain or subunit thereof, and a second $V_H$H binding to a second receptor, or domain or subunit thereof.

Wild Type: As used herein, the term "wild type" or "WT" or "native" is used to refer to an amino acid sequence or a nucleotide sequence that is found in nature and that has not been altered by the hand of man.

I. Bispecific Binding Molecules

The present disclosure provides disclosure provides bivalent binding molecules that are agonists of the IL10Rα/IL2Rγ receptor, the bivalent binding molecule comprising:

- a first single domain antibody (sdAb) that specifically binds to the extracellular domain of IL10Rα of the IL10Rα/IL2Rγ (an "anti-IL10Rα sdAb"), and
- a second single domain antibody that specifically binds to extracellular domain IL2Rγ of the IL10Rα/IL2Rγ ((an "anti-IL2Rγ sdAb"), wherein the anti-IL10Rα sdAb and anti-IL2Rγ sdAb are stably associated and first wherein contacting a cell expressing IL10Rα and IL2Rγ with an effective amount of the bivalent binding molecule results the dimerization of IL10Rα and IL2Rγ and results in intraceullar signaling. In some embodiments, one or both of the sdAbs is a an scFv. In some embodiments, one or both of the sdAbs is a VHH.

The amino acid sequence of the mature form (less the signal peptide) of IL10Rα is provided as SEQ ID NO: 7.

```
                                          (SEQ ID NO: 7)
HGTELPSPPSVWFEAEFFHHILHWTPIPNQSESTCYEVALLRYGIESWN

SISNCSQTLSYDLTAVTLDLYHSNGYRARVRAVDGSRHSNWTVTNTRFS

VDEVTLTVGSVNLEIHNGFILGKIQLPRPKMAPANDTYESIFSHFREYE

IAIRKVPGNFTFTHKKVKHENFSLLTSGEVGEFCVQVKPSVASRSNKGM

WSKEECISLTRQYFTVTNVIIFFAFVLLLSGALAYCLALQLYVRRRKKL

PSVLLFKKPSPFIFISQRPSPETQDTIHPLDEEAFLKVSPELKNLDLHG

STDSGFGSTKPSLQTEEPQFLLPDPHPQADRTLGNREPPVLGDSCSSGS

SNSTDSGICLQEPSLSPSTGPTWEQQVGSNSRGQDDSGIDLVQNSEGRA

GDTQGGSALGHHSPPEPEVPGEEDPAAVAFQGYLRQTRCAEEKATKTGC

LEEESPLTDGLGPKFGRCLVDEAGLHPPALAKGYLKQDPLEMTLASSGA

PTGQWNQPTEEWSLLALSSCSDLGISDWSFAHDLAPLGCVAAPGGLLGS

FNSDLVTLPLISSLQSSE
```

The amino acid sequence of the mature form (less the signal peptide) of IL2Rγ is provided as SEQ ID NO: 8.

```
                                          (SEQ ID No: 8)
LNTTILTPNGNEDTTADFFLTTMPTDSLSVSTLPLPEVQCFVFNVEYMN

CTWNSSSEPQPTNLTLHYWYKNSDNDKVQKCSHYLFSEEITSGCQLQKK

EIHLYQTFVVQLQDPREPRRQATQMLKLQNLVIPWAPENLTLHKLSESQ

LELNWNNRFLNHCLEHLVQYRTDWDHSWTEQSVDYRHKFSLPSVDGQKR

YTFRVRSRFNPLCGSAQHWSEWSHPIHWGSNTSKENPFLFALEAVVISV

GSMGLIISLLCVYFWLERTMPRIPTLKNLEDLVTEYHGNFSAWSGVSKG

LAESLQPDYSERLCLVSEIPPKGGALGEGPGASPCNQHSPYWAPPCYTL

KPET.
```

Provided herein is an IL10Rα/IL2Rγ binding molecule that specifically binds to IL10Rα and IL2Rγ. In some embodiments, the IL10Rα/IL2Rγ binding molecule binds to a mammalian cell expressing both IL10Rα and IL2Rγ. In some embodiments, the IL10Rα/IL2Rγ binding molecule can be a bispecific VHH2 as described below.

IL-10 of signals on T cells. The IL-10R1 receptor has a JAK associated with it and STAT3 is phosphorylated. IL-2Rg also has a JAK of course but there is NO STAT associated with this IL-2Rg. So the only signal you drive with these the IL10Rα/IL2Rγ binding molecules into these CD8 T cells is in fact coming via STAT3, just like IL-10 itself.

Single Domain Antibody Is A VHH

In some embodiments, the single domain antibody is a VHH. A $V_H$H is a type of single-domain antibody (sdAb) containing a single monomeric variable antibody domain. Like a full-length antibody, it is able to bind selectively to a specific antigen. The complementary determining regions (CDRs) of $V_H$Hs are within a single-domain polypeptide. $V_H$Hs can be engineered from heavy-chain antibodies found in camelids. An exemplary $V_H$H has a molecular weight of approximately 12-15 kDa which is much smaller than traditional mammalian antibodies (150-160 kDa) composed of two heavy chains and two light chains. $V_H$Hs can be found in or produced from Camelidae mammals (e.g., camels, llamas, dromedary, alpaca, and guanaco) which are naturally devoid of light chains. Descriptions of sdAbs and $V_H$HS can be found in, e.g., De Greve et al., *Curr Opin Biotechnol.* 61:96-101, 2019; Ciccarese, et al., *Front Genet.* 10:997, 2019; Chanier and Chames, *Antibodies* (*Basel*) 8(1), 2019; and De Vlieger et al., *Antibodies* (*Basel*) 8(1), 2018.

Exemplary Anti IL10Rα Single Domain Antibodies

Table 2 provides CDRs useful in the preparation of anti-IL10Rα sdAbs for incorporation into the bivalent binding molecules of the present disclosure. In some embodiments, the anti-IL10Rα sdAbs is a single domain antibody comprising, one or more anti-human IL10 Rα CDRs in a row of Table 2, wherein each CDR independently comprises 0, 1, 2, or 3 amino acid changes relative to the sequence of Table 2.

In some embodiments, the anti-IL10Rα sdAb comprises a sequence having at least 90% (e.g., 91%, 92%, 93%, 94%, 95%, 96%, 97%, 98%, 99%, or 100%) sequence identity to a sequence of any one the of anti-IL10Rα sdAbs provided in Table 5. In certain embodiments, the binding molecule comprises a sequence that is substantially identical to a sequence of any one of listed in a row of Table 5.

In another aspect, the disclosure provides an isolated nucleic acid encoding anti-IL10Rα sdAb described herein. Table 8 provides DNA sequences encoding the anti-IL10Rα sdAbs of Table 5, respectively. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence listed in a row Table 8.

Exemplary Anti IL2Rγ Single Domain Antibodies

Tables 3 and 4 provides CDRs useful in the preparation of anti-IL2Rγ sdAbs. In some embodiments, anti-IL2Rγ sdAb is a single domain antibody comprising, one or more anti-human IL2Rγ CDRs in a row of Table 3, wherein each CDR independently comprises 0, 1, 2, or 3 amino acid changes relative to the sequence of Table 3.

In some embodiments, anti-IL2Rγ sdAb is a single domain antibody comprising, one or more anti-murine IL2Rγ CDRs in a row of Table 4, wherein each CDR independently comprises 0, 1, 2, or 3 amino acid changes relative to the sequence of Table 4.

In some embodiments, the anti-IL2Rγ sdAb comprises a sequence having at least 90% (e.g., 91%, 92%, 93%, 94%, 95%, 96%, 97%, 98%, 99%, or 100%) sequence identity to a sequence of any one the of anti-human IL2Rγ sdAbs provided in Table 6. In certain embodiments, the binding molecule comprises a sequence that is substantially identical to a sequence of any one of listed in a row of Table 6.

In some embodiments, the anti-IL2Rγ sdAb comprises a sequence having at least 90% (e.g., 91%, 92%, 93%, 94%, 95%, 96%, 97%, 98%, 99%, or 100%) sequence identity to a sequence of any one the of anti-murine IL2Rγ sdAbs provided in Table 7. In certain embodiments, the binding molecule comprises a sequence that is substantially identical to a sequence of any one of listed in a row of Table 7.

In another aspect, the disclosure provides an isolated nucleic acid encoding anti-IL2Rγ sdAb described herein. Table 9 provides DNA sequences encoding the anti-human IL10Rα sdAbs of Table 6. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence listed in a row Table 9.

In another aspect, the disclosure provides an isolated nucleic acid encoding anti-IL2Rγ sdAb described herein. Table 10 provides DNA sequences encoding the anti-murine IL10Rα sdAbs of Table 6. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence listed in a row Table 10.

Anti IL10Rα/IL2Rγ VHH Dimer Bispecific Binding Molecules

A. "Forward Orientation"

In some embodiments, the bivalent IL10Rα/IL2Rγ binding molecule comprises a polypeptide of the structure:

$$H_2N\text{-[anti-IL10R}\alpha\text{ sdAb]-[L]}_x\text{-[anti-IL2R}\gamma\text{ sdAb]-[TAG]}_y\text{-COOH}$$

wherein and L is a polypeptide linker of 1-50 amino acids and x=0 or 1, and TAG is a chelating peptide or a subunit of an Fc domain and y=0 or 1.

In some embodiments, a bivalent IL10Rα/IL2Rγ binding molecule of the foregoing structure comprises a polypeptide from amino to carboxy terminus:

(a) an anti-IL10Rα sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR1 in a row of Table 2.
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR2 in a row of Table 2; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR3 listed in Table 2;

(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and (c) an anti-IL2Rγ sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR1 listed in Table 3 or Table 4;
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR2 listed in Table 3 or Table 4; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR3 listed in Table 3 or Table 4.

In some embodiments, the bivalent IL10Rα/IL2Rγ binding molecule comprises an anti-IL10Rα sdAb comprising a CDR1, a CDR2, and a CDR3 as listed in a row of Table 2 and an anti-IL2Rγ sdAb comprising a CDR1, a CDR2, and a CDR3 as listed in a row of Table 3 or Table 4.

In some embodiments, the anti-IL10Rα sdAb of the bivalent IL10Rα/IL2Rγ binding molecule comprises a sequence having at least 90% (e.g., 91%, 92%, 93%, 94%, 95%, 96%, 97%, 98%, 99%, or 100%) sequence identity to a sequence of any one the of anti-IL10Rα sdAbs provided in Table 5. In some embodiments, the anti-IL2Rγ sdAb of the bivalent IL10Rα/IL2Rγ binding molecule comprises a sequence having at least 90% (e.g., 91%, 92%, 93%, 94%, 95%, 96%, 97%, 98%, 99%, or 100%) sequence identity to a sequence of any one the of anti-IL2Rγ sdAbs provided in Table 6 or Table 7/

B. "Reverse Orientation"

In some embodiments, the bivalent IL10Rα/IL2Rγ binding molecule comprises a polypeptide of the structure:

$H_2N$-[anti-IL2Rγ sdAb]-$[L]_x$-[anti-IL10Rα sdAb]-$[TAG]_y$-COOH wherein and L is a polypeptide linker of 1-50 amino acids and x=0 or 1, and TAG is a chelating peptide or a subunit of an Fc domain and y=0 or 1.

In some embodiments, a bivalent IL10Rα/IL2Rγ binding molecule of the foregoing structure comprises a polypeptide from amino to carboxy terminus:

(a) an anti-IL2Rγ sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR1 listed in Table 3 or Table 4;
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR2 listed in Table 3 or Table 4; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR3 listed in Table 3 or Table 4.

(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and (c) an anti-IL10Rα sdAb comprising:

a. a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR1 in a row of Table 2.

b. a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR2 in a row of Table 2; and c. a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any CDR3 listed in Table 2;

In some embodiments, the anti-IL2Rγ sdAb comprises a sequence having at least 90% (e.g., 91%, 92%, 93%, 94%, 95%, 96%, 97%, 98%, 99%, or 100%) sequence identity to a sequence listed in a row of Table 6 or Table 7. In certain embodiments, the anti-IL10Rα sdAb comprises a sequence having at least 90% sequence identity to a sequence of any one of listed in a row of Table 5.

II. Linkers

A linker can be used to join the anti-IL10Rα sdAb and the anti-IL10Rα sdAb antibody. A linker is a linkage between two linker is a linkage between the two sdAbs in the binding molecule, e.g., protein domains. For example, a linker can simply be a covalent bond or a peptide linker. In some embodiments, the sdAbs in a binding molecule are joined directly (i.e., via a covalent bond). In a bispecific $V_HH^2$ binding molecule described herein, a linker is a linkage between the two $V_H$Hs in the binding molecule. A In some embodiments, the linker is a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids).

Examples of flexible linkers include glycine polymers (G)n, glycine-alanine polymers, alanine-serine polymers, glycine-serine polymers (for example, (GmSo)n (SEQ ID NO:306), (GSGGS)n (SEQ ID NO:307), (GmSoGm)n (SEQ ID NO:308), (GmSoGmSoGm)n (SEQ ID NO:309), (GSGGSm)n (SEQ ID NO:310), (GSGSmG)n (SEQ ID NO:311) and (GGGSm)n (SEQ ID NO:312), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Glycine and glycine-serine polymers are relatively unstructured, and therefore may serve as a neutral tether between components Exemplary flexible linkers include, but are not limited to GGGS (SEQ ID NO:9), GGGGS (SEQ ID NO: 10), GGSG (SEQ ID NO: 11), GGSGG (SEQ ID NO: 12), GSGSG (SEQ ID NO: 13), GSGGG (SEQ ID NO: 14), GGGSG (SEQ ID NO: 15) and GSSSG (SEQ ID NO: 16). In yet other embodiments, a peptide linker can contain 4 to 20 amino acids including motifs of GGSG (SEQ ID NO:11), e.g., GGSGGGSG (SEQ ID NO:17), GGSGGGSGGGSG (SEQ ID NO:18), GGSGGGSGGGSGGGSG (SEQ ID NO:19), or GGSGGGSGGGSGGGSGGGSG (SEQ ID NO:20). In other embodiments, a peptide linker can contain motifs of GGSG (SEQ ID NO:11), e.g., GGSGGGSG (SEQ ID NO:17), GGSGGGSGGGSG (SEQ ID NO:18), GGSGGGSGGGSGGGSG (SEQ ID NO:19), or GGSGGGSGGGSGGGSGGGSG (SEQ ID NO:20)

A linker can also be a chemical linker, such as a synthetic polymer, e.g., a polyethylene glycol (PEG) polymer.

The length of the linker between two sdAb in a binding molecule can be used to modulate the proximity of the two sdAb of the binding molecule. By varying the length of the linker, the overall size and length of the binding molecule can be tailored to bind to specific cell receptors or domains or subunits thereof. For example, if the binding molecule is designed to bind to two receptors or domains or subunits thereof that are located close to each other on the same cell, then a short linker can be used. In another example, if the binding molecule is designed to bind to two receptors or domains or subunits there of that are located on two different cells, then a long linker can be used.

In some embodiments, a linker joins the C-terminus of the anti-IL10Rα sdAb in the binding molecule to the N-terminus of the anti-IL2Rγ sdAb in the binding molecule. In other embodiments, a linker joins the C-terminus of the anti-IL2Rγ sdAb in the binding molecule to the N-terminus of the anti-IL10Rα sdAb in the binding molecule.

Modulation of sdAb Binding Affinity:

In some embodiments, the activity and/or specificity of the bivalent IL10Rα/IL2Rγ binding molecule of the present disclosure may be modulated by the respective binding affinities of the sdAbs for their respective receptor subunits.

It will be appreciated by one of skill in the art that the binding of the first sdAb of the bivalent IL10Rα/IL2Rγ binding molecule to the first receptor subunit ECD on the cell surface will enhance the probability of a binding interaction between the second sdAb of the bivalent IL10Rα/IL2Rγ binding molecule with the ECD of the second receptor subunit. This cooperative binding effect may result in a bivalent IL10Rα/IL2Rγ binding molecule which has a very high affinity for the receptor and a very slow "off rate" from the receptor. Typical VHH single domain antibodies have an affinity for their targets of from about $10^{-5}$M to about $10^{-10}$M. In those instances such slow off-rate kinetics are desirable in the bivalent IL10Rα/IL2Rγ binding molecule, the selection of sdAbs having high affinities (about $10^{-7}$M to about $10^{-10}$M) for incorporation into the bivalent IL10Rα/IL2Rγ binding molecule are favored.

Naturally occurring cytokine ligands typically do not exhibit a similar affinity for each subunit of a heterodimeric receptor. Consequently, in designing a bivalent IL10Rα/IL2Rγ binding molecule, selection of sdAbs for the first and second IL10Rα/IL2Rγ receptor subunit have an affinity similar to (e.g., having an affinity about 10 fold, alternatively about 20 fold, or alternatively about 50 fold higher or lower than) the cognate ligand for the respective receptor subunit may be used.

In some embodiments, the bivalent IL10Rα/IL2Rγ binding molecules of the present disclosure are partial agonists of the IL10Rα/IL2Rγ receptor. As such, the activity of the bivalent binding molecule may be modulated by selecting sdAb which have greater or lesser affinity for either one or both of the IL10Rα/IL2Rγ receptor subunits. As some heterodimeric cytokine receptors are comprised of a "proprietary subunit" (i.e., a subunit which is not naturally a subunit of another multimeric receptor) and a second "common" subunit (such as CD132) which is a shared component of multiple cytokine receptors), selectivity for the formation of such receptor may be enhanced by employing first sdAb which has a higher affinity for the proprietary receptor subunit and second sdAB which exhibits a lower affinity for the common receptor subunit. Additionally, the common receptor subunit may be expressed on a wider variety of cell types than the proprietary receptor subunit. In some embodiments wherein the receptor is a heterodimeric receptor comprising a proprietary subunit and a common subunit, the first sdAb of the bivalent IL10Rα/IL2Rγ binding molecule exhibits a significantly greater (more than 10 times greater, alternatively more than 100 times greater, alternatively more than 1000 times greater) affinity for the proprietary receptor than the second sdAb of the bivalent IL10Rα/IL2Rγ binding molecule for the common receptor subunit. In one embodiment, the present disclosure provides a bivalent IL10Rα/IL2Rγ binding molecule wherein the affinity of the anti-IL10Rα sdAb of has an affinity of more than 10 times greater, alternatively more than 100 times greater, alternatively more than 1000 times greater) affinity anti-IL2Rγ sdAb common receptor subunit.

A series of illustrative IL10Rα/IL2Rγ bivalent binding molecules of the present disclosure were prepared in accordance with the teaching of the Examples. The amino acid sequences of these illustrative IL10Rα/IL2Rγ bivalent binding molecules are provide TABLE 14 below. Bivalent constructs, optionally comprising a GGGS (SEQ ID NO: 9) and/or C-terminal GSHis8 (SEQ ID NO:22) chelating peptide were designed as indicated in Table 14. Nucleic acid sequences were isolated from the antibody producing cells of the camels and these were used for the construction of nucleic acid sequences optimized for the expression control system were generated. In particular, modification of nucleic acid sequences to facilitate insertion into the expression vector were performed, for example avoid undesired restriction sites and codon optimized for the host cell line in accordance with procedures well known in the art. The binding activity of these molecules was evaluated according to the Examples and the data provided in FIG. 15.

As discussed above, the biological activity of the IL10R binding molecules may be modulated by varying the distance between the first and second sdAbs of the IL10Rα/IL2Rγ binding molecules binding molecule in the present disclosure, the activity of the IL10Rα/IL2Rγ binding molecules dimeric VHH bivalent binding molecules of the present disclosure may be modulated by varying the length of the linker between the first and second sdAb of the IL10Rα/IL2Rγ binding molecule The IL10 activity as reflected by the level of STAT3 phosphorylation induced in each cell type in response of each of the IL10Rα/IL2Rγ binding molecules was evaluated on CD4+, CD8+ T cells and monocytes at concentrations of 0.0001 picomolar, 0.001 picomolar, 0.01 picomolar, 0.1 picomolar, 1 picomolar, 10 picomolar and 100 picomolar. To measure monocyte and CD8 T cell cytokine secretion by Meso Scale Discovery (MSD), PBMCs were first isolated from whole human blood using a commercial kit. The PBMCs were then divided into two groups to isolate monocytes and T cells. In one group, PBMCs were incubated with CD14 microbeads and monocytes were isolated using autoMACS Pro Separator. In the other group the PBMCs were incubated with CD8 T cell negative selection beads and CD8 T cells were isolated using the autoMACS Pro Separator. The monocytes were treated with 1 ng/mL LPS along with IL10R1/IL2Rg molecules (0.1 pM-100 nM). Supernatant from monocytes was collected after 48 hours and tested for cytokine secretion (IL-1β, IL-6, TNF-α, IL-8) by an MSD assay. CD8 T cells were blasted for 3 days using anti-CD2, anti-CD3, and anti-CD28 microbeads. Day 3 CD8 blasts were treated with IL10R1/IL2Rg molecules (0.1 pM-100 nM) for 72 hours. Supernatant from CD8 T cells was collected after 72 hours and tested for cytokine secretion (IFNγ, Granzyme A, Granzyme B, IL-9) by an MSD assay.

PBMCs were isolated from whole human blood. They were stained with a Live/Dead fixable dye. The cells were treated with IL10R1/IL2Rg molecules (0.1 pM-100 nM) at 37° C. for 20 minutes. The PBMCs were then fixed, permealized, and stained with CD4, CD8a, CD56, pSTAT3, CD3, CD14, and CD20 fluorescent antibodies for one hour and then run on a flow cytometer

III. Modifications to Extend Duration of Action In Vivo

The IL10Rα/IL2Rγ bivalent binding molecule described herein can be modified to provide for an extended lifetime in vivo and/or extended duration of action in a subject. In some embodiments, the binding molecule can be conjugated to carrier molecules to provide desired pharmacological properties such as an extended half-life. In some embodiments, the binding molecule can be covalently linked to the Fc domain of IgG, albumin, or other molecules to extend its half-life, e.g., by pegylation, glycosylation, and the like as known in the art. In some embodiments, the IL10Rα/IL2Rγ bivalent binding molecule modified to provide an extended duration of action in a mammalian subject has a half-life in a mammalian of greater than 4 hours, alternatively greater than 5 hours, alternatively greater than 6 hours, alternatively greater than 7 hours, alternatively greater than 8 hours, alternatively greater than 9 hours, alternatively greater than 10 hours, alternatively greater than 12 hours, alternatively greater than 18 hours, alternatively greater than 24 hours, alternatively greater than 2 days, alternatively greater than 3 days, alternatively greater than 4 days, alternatively greater than 5 days, alternatively greater than 6 days, alternatively greater than 7 days, alternatively greater than 10 days, alternatively greater than 14 days, alternatively greater than 21 days, or alternatively greater than 30 days.

Modifications of the IL10Rα/IL2Rγ bivalent binding molecule to provide an extended duration of action in a mammalian subject include (but are not limited to);

- conjugation of the IL10Rα/IL2Rγ bivalent binding molecule to one or more carrier molecules,
- conjugation of the IL10Rα/IL2Rγ bivalent binding molecule to protein carriers molecules, optionally in the form of a fusion protein with additional polypeptide sequences (e.g, IL10Rα/IL2Rγ bivalent binding molecule-Fc fusions) and
- conjugation to polymers, (e.g. water soluble polymers to provide a PEGylated IL10Rα/IL2Rγ bivalent binding molecule).

It should be noted that the more than one type of modification that provides for an extended duration of action in a mammalian subject may be employed with respect to a given IL10Rα/IL2Rγ bivalent binding molecule. For example, IL10Rα/IL2Rγ bivalent binding molecule of the present disclosure may comprise both amino acid substitutions that provide for an extended duration of action as well as conjugation to a carrier molecule such as a polyethylene glycol (PEG) molecule.

Protein Carrier Molecules:

Examples of protein carrier molecules which may be covalently attached to the IL10Rα/IL2Rγ bivalent binding molecule to provide an extended duration of action in vivo include, but are not limited to albumins, antibodies and antibody fragments such and Fc domains of IgG molecules Fc Fusions:

In some embodiments, the IL10Rα/IL2Rγ bivalent binding molecule is conjugated to a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The binding molecule described herein can be conjugated to the entire Fc region, or a smaller portion that retains the ability to extend the circulating half-life of a chimeric polypeptide of which it is a part. In addition, full-length or fragmented Fc regions can be variants of the wild-type molecule. In a typical presentation, each monomer of the dimeric Fc can carry a heterologous polypeptide, the heterologous polypeptides being the same or different.

Illustrative examples of Fc formats useful for IL10Rα/IL2Rγ bivalent binding molecules of the present disclosure are provided schematically in FIGS. 1-4 of the attached drawings.

Linkage of Bivalent Binding Molecule to Fc

As indicated, the linkage of the IL10Rα/IL2Rγ bivalent binding molecule to the Fc subunit may incorporate a linker molecule as described below between the bivalent sdAb and Fc subunit. In some embodiments, the IL10Rα/IL2Rγ bivalent binding molecule is expressed as a fusion protein with the Fc domain incorporating an amino acid sequence of a hinge region of an IgG antibody. The Fc domains engineered in accordance with the foregoing may be derived from IgG1, IgG2, IgG3 and IgG4 mammalian IgG species. In some embodiments, the Fc domains may be derived from human IgG1, IgG2, IgG3 and IgG4 IgG species. In some embodiments, the hinge region is the hinge region of an IgG1. In one particular embodiment, the IL10Rα/IL2Rγ bivalent binding is linked to an Fc domain using an human IgG1 hinge domain.

Knob-Into-Hole Fc Format

In some embodiments, when the IL10Rα/IL2Rγ bivalent binding molecule described herein is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob"), and ii) in the CH3 domain of a second heavy chain, an amino acid residue is replaced with an amino acid residue having a smaller side chain (e.g., alanine or threonine), thereby generating a cavity ("hole") at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fc region (Carter, et al. (2001) Immunol Methods 248, 7-15).

Figure 3:
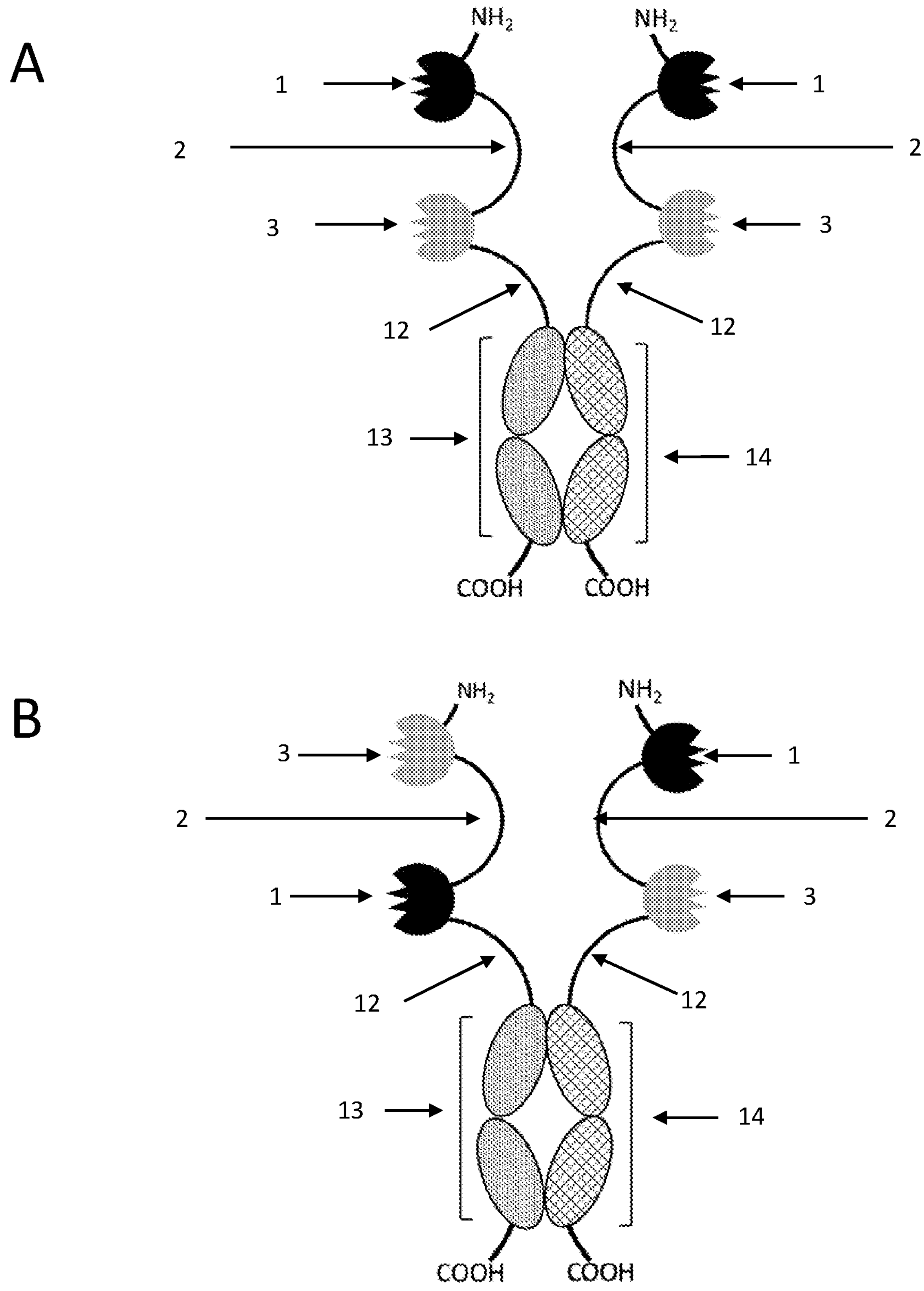
FIG. 3 of the attached drawings provides a schematic representation of two illustrative configurations of bivalent binding molecules of the present disclosure. Panel A provides a schematic representation of an illustrative bivalent binding molecule comprising a first single domain antibody (1) and a second single domain antibody (3) and a linker (2). Panel B provides a schematic representation of a bivalent binding molecule comprising two polypeptide chains, the first polypeptide chain comprising (from amino to carboxy) a first single domain antibody (1), a linker sequence, a second single domain antibody (3), an IgG hinge sequence (12) and an Fc knob domain (13) and a second polypeptide comprising an Fc hole (14) wherein the first and second polypeptides are in stable association via the interaction of the knob-into-hole Fc domain.
Figure 4:
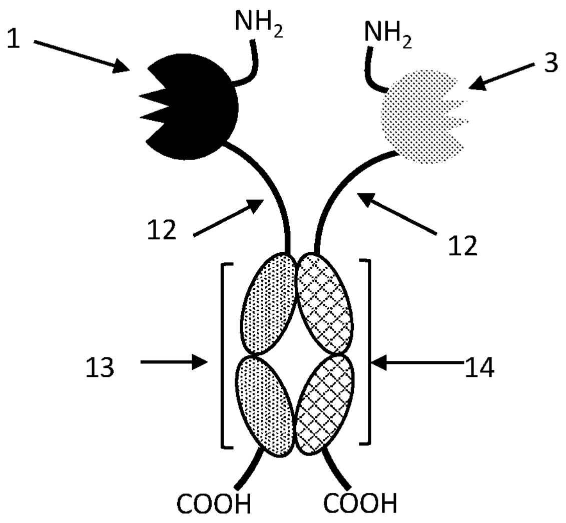
FIG. 4, Panel A provides alternative schematic representations of configurations of the bivalent binding molecules of the present disclosure where one single domain antibody is attached to each subunit of a knob-into-hole Fc domain comprising two polypeptides, the first polypeptide comprising from amino to carboxy, a first single domain antibody (1), an IgG hinge sequence (12) and a Fc knob subunit (13), the second polypeptide comprising from amino to carboxy, a second single domain antibody (3), an IgG hinge sequence (12) and a Fc hole subunit (13), wherein the first and second single domain antibodies are in stable associate via the interaction of the knob-into-hole Fc domain.
Figure 4:
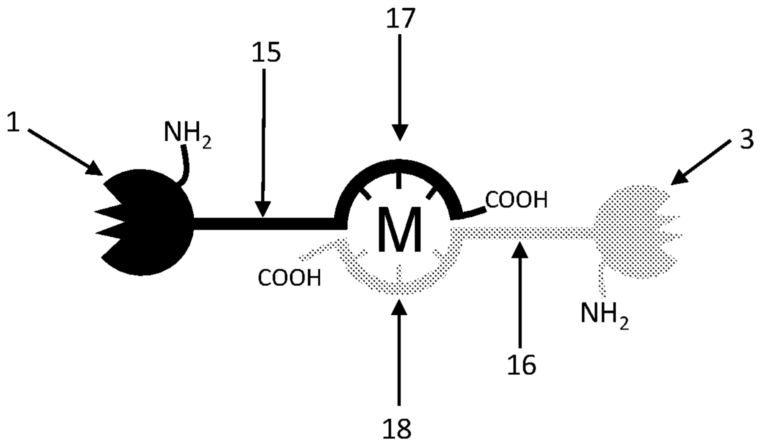

The knob-into-hole format is used to facilitate the expression of a first polypeptide on a first Fc monomer with a "knob" modification and a second polypeptide on the second Fc monomer possessing a "hole" modification to facilitate the expression of heterodimeric polypeptide conjugates. In some embodiments, the IL10Rα/IL2Rγ bivalent binding molecule covalently linked to a single subunit of the Fc as illustrated in FIG. 3, a IL10Rα/IL2Rγ bivalent binding molecule is provided on each of the subunits of the Fc as illustrated in FIG. 4A.

Albumin Carrier Molecules

In some embodiments, the IL10Rα/IL2Rγ bivalent binding molecule conjugated to an is albumin molecule (e.g., human serum albumin) which is known in the art to facilitate extended exposure in vivo. In one embodiment of the invention, the IL10Rα/IL2Rγ bivalent binding molecule is conjugated to albumin via chemical linkage or expressed as a fusion protein with an albumin molecule referred to herein as an IL10Rα/IL2Rγ bivalent binding molecule albumin fusion." The term "albumin" as used in the context αβhIL2 mutein albumin fusions include albumins such as human serum albumin (HSA), cyno serum albumin, and bovine serum albumin (BSA). In some embodiments, the HSA the HSA comprises a C34S or K573P amino acid substitution relative to the wild-type HSA sequence According to the present disclosure, albumin can be conjugated to a IL10Rα/IL2Rγ bivalent binding molecule at the carboxyl terminus, the amino terminus, both the carboxyl and amino termini, and internally (see, e.g., U.S. Pat. Nos. 5,876,969 and 7,056,701). In the HSA IL10Rα/IL2Rγ bivalent binding molecule contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a IL10Rα/IL2Rγ bivalent binding molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. As an alternative to chemical linkage between the IL10Rα/IL2Rγ bivalent binding molecule and the albumin molecule the IL10Rα/IL2Rγ bivalent binding molecule—albumin complex may be provided as a fusion protein comprising an albumin polypeptide sequence and an IL10Rα/IL2Rγ bivalent binding molecule recombinantly expressed in a host cell as a single polypeptide chain, optionally comprising a linker molecule between the albumin and IL10Rα/IL2Rγ bivalent binding molecule. Such fusion proteins may be readily prepared through recombinant technology to those of ordinary skill in the art. Nucleic acid sequences encoding such fusion proteins may be ordered from any of a variety of commercial sources. The nucleic acid sequence encoding the fusion protein is incorporated into an expression vector operably linked to one or more expression control elements, the vector introduced into a suitable host cell and the fusion protein solated from the host cell culture by techniques well known in the art.

Polymeric Carriers

In some embodiments, extended in vivo duration of action of the IL10Rα/IL2Rγ bivalent binding molecule may be achieved by conjugation to one or more polymeric carrier molecules such as XTEN polymers or water soluble polymers.

XTEN Conjugates

The IL10Rα/IL2Rγ bivalent binding molecule may further comprise an XTEN polymer. The XTEN polymer may be is conjugated (either chemically or as a fusion protein) the αβhIL2 mutein provides extended duration of akin to PEGylation and may be produced as a recombinant fusion protein in *E. coli*. XTEN polymers suitable for use in conjunction with the IL10Rα/IL2Rγ bivalent binding molecule of the present disclosure are provided in Podust, et al. (2016) "*Extension of in vivo half-life of biologically active molecules by XTEN protein polymers*", J Controlled Release 240:52-66 and Haeckel et al. (2016) "*XTEN as Biological Alternative to PEGylation Allows Complete Expression of a Protease-Activatable Killin-Based Cytostatic*" PLOS ONE-|DOI:10.1371/journal.pone.0157193 Jun. 13, 2016. The XTEN polymer may fusion protein may incorporate a protease sensitive cleavage site between the XTEN polypeptide and the hIL2 mutein such as an MMP-2 cleavage site.

Water Soluble Polymers

In some embodiments, the IL10Rα/IL2Rγ bivalent binding molecule can be conjugated to one or more water-soluble polymers. Examples of water soluble polymers useful in the practice of the present disclosure include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol,), polysaccharides), poly-alpha-hydroxy acid), polyvinyl alcohol (PVA), polyphosphazene, polyoxazolines (POZ), poly(N-acryloylmorpholine), or a combination thereof.

In some embodiments, IL10Rα/IL2Rγ bivalent binding molecule can be conjugated to one or more polyethylene glycol molecules or "PEGylated." Although the method or site of PEG attachment to the binding molecule may vary, in certain embodiments the PEGylation does not alter, or only minimally alters, the activity of the binding molecule.

PEGs suitable for conjugation to a polypeptide sequence are generally soluble in water at room temperature, and have the general formula $$R(O{-}CH_2{-}CH_2)_nO{-}R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

In some embodiments, selective PEGylation of the IL10Rα/IL2Rγ bivalent binding molecule, for example, by the incorporation of non-natural amino acids having side chains to facilitate selective PEG conjugation, may be employed. Specific PEGylation sites can be chosen such that PEGylation of the binding molecule does not affect its binding to the target receptors.

In some instances, the sequences of IL10Rα/IL2Rγ bivalent binding molecules of the present disclosure possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL10Rα/IL2Rγ binding molecules of the present disclosure, particularly when aldehyde chemistry is to be employed, the IL10Rα/IL2Rγ binding molecules possessing an amino acid at position 1 (e.g., 1Q) are substituted at position 1 with an alternative amino acid or are deleted at position 1 (e.g., des-1Q). In some embodiments, the IL10Rα/IL2Rγ binding molecules of the present disclosure comprise an amino acid substitution selected from the group Q1E and Q1D.

In certain embodiments, the increase in half-life is greater than any decrease in biological activity. PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa, or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbonst Two widely used first generation activated monomethoxy PEGs (mPEGs) are succinimdyl carbonate PEG (SC-PEG; see, e.g., Zalipsky, et al. (1992) *Biotehnol. Appl. Biochem* 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General PEGylation strategies known in the art can be applied herein.

The PEG can be bound to a binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the binding molecules is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin et al., PCT International Application No. PCT/US2018/045257 filed Aug. 3, 2018 and published Feb. 7, 2019 as International Publication Number WO 2019/028419A1.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF), a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

In some embodiments, a linker can used to join the IL10Rα/IL2Rγ bivalent binding molecule and the PEG molecule. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers are described in Section IV. Further, a multimer (e.g., 1, 2, 3, 4, 5, 6, 7, 8, 9, 10, 10-20, 20-30, or 30-50) of these linker sequences may be linked together to provide flexible linkers that may be used to conjugate two molecules. Alternative to a polypeptide linker, the linker can be a chemical linker, e.g., a PEG-aldehyde linker. In some embodiments, the binding molecule is acetylated at the N-terminus by enzymatic reaction with N-terminal acetyltransferase and, for example, acetyl CoA. Alternatively, or in addition to N-terminal acetylation, the binding molecule can be acetylated at one or more lysine residues, e.g., by enzymatic reaction with a lysine acetyltransferase. See, for example Choudhary et al. (2009) Science 325 (5942):834-840.

Fatty Acid Carriers

In some embodiments an IL10Rα/IL2Rγ bivalent binding molecule having an extended duration of action in a mammalian subject and useful in the practice of the present disclosure is achieved by covalent attachment of the IL10Rα/IL2Rγ bivalent binding molecule to a fatty acid molecule as described in Resh (2016) Progress in Lipid Research 63: 120-131. Examples of fatty acids that may be conjugated include myristate, palmitate and palmitoleic acid. Myristoylate is typically linked to an N-terminal glycine but lysines may also be myristoylated. Palmitoylation is typically achieved by enzymatic modification of free cysteine—SH groups such as DHHC proteins catalyze S-palmitoylation. Palmitoleylation of serine and threonine residues is typically achieved enzymatically using PORCN enzymes. In some embodiments, the IL10Rα/IL2Rγ bivalent binding molecule is acetylated at the N-terminus by enzymatic reaction with N-terminal acetyltransferase and, for example, acetyl CoA. Alternatively, or in addition to N-terminal acetylation, the IL10Rα/IL2Rγ bivalent binding molecule is acetylated at one or more lysine residues, e.g., by enzymatic reaction with a lysine acetyltransferase. See, for example Choudhary et al. (2009) Science 325 (5942):834L2 ortho840.

Modifications to Provide Additional Functions

In some embodiments, embodiment, the IL10Rα/IL2Rγ bivalent binding molecule may comprise a functional domain of a chimeric polypeptide. IL10Rα/IL2Rγ bivalent binding molecule fusion proteins of the present disclosure may be readily produced by recombinant DNA methodology by techniques known in the art by constructing a recombinant vector comprising a nucleic acid sequence comprising a nucleic acid sequence encoding the IL10Rα/IL2Rγ bivalent binding molecule in frame with a nucleic acid sequence encoding the fusion partner either at the N-terminus or C-terminus of the IL10Rα/IL2Rγ bivalent binding molecule, the sequence optionally further comprising a nucleic acid sequence in frame encoding a linker or spacer polypeptide.

FLAG Tags

In other embodiments, the IL10Rα/IL2Rγ bivalent binding molecule can be modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) *Science* 256:1014 and LeClair, et al. (1992) PNAS-USA 89:8145). In some embodiments, the binding molecule further comprises a C-terminal c-myc epitope tag.

Chelating Peptides

In some embodiments, the IL10Rα/IL2Rγ bivalent binding molecule (including fusion proteins of the IL10Rα/IL2Rγ bivalent binding molecule) of the present disclosure are may be covalently bonded via a peptide bond to one or more transition metal chelating polypeptide sequences. The association of the IL10Rα/IL2Rγ bivalent binding molecule with chelating peptide provides multiple utilities including: the purification of the IL10Rα/IL2Rγ bivalent binding molecule using immobilized metal affinity chromatography (IMAC) as described in Smith, et al. U.S. Pat. No. 4,569,794 issued Feb. 11, 1986; immobilization of the IL10Rα/IL2Rγ bivalent binding molecule on nitrilotriacetic acid (NTA) modified surface plasmon resonance sensor chips (e.g., Sensor Chip NTA available from Cytiva Global Life Science Solutions USA LLC, Marlborough MA as catalog number BR100407) as described in Nieba, et al. (1997) Analytical Biochemistry 252(2):217-228, or to form kinetically inert or kinetically labile complexes between the IL10Rα/IL2Rγ bivalent binding molecule and a transition metal ion as described in Anderson, et al. (U.S. Pat. No. 5,439,829 issued Aug. 8, 1995 and Hale, J. E (1996) Analytical Biochemistry 231(1):46-49. Examples of transition metal chelating polypeptides useful in the practice of the present disclosure are described in Smith, et al. supra and Dobeli, et al. U.S. Pat. No. 5,320,663 issued May 10, 1995 the entire teachings of which are hereby incorporated by reference. Particular transition metal chelating polypeptides useful in the practice of the present disclosure are peptides comprising 3-6 contiguous histidine residues (SEQ ID NO: 317) such as a six-histidine peptide $(His)_6$ (SEQ ID NO:313) anTd are frequently referred to in the art as "His-tags." In some embodiments, a purification handle is a polypeptide having the sequence Ala-Ser-His-His-His-His-His-His ("ASH6") (SEQ ID NO: 21) or Gly-Ser-His-His-His-His-His-His-His-His ("GSH8") (SEQ ID NO: 22).

Targeting Moieties:

In some embodiments, IL10Rα/IL2Rγ bivalent binding molecule is conjugated to molecule which provides ("targeting domain") to facilitate selective binding to particular cell type or tissue expressing a cell surface molecule that specifically binds to such targeting domain, optionally incorporating a linker molecule of from 1-40 (alternatively 2-20, alternatively 5-20, alternatively 10-20) amino acids between the IL10Rα/IL2Rγ bivalent binding molecule sequence and the sequence of the targeting domain of the fusion protein.

In other embodiments, a chimeric polypeptide including a IL10Rα/IL2Rγ bivalent binding molecule and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the targeting moiety is an antibody that specifically binds to at least one cell surface molecule associated with a tumor cell (i.e. at least one tumor antigen) wherein the cell surface molecule associated with a tumor cell is selected from the group consisting of GD2, BCMA, CD19, CD33, CD38, CD70, GD2, IL3Rα2, CD19, mesothelin, Her2, EpCam, Muc1, ROR1, CD133, CEA, EGR-FRVIII, PSCA, GPC3, Pan-ErbB and FAP.

Recombinant Production

Alternatively, the IL10Rα/IL2Rγ binding molecules of the present disclosure are produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide.

Construction of Nucleic Acid Sequences Encoding the IL10Rα/IL2Rγ Binding Molecule In some embodiments, the IL10Rα/IL2Rγ binding molecule is produced by recombinant methods using a nucleic acid sequence encoding the IL10Rα/IL2Rγ binding molecule (or fusion protein comprising the IL10Rα/IL2Rγ binding molecule). The nucleic acid sequence encoding the desired αβhIL10Rα/IL2Rγ binding molecule can be synthesized by chemical means using an oligonucleotide synthesizer.

The nucleic acid molecules are not limited to sequences that encode polypeptides; some or all of the non-coding sequences that lie upstream or downstream from a coding sequence can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the IL0Rα/IL2Rγ binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the IL10Rα/IL2Rγ binding molecule may be obtained from various commercial sources that provide custom made nucleic acid sequences. Amino acid sequence variants of the IL10Rα/IL2Rγ binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding a IL10Rα/IL2Rγ binding molecule and expressing those sequences in a suitably transformed host include, but are not limited to, using a PCR-assisted mutagenesis technique. Mutations that consist of deletions or additions of amino acid residues to a IL10Rα/IL2Rγ binding molecule can also be made with standard recombinant techniques. In the event of a deletion or addition, the nucleic acid molecule encoding a IL10Rα/IL2Rγ binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A IL10Rα/IL2Rγ binding molecule of the present disclosure may be produced recombinantly not only directly, but also as a fusion polypeptide with a heterologous polypeptide, e.g. a signal sequence or other polypeptide having a specific cleavage site at the N-terminus or C-terminus of the mature IL10Rα/IL2Rγ binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. The inclusion of a signal sequence depends on whether it is desired to secrete the IL10Rα/IL2Rγ binding molecule from the recombinant cells in which it is made. If the chosen cells are prokaryotic, it generally is preferred that the DNA sequence not encode a signal sequence. When the recombinant host cell is a yeast cell such as *Saccharomyces cerevisiae*, the alpha mating factor secretion signal sequence may be employed to achieve extracellular secretion of the IL10Rα/IL2Rγ binding molecule into the culture medium as described in Singh, U.S. Pat. No. 7,198,919 B1 issued Apr. 3, 2007.

In the event the IL10Rα/IL2Rγ binding molecule to be expressed is to be expressed as a chimera (e.g., a fusion protein comprising a IL10Rα/IL2Rγ binding molecule and a heterologous polypeptide sequence), the chimeric protein can be encoded by a hybrid nucleic acid molecule comprising a first sequence that encodes all or part of the IL10Rα/IL2Rγ binding molecule and a second sequence that encodes all or part of the heterologous polypeptide. For example, subject IL10Rα/IL2Rγ binding molecules described herein may be fused to a hexa-/octa-histidine (SEQ ID NOS 313-314, respectively) tag to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the IL10Rα/IL2Rγ binding molecule. For example, the N-terminus may be linked to a targeting domain and the C-terminus linked to a hexa-histidine (SEQ ID NO:313) tag purification handle.

The complete amino acid sequence of the polypeptide (or fusion/chimera) to be expressed can be used to construct a back-translated gene. A DNA oligomer containing a nucleotide sequence coding a IL10Rα/IL2Rγ binding molecule can be synthesized. For example, several small oligonucleotides coding for portions of the desired polypeptide can be synthesized and then ligated. The individual oligonucleotides typically contain 5' or 3' overhangs for complementary assembly.

Codon Optimization: In some embodiments, the nucleic acid sequence encoding the IL10Rα/IL2Rγ binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors:

Once assembled (by synthesis, site-directed mutagenesis or another method), the nucleic acid sequence encoding an a IL10Rα/IL2Rγ binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors.

To facilitate efficient expression of the recombinant polypeptide, the nucleic acid sequence encoding the polypeptide sequence to be expressed is operably linked to transcriptional and translational regulatory control sequences that are functional in the chosen expression host.

Selectable Marker:

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences:

Expression vectors for a IL10Rα/IL2Rγ binding molecules of the present disclosure contain a regulatory sequence that is recognized by the host organism and is operably linked to nucleic acid sequence encoding the IL10Rα/IL2Rγ binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject a IL10Rα/IL2Rγ binding molecule, particularly as regards potential secondary structures.

Promoters:

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers:

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells:

The present disclosure further provides prokaryotic or eukaryotic cells that contain and express a nucleic acid molecule that encodes a IL10Rα/IL2Rγ binding molecule. A cell of the present disclosure is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant IL10Rα/IL2Rγ binding molecule can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast S. cerenvisiae include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The IL10Rα/IL2Rγ binding molecule may be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, a IL10Rα/IL2Rγ binding molecule obtained will be glycosylated or unglycosylated depending on the host organism used to produce the mutein. If bacteria are chosen as the host then the a IL10Rα/IL2Rγ binding molecule produced will be unglycosylated. Eukaryotic cells, on the other hand, will typically result in glycosylation of the IL10Rα/IL2Rγ binding molecule.

In some embodiments, it is possible that an amino acid sequence (particularly a CDR sequence) of an sdAb to be incorporated into a bivalent IL10Rα/IL2Rγ binding molecule may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation motif.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The expression constructs of the can be introduced into host cells to thereby produce a IL10Rα/IL2Rγ binding molecule disclosed herein. The expression vector comprising a nucleic acic sequence encoding IL10Rα/IL2Rγ binding molecule is introduced into the prokaryotic or eukaryotic host cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals. To facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced IL10Rα/IL2Rγ binding molecule polypeptides can be recovered from the culture medium as a secreted polypeptide if a secretion leader sequence is employed. Alternatively, the IL10Rα/IL2Rγ binding molecule polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

A recombinantly IL10Rα/IL2Rγ binding molecule by the transformed host can be purified according to any suitable method. Recombinant IL10Rα/IL2Rγ binding molecules can be isolated from inclusion bodies generated in *E. coli*, or from conditioned medium from either mammalian or yeast cultures producing a given mutein using cation exchange, gel filtration, and or reverse phase liquid chromatography. The substantially purified forms of the recombinant a IL10Rα/IL2Rγ binding molecule can be purified from the expression system using routine biochemical procedures, and can be used, e.g., as therapeutic agents, as described herein.

In some embodiments, where the IL10Rα/IL2Rγ binding molecule is expressed with a purification tag as discussed above, this purification handle may be used for isolation of the IL10Rα/IL2Rγ binding molecule from the cell lysate or cell medium. Where the purification tag is a chelating peptide, methods for the isolation of such molecules using immobilized metal affinity chromatography are well known in the art. See, e.g., Smith, et al. U.S. Pat. No. 4,569,794.

The biological activity of the IL10Rα/IL2Rγ binding molecules recovered can be assayed for activating by any suitable method known in the art and may be evaluated as substantially purified forms or as part of the cell lysate or cell medium when secretion leader sequences are employed for expression.

Pharmaceutical Formulations

In some embodiments, the subject IL10Rα/IL2Rγ binding molecule (and/or nucleic acids encoding the IL10Rα/IL2Rγ binding molecule or recombinant cells incorporating a nucleic acid sequence and modified to express the IL10Rα/IL2Rγ binding molecule) can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the IL10Rα/IL2Rγ binding molecule is to be administered to the subject in need of treatment or prophyaxis.

Carriers:

Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor ELTM (BASF, Parsippany, N.J.) or phosphate buffered saline (PBS).

Buffers:

The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions:

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives:

The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite; chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents:

In many cases, it will be preferable to include isotonic agents, for example, sugars, polyalcohols such as mannitol, sorbitol, sodium chloride in the composition.

Routes of Administration:

In some embodiments of the therapeutic methods of the present disclosure involve the administration of a pharmaceutical formulation comprising a IL10Rα/IL2Rγ binding molecule (and/or nucleic acids encoding the IL10Rα/IL2Rγ binding molecule or recombinantly modified host cells expressing the IL10Rα/IL2Rγ binding molecule) to a subject in need of treatment. The pharmaceutical formulation comprising a IL10Rα/IL2Rγ binding molecules of the present disclosure may be administered to a subject in need of treatment or prophyaxis by a variety of routes of administration, including parenteral administration, oral, topical, or inhalation routes.

Parenteral Administration:

In some embodiments, the methods of the present disclosure involve the parenteral administration of a pharmaceutical formulation comprising a IL10Rα/IL2Rγ binding molecule (and/or nucleic acids encoding the IL10Rα/IL2Rγ binding molecule or recombinantly modified host cells expressing the IL10Rα/IL2Rγ binding molecule) to a subject in need of treatment. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion. The parenteral preparation can be enclosed in ampoules, disposable syringes or multiple dose vials made of glass or plastic. In one embodiment, the formulation is provided in a prefilled syringe for parenteral administration.

Oral Administration:

In some embodiments, the methods of the present disclosure involve the oral administration of a pharmaceutical formulation comprising a IL10Rα/IL2Rγ binding molecule (and/or nucleic acids encoding the IL10Rα/IL2Rγ binding molecule or recombinantly modified host cells expressing the IL10Rα/IL2Rγ binding molecule) to a subject in need of treatment. Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

Inhalation Formulations:

In some embodiments, the methods of the present disclosure involve the inhaled administration of a pharmaceutical formulation comprising a IL10Rα/IL2Rγ binding molecule (and/or nucleic acids encoding the IL10Rα/IL2Rγ binding molecule or recombinantly modified host cells expressing the IL10Rα/IL2Rγ binding molecule) to a subject in need of treatment. In the event of administration by inhalation, subject IL10Rα/IL2Rγ binding molecules, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal Formulations:

In some embodiments, the methods of the present disclosure involve the mucosal or transdermal administration of a pharmaceutical formulation comprising a IL10Rα/IL2Rγ binding molecule (and/or nucleic acids encoding the IL10Rα/IL2Rγ binding molecule or recombinantly modified host cells expressing the IL10Rα/IL2Rγ binding molecule) to a subject in need of treatment. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations:

In some embodiments of the method of the present disclosure, the IL10Rα/IL2Rγ binding molecule is administered to a subject in need of treatment in a formulation to provide extended release of the IL10Rα/IL2Rγ binding molecule agent. Examples of extended release formulations of the injectable compositions can be brought about by including in the composition an agent which delays absorption, for example, aluminum monostearate and gelatin. In one embodiment, the subject IL10Rα/IL2Rγ binding molecules or nucleic acids are prepared with carriers that will protect the IL10Rα/IL2Rγ binding molecules against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the IL10Rα/IL2Rγ Binding Molecule:

In some embodiments of the method of the present disclosure, delivery of the the IL10Rα/IL2Rγ binding molecule to a subject in need of treatment is achieved by the administration of a nucleic acid encoding the IL10Rα/IL2Rγ binding molecule. Methods for the administration nucleic acid encoding the IL10Rα/IL2Rγ binding molecule to a subject is achieved by transfection or infection using methods known in the art, including but not limited to the methods described in McCaffrey et al. (Nature (2002) 418: 6893), Xia et al. (Nature Biotechnol. (2002) 20:1006-1010), or Putnam (Am. J. Health Syst. Pharm. (1996) 53: 151-160 erratum at Am. J. Health Syst. Pharm. (1996) 53:325). In some embodiments, the IL10Rα/IL2Rγ binding molecule is administered to a subject by the administration of a pharmaceutically acceptable formulation of recombinant expression vector comprising a nucleic acid sequence encoding the IL10Rα/IL2Rγ binding molecule operably linked to one or more expression control sequences operable in a mammalian subject. In some embodiments, the expression control sequence may be selected that is operable in a limited range of cell types (or single cell type) to facilitate the selective expression of the IL10Rα/IL2Rγ binding molecule in a particular target cell type. In one embodiment, the recombinant expression vector is a viral vector. In some embodiments, the recombinant vector is a recombinant viral vector. In some embodiments the recombinant viral vector is a recombinant adenoassociated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in the target cell type.

In some embodiments, particularly for administration of IL10Rα/IL2Rγ binding molecules to the subject, particular for treatment of diseases of the intestinal tract or bacterial infections in a subject, the nucleic acid encoding the IL10Rα/IL2Rγ binding molecule may be delivered to the subject by the administration of a recombinantly modified bacteriophage vector encoding the IL10Rα/IL2Rγ binding molecule. As used herein, the terms 'procaryotic virus," "bacteriophage" and "phage" are used interchangeably hereinto describe any of a variety of bacterial viruses that infect and replicate within a bacterium. Bacteriophage selectively infect procaryotic cells, restricting the expression of the IL10Rα/IL2Rγ binding molecule to procaryotic cells in the subject while avoiding expression in mammalian cells. A wide variety of bacteriophages capable of selection a broad range of bacterial cells have been identified and characterized extensively in the scientific literature. In some embodiments, the phage is modified to remove adjacent motifs (PAM). Elimination of the of Cas9 sequences from the phage genome reduces ability of the Cas9 endonuclease of the target procaryotic cell to neutralize the invading phage encoding the IL10Rα/IL2Rγ binding molecule.

Administration of Recombinantly Modified Cells Expressing the IL10Rα/IL2Rγ Binding Molecule:

In some embodiments of the method of the present disclosure, delivery of the the IL10Rα/IL2Rγ binding molecule to a subject in need of treatment is achieved by the administration of recombinant host cells modified to express the IL10Rα/IL2Rγ binding molecule may be administered in the therapeutic and prophylactic applications described herein. In some embodiments, the recombinant host cells are mammalian cells, e.g., human cells.

In some embodiments, the nucleic acid sequence encoding the IL10Rα/IL2Rγ binding molecule (or vectors comprising same) may be maintained extrachromosomally in the recombinantly modified host cell for administration. In other embodiments, the nucleic acid sequence encoding the IL10Rα/IL2Rγ binding molecule may be incorporated into the genome of the host cell to be administered using at least one endonuclease to facilitate incorporate insertion of a nucleic acid sequence into the genomic sequence of the cell. As used herein, the term "endonuclease" is used to refer to a wild-type or variant enzyme capable of catalyzing the cleavage of bonds between nucleic acids within a DNA or RNA molecule, preferably a DNA molecule. Endonucleases are referred to as "rare-cutting" endonucleases when such endonucleases have a polynucleotide recognition site greater than about 12 base pairs (bp) in length, more preferably of 14-55 bp. Rare-cutting endonucleases can be used for inactivating genes at a locus or to integrate transgenes by homologous recombination (HR) i.e. by inducing DNA double-strand breaks (DSBs) at a locus and insertion of exogenous DNA at this locus by gene repair mechanism. Examples of rare-cutting endonucleases include homing endonucleases (Grizot, et al (2009) Nucleic Acids Research 37(16):5405-5419), chimeric Zinc-Finger nucleases (ZFN) resulting from the fusion of engineered zinc-finger domains (Porteus M and Carroll D., *Gene targeting using zinc finger nucleases* (2005) Nature Biotechnology 23(3):967-973, a TALEN-nuclease, a Cas9 endonuclease from CRISPR system as or a modified restriction endonuclease to extended sequence specificity (Eisenschmidt, et al. 2005; 33(22): 7039-7047).

In some embodiments, particularly for administration of IL10Rα/IL2Rγ binding molecules to the intestinal tract, the IL10Rα/IL2Rγ binding molecule may be delivered to the subject by a recombinantly modified procaryotic cell (e.g., *Lactobacillus lacti*). The use of engineered procaryotic cells for the delivery of recombinant proteins to the intestinal tract are known in the art. See, e.g. Lin, et al. (2017) Microb Cell Fact 16:148. In some embodiments, the engineered bacterial cell expressing the IL10Rα/IL2Rγ binding molecule may be administered orally, typically in aqueous suspension, or rectally (e.g. enema).

Therapeutic Applications

The present disclosure further provides methods of treating a subject suffering from a disease disorder or condition by the administration of a therapeutically effective amount of an IL10Rα/IL2Rγ binding molecule (or nucleic acid encoding an IL10Rα/IL2Rγ binding molecule including recombinant viruses encoding the IL10Rα/IL2Rγ binding molecule) of the present disclosure.

Neoplastic Diseases

The present disclosure provides methods of use of binding proteins that bind to IL10Rα and IL2Rγ in the treatment of subjects suffering from a neoplastic disease, disorder, or condition, including benign and malignant neoplasms, by the administration of a therapeutically effective amount of a binding protein (or nucleic acid encoding a binding protein including recombinant vectors encoding the binding protein) as described herein. IL10 agonists have been identified as useful in the treatment of neoplastic disease as described in Oft, M. (2014) Cancer Immunology Research 2(3):194-199; Naing, et al. (2108) Cancer Cell 34(5):775-791; and Mumm, J. and Oft, M (2013) Bioessays 35(7):623-631.

Neoplastic diseases include but are not limited to, cancer (e.g., a solid tumor cancer; e.g., non-small-cell lung carcinoma (NSCLC), renal cell carcinoma (RCC), or melanoma). The binding protein binds to and activates CD8+ T cells and/or CD4+ T cells. In certain embodiments, the method does not cause anemia. It is known that IL10 has activities on macrophages and T cells. In some embodiments, the method provided herein uses a binding molecule of the present disclosure that binds to IL10Rα and IL2Rγ resulting in the selective activation of T cells relative to activation of macrophages. The selective activation of T cells relative to macrophages is beneficial because IL10-activated macrophages can phagocytose aging red blood cells, which manifests itself as anemia in a patient receiving IL10. Binding proteins as described herein that provide for the selective substantial activation of T cells while providing a minimal activation of macrophages result in a molecule that produces lower side effects, such as anemia, relative to the native IL10 ligand. Other problems and toxicities related to IL10 activation are described in, e.g., Fioranelli and Grazia, J Integr Cardiol 1(1):2-6, 2014. Such problems can be avoided by using a binding protein of the present disclosure that specifically binds to IL10Rα and IL2Rγ.

In some embodiments, the binding protein that binds to IL10Rα and IL2Rγ can trigger different levels of downstream signaling in different cell types. For example, by varying the length of the linker between the antiIL10Rα VHH antibody and the antiIL2Rγ VHH antibody in the binding protein, the downstream signaling of the binding protein is modulated in CD8+ T cells compared to other T cells. In other embodiments, different antiIL10Rα VHH antibodies with different binding affinities and different antiIL2Rγ VHH antibodies with different binding affinities can be combined to make different binding proteins. Further, the orientation of the two antibodies in the binding protein can also be changed to make a different binding protein (i.e., antiIL10Rα VHH antibody-linker-antiIL2Rγ VHH antibody, or antiIL2Rγ VHH antibody-linker-antiIL10Rα VHH antibody). Different binding proteins can be screened to find the ideal binding protein that causes a higher level of downstream signaling in desired cell types compared to undesired cell types. In some embodiments, the level of downstream signaling in CD8+ T cells is at least 1.1, 1.5, 2, 3, 5, or 10 times of the level of downstream signaling in other T cells.

Examples benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including, but not limited to, breast cancers, sarcomas (including but not limited to osteosarcomas and angiosarcomas and fibrosarcomas), leukemias, lymphomas, genitourinary cancers (including but not limited to ovarian, urethral, bladder, and prostate cancers), gastrointestinal cancers (including but not limited to colon esophageal and stomach cancers), lung cancers, myelomas, pancreatic cancers, liver cancers, kidney cancers, endocrine cancers, skin cancers, and brain or central and peripheral nervous (CNS) system tumors, malignant or benign, including gliomas and neuroblastomas, astrocytomas, myelodysplastic disorders, cervical carcinoma-in-situ, intestinal polyposes, oral leukoplakias, histiocytoses, hyperprofroliferative scars including keloid scars, hemangiomas, hyperproliferative arterial stenosis, psoriasis, inflammatory arthritis, hyperkeratoses, and papulosquamous eruptions including arthritis.

The term "neoplastic disease" includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic/neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML), and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL), and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease, and Reed-Steinberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

Assessing Anti-Neoplastic Efficacy

The determination of efficacy of the methods of the present disclosure in the treatment of cancer is generally associated with the achievement of one or more art recognized parameters such as reduction in lesions particularly reduction of metastatic lesion, reduction in metastatsis, reduction in tumor volume, improvement in ECOG score, and the like. Determining response to treatment can be assessed through the measurement of biomarker that can provide reproducible information useful in any aspect of binding protein therapy, including the existence and extent of a subject's response to such therapy and the existence and extent of untoward effects caused by such therapy. By way of example, but not limitation, biomarkers include enhancement of IFNγ, and upregulation of granzyme A, granzyme B, and perform; increase in $CD8^+$ T-cell number and function; enhancement of IFNγ, an increase in ICOS expression on $CD8^+$ T-cells, enhancement of IL10 expressing $T_{Reg}$ cells. The response to treatment may be characterized by improvements in conventional measures of clinical efficacy may be employed such as Complete Response (CR), Partial Response (PR), Stable Disease (SD) and with respect to target lesions, Complete Response (CR)," Incomplete Response/Stable Disease (SD) as defined by RECIST as well as immune-related Complete Response (irCR), immune-related Partial Response (irPR), and immune-related Stable Disease (irSD) as defined Immune-Related Response Criteria (irRC) are considered by those of skill in the art as evidencing efficacy in the treatment of neoplastic disease in mammalian (e.g., human) subjects.

Further embodiments comprise a method or model for determining the optimum amount of an agent(s) in a combination. An optimum amount can be, for example, an amount that achieves an optimal effect in a subject or subject population, or an amount that achieves a therapeutic effect while minimizing or eliminating the adverse effects associated with one or more of the agents. In some embodiments, the methods involving the combination of a binding protein described herein and a supplementary agent which is known to be, or has been determined to be, effective in treating or preventing a disease, disorder or condition described herein (e.g., a cancerous condition) in a subject (e.g., a human) or a subject population, and an amount of one agent is titrated while the amount of the other agent(s) is held constant. By manipulating the amounts of the agent(s) in this manner, a clinician is able to determine the ratio of agents most effective for, for example, treating a particular disease, disorder or condition, or eliminating the adverse effects or reducing the adverse effects such that are acceptable under the circumstances.

Combination of Binding Proteins with Supplementary Therapeutic Agents

The present disclosure provides the for the use of the binding proteins of the present disclosure in combination with one or more additional active agents ("supplementary agents"). Such further combinations are referred to interchangeably as "supplementary combinations" or "supplementary combination therapy" and those therapeutic agents that are used in combination with binding proteins of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the binding proteins.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., a binding protein described herein) is considered to be administered in combination with a second agent (e.g. a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g. nivolumab or pembrolizumab) are typically administered by IV infusion every two weeks or every three weeks while the binding proteins of the present disclosure are typically administered more frequently, e.g. daily, BID, or weekly. However, the administration of the first agent (e.g. pembrolizumab) provides a therapeutic effect over an extended time and the administration of the second agent (e.g., a binding protein described herein) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the binding protein and the supplementary agent(s) are administered or applied sequentially, e.g., where one agent is administered prior to one or more other agents. In other embodiments, the binding protein and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Chemotherapeutic Agents

In some embodiments, the supplementary agent is a chemotherapeutic agent. In some embodiments the supplementary agent is a "cocktail" of multiple chemotherapeutic agents. The use of IL-10 agents in combination with chemotherapeutic agents is described in Oft, et al., U.S. Pat. No. 9,833,514B2 issued Dec. 5, 2017, the teaching of which is herein incorporated by reference. In some embodiments the chemotherapeutic agent or cocktail is administered in combination with one or more physical methods (e.g., radiation therapy). The term "chemotherapeutic agents" includes but is not limited to alkylating agents such as thiotepa and cyclosphosphamide, alkyl sulfonates such as busulfan, improsulfan and piposulfan, aziridines such as benzodopa, carboquone, meturedopa, and uredopa, ethylenimines and methylamelamines including altretamine, triethylenemelamine, trietylenephosphoramide, triethylenethiophosphaoramide and trimethylolomelamime, nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, nitrosureas such as carmustine, chlorozotocin, fotemustine, lomustine, nimustine, ranimustine, antibiotics such as aclacinomysins, actinomycin, authramycin, azaserine, bleomycins such as bleomycin A2, cactinomycin, calicheamicin, carabicin, caminomycin, carzinophilin, chromomycins, dactinomycin, daunorubicin and derivaties such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, anti-metabolites such as methotrexate and 5-fluorouracil (5-FU), folic acid analogues such as denopterin, methotrexate, pteropterin, trimetrexate, dideazatetrahydrofolic acid, and folinic acid, purine analogs such as fludarabine, 6-mercaptopurine, thiamiprine, thioguanine, pyrimidine analogs such as ancitabine, azacitidine, 6-azauridine, carmofur, cytarabine, dideoxyuridine, doxifluridine, enocitabine, floxuridine, 5-FU, androgens such as calusterone, dromostanolone propionate, epitiostanol, mepitiostane, testolactone, anti-adrenals such as aminoglutethimide, mitotane, trilostane, folic acid replenisher such as frolinic acid, aceglatone, aldophosphamide glycoside, aminolevulinic acid, amsacrine, bestrabucil, bisantrene, edatraxate, defofamine, demecolcine, diaziquone, elformithine, elliptinium acetate, etoglucid, gallium nitrate, hydroxyurea, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, tenuazonic acid, triaziquone, 2,2',2"-trichlorotriethylamine, urethan, vindesine, dacarbazine, mannomustine, mitobronitol, mitolactol, pipobroman, gacytosine, arabinoside (Ara-C), cyclophosphamide, thiotepa, taxoids, e.g., paclitaxel, nab-paclitaxel and doxetaxel, chlorambucil, gemcitabine, 6-thioguanine, mercaptopurine, methotrexate, platinum and platinum coordination complexes such as cisplatin, oxaplatin and carboplatin, vinblastine, etoposide (VP-16), ifosfamide, mitomycin C, mitoxantrone, vincristine, vinorelbine, navelbine, novantrone, teniposide, daunomycin, aminopterin, xeloda, ibandronate, CPT11, topoisomerase inhibitors, difluoromethylornithine (DMFO), retinoic acid, esperamicins, capecitabine, taxanes such as paclitaxel, docetaxel, cabazitaxel, carminomycin, adriamycins such as 4'-epiadriamycin, 4-adriamycin-14-benzoate, adriamycin-14-octanoate, adriamycin-14-naphthaleneacetate, cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary agent is one or more chemical or biological agents identified in the art as useful in the treatment of neoplastic disease, including, but not limited to, a cytokines or cytokine antagonists such as IL12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), antitumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-β1a (Avonex®), and interferon-β1b (Betaseron®) as well as combinations of one or more of the foregoing as practiced in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the binding protein is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

Combination with Therapeutic Antibodies

In some embodiments, a "supplementary agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs). The use of IL10 agents in combination with therapeutic antibodies in the treatment of neoplastic diseases is described in Mumm, et al., U.S. Pat. No. 10,618,970B2 issued Apr. 14, 2020.

In some embodiments, the therapeutic antibody is an antibody that binds to at least one tumor antigen selected from the group consisting of HER2 (e.g. trastuzumab, pertuzumab, ado-trastuzumab emtansine), nectin-4 (e.g. enfortumab), CD79 (e.g. polatuzumab vedotin), CTLA4 (e.g. ipilumumab), CD22 (e.g. moxetumomab pasudotox), CCR4 (e.g. magamuizumab), IL23p19 (e.g. tildrakizumab), PDL1 (e.g. durvalumab, avelumab, atezolizumab), IL17a (e.g. ixekizumab), CD38 (e.g. daratumumab), SLAMF7 (e.g. elotuzumab), CD20 (e.g. rituximab, tositumomab, ibritumomab and ofatumumab), CD30 (e.g. brentuximab vedotin), CD33 (e.g. gemtuzumab ozogamicin), CD52 (e.g. alemtuzumab), EpCam, CEA, fpA33, TAG-72, CAIX, PSMA, PSA, folate binding protein, GD2 (e.g. dinuntuximab), GD3, IL6 (e.g. silutxumab) GM2, $Le^y$, VEGF (e.g. bevacizumab), VEGFR, VEGFR2 (e.g. ramucirumab), PDGFRα (e.g. olartumumab), EGFR (e.g. cetuximab, panitumumab and necitumumab), ERBB2 (e.g. trastuzumab), ERBB3, MET, IGF1R, EPHA3, TRAIL R1, TRAIL R2, RANKL RAP, tenascin, integrin αVβ3, and integrin α4β1.

Examples of antibody therapeutics which are FDA approved and may be used as supplementary agents for use in the treatment of neoplastic disease indication include those provided in Table 11.

In some embodiments, where the antibody is a bispecific antibody targeting a first and second tumor antigen such as HER2 and HER3 (abbreviated HER2 x HER3), FAP x DR-5 bispecific antibodies, CEA x CD3 bispecific antibodies, CD20 x CD3 bispecific antibodies, EGFR-EDV-miR16 trispecific antibodies, gp100 x CD3 bispecific antibodies, Ny-eso x CD3 bispecific antibodies, EGFR x cMet bispecific antibodies, BCMA x CD3 bispecific antibodies, EGFR-EDV bispecific antibodies, CLEC12A x CD3 bispecific antibodies, HER2 x HER3 bispecific antibodies, Lgr5 x EGFR bispecific antibodies, PD1 x CTLA-4 bispecific antibodies, CD123 x CD3 bispecific antibodies, gpA33 x CD3 bispecific antibodies, B7-H3 x CD3 bispecific antibodies, LAG-3 x PD1 bispecific antibodies, DLL4 x VEGF bispecific antibodies, Cadherin-P x CD3 bispecific antibodies, BCMA x CD3 bispecific antibodies, DLL4 x VEGF bispecific antibodies, CD20 x CD3 bispecific antibodies, Ang-2 x VEGF-A bispecific antibodies, CD20 x CD3 bispecific antibodies, CD123 x CD3 bispecific antibodies, SSTR2 X CD3 bispecific antibodies, PD1 x CTLA-4 bispecific antibodies, HER2 x HER2 bispecific antibodies, GPC3 x CD3 bispecific antibodies, PSMA x CD3 bispecific antibodies, LAG-3 x PD-L1 bispecific antibodies, CD38 x CD3 bispecific antibodies, HER2 x CD3 bispecific antibodies, GD2 x CD3 bispecific antibodies, and CD33 x CD3 bispecific antibodies.

Such therapeutic antibodies may be further conjugated to one or more chemotherapeutic agents (e.g., antibody drug conjugates or ADCs) directly or through a linker, especially acid, base or enzymatically labile linkers.

Combination with Physical Methods

In some embodiments, a supplementary agent is one or more non-pharmacological modalities (e.g., localized radiation therapy or total body radiation therapy or surgery). By way of example, the present disclosure contemplates treatment regimens wherein a radiation phase is preceded or followed by treatment with a treatment regimen comprising a binding protein and one or more supplementary agents. In some embodiments, the present disclosure further contemplates the use of a binding protein in combination with surgery (e.g. tumor resection). In some embodiments, the present disclosure further contemplates the use of a binding protein in combination with bone marrow transplantation, peripheral blood stem cell transplantation or other types of transplantation therapy.

Combination with Immune Checkpoint Modulators:

In some embodiments, a “supplementary agent” is an immune checkpoint modulator for the treatment and/or prevention neoplastic disease in a subject as well as diseases, disorders or conditions associated with neoplastic disease. The use of IL10 agents in combination with immune checkpoint modulators in the treatment of neoplastic disease is described in Oft, United States Patent Publication US2020/0353050 published Nov. 12, 2020. The term “immune checkpoint pathway” refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as “immune checkpoints.” The biological responses modulated by such immune checkpoint pathways are mediated by intracellular signaling pathways that lead to downstream immune effector pathways, such as cell activation, cytokine production, cell migration, cytotoxic factor secretion, and antibody production. Immune checkpoint pathways are commonly triggered by the binding of a first cell surface expressed molecule to a second cell surface molecule associated with the immune checkpoint pathway (e.g. binding of PD1 to PDL1, CTLA4 to CD28, etc.). The activation of immune checkpoint pathways can lead to stimulation or inhibition of the immune response.

An immune checkpoint whose activation results in inhibition or downregulation of the immune response is referred to herein as a “negative immune checkpoint pathway modulator.” The inhibition of the immune response resulting from the activation of a negative immune checkpoint modulator diminishes the ability of the host immune system to recognize foreign antigen such as a tumor-associated antigen. The term negative immune checkpoint pathway includes, but is not limited to, biological pathways modulated by the binding of PD1 to PDL1, PD1 to PDL2, and CTLA4 to CDCD80/86. Examples of such negative immune checkpoint antagonists include but are not limited to antagonists (e.g. antagonist antibodies) that bind T-cell inhibitory receptors including but not limited to PD1 (also referred to as CD279), TIM3 (T-cell membrane protein 3; also known as HAVcr2), BTLA (B and T lymphocyte attenuator; also known as CD272), the VISTA (B7-H5) receptor, LAG3 (lymphocyte activation gene 3; also known as CD233) and CTLA4 (cytotoxic T-lymphocyte associated antigen 4; also known as CD152).

In one embodiment, an immune checkpoint pathway the activation of which results in stimulation of the immune response is referred to herein as a “positive immune checkpoint pathway modulator.” The term positive immune checkpoint pathway modulator includes, but is not limited to, biological pathways modulated by the binding of ICOSL to ICOS(CD278), B7-H6 to NKp30, CD155 to CD96, OX40L to OX40, CD70 to CD27, CD40 to CD40L, and GITRL to GITR. Molecules which agonize positive immune checkpoints (such natural or synthetic ligands for a component of the binding pair that stimulates the immune response) are useful to upregulate the immune response. Examples of such positive immune checkpoint agonists include but are not limited to agonist antibodies that bind T-cell activating receptors such as ICOS (such as JTX-2011, Jounce Therapeutics), OX40 (such as MEDI6383, Medimmune), CD27 (such as varlilumab, Celldex Therapeutics), CD40 (such as dacetuzmumab CP-870,893, Roche, Chi Lob 7/4), HVEM, CD28, CD137 4-1BB, CD226, and GITR (such as MEDI1873, Medimmune; INCAGN1876, Agenus).

As used herein, the term “immune checkpoint pathway modulator” refers to a molecule that inhibits or stimulates the activity of an immune checkpoint pathway in a biological system including an immunocompetent mammal. An immune checkpoint pathway modulator may exert its effect by binding to an immune checkpoint protein (such as those immune checkpoint proteins expressed on the surface of an antigen presenting cell (APC) such as a cancer cell and/or immune T effector cell) or may exert its effect on upstream and/or downstream reactions in the immune checkpoint pathway. For example, an immune checkpoint pathway modulator may modulate the activity of SHP2, a tyrosine phosphatase that is involved in PD-1 and CTLA-4 signaling. The term “immune checkpoint pathway modulators” encompasses both immune checkpoint pathway modulator(s) capable of down-regulating at least partially the function of an inhibitory immune checkpoint (referred to herein as an “immune checkpoint pathway inhibitor” or “immune checkpoint pathway antagonist”) and immune checkpoint pathway modulator(s) capable of up-regulating at least partially the function of a stimulatory immune checkpoint (referred to herein as an “immune checkpoint pathway effector” or “immune checkpoint pathway agonist.”).

The immune response mediated by immune checkpoint pathways is not limited to T-cell mediated immune response. For example, the KIR receptors of NK cells modulate the immune response to tumor cells mediated by NK cells. Tumor cells express a molecule called HLA-C, which inhibits the KIR receptors of NK cells leading to a dimunition or the antitumor immune response. The administration of an agent that antagonizes the binding of HLA-C to the KIR receptor such an anti-KIR3 mab (e.g. lirilumab, BMS) inhibits the ability of HLA-C to bind the NK cell inhibitory receptor (KIR) thereby restoring the ability of NK cells to detect and attack cancer cells. Thus, the immune response mediated by the binding of HLA-C to the KIR receptor is an example a negative immune checkpoint pathway the inhibition of which results in the activation of a of non-T-cell mediated immune response.

In one embodiment, the immune checkpoint pathway modulator is a negative immune checkpoint pathway inhibitor/antagonist. In another embodiment, immune checkpoint pathway modulator employed in combination with the binding protein is a positive immune checkpoint pathway agonist. In another embodiment, immune checkpoint pathway modulator employed in combination with the binding protein is an immune checkpoint pathway antagonist.

The term "negative immune checkpoint pathway inhibitor" refers to an immune checkpoint pathway modulator that interferes with the activation of a negative immune checkpoint pathway resulting in the upregulation or enhancement of the immune response. Exemplary negative immune checkpoint pathway inhibitors include but are not limited to programmed death-1 (PD1) pathway inhibitors, programed death ligand-1 (PDL1) pathway inhibitors, TIM3 pathway inhibitors and anti-cytotoxic T-lymphocyte antigen 4 (CTLA4) pathway inhibitors.

In one embodiment, the immune checkpoint pathway modulator is an antagonist of a negative immune checkpoint pathway that inhibits the binding of PD1 to PDL1 and/or PDL2 ("PD1 pathway inhibitor"). PD1 pathway inhibitors result in the stimulation of a range of favorable immune response such as reversal of T-cell exhaustion, restoration cytokine production, and expansion of antigen-dependent T-cells. PD1 pathway inhibitors have been recognized as effective variety of cancers receiving approval from the USFDA for the treatment of variety of cancers including melanoma, lung cancer, kidney cancer, Hodgkins lymphoma, head and neck cancer, bladder cancer and urothelial cancer.

The term PD1 pathway inhibitors includes monoclonal antibodies that interfere with the binding of PD1 to PDL1 and/or PDL2. Antibody PD1 pathway inhibitors are well known in the art. Examples of commercially available PD1 pathway inhibitors that monoclonal antibodies that interfere with the binding of PD1 to PDL1 and/or PDL2 include nivolumab (Opdivo®, BMS-936558, MDX1106, commercially available from BristolMyers Squibb, Princeton NJ), pembrolizumab (Keytruda®MK-3475, lambrolizumab, commercially available from Merck and Company, Kenilworth NJ), and atezolizumab (Tecentriq®, Genentech/Roche, South San Francisco CA). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105, BristolMyers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011.

The term PD1 pathway inhibitors are not limited to antagonist antibodies. Non-antibody biologic PD1 pathway inhibitors are also under clinical development including AMP-224, a PD-L2 IgG2a fusion protein, and AMP-514, a PDL2 fusion protein, are under clinical development by Amplimmune and Glaxo SmithKline. Aptamer compounds are also described in the literature useful as PD1 pathway inhibitors (Wang, et al. (2018) 145:125-130.).

The term PD1 pathway inhibitors includes peptidyl PD1 pathway inhibitors such as those described in Sasikumar, et al., U.S. Pat. No. 9,422,339 issued Aug. 23, 2016, and Sasilkumar, et al., U.S. Pat. No. 8,907,053 issued Dec. 9, 2014. CA-170 (AUPM-170, Aurigene/Curis) is reportedly an orally bioavailable small molecule targeting the immune checkpoints PDL1 and VISTA. Pottayil Sasikumar, et al. Oral immune checkpoint antagonists targeting PD-L1/VISTA or PD-L1/Tim3 for cancer therapy. [abstract]. In: Proceedings of the 107th Annual Meeting of the American Association for Cancer Research; 2016 Apr. 16-20; New Orleans, LA. Philadelphia (PA): AACR; Cancer Res 2016; 76(14 Suppl): Abstract No. 4861. CA-327 (AUPM-327, Aurigene/Curis) is reportedly an orally available, small molecule that inhibit the immune checkpoints, Programmed Death Ligand-1 (PDL1) and T-cell immunoglobulin and mucin domain containing protein-3 (TIM3).

The term PD1 pathway inhibitors includes small molecule PD1 pathway inhibitors. Examples of small molecule PD1 pathway inhibitors useful in the practice of the present invention are described in the art including Sasikumar, et al., 1,2,4-oxadiazole and thiadiazole compounds as immunomodulators (PCT/IB2016/051266 filed Mar. 7, 2016, published as WO2016142833A1 Sep. 15, 2016) and Sasikumar, et al. 3-substituted-1,2,4-oxadiazole and thiadiazole PCT/IB2016/051343 filed Mar. 9, 2016 and published as WO2016142886A2), BMS-1166 and Chupak L S and Zheng X. Compounds useful as immunomodulators. Bristol-Myers Squibb Co. (2015) WO 2015/034820 A1, EP3041822 B1 granted Aug. 9, 2017; WO2015034820 A1; and Chupak, et al. Compounds useful as immunomodulators. Bristol-Myers Squibb Co. (2015) WO 2015/160641 A2. WO 2015/160641 A2, Chupak, et al. Compounds useful as immunomodulators. Bristol-Myers Squibb Co. Sharpe, et al. Modulators of immunoinhibitory receptor PD-1, and methods of use thereof, WO 2011082400 A2 published Jul. 7, 2011; U.S. Pat. No. 7,488,802 (Wyeth) issued Feb. 10, 2009;

In some embodiments, combination of binding proteins described herein and one or more PD1 immune checkpoint modulators are useful in the treatment of neoplastic conditions for which PD1 pathway inhibitors have demonstrated clinical effect in human beings either through FDA approval for treatment of the disease or the demonstration of clinical efficacy in clinical trials including but not limited to melanoma, non-small cell lung cancer, small cell lung cancer, head and neck cancer, renal cell cancer, bladder cancer, ovarian cancer, uterine endometrial cancer, uterine cervical cancer, uterine sarcoma, gastric cancer, esophageal cancer, DNA mismatch repair deficient colon cancer, DNA mismatch repair deficient endometrial cancer, hepatocellular carcinoma, breast cancer, Merkel cell carcinoma, thyroid cancer, Hodgkins lymphoma, follicular lymphoma, diffuse large B-cell lymphoma, mycosisfungoides, peripheral T-cell lymphoma. In some embodiments, the combination of binding proteins and an PD1 immune checkpoint modulator is useful in the treatment of tumors characterized by high levels of expression of PDL1, where the tumor has a tumor mutational burden, where there are high levels of $CD8^+$ T-cell in the tumor, an immune activation signature associated with IFNγ and the lack of metastatic disease particularly liver metastasis.

In some embodiments, the binding protein is administered in combination with an antagonist of a negative immune checkpoint pathway that inhibits the binding of CTLA4 to CD28 ("CTLA4 pathway inhibitor"). Examples of CTLA4 pathway inhibitors are well known in the art (See, e.g., U.S. Pat. No. 6,682,736 (Abgenix) issued Jan. 27, 2004; U.S. Pat. No. 6,984,720 (Medarex, Inc.) issued May 29, 2007; U.S. Pat. No. 7,605,238 (Medarex, Inc.) issued Oct. 20, 2009)

In some embodiments, the binding protein is administered in combination with an antagonist of a negative immune checkpoint pathway that inhibits the binding of BTLA to HVEM ("BTLA pathway inhibitor"). A number of approaches targeting the BTLA/HVEM pathway using anti-BTLA antibodies and antagonistic HVEM-Ig have been evaluated, and such approaches have suggested promising utility in a number of diseases, disorders and conditions, including transplantation, infection, tumor, and autoimmune disease (See e.g. Wu, et al., (2012) *Int. J. Biol. Sci.* 8:1420-30).

In some embodiments, the binding protein is administered in combination with an antagonist of a negative immune checkpoint pathway that inhibits the ability TIM3 to binding to TIM3-activating ligands ("TIM3 pathway inhibitor"). Examples of TIM3 pathway inhibitors are known in the art and with representative non-limiting examples described in United States Patent Publication No. PCT/US2016/021005 published Sep. 15, 2016; Lifke, et al. United States Patent Publication No. US 20160257749 A1 published Sep. 8, 2016 (F. Hoffman-LaRoche), Karunsky, U.S. Pat. No. 9,631,026 issued Apr. 27, 2017; Karunsky, Sabatos-Peyton, et al. U.S. Pat. No. 8,841,418 issued Sep. 23, 2014; U.S. Pat. No. 9,605,070; Takayanagi, et al., U.S. Pat. No. 8,552,156 issued Oct. 8, 2013.

In some embodiments, the binding protein is administered in combination with an inhibitor of both LAG3 and PD1 as the blockade of LAG3 and PD1 has been suggested to synergistically reverse anergy among tumor-specific $CD8^+$ T-cells and virus-specific $CD8^+$ T-cells in the setting of chronic infection. IMP321 (ImmuFact) is being evaluated in melanoma, breast cancer, and renal cell carcinoma. See generally Woo et al., (2012) *Cancer Res* 72:917-27; Goldberg et al., (2011) *Curr. Top. Microbiol. Immunol.* 344:269-78; Pardoll (2012) *Nature Rev. Cancer* 12:252-64; Grosso et al., (2007) *J. Clin. Invest.* 117:3383-392.

In some embodiments, the binding protein is administered in combination with an A2aR inhibitor. A2aR inhibits T-cell responses by stimulating $CD4^+$ T-cells towards developing into $T_{Reg}$ cells. A2aR is particularly important in tumor immunity because the rate of cell death in tumors from cell turnover is high, and dying cells release adenosine, which is the ligand for A2aR. In addition, deletion of A2aR has been associated with enhanced and sometimes pathological inflammatory responses to infection. Inhibition of A2aR can be effected by the administration of molecules such as antibodies that block adenosine binding or by adenosine analogs. Such agents may be used in combination with the binding proteins for use in the treatment disorders such as cancer and Parkinson's disease.

In some embodiments, the binding protein is administered in combination with an inhibitor of IDO (Indoleamine 2,3-dioxygenase). IDO down-regulates the immune response mediated through oxidation of tryptophan resulting in in inhibition of T-cell activation and induction of T-cell apoptosis, creating an environment in which tumor-specific cytotoxic T lymphocytes are rendered functionally inactive or are no longer able to attack a subject's cancer cells. Indoximod (NewLink Genetics) is an IDO inhibitor being evaluated in metastatic breast cancer.

As previously described, the present invention provides for a method of treatment of neoplastic disease (e.g., cancer) in a mammalian subject by the administration of a binding protein in combination with an agent(s) that modulate at least one immune checkpoint pathway including immune checkpoint pathway modulators that modulate two, three or more immune checkpoint pathways.

In some embodiments the binding protein is administered in combination with an immune checkpoint modulator that is capable of modulating multiple immune checkpoint pathways. Multiple immune checkpoint pathways may be modulated by the administration of multi-functional molecules which are capable of acting as modulators of multiple immune checkpoint pathways. Examples of such multiple immune checkpoint pathway modulators include but are not limited to bi-specific or poly-specific antibodies. Examples of poly-specific antibodies capable of acting as modulators or multiple immune checkpoint pathways are known in the art. For example, United States Patent Publication No. 2013/0156774 describes bispecific and multispecific agents (e.g., antibodies), and methods of their use, for targeting cells that co-express PD1 and TIM3. Moreover, dual blockade of BTLA and PD1 has been shown to enhance antitumor immunity (Pardoll, (April 2012) *Nature Rev. Cancer* 12:252-64). The present disclosure contemplates the use of binding proteins in combination with immune checkpoint pathway modulators that target multiple immune checkpoint pathways, including but limited to bi-specific antibodies which bind to both PD1 and LAG3. Thus, antitumor immunity can be enhanced at multiple levels, and combinatorial strategies can be generated in view of various mechanistic considerations.

In some embodiments, the binding protein may be administered in combination with two, three, four or more checkpoint pathway modulators. Such combinations may be advantageous in that immune checkpoint pathways may have distinct mechanisms of action, which provides the opportunity to attack the underlying disease, disorder or conditions from multiple distinct therapeutic angles.

It should be noted that therapeutic responses to immune checkpoint pathway inhibitors often manifest themselves much later than responses to traditional chemotherapies such as tyrosine kinase inhibitors. In some instance, it can take six months or more after treatment initiation with immune checkpoint pathway inhibitors before objective indicia of a therapeutic response are observed. Therefore, a determination as to whether treatment with an immune checkpoint pathway inhibitors(s) in combination with a binding protein of the present disclosure must be made over a time-to-progression that is frequently longer than with conventional chemotherapies. The desired response can be any result deemed favorable under the circumstances. In some embodiments, the desired response is prevention of the progression of the disease, disorder or condition, while in other embodiments the desired response is a regression or stabilization of one or more characteristics of the disease, disorder or conditions (e.g., reduction in tumor size). In still other embodiments, the desired response is reduction or elimination of one or more adverse effects associated with one or more agents of the combination.

Cell Therapy Agents and Methods as Supplementary Agents

In some embodiments, the methods of the disclosure may include the combination of the administration of a binding protein with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more activated CAR-T cells, engineered TCR cells, tumor infiltrating lymphocytes (TILs), engineered Treg cells. As engineered T-cell products are commonly activated ex vivo prior to their administration to the subject and therefore provide upregulated levels of CD25, cell products comprising such activated engineered T cells types are amenable to further support via the administration of a CD25 biased binding protein as described herein.

CAR-T Cells

In some embodiments of the methods of the present disclosure, the supplementary agent is a "chimeric antigen receptor T-cell" and "CAR-T cell" are used interchangeably to refer to a T-cell that has been recombinantly modified to express a chimeric antigen receptor. The use of IL10 agents in combination with CAR-T cells for the treatment of neoplastic disease is described in Mumm, et al., U.S. Pat. No. 10,195,274 issued Feb. 5, 2019. As used herein, the terms "chimeric antigen receptor" and "CAR" are used interchangeably to refer to a chimeric polypeptide comprising multiple functional domains arranged from amino to carboxy terminus in the sequence: (a) an antigen binding domain (ABD), (b) a transmembrane domain (TD); and (c) one or more cytoplasmic signaling domains (CSDs) wherein the foregoing domains may optionally be linked by one or more spacer domains. The CAR may also further comprise a signal peptide sequence which is conventionally removed during post-translational processing and presentation of the CAR on the cell surface of a cell transformed with an expression vector comprising a nucleic acid sequence encoding the CAR. CARs useful in the practice of the present invention are prepared in accordance with principles well known in the art. See e.g., Eshhaar et al. U.S. Pat. No. 7,741,465 B1 issued Jun. 22, 2010; Sadelain, et al (2013) Cancer Discovery 3(4):388-398; Jensen and Riddell (2015) Current Opinions in Immunology 33:9-15; Gross, et al. (1989) PNAS (USA) 86(24):10024-10028; Curran, et al. (2012) J Gene Med 14(6):405-15. Examples of commercially available CAR-T cell products that may be modified to incorporate an orthogonal receptor of the present invention include axicabtagene ciloleucel (marketed as Yescarta® commercially available from Gilead Pharmaceuticals) and tisagenlecleucel (marketed as Kymriah® commercially available from Novartis).

As used herein, the term antigen binding domain (ABD) refers to a polypeptide that specifically binds to an antigen expressed on the surface of a target cell. The ABD may be any polypeptide that specifically binds to one or more cell surface molecules (e.g. tumor antigens) expressed on the surface of a target cell. In some embodiments, the ABD is a polypeptide that specifically binds to a cell surface molecule associated with a tumor cell is selected from the group consisting of GD2, BCMA, CD19, CD33, CD38, CD70, GD2, IL3Rα2, CD19, mesothelin, Her2, EpCam, Muc1, ROR1, CD133, CEA, EGRFRVIII, PSCA, GPC3, Pan-ErbB and FAP. In some embodiments, the ABD is an antibody (as defined hereinabove to include molecules such as one or more VHHs, scFvs, etc.) that specifically binds to at least one cell surface molecule associated with a tumor cell (i.e. at least one tumor antigen) wherein the cell surface molecule associated with a tumor cell is selected from the group consisting of GD2, BCMA, CD19, CD33, CD38, CD70, GD2, IL3Ra2, CD19, mesothelin, Her2, EpCam, Muc1, ROR1, CD133, CEA, EGRFRVIII, PSCA, GPC3, Pan-ErbB and FAP. Examples of CAR-T cells useful as supplementary agents in the practice of the methods of the present disclosure include but are not limited to CAR-T cells expressing CARs comprising an ABD further comprising at least one of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Muc1 antibodies, anti-ROR1 antibodies, anti-CD133 antibodies, anti-CEA antibodies, anti-PSMA antibodies, anti-EGR-FRVIII antibodies, anti-PSCA antibodies, anti-GPC3 antibodies, anti-Pan-ErbB antibodies, anti-FAP antibodies, CARs of CAR-T cells useful in the practice of the methods of the present disclosure further comprise a transmembrane domain joining the ABD (or linker, if employed, see discussion of linkers below) to the intracellular cytoplasmic domain of the CAR. The transmembrane domain is comprised of any polypeptide sequence which is thermodynamically stable in a eukaryotic cell membrane. The transmembrane spanning domain may be derived from the transmembrane domain of a naturally occurring membrane spanning protein or may be synthetic. In designing synthetic transmembrane domains, amino acids favoring alpha-helical structures are preferred. Transmembrane domains useful in construction of CARs are comprised of approximately 10, 11, 12, 13, 14, 15, 16, 17, 18, 19, 20, 21, 22, 22, 23, or 24 amino acids favoring the formation having an alpha-helical secondary structure. Amino acids having a to favor alpha-helical conformations are well known in the art. See, e.g Pace, et al. (1998) Biophysical Journal 75: 422-427. Amino acids that are particularly favored in alpha helical conformations include methionine, alanine, leucine, glutamate, and lysine. In some embodiments, the CAR transmembrane domain may be derived from the transmembrane domain from type I membrane spanning proteins, such as CD3ζ, CD4, CD8, CD28, etc.

The cytoplasmic domain of the CAR polypeptide comprises one or more intracellular signal domains. In one embodiment, the intracellular signal domains comprise the cytoplasmic sequences of the T-cell receptor (TCR) and co-receptors that initiate signal transduction following antigen receptor engagement and functional derivatives and sub-fragments thereof. A cytoplasmic signaling domain, such as those derived from the T cell receptor zeta-chain, is employed as part of the CAR in order to produce stimulatory signals for T lymphocyte proliferation and effector function following engagement of the chimeric receptor with the target antigen. Examples of cytoplasmic signaling domains include but are not limited to the cytoplasmic domain of CD27, the cytoplasmic domain S of CD28, the cytoplasmic domain of CD137 (also referred to as 4-1BB and TNFRSF9), the cytoplasmic domain of CD278 (also referred to as ICOS), p110α, β, or δ catalytic subunit of PI3 kinase, the human CD3 ζ-chain, cytoplasmic domain of CD134 (also referred to as OX40 and TNFRSF4), FcεR1γ and β chains, MB1 (Igα) chain, B29 (Igβ) chain, etc.), CD3 polypeptides (δ, Δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28.

In some embodiments, the CAR may also provide a co-stimulatory domain. The term "co-stimulatory domain" ("CSD") refers to a stimulatory domain, typically an endodomain, of a CAR that provides a secondary non-specific activation mechanism through which a primary specific stimulation is propagated. The co-stimulatory domain refers to the portion of the CAR which enhances the proliferation, survival or development of memory cells. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved are described in Chen & Flies (2013) Nat Rev Immunol 13(4):227-42. In some embodiments of the present disclosure, the CSD comprises one or more of members of the TNFR superfamily, CD28, CD137 (4-1BB), CD134 (OX40), Dap10, CD27, CD2, CD5, ICAM-1, LFA-1 (CD11a/CD18), Lck, TNFR-I, TNFR-II, Fas, CD30, CD40 or combinations thereof.

CARs useful in the practice of the methods of the present disclosure may optionally include one or more polypeptide spacers linking the domains of the CAR, in particular the linkage between the ABD to the transmembrane spanning domain of the CAR. Although not an essential element of the CAR structure, the inclusion of a spacer domain is generally considered desirable to facilitate antigen recognition by the ARD. As used in conjunction with the CAR-T cell technology described herein, the terms "linker", "linker domain" and "linker region" refer to a polypeptide from about 1 to 100 amino acids in length. Linkers are typically be composed of amino acid residues which permit flexibility of the polypeptide (e.g. glycine and serine) so that the adjacent domains of the CAR are provided greater freedom of movement relative to one another. Although there is no particularly defined length or sequence of amino acids that is necessary for the spacer to achieve its function, but the typical properties of the spacer are flexibility to enable freedom of movement of the ABD to facilitate targeting antigen recognition. Similarly, it has been found that there is there is substantial leniency in spacer length while retaining CAR function. Jensen and Riddell (2014) Immunol. Review 257(1) 127-144. Sequences useful as spacers in the construction of CARs useful in the practice of the present invention include but are not limited to the hinge region of IgG1, the immunoglobulin 1 CH2-CH3 region, IgG4 hinge-CH2-CH3, IgG4 hinge-CH3, and the IgG4 hinge. The hinge and transmembrane domains may be derived from the same molecule such as the hinge and transmembrane domains of CD8-alpha. Imai, et al. (2004) Leukemia 18(4):676-684.

CARs are often referred to as first, second, third or fourth generation. The term first-generation CAR refers to a CAR wherein the cytoplasmic domain transmits the signal from antigen binding through only a single signaling domain, for example a signaling domain derived from the high-affinity receptor for IgE FcεR1γ or the CD3ζ chain. The domain contains one or three immunoreceptor tyrosine-based activating motif(s) [ITAM(s)] for antigen-dependent T-cell activation. The ITAM-based activating signal endows T-cells with the ability to lyse the target tumor cells and secret cytokines in response to antigen binding. Second-generation CARs include a co-stimulatory signal in addition to the CD3ζ signal. Coincidental delivery of the co-stimulatory signal enhances cytokine secretion and antitumor activity induced by CAR-transduced T-cells. The co-stimulatory domain is usually be membrane proximal relative to the CD3ζ domain. Third-generation CARs include a tripartite signaling domain, comprising for example a CD28, CD3ζ, OX40 or 4-1BB signaling region. In fourth generation, or "armored car" CAR T-cells are further modified to express or block molecules and/or receptors to enhance immune activity such as the expression of IL12, IL18, IL7, and/or IL10; 4-1BB ligand, CD-40 ligand. Examples of intracellular signaling domains comprising may be incorporated into the CAR of the present invention include (amino to carboxy): CD3ζ; CD28-41BB-CD3ζ; CD28-OX40-CD3ζ; CD28-41BB-CD3ζ; 41BB-CD-28-CD3ζ and 41BB-CD3ζ.

The term CAR includes CAR variants including but not limited split CARs, ON-switch CARS, bispecific or tandem CARs, inhibitory CARs (iCARs) and induced pluripotent stem (iPS) CAR-T cells. The term "Split CARs" refers to CARs wherein the extracellular portion, the ABD and the cytoplasmic signaling domain of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR molecules and derivatives thereof (i.e., CAR variants) are described, e.g., in PCT Application Nos. US2014/016527, US1996/017060, US2013/063083; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2):141-4; Pegram et al. *Cancer J* (2014) 20(2): 127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety. The term "bispecific or tandem CARs" refers to CARs which include a secondary CAR binding domain that can either amplify or inhibit the activity of a primary CAR. The term "inhibitory chimeric antigen receptors" or "iCARs" are used interchangeably herein to refer to a CAR where binding iCARs use the dual antigen targeting to shut down the activation of an active CAR through the engagement of a second suppressive receptor equipped with inhibitory signaling domains of a secondary CAR binding domain results in inhibition of primary CAR activation. Inhibitory CARs (iCARs) are designed to regulate CAR-T cells activity through inhibitory receptors signaling modules activation. This approach combines the activity of two CARs, one of which generates dominant negative signals limiting the responses of CAR-T cells activated by the activating receptor. iCARs can switch off the response of the counteracting activator CAR when bound to a specific antigen expressed only by normal tissues. In this way, iCARs-T cells can distinguish cancer cells from healthy ones, and reversibly block functionalities of transduced T cells in an antigen-selective fashion. CTLA-4 or PD-1 intracellular domains in iCARs trigger inhibitory signals on T lymphocytes, leading to less cytokine production, less efficient target cell lysis, and altered lymphocyte motility. The term "tandem CAR" or "TanCAR" refers to CARs which mediate bispecific activation of T cells through the engagement of two chimeric receptors designed to deliver stimulatory or costimulatory signals in response to an independent engagement of two different tumor associated antigens.

Typically, the chimeric antigen receptor T-cells (CAR-T cells) are T-cells which have been recombinantly modified by transduction with an expression vector encoding a CAR in substantial accordance with the teaching above.

In some embodiments, the engineered T cell is allogeneic with respect to the individual that is treated. Graham et al. (2018) Cell 7(10) E155. In some embodiments an allogeneic engineered T cell is fully HLA matched. However not all patients have a fully matched donor and a cellular product suitable for all patients independent of HLA type provides an alternative.

Because the cell product may consist of a subject's own T-cells, the population of the cells to be administered is to the subject is necessarily variable. Consequently, identifying the optimal concentration of the CAR-T cell will be optimized by the caregiver in accordance with the needs of the subject to be treated and monitored by conventional laboratory testing. Additionally, since the CAR-T cell agent is variable, the response to such agents can vary and thus involves the ongoing monitoring and management of therapy related toxicities which are managed with a course of pharmacologic immunosuppression or B cell depletion prior to the administration of the CAR-T cell treatment. Usually, at least $1\times10^6$ cells/kg will be administered, at least $1\times10^7$ cells/kg, at least $1\times10^8$ cells/kg, at least $1\times10^9$ cells/kg, at least $1\times10^{10}$ cells/kg, or more, usually being limited by the number of T cells that are obtained during collection. The engineered cells may be infused to the subject in any physiologically acceptable medium by any convenient route of administration, normally intravascularly, although they may also be introduced by other routes, where the cells may find an appropriate site for growth If the T cells used in the practice of the present invention are allogeneic T cells, such cells may be modified to reduce graft versus host disease. For example, the engineered cells of the present invention may be TCRαβ receptor knock-outs achieved by gene editing techniques. TCRαβ is a heterodimer and both alpha and beta chains need to be present for it to be expressed. A single gene codes for the alpha chain (TRAC), whereas there are 2 genes coding for the beta chain, therefore TRAC loci KO has been deleted for this purpose. A number of different approaches have been used to accomplish this deletion, e.g. CRISPR/Cas9; meganuclease; engineered I-CreI homing endonuclease, etc. See, for example, Eyquem et al. (2017) Nature 543:113-117, in which the TRAC coding sequence is replaced by a CAR coding sequence; and Georgiadis et al. (2018) Mol. Ther. 26:1215-1227, which linked CAR expression with TRAC disruption by clustered regularly interspaced short palindromic repeats (CRISPR)/Cas9 without directly incorporating the CAR into the TRAC loci. An alternative strategy to prevent GVHD modifies T cells to express an inhibitor of TCRαβ signaling, for example using a truncated form of CD3ζ as a TCR inhibitory molecule.

Chemokine and Cytokine Agents as Supplementary Agents:

In some embodiments the binding protein is administered in combination with additional cytokines including but not limited to IL2, IL7, IL12, IL15 (See U.S. Pat. No. 10,398,761 issued Sep. 13, 2019) and IL18 including analogs and variants of each thereof.

Activation-Induced Cell Death Inhibitors

In some embodiments the binding protein is administered in combination with one or more supplementary agents that inhibit Activation-Induced Cell Death (AICD). AICD is a form of programmed cell death resulting from the interaction of Fas receptors (e.g., Fas, CD95) with Fas ligands (e.g., FasL, CD95 ligand), helps to maintain peripheral immune tolerance. The AICD effector cell expresses FasL, and apoptosis is induced in the cell expressing the Fas receptor. Activation-induced cell death is a negative regulator of activated T lymphocytes resulting from repeated stimulation of their T-cell receptors. Examples of agents that inhibit AICD that may be used in combination with the binding proteins described herein include but are not limited to cyclosporin A (Shih, et al., (1989) Nature 339:625-626, IL16 and analogs (including rhIL16, Idziorek, et al., (1998) Clinical and Experimental Immunology 112:84-91), TGFb1 (Genesteir, et al., (1999) J Exp Med 189(2): 231-239), and vitamin E (Li-Weber, et al., (2002) J Clin Investigation 110(5):681-690).

Physical Methods

In some embodiments, the supplementary agent is an anti-neoplastic physical methods including but not limited to radiotherapy, cryotherapy, hyperthermic therapy, surgery, laser ablation, and proton therapy.

Immune Diseases

The present disclosure further provides methods of treating a subject suffering from a disease, disorder, or condition by the administration of a therapeutically effective amount of an IL10Rα/IL2Rγ binding protein (or nucleic acid encoding an IL10Rα/IL2Rγ binding protein including recombinant viruses encoding the IL10Rα/IL2Rγ binding protein) of the present disclosure. Disorders amenable to treatment with IL10Rα/IL2Rγ binding proteins (including pharmaceutically acceptable formulations comprising IL10Rα/IL2Rγ binding proteins and/or the nucleic acid molecules that encode them including recombinant viruses encoding such IL10Rα/IL2Rγ binding proteins) of the present disclosure include inflammatory or autoimmune diseases including but not limited to, viral infections (e.g., AIDS, influenza, chronic HCV, chronic viral hepatitis B, C or D), heliobacter pylori infection, HTLV, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome). In certain embodiments, the method does not cause anemia.

Other examples of proliferative and/or differentiative disorders amenable to treatment with IL10Rα/IL2Rγ binding proteins (including pharmaceutically acceptable formulations comprising IL10Rα/IL2Rγ binding proteins and/or the nucleic acid molecules that encode them including recombinant viruses encoding such IL10Rα/IL2Rγ binding proteins) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

The compositions of the present disclosure (including pharmaceutically acceptable formulations comprising IL10Rα/IL2Rγ binding proteins and/or the nucleic acid molecules that encode them including recombinant viruses encoding such IL10Rα/IL2Rγ binding proteins) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Combination of IL10Rα/IL2Rγ Binding Proteins with Additional Therapeutic Agents for Autoimmune Disease:

The present disclosure provides the for the use of the IL10Rα/IL2Rγ binding proteins of the present disclosure in combination with one or more additional active agents ("supplementary agents") in the treatment of autoimmune disease. As used herein, the term "supplementary agents" includes agents that can be administered or introduced separately, for example, formulated separately for separate administration (e.g., as may be provided in a kit) and/or therapies that can be administered or introduced in combination with the IL10Rα/IL2Rγ binding proteins.

As used herein, the term "in combination with" when used in reference to the administration of multiple agents to a subject refers to the administration of a first agent at least one additional (i.e., second, third, fourth, fifth, etc.) agent to a subject. For purposes of the present invention, one agent (e.g., IL10Rα/IL2Rγ binding protein) is considered to be administered in combination with a second agent (e.g. a therapeutic autoimmune antibody such as Humira®) if the biological effect resulting from the administration of the first agent persists in the subject at the time of administration of the second agent such that the therapeutic effects of the first agent and second agent overlap. For example, the therapeutic antibodies are sometimes administered by IV infusion every two weeks (e.g. adalimumab in the treatment of Crohn's disease) while the IL10Rα/IL2Rγ binding proteins of the present disclosure may be administered more frequently, e.g. daily, BID, or weekly. However, the administration of the first agent (e.g. entaercept) provides a therapeutic effect over an extended time and the administration of the second agent (e.g. an IL10Rα/IL2Rγ binding protein) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL10Rα/IL2Rγ binding protein and the supplementary agent(s) are administered or applied sequentially, e.g., where one agent is administered prior to one or more other agents. In other embodiments, the IL10Rα/IL2Rγ binding protein and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies. Examples of therapeutic antibodies that may be administered as supplementary agents in combination with the IL10Rα/IL2Rγ binding proteins of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL6R antibodies (e.g. tocilizumab), anti-TNFα antibodies (e.g. adalimumab (Humira®), golimumab, and infliximab), anti-integrin-α4β7 antibodies (e.g. vedolizumab), anti-IL17a antibodies (e.g. brodalumab or secukinumab), anti-IL4Rα antibodies (e.g. dupilumab), anti-RANKL antibodies, IL6R antibodies, anti-IL1β antibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IL10Rα/IL2Rγ binding proteins of the present disclosure (and optionally additional supplementary agents) for the treatment of the indicated autoimmune disease are provided in Table 12.

The foregoing antibodies useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

In some embodiments the supplementary agent is a vaccine. The IL10Rα/IL2Rγ binding proteins of the present invention may be administered to a subject in combination with vaccines as an adjuvant to enhance the immune response to the vaccine in accordance with the teaching of Doyle, et al U.S. Pat. No. 5,800,819 issued Sep. 1, 1998. Examples of vaccines that may be combined with the IL10Rα/IL2Rγ binding proteins of the present invention include are HSV vaccines, *Bordetella pertussis, Escherichia coli* vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, *Haemophilus influenzae* type B vaccines, human papilloma virus vaccines such as Gardasil®, polio vaccines, Leptospirosis vaccines, combination respiratory vaccine, *Moraxella* vaccines, and attenuated live or killed virus vaccine products such as bovine respiratory disease vaccine (RSV), multivalent human influenza vaccines such as Fluzone® and Quadravlent Fluzone®), feline leukemia vaccine, transmissible gastroenteritis vaccine, COVID-19 vaccine, and rabies vaccine.

Selective Activation

It is known that IL10 has activities on macrophages (e.g., monocytes) and T cells (e.g., $CD4^+$ T cells and $CD8^+$ T cells). In some embodiments, the method provided herein uses a binding protein of the present disclosure that binds to IL10Rα and IL2Rγ resulting in the selective activation of T cells relative to activation of macrophages. Macrophages is a cell type that expresses both IL10Rα and IL10Rβ receptors but when activated too potently can cause side effects such as anemia. The selective activation of T cells relative to macrophages is beneficial because IL10-activated macrophages can phagocytose aging red blood cells, which manifests itself as anemia in a patient receiving IL10. Binding proteins as described herein that provide for the selective substantial activation of T cells while providing a minimal activation of macrophages can result in a molecule that produces lower side effects, such as anemia, relative to the native IL10 ligand. Other problems and toxicities related to IL10 activation are described in, e.g., Fioranelli and Grazia, *J Integr Cardiol* 1(1):2-6, 2014. Such problems can be avoided by using a binding protein of the present disclosure that specifically binds to IL10Rα and IL2Rγ.

In some embodiments, provided herein are methods to selectively induce activity in one or more of a first cell type over one or more of a second cell type by contacting a population of cells comprising both the first and second cell types with an IL10Rα/IL2Rγ binding protein described herein. In particular embodiments, the first cell type is $CD4^+$ T cells, $CD8^+$ T cells, B cells, and/or NK cells and the second cell type is monocytes. In other embodiments, the first cell type is $CD4^+$ T cells and/or $CD8^+$ T cells and the second cell type is NK cells, B cells, and/or monocytes. In certain embodiments, the activity of the first cell type induced by an IL10Rα/IL2Rγ is at least 1.2 fold more than the activity of the second cell type.

Use in Combination with Supplementary Agents:

In some embodiments of the therapeutic uses of the compositions of the present disclosure, the administration of a therapeutically effective amount of an IL10Rα/IL2Rγ binding molecule (or nucleic acid encoding an IL10Rα/IL2Rγ binding molecule including recombinant viruses encoding the IL10Rα/IL2Rγ binding molecule) are administered in combination with one or more additional active agents ("supplementary agents").

As used herein, the term "in combination with" when used in reference to the administration of multiple agents to a subject refers to the administration of a first agent at least one additional (i.e., second, third, fourth, fifth, etc.) agent to a subject. For purposes of the present invention, one agent (e.g., IL10Rα/IL2Rγ binding molecule) is considered to be administered in combination with a second agent (e.g. a therapeutic autoimmune antibody such as Humira®) if the biological effect resulting from the administration of the first agent persists in the subject at the time of administration of the second agent such that the therapeutic effects of the first agent and second agent overlap. For example, the therapeutic antibodies are sometimes administered by IV infusion every two weeks while the IL10Rα/IL2Rγ binding molecules of the present disclosure may be administered more frequently, e.g. daily, BID, or weekly. However, the administration of the first agent (e.g. entaercept) provides a therapeutic effect over an extended time and the administration of the second agent (e.g. an IL10Rα/IL2Rγ binding molecule) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL10Rα/IL2Rγ binding molecule and the supplementary agent(s) are administered or applied sequentially, e.g., where one agent is administered prior to one or more other agents.

In other embodiments, the IL10Rα/IL2Rγ binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplementary agents may administered or introduced separately, for example, formulated separately for separate administration (e.g., as may be provided in a kit) and/or therapies that can be administered or introduced in combination with the IL10Rα/IL2Rγ binding molecules.

Prophylactic Applications

In some embodiments where the IL10Rα/IL2Rγ binding molecule is used in prophylaxis of disease, the supplementary agent may be a vaccine. The IL10Rα/IL2Rγ binding molecule of the present invention may be administered to a subject in combination with vaccines as an adjuvant to enhance the immune response to the vaccine in accordance with the teaching of Doyle, et al U.S. Pat. No. 5,800,819 issued Sep. 1, 1998. Examples of vaccines that may be combined with the IL10Rα/IL2Rγ binding molecule of the present invention include are HSV vaccines, *Bordetella pertussis, Escherichia coli* vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, Haemophilus influenzae type B vaccines, human papilloma virus vaccines such as Garasil®, polio vaccines, Leptospirosis vaccines, combination respiratory vaccine, Moraxella vaccines, and attenuated live or killed virus vaccine products such as bovine respiratory disease vaccine (RSV), multivalent human influenza vaccines such as Fluzone® and Quadravlent Fluzone®), feline leukemia vaccine, transmissible gastroenteritis vaccine, COVID-19 vaccine, and rabies vaccine.

Dosage

Dosage, toxicity and therapeutic efficacy of such binding proteins or nucleic acids compounds can be determined by standard pharmaceutical procedures in cell cultures or experimental animals. The data obtained from the cell culture assays and animal studies can be used in formulating a range of dosage for use in humans. The dosage of such compounds lies preferably within a range of circulating concentrations that include the ED50 with minimal acceptable toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 as determined in cell culture. Such information can be used to more accurately determine useful doses in humans. Levels in plasma may be measured, for example, by high performance liquid chromatography.

As defined herein, a therapeutically effective amount of a subject binding protein (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered.

In some embodiments, the pharmaceutically acceptable forms of the binding proteins of the present disclosure are administered to a subject in accordance with a "low-dose" treatment protocol as described in Klatzman, et al. U.S. Pat. Nos. 9,669,071 and 10,293,028B2 the entire teachings of which are herein incorporated by reference. Additional low dose protocols are described in Smith, K. A. (1993) Blood 81(6):1414-1423, He, et al., (2016) Nature Medicine 22(9): 991-993

In some embodiments of the present disclosure provides methods and compositions for the treatment and/or prevention of neoplastic diseases, disorders or conditions in a subject by the administration to the subject a therapeutically effective amount of a binding protein of the present disclosure wherein the serum concentration of is maintained for a majority (i.e., greater than about 50% of the period of time, alternatively greater than about 60%, alternatively greater than about 70%, alternatively greater than about 80%, alternatively greater than about 90%) of a period of time (e.g. at least 24 hours, alternatively at least 48 hours, alternatively at least 72 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer) at a serum concentration at or above the effective concentration of the binding protein sufficient to promote proliferation of CD3-activated primary human T-cells (e.g., at or above $EC_{10}^{PRO}$, alternatively at or above $EC_{20}^{PRO}$, alternatively at or above $EC_{30}^{PRO}$, alternatively at or above $EC_{40}^{PRO}$, at or above $EC_{50}^{PRO}$, alternatively at or above $EC_{60}^{PRO}$) with respect to such binding protein but at a serum concentration at or below of the effective concentration at a serum concentration of such binding protein sufficient to induce activation of T-cells (e.g., at or below $EC_{100}^{PRO}$ alternatively at or below $EC_{90}^{PRO}$, alternatively at or below $EC_{80}^{PRO}$, alternatively at or below $EC_{70}^{PRO}$, at or below $EC_{60}^{PRO}$, alternatively at or below $EC_{50}^{PRO}$) with respect to such binding protein.

In some embodiments of the present disclosure provides methods and compositions for the treatment and/or prevention of neoplastic diseases, disorders or conditions in a subject by the administration to the subject a therapeutically effective amount of a binding protein described herein sufficient to maintain a serum concentration of the binding protein for more than about 50%, alternatively greater than about 60%, alternatively greater than about 70%, alternatively greater than about 80%, alternatively greater than about 90%) of a period of time of at least 24 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer.

In some embodiments of the present disclosure provides methods and compositions for the treatment and/or prevention of neoplastic diseases, disorders or conditions in a subject by the administration to the subject a therapeutically effective amount of a binding protein sufficient to maintain a serum concentration of the binding protein at or above the effective concentration for more than about 50%, alternatively greater than about 60%, alternatively greater than about 70%, alternatively greater than about 80%, alternatively greater than about 90%) of a period of time of at least 24 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer.

In accordance with another aspect, there is provided a method for stimulating the immune system of an animal by administering the binding proteins of the present disclosure. The method is useful to treat disease states where the host immune response is deficient. In treating a subject, a therapeutically effective dose of compound (i.e., active ingredient) is administered. A therapeutically effective dose refers to that amount of the active ingredient that produces amelioration of symptoms or a prolongation of survival of a subject. An effective dose will vary with the characteristics of the binding protein to be administered, the physical characteristics of the subject to be treated, the nature of the disease or condition, and the like. A single administration can range from about 50,000 IU/kg to about 1,000,000 IU/kg or more, more typically about 600,000 IU/kg. This may be repeated several times a day (e.g., 2-3 times per day) for several days (e.g., about 3-5 consecutive days) and then may be repeated one or more times following a period of rest (e.g., about 7-14 days). Thus, an effective dose may comprise only a single administration or many administrations over a period of time (e.g., about 20-30 individual administrations of about 600,000 IU/kg each given over about a 10-20 day period).

The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the binding proteins can include a single treatment or, can include a series of treatments. In one embodiment, the compositions are administered every 8 hours for five days, followed by a rest period of 2 to 14 days, e.g., 9 days, followed by an additional five days of administration every 8 hours. In another embodiment, the compositions are administered every other day for a period of at least 6 days, optionally at least 10 days, optionally at least 14 days, optionally at least 30 days, optionally at least 60 days.

The pharmaceutical compositions can be included in a container, pack, or dispenser together with instructions for administration.

While compounds that exhibit toxic side effects may be used, care should be taken to design a delivery system that targets such compounds to the site of affected tissue in order to minimize potential damage to uninfected cells and, thereby, reduce side effects. Toxicity and therapeutic efficacy of a binding protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LC_{50}/EC_{50}$. Binding proteins that exhibit large therapeutic indices are preferred. The data obtained from these cell culture assays and animal studies can be used in formulating a range of dosages suitable for use in humans. The dosage of such mutants lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

A therapeutically effective dose can be estimated initially from cell culture assays by determining an $EC_{50}$. A dose can then be formulated in animal models to achieve a circulating plasma concentration range that includes the $EC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition.

The attending physician for patients treated with binding proteins of the present disclosure would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

EXAMPLES

Example 1—$V_H$H Generation

Camels were acclimated at research facility for at least 7 days before immunization. Antigen was diluted with 1×PBS (antigen total about 1 mg). The quality of the antigen was assessed by SDS-PAGE to ensure purity (e.g., >80%). For the first time, 10 mL CFA (then followed 6 times using IFA) was added into mortar, then 10 mL antigen in 1×PBS was slowly added into the mortar with the pestle grinding. The antigen and CFA/IFA were ground until the component showed milky white color and appeared hard to disperse. Camels were injected with antigen emulsified in CFA subcutaneously at at least six sites on the body, injecting about 2 mL at each site (total of 10 mL per camel). A stronger immune response was generated by injecting more sites and in larger volumes. The immunization was conducted every week (7 days), for 7 times. The needle was inserted into the subcutaneous space for 10 to 15 seconds after each injection to avoid leakage of the emulsion. Alternatively, a light pull on the syringe plunger also prevented leakage. The blood sample was collected three days later after $7^{th}$ immunization.

After immunization, the library was constructed. Briefly, RNA was extracted from blood and transcribed to cDNA. The $V_H$H regions were obtained via two-step PCR, which fragment about 400 bp. The PCR outcomes and the vector of pMECS phagemid were digested with Pst I and Not I, subsequently, ligated to pMECS/Nb recombinant. After ligation, the products were transformed into *Escherichia coli* (*E. coli*) TG1 cells by electroporation. Then, the transformants were enriched in growth medium and planted on plates. Finally, the library size was estimated by counting the number of colonies.

Library biopanning was conducted to screen candidates against the antigens after library construction. Phage display technology was applied in this procedure. Positive colonies were identified by PE-ELISA.

Example 2—Recombinant Production and Purification

Codon optimized DNA inserts were cloned into modified pcDNA3.4 (Genscript) for small scale expression in HEK293 cells in 24 well plates. The binding molecules were purified in substantial accordance with the following procedure. Using a Hamilton Star automated system, 96×4 mL of supernatants in 4×24-well blocks were re-arrayed into 4×96-well, 1 mL blocks. PhyNexus micropipette tips (Biotage, San Jose CA) holding 80 μL of Ni-Excel IMAC resin (Cytiva) are equilibrated wash buffer: PBS pH 7.4, 30 mM imidazole. PhyNexus tips were dipped and cycled through 14 cycles of 1 mL pipetting across all 4×96-well blocks. PhyNexus tips were washed in 2×1 mL blocks holding wash buffer. PhyNexus tips were eluted in 3×0.36 mL blocks holding elution buffer: PBS pH 7.4, 400 mM imidazole. PhyNexus tips were regenerated in 3×1 mL blocks of 0.5 M sodium hydroxide.

The purified protein eluates were quantified using a Biacore® T200 as in substantial accordance with the following procedure. 10 μL of the first 96×0.36 mL eluates were transferred to a Biacore® 96-well microplate and diluted to 60 uL in HBS-EP+ buffer (10 mM Hepes pH 7.4, 150 mM NaCl, 1 mM EDTA, 0.05% Tween 20). Each of the 96 samples was injected on a CM5 series S chip previously functionalized with anti-histidine capture antibody (Cytiva): injection is performed for 18 seconds at 5 μL/min. Capture levels were recorded 60 seconds after buffer wash. A standard curve of known $V_H$H concentrations (270, 90, 30, 10, 3.3, 1.1 μg/mL) was acquired in each of the 4 Biacore chip flow cells to eliminate cell-to-cell surface variability. The 96 captures were interpolated against the standard curve using a non-linear model including specific and unspecific, one-site binding. Concentrations in the first elution block varied from 12 to 452 μg/mL corresponding to a 4-149 μg. SDS-PAGE analysis of 5 randomly picked samples was performed to ensure molecular weight of eluates corresponded to expected values (~30 kDa).

The concentration of the proteins was normalized using the Hamilton Star automated system in substantial accordance with the following procedure. Concentration values are imported in an Excel spreadsheet where pipetting volumes were calculated to perform dilution to 50 μg/mL in 0.22 mL. The spreadsheet was imported in a Hamilton Star method dedicated to performing dilution pipetting using the first elution block and elution buffer as diluent. The final, normalized plate was sterile filtered using 0.22 μm filter plates (Corning).

Example 3. Evaluation of Binding Affinity of IL10Ra/IL2Rg Dimers Via SPR

All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with Protein A or CAP biotin chips (Cytiva). For experiments on Protein A chips, Fc-fused ligands were flowed at 5 μl/min for variable time ranging from 18 to 300 seconds, reaching the capture loads listed in the tables below. Following ligand capture, injections of a 2-fold dilution series of analyte typically comprising at least five concentrations between 1 μM and 1 nM were performed in either high performance or single cycle kinetics mode. Surface regeneration was achieved by flowing 10 mM glycine-HCl, pH 1.5 (60 seconds, 50 μL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Experiments on CAP chips were performed as described above with an additional capture step of Biotin CAPture reagent (10 seconds, 40 uL/min) performed prior to capture of biotinylated ligands. Calculated Rmax were generated using the equation Rmax=Load (RU) x valency of ligand x (Molecular weight of analyte/Molecular weight of ligand. Surface activity was defined as the ratio experimental/calculated Rmax. The results of these experiments are provided in below for sample information and experimental results.

TABLES

TABLE 2 anti-human IL10Ra sdAb CDRs

| Name | CDR 1 | SEQ ID NO: | CDR 2 | SEQ ID NO: | CDR 3 | SEQ ID NO: |
|---|---|---|---|---|---|---|
| hIL10Ra_ VHH1 | YLYSIDYMA | 25 | VIYTASGATFYPDSVKG | 43 | VRKTDSYLFDAQS FTY | 61 |
| hIL10Ra_ VHH2 | YLYSTNYMA | 26 | VIYTASGATLYTDSVKG | 44 | VRKTDSYLFDAQS FTY | 62 |
| hIL10Ra_ VHH3 | YLYSTNYMA | 27 | VIYTASGATLYTDSVKG | 45 | VRKTDSYLFDAQS FTY | 63 |
| hIL10Ra_ VHH4 | YLYSIDYMA | 28 | VIYTASGATFYPDSVKG | 46 | VRKTDSYLFDAQS FTY | 64 |
| hIL10Ra_ VHH5 | YLYSTNYMA | 29 | AIYTASGATLYSDSNKG | 47 | VRKTGSYLFDAQS FTY | 65 |
| hIL10Ra_ VHH6 | FTYSSYCMG | 30 | SIDSDGSTSYTDSVKG | 48 | DLMSTVVPGFCGF LLSAGMDY | 66 |
| hIL10Ra_ VHH7 | YTFNSNCMG | 31 | TIYTGVGSTYYADSVKG | 49 | EPLSRVYGGSCPTP TFGY | 67 |

TABLE 2-continued

| anti-human IL10Ra sdAb CDRs | | | | | | |
|---|---|---|---|---|---|---|
| Name | CDR 1 | SEQ ID NO: | CDR 2 | SEQ ID NO: | CDR 3 | SEQ ID NO: |
| hIL10Ra_ VHH8 | YTYSMYCMG | 32 | QINSDGSTSYADSVKG | 50 | DSRVYGGSWYERL CGPYTYEYNY | 68 |
| hIL10Ra_ VHH9 | YAYSTYCMG | 33 | AIDSGGSTSYADSVKG | 51 | VPPPPDGGSCLFLG PEIKVSKADFRY | 69 |
| hIL10Ra_ VHH10 | YLYSIDYMA | 34 | VIYTASGATFYPDSVKG | 52 | VRKTDSYLFDAQS FTY | 70 |
| hIL10Ra_ VHH11 | YTYSSYCMG | 35 | VIDSDGSTSYADSVKG | 53 | DLGHYRPPCGVLY LGMDY | 71 |
| hIL10Ra_ VHH12 | YTYSSNCMG | 36 | TIYTGGGNTYYADSVKG | 54 | EPLSRVYGGSCPTP TFDY | 72 |
| hIL10Ra_ VHH13 | YSYSSNCMG | 37 | TIHTGGGSTYYADSVKG | 55 | EPLSRLYGGSCPTP TFGY | 73 |
| hIL10Ra_ VHH14 | YTYSSYCMG | 38 | VIDSDGSTSYADSVKG | 56 | DLGHYRPPCGVLY LGMDY | 74 |
| hIL10Ra_ VHH15 | YTYSGYCMG | 39 | VIDSDGSTSYADSVKG | 57 | DLGHYRPPCGVLY LGMDY | 75 |
| hIL10Ra_ VHH16 | YTYSNYCMG | 40 | TIDSDGNTSYADSVKG | 58 | DLGHYRPPCGAYY YGMDY | 76 |
| hIL10Ra_ VHH17 | YSNCSYDMT | 41 | AIHSDGSTRYADSVKG | 59 | DPLHCRAHGGSW YSVRANY | 77 |
| hIL10Ra_ VHH18 | YTYNSNCMG | 42 | TIYTGVGSTYYADSVKG | 60 | EPLSRVYGGSCPTP TFGY | 78 |

TABLE 3

| human anti-IL2Rg sdAb CDRs | | | | | | |
|---|---|---|---|---|---|---|
| Name | CDR | SEQ ID NO: | CDR | SEQ ID NO: | CDR | SEQ ID NO: |
| hIL2Rg_VHH-1 | FTFDDSDMG | 79 | TISSDGSTYYADSVKG | 102 | DFMIAIQAPGAGC | 125 |
| hIL2Rg_VHH-2 | FSFSSYPMT | 80 | TIASDGGSTAYAASVE G | 103 | GYGDGTPA | 126 |
| hIL2Rg_VHH-3 | FTFDDREMN | 81 | TISSDGSTYYADSVKG | 104 | DFMIAIQAPGAGC | 127 |
| hIL2Rg_VHH-4 | FTFDDSDMG | 82 | TISSDGNTYYTDSVKG | 105 | EPRGYYSNYGGRRE CNY | 128 |
| hIL2Rg_VHH-5 | FSFSSYPMT | 83 | TIASDGGSTAYAASVE G | 106 | GYGDGTPA | 129 |
| hIL2Rg_VHH-6 | FTFSNAHMS | 84 | SIYSGGSTWYADSVKG | 107 | NRLHYYSDDDSL | 130 |
| hIL2Rg_VHH-7 | FTFDDREMN | 85 | TISSDGSTYYADSVKG | 108 | DFMIAIQAPGAGC | 131 |
| hIL2Rg_VHH-8 | YTFSSYCMG | 86 | ALGGGSTYYADSVKG | 109 | AWVACLEFGGSWY DLARYKH | 132 |
| hIL2Rg_VHH-9 | FTFDDSDMG | 87 | TISSDGSTYYADSVKG | 110 | EPRGYYSNYGGRRE CNY | 133 |
| hIL2Rg_VHH-10 | SIYSSAYIG | 88 | GIYTRDGSTAYADSVK G | 111 | GRRTKSYVYIFRPE EYNY | 134 |
| hIL2Rg_VHH-11 | FTFSSAHMS | 89 | SIYSGGGTFYADSVKG | 112 | NRLHYYSDDDSL | 135 |
| hIL2Rg_VHH-12 | FTFSNAHMS | 90 | SIYSGGSTWYADSVKG | 113 | NRLHYYSDDDSL | 136 |

TABLE 3-continued

| human anti-IL2Rg sdAb CDRs | | | | | | |
|---|---|---|---|---|---|---|
| Name | CDR | SEQ ID NO: | CDR | SEQ ID NO: | CDR | SEQ ID NO: |
| hIL2Rg_VHH-13 | FIFDDSDMG | 91 | TISSDGSTYYADSVKG | 114 | EPRGYYSNYGGRRE CNY | 137 |
| hIL2Rg_VHH-14 | FTADDSDMG | 92 | TISSDGSTYYADSVKG | 115 | EPRGYYSNYGGRRE CNY | 138 |
| hIL2Rg_VHH-15 | FTFSSAHMS | 93 | SIYSGGGTFYADSVKG | 116 | NRLHYYSDDDSL | 139 |
| hIL2Rg_VHH-16 | FTFSNAHMS | 94 | SIYSGGSTWYADSVKG | 117 | NRLHYYSDDDSL | 140 |
| hIL2Rg_VHH-17 | FTFSNAHMS | 95 | SIYSGGSTWYADSVKG | 118 | NRLHYYSDDDSL | 141 |
| hIL2Rg_VHH-18 | FTFSSYPMT | 96 | TIASDGGSTAYAASVE G | 119 | GYGDGTPA | 142 |
| hIL2Rg_VHH-19 | FTFDDREMN | 97 | TISSDGSTYYADSVKG | 120 | DFMIAIQAPGAGC | 143 |
| hIL2Rg_VHH-20 | FTFDDSDMG | 98 | TISSDGSTYYADSVKG | 121 | EPRGYYSNYGGRRE CNY | 144 |
| hIL2Rg_VHH-21 | YTSCMG | 99 | TIYTRGRSIYYADSVK G | 122 | GGYSWSAGCEFNY | 145 |
| hIL2Rg_VHH-22 | FSFSSYPMT | 100 | TIASDGGSTAYAASVE G | 123 | GYGDGTPA | 146 |
| hIL2Rg_VHH-23 | FSFSSYPMT | 101 | TIASDGGSTAYAASVE G | 124 | GYGDGTPA | 147 |

TABLE 4

| mouse anti-IL2Rg sdAb CDRs | | | | | | |
|---|---|---|---|---|---|---|
| Name | CDR 1 | SEQ ID NO: | CDR 2 | SEQ ID NO: | CDR 3 | SEQ ID NO: |
| mIL2Rg_VHH1 | YGYNYIG | 148 | VIYTGGGDTYYA DSVKG | 163 | SVYACLRGGHDEY AH | 178 |
| mIL2Rg_VHH2 | STYANYLMG | 149 | AIYSGGGSTYYA DSVKG | 164 | ASAVKGDKGDIVV VVTGTQRMEYDY | 179 |
| mIL2Rg_VHH3 | FTFDESVMS | 150 | IISSDDNTYYDDS VKG | 165 | RRRRPVYDSDYEL RPRPLCGDFGV | 180 |
| mIL2Rg_VHH4 | LPFDEDDMG | 151 | SISSDGTAYYAD SVKG | 166 | GVHRQFGGSSSCG DAFYGMDY | 181 |
| mIL2Rg_VHH5 | DVYGRNSM A | 152 | VGYSVVTTTYYA DSVKG | 167 | DGNLWRGLRPSEY TY | 182 |
| mIL2Rg_VHH6 | FPYSRYCMG | 153 | AIEPDGSTSYADS VKG | 168 | DERCFYLKDYDLR RPAQYRY | 183 |
| mIL2Rg_VHH7 | FTFDESDMG | 154 | VITSDDNPYYDD SVKG | 169 | RSRQPVYSRDYEL RPRPLCGDFGV | 184 |
| mIL2Rg_VHH8 | FTFDDFDMG | 155 | TISDDGSTYYAD SVKG | 170 | EGALGSKTNCGW VGNFGY | 185 |
| mIL2Rg_VHH9 | FTFDDFDMG | 156 | TISDDGSTYYAD SVKG | 171 | EGALGSKTNCGW VGNFGY | 186 |
| mIL2Rg_VHH10 | FTFDDFDMG | 157 | TISDDGSTYYAD SVKG | 172 | EGALGSKTNCGW VGNFGY | 187 |
| mIL2Rg_VHH11 | FTFSDRDMG | 158 | TISDDGSTYYAD SVKG | 173 | EGALGSKTNCGW VGNFGY | 188 |

TABLE 4-continued

| mouse anti-IL2Rg sdAb CDRs | | | | | | |
|---|---|---|---|---|---|---|
| Name | CDR 1 | SEQ ID NO: | CDR 2 | SEQ ID NO: | CDR 3 | SEQ ID NO: |
| mIL2Rg_VHH12 | YGYNYIG | 159 | VIYIGGGDTYYA DSVKG | 174 | RYCVGSVYACLRG GHDEYAH | 189 |
| mIL2Rg_VHH13 | YGYNYIG | 160 | VIYTGGGDTYYA DSVKG | 175 | RYCVGSVYACLRG GHDEYAH | 190 |
| mIL2Rg_VHH14 | FTFDDFDMG | 161 | TISDDGSTYYAN SVKG | 176 | EGALGSKTNCGW VGNFGY | 191 |
| mIL2Rg_VHH15 | FTFDDFDMG | 162 | TISDDGSTYYAD SVKG | 177 | EGALGSKMNCGW VGNFGY | 192 |

TABLE 5

| human anti-IL10Ra VHH Amino Acid Sequences | | |
|---|---|---|
| Name | VHH Sequence | SEQ ID NO: |
| hIL10Ra_VHH1 | QVQLQESGGGSIQAGGSLRLSCAASR YLYSIDYMAWFRQSPGKEREPVAVIY TASGATFYPDSVKGRFTISQDNAKMT VYLQMNSLKSEDTAMYYCAAVRKT DSYLFDAQSFTYWGQGTQVTVSS | 193 |
| hIL10Ra_VHH2 | QVQLQESGGGSVQAGGSLRLSCVAS RYLYSTNYMAWFRQSPGKEREAVAV IYTASGATLYTDSVKGRFTISQDNAK MTVYLQMNRLKSEDTAMYYCAAVR KTDSYLFDAQSFTYWGQGTQVTVSS | 194 |
| hIL10Ra_VHH3 | QVQLQESGGGSIQAGGSLRLSCVASR YLYSTNYMAWFRQSPGKEREAVAVI YTASGATLYTDSVKGRFTISQDNAK MTVYLQMNRLKSEDTAMYYCAAVR KTDSYLFDAQSFTYWGQGTQVTVSS | 195 |
| hIL10Ra_VHH4 | QVQLQESGGGSIQAGGSLRLSCAASR YLYSIDYMAWFRQSPGKEREPAAVIY TASGATFYPDSVKGRFTISQDNAKMT VYLQMNSLKSEDTAMYYCAAVRKT DSYLFDAQSFTYWGQGTQVTVSS | 196 |
| hIL10Ra_VHH5 | QVQLQESGGGSIQAGGSLRLSCVASK YLYSTNYMAWFRQSPGKEREAVAAI YTASGATLYSDSNKGRFTISQDNAK MTVYLQMNSLKSEDTAMYYCAAVR KTGSYLFDAQSFTYWGQGTQVTVSS | 197 |
| hIL10Ra_VHH6 | QVQLQESGGGSVQAGGSLRLSCAAS RFTYSSYCMGWFRQAPGKEREGVAS IDSDGSTSYTDSVKGRFTISKDNAKN TLYLQMNSLKPEDTAMYYCALDLMS TVVPGFCGFLLSAGMDYWGKGTQVT VSS | 198 |
| hIL10Ra_VHH7 | QVQLQESGGGSVQAGGSLRLSCAVS GYTFNSNCMGWFRQAPGKEREGVAT IYTGVGSTYYADSVKGRFTISQDNAK NTVYLQMNSLKPEDTAMYYCAAEPL SRVYGGSCPTPTFGYWGQGTQVTVS S | 199 |
| hIL10Ra_VHH8 | QVQLQESGGGSVQAGGSLRLSCAAS GYTYSMYCMGWFRQAPGKEREGVA QINSDGSTSYADSVKGRFTISKDNAK NTLYLQMNSLKPEDTAMYYCAADSR VYGGSWYERLCGPYTYEYNYWGQG TQVTVSS | 200 |

TABLE 5-continued

| human anti-IL10Ra VHH Amino Acid Sequences | | |
|---|---|---|
| Name | VHH Sequence | SEQ ID NO: |
| hIL10Ra_VHH9 | QVQLQESGGGSVQAGGSLRLSCAVS GYAYSTYCMGWFRQAPGKEREGVA AIDSGGSTSYADSVKGRFTISKDNAK NTLYLRMNSLKPEDTAMYYCAAVPP PPDGGSCLFLGPEIKVSKADFRYWGQ GTQVTVSS | 201 |
| hIL10Ra_VHH10 | QVQLQESGGGSVQAGGSLRLSCAAS RYLYSIDYMAWFRQSPGKEREPVAVI YTASGATFYPDSVKGRFTISQDNAKM TVYLQMNSLKSEDTAMYYCAAVRK TDSYLFDAQSFTYWGQGTQVTVSS | 202 |
| hIL10Ra_VHH11 | QVQLQESGGGSVQAGGSLRLSCGAS RYTYSSYCMGWFRQAPGKEREGVA VIDSDGSTSYADSVKGRFTISKDNGK NTLYLQMNSLKPEDTAMYYCAADL GHYRPPCGVLYLGMDYWGKGTQVT VSS | 203 |
| hIL10Ra_VHH12 | QVQLQESGGGSVQAGGSLRLSCTVS GYTYSSNCMGWFRQAPGKEREGVAT TYTGGGNTYYADSVKGRFTISQDNAK NTVYLQMNNLKPEDTAMYYCAAEP LSRVYGGSCPTPTFDYWGQGTQVTV SS | 204 |
| hIL10Ra_VHH13 | QVQLQESGGGSVQAGGSLRLSCAVS GYSYSSNCMGWFRQAPGKEREGVAT IHTGGGSTYYADSVKGRFTISQDNAK NTVYLQMNSLKPEDTAMYYCAAEPL SRLYGGSCPTPTFGYWGQGTQVTVSS | 205 |
| hIL10Ra_VHH14 | QVQLQESGGGSVQAGGSLRLSCGAS GYTYSSYCMGWFRQVPGKEREGVA VIDSDGSTSYADSVKGRFTISKDNGK NTLYLQMNSLKPEDTAMYYCAADL GHYRPPCGVLYLGMDYWGKGTQVT VSS | 206 |
| hIL10Ra_VHH15 | QVQLQESGGGSVQAGGSLRLSCGAS GYTYSGYCMGWFRQAPGKEREGVA VIDSDGSTSYADSVKGRFTISKDNGK NTLYLQMNSLKPEDTAMYYCAADL GHYRPPCGVLYLGMDYWGKGTQVT VSS | 207 |

TABLE 5-continued

| human anti-IL10Ra VHH Amino Acid Sequences | | |
|---|---|---|
| Name | VHH Sequence | SEQ ID NO: |
| hIL10Ra_VHH16 | QVQLQESGGGSVQAGGSLRLACAASRYTYSNYCMGWFRQAPGKEREGVATIDSDGNTSYADSVKGRFTISRDNAKNTLYLQMNSLKPGDTAMYYCAADLGHYRPPCGAYYYGMDYWGKGTQVTVSS | 208 |
| hIL10Ra_VHH17 | QVQLQESGGGSVQAGGSLRLSCAASGYSNCSYDMTWYRQAPGKEREFVSAIHSDGSTRYADSVKGRFFISQDNAKNTVYLQMNSLKPEDTAMYYCKTDPLHCRAHGGSWYSVRANYWGQGTQVTVSS | 209 |
| hIL10Ra_VHH18 | QVQLQESGGGSVQAGGSLRLSCAVSGYTYNSNCMGWFRQAPGKEREGVATIYTGVGSTYYADSVKGRFTISQDNAKNTVYLQMNSLKPEDTAMYYCAAEPLSRVYGGSCPTPTFGYWGQGTQVTVSS | 210 |

TABLE 6

| human anti-IL2Rg VHH Amino Acid Sequences | | |
|---|---|---|
| Name | VHH Sequence (CDRs are underlined) | SEQ ID NO: |
| hIL2Rg_VHH-1 | QVQLQESGGGSVQAGGSLRLSCAASGFTFDDSDMGWYRQAPGNECDLVSTISSDGSTYYADSVKGRFTISQDNAKNTVYLQMDSVKPEDTAVYYCAADFMIAIQAPGAGCWGQGTQVTVSS | 211 |
| hIL2Rg_VHH-2 | QVQLQESGGGSVPAGGSLKLSCAASGFSFSSYPMTWARQAPGKGLEWVSTIASDGGSTAYAASVEGRFTISRDNAKSTLYLQLNSLKTEDTAMYYCTKGYGDGTPAPGQGTQVTVSS | 212 |
| hIL2Rg_VHH-3 | QVQLQESGGGSVQTGGSLRLSCTASGFTFDDREMNWYRQAPGNECELVSTISSDGSTYYADSVKGRFTISQDNAKNTVYLQMDSVKPEDTAVYYCAADFMIAIQAPGAGCWGQGTQVTVSS | 213 |
| hIL2Rg_VHH-4 | QVQLQESGGGSVQAGGSLRLSCTASGFTFDDSDMGWYRQAPGNECELVSTISSDGNTYYTDSVKGRFTISQDNAKNTVYLQMNSLGPEDTAVYYCAAEPRGYYSNYGGRRECNYWGQGTQVTVSS | 214 |
| hIL2Rg_VHH-5 | QVQLQESGGGSVQAGGSLRLSCAASGFSFSSYPMTWARQAPGKGLEWVSTIASDGGSTAYAASVEGRFTISRDNAKSTLYLQLNSLKTEDTAMYYCTKGYGDGTPAPGQGTQVTVSS | 215 |
| hIL2Rg_VHH-6 | QVQLQESGGGAVQAGGSLRLSCAASGFTFSNAHMSWVRQAPGKGREWISSIYSGGSTWYADSVKGRFTISRDNSKNTLYLQLNSLKTEDTAMYYCAENRLHYYSDDDSLRGQGTQVTVSS | 216 |
| hIL2Rg_VHH-7 | QVQLQESGGGLVQPGGSLRLSCAASGFTFDDREMNWYRQAPGNECELVSTISSDGSTYYADSVKGRFTISQDNAKNTVYLQMDSVKPEDTAVYYCAADFMIAIQAPGAGCWGQGTQVTVSS | 217 |
| hIL2Rg_VHH-8 | QVQLQESGGGSVQAGGSLRLSCVASGYTFSSYCMGWFRQAPGKEREGVAALGGGSTYYADSVKGRFTISQDNAKNTLYLQMNSLKPEDTAMYYCAAAWVACLEFGGSWYDLARYKHWGQGTQVTVSS | 218 |
| hIL2Rg_VHH-9 | QVQLQESGGGSVQAGGSLRLSCTASGFTFDDSDMGWYRQAPGGECELVTISSDGSTYYADSVKGRFTISQDNAKNTVYLQMNSLKPEDTAVYYCAAEPRGYYSNYGGRRECNYWGQGTQVTVSS | 219 |
| hIL2Rg_VHH-10 | QVQLQESGGGSVQAGGSLRLSCAASGSIYSSAYIGWFRQAPGKKREGVAGIYTRDGSTAYADSVKGRFTISQDSAKKTVYLQMNSLKPEDTAMYYCAAGRRTKSYVYIFRPEEYNYWGQGTQVTVSS | 220 |

TABLE 6-continued human anti-IL2Rg VHH Amino Acid Sequences

| Name | VHH Sequence (CDRs are underlined) | SEQ ID NO: |
|---|---|---|
| hIL2Rg_VHH-11 | QVQLQESGGGSVQAGGSLRLSCAASGFTFSSAHMSWVRQAPGKGREWIASIYSGGGTFYADSVKGRFTISRDNAKNTLYLQLNSLKTEDTAMYYCATNRLHYYSDDDSLRGQGTQVTVSS | 221 |
| hIL2Rg_VHH-12 | QVQLQESGGGSVQAGGSLRLSCAASGFTFSNAHMSWVRQAPGKGREWISSIYSGGSTWYADSVKGRFTISRDNSKNTLYLQLNSLKTEDTAMYYCAENRLHYYSDDDSLRGQGTQVTVSS | 222 |
| hIL2Rg_VHH-13 | QVQLQESGGGSVQAGGSLRLSCTASRFIFDDSDMGWYRQAPGNECELVSTISSDGSTYYADSVKGRFTISRDNAKNTVYLQMNSLKPEDTAVYYCAAEPRGYYSNYGGRRECNYWGQGTQVTVSS | 223 |
| hIL2Rg_VHH-14 | QVQLQESGGGSVQAGGSLKLSCTVSGFTADDSDMGWYRQGPGNECELVTISSDGSTYYADSVKGRFTISQDNAKNTVYLQMNSLKPEDTAVYYCAAEPRGYYSNYGGRRECNYWGQGTQVTVSS | 224 |
| hIL2Rg_VHH-15 | QVQLQESGGGLVQPGGSLRLSCAASGFTFSSAHMSWVRQAPGKGREWIASIYSGGGTFYADSVKGRFTISRDNAKNTLYLQLNSLKAEDTAMYYCATNRLHYYSDDDSLRGQGTQVTVSS | 225 |
| hIL2Rg_VHH-16 | QVQLQESGGGLVQPGGSLRLSCVASGFTFSNAHMSWVRQAPGKGREWISSIYSGGSTWYADSVKGRFTISRDNSKNTLYLQLNSLKTEDTAMYYCAENRLHYYSDDDSLRGQGTQVTVSS | 226 |
| hIL2Rg_VHH-17 | QVQLQESGGGLVQPGGSLRLSCAASGFTFSNAHMSWVRQAPGKGREWISSIYSGGSTWYADSVKGRFTISRDNSKNTLYLQLNSLKTEDTAMYYCAENRLHYYSDDDSLRGQGTQVTVSS | 227 |
| hIL2Rg_VHH-18 | QVQLQESGGGLVQPGGSLRLSCAASGFTFSSYPMTWARQAPGKGLEWVSTIASDGGSTAYAASVEGRFTISRDNAKSTLYLQLNSLKTEDTAMYYCTKGYGDGTPAPGQGTQVTVSS | 228 |
| hIL2Rg_VHH-19 | QVQLQESGGGSVQAGGSLRLSCTASGFTFDDREMNWYRQAPGNECELVSTISSDGSTYYADSVKGRFTISQDNAKNTVYLQMDSVKPEDTAVYYCAADFMIAIQAPGAGCWGQGTQVTVSS | 229 |
| hIL2Rg_VHH-20 | QVQLQESGGGSVQAGGSLRLSCTASGFTFDDSDMGWYRQAPGNECELVSTISSDGSTYYADSVKGRFTISQDNAKNTVYLQMNSLKPEDTAVYYCAAEPRGYYSNYGGRRECNYWGQGTQVTVSS | 230 |
| hIL2Rg_VHH-21 | QVQLQESGGGSVQAGGSLRLSCVASGYTSCMGWFRQAPGKEREAVATIYTRGRSIYYADSVKGRFTISQDNAKNTLYLQMNSLKPEDIAMYSCAAGGYSWSAGCEFNYWGQGTQVTVSS | 231 |
| hIL2Rg_VHH-22 | QVQLQESGGGLVQPGGSLRLSCTASGFSFSSYPMTWARQAPGKGLEWVSTIASDGGSTAYAASVEGRFTISRDNAKSTLYLQLNSLKTEDTAMYYCTKGYGDGTPAPGQGTQVTVSS | 232 |
| hIL2Rg_VHH-23 | QVQLQESGGGLVQPGGSLRLSCAASGFSFSSYPMTWARQAPGKGLEWVSTIASDGGSTAYAASVEGRFTISRDNAKSTLYLQLNSLKTEDTAMYYCTKGYGDGTPAPGQGTQVTVSS | 233 |

TABLE 7

| murine anti-IL2Rg VHH Amino Acid Sequences | | |
|---|---|---|
| Name | VHH AA Sequence (CDRs Underlined) | SEQ ID NO: |
| mIL2Rg_VHH1 | QVQLQESGGGSVLAGGSLRLSCVASGYGYNYIGWFRQTPGKERE GVAVIYTGGGDTYYADSVKGRFTASRDNAKSTLYLQMNSLEPED TAMYYGVARYCVGSVYACLRGGHDEYAHWGQGTQVTVSS | 234 |
| mIL2Rg_VHH2 | QVQLQESGGGSVQPGGSLRLSCAASGSTYANYLMGWFRQAPGK EREGVAAIYSGGGSTYYADSVKGRFTISQDNAKNTLYLQMNSLK PEDTAMYYCAAASAVKGDKGDIVVVVTGTQRMEYDYWGHGTQ VTVSS | 235 |
| mIL2Rg_VHH3 | QVQLQESGGGSVQAGASLRLSCSVSGFTFDESVMSWLRQGPGNE CDAVAIISSDDNTYYDDSVKGRFTISEDNAKNMVYLQMNSLKPE DTAVYYCAARRRRPVYDSDYELRPRPLCGDFGVWGQGTQVTVS S | 236 |
| mIL2Rg_VHH4 | QVQLQESGGGSVQAGGSLRLSCIGSGLPFDEDDMGWYRQAPGNE CELVSSISSDGTAYYADSVKGRFTISRDNAKNTVLLQMNSLKPED TAVYYCAAGVHRQFGGSSSCGDAFYGMDYWGKGTQVTVSS | 237 |
| mIL2Rg_VHH5 | QVQLQESGGGSVQAGGSLRLSCVASGDVYGRNSMAWFRQAPGK EREGVAVGYSVVTTTYYADSVKGRFTISEDNDKNTVYLEMNSLK PEDTAMYYCAADGNLWRGLRPSEYTYWGQGTQVTVSS | 238 |
| mIL2Rg_VHH6 | QVQLQESGGGSVQAGGSLRLSCATSGFPYSRYCMGWFRQAPGKE REGVAAIEPDGSTSYADSVKGRFTISQDNAVNTLYLQMNNLKPE DTAMYYCAADERCFYLKDYDLRRPAQYRYWGQGTQVTVSS | 239 |
| mIL2Rg_VHH7 | QVQLQESGGGLVQPGGSLRLSCTVSGFTFDESDMGWLRQNPGNE CGVVSVITSDDNPYYDDSVKGRFTISEDNAKNMVYLQMNSLKPE DTGVYYCATRSRQPVYSRDYELRPRPLCGDFGVWGQGTQVTVSS | 240 |
| mIL2Rg_VHH8 | QVQLQESGGGSVQAGGSLRLSCTASGFTFDDFDMGWYRQAPGN ECELVSTISDDGSTYYADSVKGRSSISRDNAKNTVYLQMNRLKPE DTGVYYCAAEGALGSKTNCGWVGNFGYWGQGTQVTVSS | 241 |
| mIL2Rg_VHH9 | QVQLQESGGGSVQAGGSLRLSCAASGFTFDDFDMGWYRQAPGN ECELVSTISDDGSTYYADSVKGRSSISRDNAKNTVYLQMNSLKPE DTAVYYCAAEGALGSKTNCGWVGNFGYWGQGTQVTVSS | 242 |
| mIL2Rg_VHH10 | QVQLQESGGGLVQPGGSLRLSCAASGFTFDDFDMGWYRQAPGN ECELVSTISDDGSTYYADSVKGRSSISRDNAKSTVYLQMNRLKPE DTGVYYCAAEGALGSKTNCGWVGNFGYWGQGTQVTVSS | 243 |
| mIL2Rg_VHH11 | QVQLQESGGGLVQPGGSLKLSCAASGFTFSDRDMGWYRQAPGN ECERVSTISDDGSTYYADSVKGRSSISRDNAKNTVYLQMNSLKPE DTAVYYCAAEGALGSKTNCGWVGNFGYWGQGTQVTVSS | 244 |
| mIL2Rg_VHH12 | QVQLQESGGGSVLAGGSLRLSCVASGYGYNYIGWFRQTPGKERE GVAVIYIGGGDTYYADSVKGRFTASRDNAKSTLYLQMNSLEPED TAMYYCVARYCVGSVYACLRGGHDEYAHWGQGTQVTVSS | 245 |
| mIL2Rg_VHH13 | QVQLQESGGGSVLAGGSLRLSCVASGYGYNYIGWFRQTPGKERE GVAVIYTGGGDTYYADSVKGRFTASRDNAKSTLYLQMNSLEPED TAMYYCVARYCVGSVYACLRGGHDEYAHWGQGTQVTVSS | 246 |
| mIL2Rg_VHH14 | QVQLQESGGGSVQAGGSLRLSCAASGFTFDDFDMGWYRQAPGN ECELVSTISDDGSTYYANSVKGRSSISRDNAKNMVYLQMNSLKPE DTAVYYCAAEGALGSKTNCGWVGNFGYWGQGTQVTVSS | 247 |
| mIL2Rg_VHH15 | QVQLQESGGGSVQAGGSLRLSCTASGFTFDDFDMGWYRQAPGN ECELVSTISDDGSTYYADSVKGRSSISRDNAKNTVYLQMNRLKPE DTGVYYCAAEGALGSKMNCGWVGNFGYWGQGTQVTVSS | 248 |

TABLE 8

| anti-IL10Ra sdAb VHH DNA SEQUENCE | | |
|---|---|---|
| Table 2. hIL10Ra VHH DNA Sequences | | |
| Name | Sequence | SEQ ID NO: |
| hIL10Ra_VHH1 | CAGGTTCAGCTTCAGGAGTCCGGTGGAGGCTCCA TCCAGGCCGGGGGCTCTCTCCGCCTGTCTTGCGCC | 249 |

TABLE 8-continued anti-IL10Ra sdAb VHH DNA SEQUENCE

Table 2. hIL10Ra VHH DNA Sequences

| Name | Sequence | SEQ ID NO: |
|---|---|---|
| | GCTTCCAGATACCTCTACAGTATCGACTACATGG CTTGGTTTCGTCAGAGCCCAGGAAAAGAGCGGGA ACCCGTGGCAGTAATCTACACTGCCTCAGGTGCC ACATTTTACCCCGACTCTGTCAAGGGCAGGTTCA CCATCTCTCAGGATAATGCCAAGATGACAGTGTA CTTGCAGATGAACTCCCTGAAATCTGAGGATACC GCTATGTATTACTGTGCCGCAGTGCGCAAGACCG ATTCTTACCTGTTCGACGCTCAGAGTTTTACCTAC TGGGGCCAGGGCACTCAGGTCACCGTCAGCAGC | |
| hIL10Ra_VHH2 | CAGGTGCAGTTGCAGGAGTCCGGCGGGGGTTCCG TGCAAGCAGGCGGATCTCTGCGCCTGTCCTGCGT GGCCTCTCGTTATTTGTATAGCACCAACTACATGG CTTGGTTCCGTCAGTCCCCAGGCAAAGAGCGCGA AGCCGTAGCCGTAATCTATACGGCCTCTGGGGCA ACACTCTATACCGACTCAGTGAAGGGACGCTTCA CGATTTCCCAAGACAATGCAAAGATGACCGTGTA CTTGCAGATGAACCGCCTGAAGAGCGAGGACACG GCTATGTATTACTGCGCAGCCGTGCGCAAGACCG ACTCCTACTTGTTTGACGCTCAGTCCTTCACTTAT TGGGGCCAGGGTACACAGGTCACCGTGAGCAGT | 250 |
| hIL10Ra_VHH3 | CAAGTACAGCTCCAGGAGAGCGGCGGTGGATCTA TCCAAGCAGGGGGTAGCCTTAGGTTGTCCTGTGT GGCGTCCAGATACCTGTATAGCACGAACTACATG GCATGGTTCAGACAGTCCCCAGGCAAGGAACGCG AGGCAGTCGCCGTTATTTACACTGCATCTGGGGC CACCCTCTATACGGACAGCGTGAAGGGAAGGTTT ACAATCTCCCAGGACAACGCGAAGATGACCGTGT ACCTTCAGATGAACCGCCTGAAGTCCGAGGACAC CGCCATGTATTACTGTGCAGCGGTGCGCAAGACC GACAGCTATCTGTTCGACGCGCAGTCATTCACTTA TTGGGGCCAAGGAACCCAAGTGACCGTCAGCTCA | 251 |
| hIL10Ra_VHH4 | CAGGTGCAGCTCCAAGAGTCCGGGGGAGGCTCTA TCCAGGCGGGAGGCAGTCTGCGCTTGTCCTGCGC CGCAAGTCGTTATCTGTACTCCATTGATTACATGG CATGGTTCCGCCAGTCCCCAGGTAAGGAACGTGA ACCTGCCGCTGTGATCTACACCGCTTCTGGAGCA ACCTTTTATCCTGATAGCGTTAAGGGTCGCTTCAC CATCTCTCAGGATAACGCCAAAATGACAGTGTAC CTCCAGATGAACAGCCTGAAGTCTGAGGACACTG CCATGTACTATTGTGCGGCTGTGCGCAAGACCGA CTCCTATCTGTTTGATGCACAGAGCTTTACCTATT GGGGTCAGGGCACCCAGGTGACTGTGTCTAGC | 252 |
| hIL10Ra_VHH5 | CAGGTCCAGTTGCAGGAGTCCGGTGGAGGTTCCA TCCAGGCGGGTGGGTCCCTTCGTCTCTCCTGCGTG GCCTCTAAGTACCTGTATTCAACCAACTACATGG CATGGTTCAGACAGTCTCCCGGCAAAGAGCGTGA GGCAGTGGCCGCGATCTATACAGCTTCTGGGGCC ACCCTGTACTCTGATTCCAATAAGGGAAGGTTCA CTATCTCACAGGATAACGCCAAAATGACCGTCTA CCTTCAGATGAACAGCCTCAAGTCTGAAGACACG GCAATGTATTACTGTGCAGCCGTGCGCAAAACTG GGAGCTACCTGTTTGACGCTCAGTCTTTCACTTAT TGGGGCCAGGGTACGCAGGTGACAGTCTCTTCT | 253 |
| hIL10Ra_VHH6 | CAGGTGCAACTCCAGGAGAGCGGAGGCGGTTCTG TTCAGGCAGGAGGTTCCCTGAGACTGTCCTGTGC CGCGTCTCGCTTTACGTATTCATCCTACTGCATGG GATGGTTCAGACAAGCGCCGGGGAAAGAAAGGG AAGGCGTGGCCTCCATTGACTCCGACGGCTCAAC TTCATACACTGATAGCGTGAAAGGCCGGTTCACC ATCTCTAAGGACAACGCGAAGAACACCCTGTATC TCCAGATGAACAGCCTCAAGCCTGAGGATACTGC CATGTACTATTGCGCACTCGACCTGATGTCTACTG TGGTCCCAGGCTTCTGCGGGTTCCTGCTCTCTGCT GGCATGGACTACTGGGGAAGGGCACTCAGGTA ACGGTTAGCTCC | 254 |
| hIL10Ra_VHH7 | CAGGTGCAGCTTCAGGAATCTGGCGGGGGCTCCG TGCAGGCCGGGGGCTCCCTCAGACTTTCCTGTGC CGTCTCCGGTTACACATTTAACAGTAACTGTATGG | 255 |

TABLE 8-continued anti-IL10Ra sdAb VHH DNA SEQUENCE

Table 2. hIL10Ra VHH DNA Sequences

| Name | Sequence | SEQ ID NO: |
|---|---|---|
| | GCTGGTTCCGCCAGGCACCAGGCAAGGAGAGGG<br>AAGGTGTGGCCACAATCTATACTGGTGTTGGGAG<br>TACGTACTATGCTGATTCCGTGAAAGGTCGCTTCA<br>CAATTTCCCAGGACAACGCGAAGAACACTGTGTA<br>CTTGCAGATGAATAGCCTGAAGCCTGAAGATACC<br>GCAATGTATTACTGCGCTGCCGAGCCACTCTCCC<br>GCGTATATGGTGGAAGTTGCCCCACCCCCACTTTC<br>GGTTACTGGGGCCAGGGCACTCAAGTGACCGTGT<br>CCTCT | |
| hIL10Ra_VHH8 | CAGGTTCAGCTTCAGGAGTCTGGGGGCGGTTCAG<br>TGCAGGCTGGCGGTTCTCTCCGCCTGTCCTGCGCT<br>GCCAGCGGCTATACTTACAGCATGTACTGCATGG<br>GCTGGTTCCGGCAAGCCCCCGGCAAAGAGCGTGA<br>GGGCGTCGCTCAAATCAACAGCGACGGGTCAACC<br>AGCTACGCCGATTCTGTCAAGGGCAGATTTACTA<br>TCAGCAAGGACAACGCCAAAAACACACTGTACCT<br>CCAGATGAACTCTTTGAAGCCTGAGGACACCGCG<br>ATGTATTACTGCGCCGCTGACAGCCGCGTGTACG<br>GTGGCAGCTGGTATGAGAGGCTGTGCGGCCCGTA<br>CACCTACGAGTACAACTATTGGGGACAGGGCACG<br>CAGGTGACAGTTAGCTCC | 256 |
| hIL10Ra_VHH9 | CAGGTGCAACTGCAAGAGAGTGGCGGAGGCTCC<br>GTCCAGGCTGGAGGTTCCCTGCGGCTGTCTTGCG<br>CCGTCAGCGGCTACGCATATTCCACTTACTGTATG<br>GGTTGGTTCCGCCAGGCCCCTGGAAAGGAACGCG<br>AGGGTGTTGCCGCTATTGATAGCGGAGGCTCCAC<br>ATCCTATGCGGACTCCGTGAAAGGTCGTTTCACC<br>ATCTCCAAGGATAACGCCAAGAACACTCTGTACC<br>TGCGCATGAACTCTCTGAAGCCTGAGGACACTGC<br>CATGTATTACTGCGCCGCTGTGCCCCCTCCACCCG<br>ACGGGGGCTCTTGTCTGTTTCTTGGCCCGGAGATC<br>AAGGTGTCCAAGGCTGATTTCCGTTATTGGGGCC<br>AGGGAACTCAAGTCACCGTGTCTTCC | 257 |
| hIL10Ra_VHH10 | CAGGTCCAGCTCCAGGAGTCCGGTGGAGGCTCCG<br>TTCAGGCCGGTGGCAGCTTGCGTCTGAGCTGCGC<br>GGCTTCAAGATACCTGTACTCCATTGATTACATGG<br>CATGGTTCCGTCAGTCTCCTGGCAAGGAGCGCGA<br>GCCCGTCGCTGTGATCTATACCGCCAGCGGAGCC<br>ACGTTCTACCCTGATTCCGTCAAGGGCCGCTTCAC<br>CATTAGCCAAGACAACGCTAAGATGACGGTGTAC<br>CTCCAAATGAATAGCCTGAAAAGCGAGGACACA<br>GCGATGTATTACTGCGCCGCTGTTAGGAAAACTG<br>ATAGTTACCTGTTCGATGCACAGTCTTTCACTTAC<br>TGGGGGCAGGGCACCCAAGTTACCGTCTCCTCT | 258 |
| hIL10Ra_VHH11 | CAGGTGCAGCTCCAGGAATCTGGAGGGGGCAGTG<br>TGCAGGCCGGGGGCTCCCTGCGCTTGAGCTGTGG<br>AGCCAGCCGCTACACGTATTCCAGTTACTGTATG<br>GGCTGGTTCAGACAAGCTCCGGGTAAGGAGAGA<br>GAGGGAGTTGCCGTAATTGATTCTGACGGGTCCA<br>CTAGCTATGCGGATTCAGTCAAGGGCCGGTTCAC<br>CATCAGCAAGGACAATGGTAAGAACACACTGTAC<br>CTGCAAATGAACAGCCTGAAGCCCGAGGACACCG<br>CCATGTACTATTGTGCCGCTGATCTCGGACATTAC<br>CGCCCTCCCTGCGGTGTGCTCTATCTCGGGATGGA<br>CTATTGGGGTAAGGGCACCCAGGTGACCGTGTCC<br>TCT | 259 |
| hIL10Ra_VHH12 | CAGGTGCAGCTCCAGGAAAGCGGCGGGGGTAGC<br>GTTCAAGCAGGTGGGTCCCTGCGCTTGAGCTGTA<br>CTGTGTCCGGCTACACCTACTCAAGCAACTGCAT<br>GGGATGGTTCCGTCAGGCCCCTGGCAAGGAACGC<br>GAAGGCGTGGCTACTATCTACACCGGCGGTGGCA<br>ACACTTATTACGCCGACTCCGTTAAGGGGCGTTTC<br>ACTATCAGCCAAGACAACGCCAAGAACACCGTGT<br>ATCTGCAAATGAATAACCTGAAGCCTGAAGACAC<br>CGCCATGTATTACTGTGCTGCCGAGCCCCTTTCCC<br>GCGTTTACGGCGGTTCTTGTCCTACCCCTACCTTT<br>GACTACTGGGGTCAGGGAACACAGGTGACAGTGT<br>CCAGT | 260 |

TABLE 8-continued anti-IL10Ra sdAb VHH DNA SEQUENCE

Table 2. hIL10Ra VHH DNA Sequences

| Name | Sequence | SEQ ID NO: |
|---|---|---|
| hIL10Ra_VHH13 | CAAGTCCAACTCCAGGAATCTGGGGGAGGCTCCG TACAGGCTGGCGGTTCCCTTCGTCTGTCCTGTGCT GTGTCAGGGTACTCCTACTCCAGTAACTGTATGG GCTGGTTCCGGCAAGCCCCCGGAAAGGAGCGCGA GGGCGTGGCTACCATCCACACAGGGGGCGGTTCC ACATATTACGCCGATAGTGTCAAGGGCCGCTTCA CCATTAGTCAGGACAACGCCAAGAATACCGTTTA CCTTCAAATGAACTCTTTGAAACCTGAGGACACT GCGATGTATTACTGTGCGGCAGAGCCTTTGTCCC GCCTGTACGGGGGATCTTGTCCGACCCCGACTTTC GGGTACTGGGGACAGGGCACCCAGGTGACAGTGT CCTCC | 261 |
| hIL10Ra_VHH14 | CAGGTGCAGTTGCAGGAAAGCGGGGGTGGCAGC GTCCAAGCCGGTGGCAGCCTGCGTCTGTCCTGCG GTGCCTCCGGCTATACTTACTCCAGCTATTGCATG GGTTGGTTCCGCCAAGTGCCAGGAAAGGAGCGTG AGGGGGTGGCTGTAATTGATTCAGATGGGTCAAC AAGCTACGCTGACAGCGTTAAAGGTCGCTTCACC ATCAGTAAGGACAACGGCAAGAACACCCCTCTACC TGCAAATGAACTCCCTGAAGCCGGAGGATACCGC AATGTATTACTGTGCCGCTGACTTGGGACACTAC CGCCCTCCGTGCGGTGTGCTTTATCTGGGCATGGA TTACTGGGGTAAGGGAACCCAAGTGACGGTGTCT TCT | 262 |
| hIL10Ra_VHH15 | CAGGTACAACTCCAGGAGTCTGGCGGTGGGTCCG TGCAGGCAGGTGGCAGCCTTCGCCTCTCCTGCGG GGCCTCCGGGTACACCTATAGTGGCTACTGCATG GGGTGGTTCAGGCAAGCCCCCGGTAAGGAACGTG AGGGAGTTGCTGTGATTGATTCAGATGGGTCCAC GAGTTACGCTGACTCCGTGAAAGGTAGGTTCACA ATCTCCAAAGATAATGGCAAGAACACCCTCTACC TTCAGATGAATAGCCTGAAGCCAGAAGACACCGC CATGTATTACTGTGCTGCCGACCTGGGACACTATC GCCCTCCGTGCGGGGTCCTGTACTTGGGCATGGA CTATTGGGGCAAGGGGACCCAGGTGACTGTGTCC TCT | 263 |
| hIL10Ra_VHH16 | CAGGTGCAGTTGCAGGAATCCGGTGGAGGCTCTG TTCAGGCCGGGGGCTCTCTCCGCCTGGCCTGCGC AGCCTCCAGGTATACTTACAGCAACTACTGCATG GGGTGGTTTCGCCAGGCTCCGGGCAAAGAGCGTG AGGGAGTGGCTACTATTGATTCCGATGGAAACAC CAGCTACGCCGATAGCGTGAAGGGCAGATTTACT ATCAGCAGAGATAACGCTAAAAACACGTTGTACC TCCAGATGAACTCACTCAAGCCGGGGGACACAGC TATGTATTACTGCGCAGCCGATCTGGGTCACTACC GCCCGCCCTGCGGCGCATATTACTATGGCATGGA CTACTGGGGCAAGGGCACCCAGGTGACCGTGTCC AGT | 264 |
| hIL10Ra_VHH17 | CAGGTGCAGCTCCAAGAGTCTGGCGGGGGTTCCG TGCAAGCCGGTGGCTCACTCAGGTTGAGTTGCGC AGCCAGCGGCTATAGCAACTGTTCCTATGACATG ACTTGGTATCGCCAGGCCCCTGGCAAAGAGCGTG AGTTCGTGTCAGCTATTCACTCCGACGGCTCCACT CGTTATGCGGACTCTGTGAAGGGCCGGTTTTTCAT CTCCCAGGACAACGCTAAAAACACTGTCTATTTG CAGATGAACTCTCTGAAACCCGAAGATACCGCCA TGTACTATTGCAAAACCGATCCTCTGCATTGTCGC GCCCACGGCGGGAGTTGGTACTCTGTGCGGGCCA ACTATTGGGGCCAGGGCACCCAGGTCACCGTGTC CTCA | 265 |
| hIL10Ra_VHH18 | CAGGTACAACTCCAGGAGTCTGGCGGTGGCAGCG TGCAGGCAGGCGGAAGCCTGAGGCTGTCCTGCGC TGTATCTGGCTACACTTATAATTCCAACTGCATGG GTTGGTTTCGGCAGGCTCCAGGTAAGGAGCGCGA GGGCGTCGCCACCATTTATACAGGTGTTGGCAGC ACATATTACGCCGACAGCGTGAAGGGAAGGTTCA CCATCTCCCAAGACAATGCGAAAAACACAGTGTA TCTCCAGATGAATAGCCTGAAGCCCGAGGACACG GCTATGTATTACTGCGCTGCCGAGCCACTGAGCA | 266 |

TABLE 8-continued anti-IL10Ra sdAb VHH DNA SEQUENCE

Table 2. hIL10Ra VHH DNA Sequences

| Name | Sequence | SEQ ID NO: |
|---|---|---|
| | GAGTGTATGGGGGCAGCTGTCCTACACCCACTTT CGGCTATTGGGGTCAAGGCACCCAGGTTACAGTC AGCTCC | |

TABLE 9 anti-IL2Rg VHH DNA sequences

| Name | Sequence | SEQ ID NO: |
|---|---|---|
| hIL2Rg_VHH-1 | CAGGTCCAGCTCCAGGAGAGCGGGGG CGGTTCTGTGCAAGCCGGAGGCTCATT GAGACTCTCATGCGCTGCAAGTGGTTT TACCTTCGATGACAGCGATATGGGATG GTATCGTCAGGCTCCGGGCAATGAGTG TGATCTGGTCTCCACTATCTCCTCTGAT GGTTCCACATACTATGCTGACTCTGTCA AGGGGCGCTTTACCATCTCCCAAGATA ATGCCAAGAACACCGTGTACCTTCAGA TGGATTCAGTTAAGCCCGAGGACACAG CCGTCTATTACTGCGCTGCGGATTTTAT GATTGCCATCCAAGCTCCCGGAGCGGG ATGCTGGGGCCAGGGAACCCAGGTCAC TGTGAGCAGT | 267 |
| hIL2Rg_VHH-2 | CAGGTGCAGTTGCAGGAGTCCGGCGGG GGTTCTGTGCCAGCGGGTGGGAGCCTC AAGCTCTCCTGTGCCGCTTCCGGCTTCT CATTCTCCTCTTACCCTATGACCTGGGC ACGCCAAGCGCCCGGCAAGGGACTGG AATGGGTGTCCACCATTGCTTCCGATG GCGGTAGTACAGCCTACGCCGCGTCAG TGGAGGGTCGGTTCACGATCAGCCGGG ACAACGCGAAGAGCACACTCTACCTCC AGCTGAACTCTCTGAAGACCGAGGACA CCGCCATGTACTATTGCACAAAGGGCT ACGGCGACGGCACCCCGGCACCCGGCC AGGGCACCCAGGTGACAGTCTCTTCC | 268 |
| hIL2Rg_VHH-3 | CAGGTGCAGTTGCAGGAAAGTGGTGGA GGGAGTGTGCAGACTGGGGGCTCTCTC CGCCTCAGCTGCACAGCCTCTGGATTT ACCTTCGATGATCGCGAGATGAACTGG TATCGCCAGGCTCCGGGAAACGAGTGC GAACTGGTGTCTACAATCAGTTCTGAC GGGTCCACCTATTACGCTGATAGTGTC AAGGGCCGCTTCACTATCTCTCAGGAC AACGCGAAGAACACCGTTTACTTGCAG ATGGATAGCGTGAAGCCTGAAGATACA GCGGTGTATTACTGCGCTGCCGACTTT ATGATTGCCATCCAGGCACCGGGGGCG GGGTGTTGGGGACAGGGAACTCAGGTG ACTGTGTCCTCC | 269 |
| hIL2Rg_VHH-4 | CAGGTTCAACTCCAAGAGAGTGGTGGC GGAAGCGTGCAGGCGGGCGGTTCTCTG CGTCTGAGTTGCACTGCCAGCGGATTT ACCTTCGACGATTCCGACATGGGATGG TACAGACAGGCCCCTGGTAACGAGTGC GAACTCGTGAGTACTATCAGCTCCGAC GGCAACACCTATTACACCGATTCTGTG AAGGGCAGGTTCACCATCTCCCAGGAC AACGCTAAGAACACTGTGTACCTGCAA ATGAATAGCCTGGGACCCGAGGACACA GCGGTCTATTACTGCGCGGCAGAGCCG CGCGGCTATTACAGCAACTACGGCGGT AGACGCGAGTGCAACTACTGGGGGCA GGGGACGCAAGTGACTGTCTCCTCC | 270 |
| hIL2Rg_VHH-5 | CAAGTGCAGCTTCAGGAGTCCGGGGGT GGCAGCGTCCAGGCTGGGGGCAGCTTG CGCCTGTCTTGCGCTGCGTCTGGGTTCA GCTTTAGCTCCTACCCTATGACCTGGGC TAGACAGGCCCCCGGCAAGGGGCTGG AGTGGGTGAGTACAATCGCCTCCGACG GAGGTAGTACGGCCTACGCAGCGTCCG TCGAGGGTCGCTTCACCATCAGCCGGG ATAACGCTAAGTCCACCCTGTACCTTC AGCTCAATTCTCTCAAAACGGAGGATA CCGCCATGTACTATTGCACCAAGGGAT ATGGCGACGGCACCCCAGCTCCTGGAC AGGGCACACAGGTCACCGTTAGCTCC | 271 |
| hIL2Rg_VHH-6 | CAGGTCCAGCTTCAGGAGTCTGGCGGG GGCGCAGTACAGGCAGGGGGTTCTCTG CGTCTGTCCTGCGCCGCGTCCGGCTTTA CTTTCAGCAACGCACACATGAGTTGGG TGCGCCAAGCGCCCGGCAAGGGCCGG GAATGGATCAGTAGCATCTACAGTGGA GGCAGCACATGGTACGCCGACTCTGTT AAGGGTCGTTTTACGATCTCTCGTGAC AACTCCAAGAACACTTTGTACCTCCAG CTCAATTCTCTCAAGACCGAGGACACC GCGATGTACTATTGTGCCGAGAACAGG CTGCACTACTATTCCGACGATGACTCTC TCAGGGGCCAGGGAACTCAAGTTACCG TGTCCAGC | 272 |
| hIL2Rg_VHH-7 | CAAGTGCAGCTCCAAGAGAGTGGTGGC GGGCTGGTTCAGCCAGGGGGCAGCTTG AGACTCTCCTGCGCAGCTTCAGGCTTT ACCTTCGATGACCGTGAGATGAACTGG TATCGTCAGGCCCCAGGCAACGAGTGT GAGCTGGTTAGCACGATTTCTTCCGAC GGTTCCACCTATTACGCCGACTCTGTG AAGGGACGTTTCACTATCTCCCAGGAC AATGCCAAGAACACCGTGTACCTCCAG ATGGACAGCGTGAAGCCGGAGGATACT GCTGTGTATTACTGCGCTGCCGACTTTA TGATCGCCATCCAGGCCCCTGGCGCGG GTTGCTGGGGCCAGGGCACTCAGGTGA CCGTGTCTTCC | 273 |
| hIL2Rg_VHH-8 | CAAGTGCAACTGCAAGAGTCCGGCGGT GGATCTGTGCAGGCCGGAGGCAGCCTG CGGCTGAGCTGTGTAGCTTCCGGGTAT ACCTTTAGCTCATACTGTATGGGCTGGT TTCGTCAGGCCCCCGGTAAGGAGCGCG AGGGCGTGGCCGCTCTTGGTGGAGGCT CCACCTATTACGCCGATTCCGTGAAGG GCAGGTTTACTATCTCCCAGGACAACG CGAAGAATACGCTCTATCTCCAGATGA ATAGCCTGAAGCCCGAGGATACAGCTA TGTATTACTGTGCTGCCGCTTGGGTAGC CTGCCTGGAGTTCGGTGGCTCCTGGTA CGATCTGGCACGGTACAAACATTGGGG GCAGGGCACCCAGGTCACCGTGTCTAG C | 274 |

TABLE 9-continued anti-IL2Rg VHH DNA sequences

| Name | Sequence | SEQ ID NO: |
|---|---|---|
| hIL2Rg_VHH-9 | CAGGTCCAGTTGCAGGAATCTGGGGGC GGTTCCGTACAAGCAGGTGGCTCCCTT CGGTTGAGCTGTACCGCATCCGGCTTT ACTTTCGACGATAGCGATATGGGCTGG TATCGTCAGGCCCCAGGGGGCGAGTGC GAGCTGGTTACAATCTCCTCTGACGGC AGTACCTATTACGCAGACTCCGTCAAG GGCAGGTTCACTATCAGTCAGGACAAT GCAAAGAACACTGTGTATCTCCAGATG AACTCTCTGAAGCCAGAAGATACTGCC GTGTATTACTGCGCTGCGGAACCGAGA GGCTATTACTCTAATTATGGCGGGCGT CGGGAGTGTAATTATTGGGGACAGGGA ACCCAGGTGACCGTGTCCTCC | 275 |
| hIL2Rg_VHH-10 | CAGGTGCAGCTCCAGGAGAGTGGCGG AGGCTCCGTGCAGGCTGGGGGCTCTCT GCGTCTGAGCTGTGCCGCAAGCGGTAG CATTTACAGCTCTGCCTACATCGGGTG GTTTCGTCAAGCGCCGGGCAAAAAGCG CGAAGGCGTGGCCGGAATCTACACGCG CGATGGCTCCACCGCTTATGCTGACAG CGTTAAGGGACGTTTTACGATCAGCCA GGACTCTGCCAAAAAGACTGTGTATCT CCAGATGAACTCCCTGAAACCTGAGGA CACAGCCATGTATTACTGCGCCGCTGG CCGCCGTACAAAGAGCTATGTTTACAT CTTTCGCCCCGAAGAGTACAACTACTG GGGCCAGGGAACCCAAGTGACTGTGTC CAGT | 276 |
| hIL2Rg_VHH-11 | CAGGTTCAGTTGCAGGAGTCCGGCGGA GGCAGCGTGCAGGCCGGAGGCTCCTTG CGCTTGTCCTGTGCGGCTTCTGGCTTCA CCTTCTCATCTGCTCACATGAGTTGGGT GCGTCAGGCCCCAGGGAAAGGTCGCG AGTGGATTGCCTCCATCTACAGCGGTG GGGGCACTTTTTATGCGGACAGCGTGA AGGGCCGCTTTACCATCAGCCGTGACA ACGCTAAGAACACCCTGTATCTCCAAC TCAATTCCCTCAAGACCGAGGATACAG CGATGTACTATTGTGCAACCAACCGCC TTCACTATTACTCCGACGATGACAGCC TGCGCGGACAGGGGACCCAGGTGACG GTGTCCAGC | 277 |
| hIL2Rg_VHH-12 | CAGGTGCAACTCCAGGAAAGTGGCGG AGGCTCAGTGCAGGCAGGTGGCTCTCT CCGCCTTTCCTGCGCTGCCAGCGGATTC ACCTTCTCTAACGCTCACATGAGCTGG GTTCGTCAGGCTCCCGGCAAAGGCCGT GAATGGATTAGCTCCATCTATAGTGGC GGAAGTACTTGGTACGCAGATAGCGTC AAGGGCCGCTTCACTATTAGTCGGGAT AACTCCAAGAACACTCTGTACCTCCAG CTGAACTCATTGAAAACCGAGGACACG GCTATGTACTATTGTGCTGAGAACAGG CTGCACTATTACTCCGACGATGACTCTC TGAGGGGTCAGGGCACCCAGGTGACCG TCAGCTCC | 278 |
| hIL2Rg_VHH-13 | CAGGTCCAACTCCAGGAGTCCGGCGGA GGCAGCGTGCAGGCTGGAGGCTCTCTC CGCCTGAGCTGCACAGCTTCCAGATTC ATCTTCGATGACTCCGACATGGGCTGG TATCGCCAGGCTCCAGGGAACGAGTGC GAACTGGTGAGCACCATCTCTTCAGAC GGTAGCACCTATTACGCCGACAGTGTG AAGGGGCGCTTCACCATCTCCCGCGAC AATGCTAAAAATACGGTGTATCTCCAG ATGAACTCCCTCAAACCGGAGGACACA GCTGTATATTACTGTGCTGCGGAACCA CGGGGCTACTATAGCAACTATGGTGGA AGGCGCGAGTGCAACTACTGGGGTCAG GGCACACAGGTGACGGTTTCCTCC | 279 |
| hIL2Rg_VHH-14 | CAGGTGCAGCTCCAGGAGAGCGGCGGT GGCTCCGTGCAGGCTGGTGGCAGCCTG AAGCTGTCCTGCACCGTGAGTGGCTTC ACAGCCGACGATTCTGATATGGGCTGG TATCGCCAAGGCCCCGGCAATGAGTGC GAGCTGGTAACCATTAGCTCAGACGGC TCTACATACTATGCCGATTCTGTTAAGG GCCGCTTTACTATCTCACAGGATAATG CCAAGAACACAGTGTACTTGCAGATGA ACTCTCTGAAACCGGAAGACACAGCTG TGTATTACTGTGCTGCGGAGCCTAGAG GGTATTACAGCAATTACGGGGGCCGGA GAGAGTGTAACTATTGGGGGCAGGGCA CCCAAGTGACCGTTTCCTCC | 280 |
| hIL2Rg_VHH-15 | CAGGTCCAGCTTCAGGAATCTGGGGGC GGTCTCGTGCAGCCCGGCGGGTCCCTG CGTCTGTCTTGTGCTGCGAGCGGCTTCA CGTTCTCAAGTGCCCACATGAGCTGGG TAAGGCAGGCACCGGGCAAGGGGCGC GAGTGGATTGCAAGCATCTATTCAGGC GGGGGCACATTCTACGCCGACAGCGTG AAGGGACGTTTTACAATCTCCAGAGAT AACGCAAAGAACACTCTCTACCTCCAA CTCAACTCCTTGAAGGCGGAAGATACT GCAATGTATTACTGTGCTACTAACCGT CTTCATTATTACTCTGACGATGACTCCC TGCGGGGGCAGGGTACACAGGTGACA GTGAGTTCC | 281 |
| hIL2Rg_VHH-16 | CAGGTGCAGCTGCAAGAATCTGGTGGA GGGCTGGTCCAGCCTGGGGGCTCCCTG CGCCTCTCATGTGTCGCATCTGGCTTCA CCTTCAGCAACGCCCACATGAGCTGGG TTCGCCAAGCCCCTGGGAAGGGCCGGG AGTGGATCTCCAGTATCTATTCCGGCG GAAGCACTTGGTATGCAGACAGCGTCA AAGGACGGTTCACTATTTCTCGTGATA ATTCTAAGAACACCCTGTACCTTCAGC TGAACAGCCTGAAGACCGAGGACACTG CTATGTACTATTGTGCTGAGAATCGCCT GCATTACTATAGCGACGATGACAGTCT GCGCGGACAGGGGACCCAGGTCACCGT GTCCTCT | 282 |
| hIL2Rg_VHH-17 | CAGGTTCAGTTGCAGGAATCAGGAGGC GGTCTGGTGCAGCCTGGGGGCTCTCTG CGTCTCTCCTGCGCCGCTTCCGGCTTCA CATTCTCCAACGCCCACATGAGCTGGG TCCGCCAGGCCCCTGGGAAGGGCCGCG AGTGGATCTCCAGTATCTACAGCGGGG GCTCCACTTGGTACGCAGACAGCGTCA AAGGGAGGTTTACCATTAGCCGTGACA ATTCTAAGAACACATTGTATTTGCAGC TGAACTCTCTTAAAACCGAGGACACCG CCATGTACTATTGTGCTGAGAACAGGC TCCACTATTACTCAGACGATGACTCAC TTCGCGGGCAGGGAACCCAGGTCACCG TCTCCTCT | 283 |
| hIL2Rg_VHH-18 | CAAGTCCAGCTCCAGGAAAGCGGCGGT GGCCTGGTGCAACCTGGCGGGTCTCTG CGCTTGTCATGCGCTGCCTCCGGCTTCA CCTTCTCATCTTACCCTATGACCTGGGC GCGTCAGGCTCCCGGCAAGGGATTGGA GTGGGTGTCTACTATTGCCTCCGACGG TGGCAGCACGGCCTACGCAGCGTCTGT AGAAGGACGCTTCACAATTAGCAGAGA CAACGCAAAATCTACTTTGTACCTTCA GCTCAACAGCCTGAAGACCGAAGACAC AGCTATGTATTACTGCACAAAAGGCTA | 284 |

TABLE 9-continued anti-IL2Rg VHH DNA sequences

| Name | Sequence | SEQ ID NO: |
|---|---|---|
| | CGGGGACGGCACGCCAGCGCCTGGAC<br>AGGGGACACAGGTGACCGTATCTTCT | |
| hIL2Rg_VHH-19 | CAGGTGCAGTTGCAGGAATCAGGGGGT<br>GGCTCTGTGCAGGCCGGGGGCTCCCTG<br>CGTCTGTCCTGTACTGCGAGCGGCTTC<br>ACCTTTGATGACCGCGAGATGAACTGG<br>TATCGCCAGGCTCCGGGGAACGAGTGC<br>GAACTCGTGTCTACAATTAGCTCCGAT<br>GGTTCAACATACTATGCTGATTCTGTCA<br>AAGGTCGCTTTACCATCTCACAGGACA<br>ACGCCAAGAACACCGTCTACCTCCAGA<br>TGGACTCTGTGAAGCCTGAAGATACCG<br>CCGTATACTATTGCGCCGCTGACTTTAT<br>GATTGCCATTCAGGCTCCGGGTGCTGG<br>ATGCTGGGGTCAGGGGACTCAGGTGAC<br>CGTGTCTTCA | 285 |
| hIL2Rg_VHH-20 | CAAGTGCAGTTGCAGGAAAGCGGCGGT<br>GGGTCCGTGCAAGCCGGAGGTTCTCTC<br>CGCCTGTCTTGCACTGCCTCAGGTTTTA<br>CCTTCGACGATTCCGATATGGGCTGGT<br>ACAGGCAGGCTCCCGGCAATGAGTGCG<br>AGCTGGTGTCTACGATCTCAAGTGATG<br>GCTCCACCTACTATGCCGATAGCGTAA<br>AAGGAAGGTTTACTATTAGCCAGGATA<br>ACGCGAAGAACACGGTGTACCTCCAGA<br>TGAACAGTCTCAAGCCGGAGGATACTG<br>CCGTGTATTACTGTGCTGCCGAGCCGC<br>GTGGCTATTACTCCAACTACGGTGGCA<br>GACGTGAATGCAATTACTGGGGACAGG<br>GTACTCAGGTTACCGTGTCCTCT | 286 |
| hIL2Rg_VHH-21 | CAGGTTCAACTTCAGGAATCCGGGGGC<br>GGTTCCGTGCAAGCCGGGGGTAGCCTG<br>CGTCTGTCTTGCGTGGCCAGCGGCTAT<br>ACCTCCTGTATGGGTTGGTTTCGGCAG<br>GCTCCTGGGAAGGAGCGCGAAGCCGTG | 287 |

TABLE 9-continued anti-IL2Rg VHH DNA sequences

| Name | Sequence | SEQ ID NO: |
|---|---|---|
| | GCGACCATCTACACACGGGGCCGCAGC<br>ATCTATTACGCTGACAGTGTGAAGGGC<br>CGCTTCACCATCTCCCAGGATAACGCC<br>AAGAATACCCTGTATCTGCAAATGAAC<br>TCCCTGAAGCCTGAGGACATCGCCATG<br>TATTCCTGCGCAGCTGGAGGGTACTCA<br>TGGTCCGCTGGGTGCGAGTTTAATTATT<br>GGGGCCAAGGAACCCAGGTGACCGTCT<br>CCTCA | |
| hIL2Rg_VHH-22 | CAAGTGCAGCTCCAGGAGTCTGGCGGG<br>GGCCTGGTTCAGCCTGGTGGGTCCCTG<br>CGCCTGTCTTGCACGGCTTCCGGCTTTA<br>GCTTCTCCTCATATCCAATGACCTGGGC<br>ACGCCAGGCTCCTGGTAAGGGCCTGGA<br>GTGGGTCTCCACCATCGCCTCTGATGG<br>TGGGTCAACTGCCTATGCTGCCTCCGTC<br>GAGGGTAGATTCACAATCAGCAGAGAC<br>AACGCCAAATCCACGCTGTACCTGCAA<br>CTCAACTCCTTGAAGACCGAGGACACA<br>GCTATGTATTACTGTACCAAAGGCTAC<br>GGCGACGGCACTCCTGCTCCCGGACAG<br>GGGACCCAGGTGACTGTGTCTAGC | 288 |
| hIL2Rg_VHH-23 | CAGGTCCAACTTCAGGAAAGCGGGGGT<br>GGACTGGTACAGCCAGGGGGCAGTCTG<br>CGCCTGTCCTGTGCCGCAAGCGGGTTT<br>TCTTTCTCCAGTTACCCCATGACCTGGG<br>CTCGCCAAGCACCTGGAAAGGGACTGG<br>AGTGGGTGTCTACTATTGCGTCAGATG<br>GTGGGAGTACGGCTTACGCCGCGAGCG<br>TGGAGGGTCGTTTTACGATCAGTAGGG<br>ACAACGCCAAAAGCACTCTGTACCTCC<br>AGCTTAACAGCCTGAAGACCGAGGACA<br>CCGCCATGTATTACTGTACCAAGGGCT<br>ACGGAGACGGCACCCCTGCGCCGGGGC<br>AAGGCACCCAGGTGACCGTAAGTTCA | 289 |

TABLE 10 murine anti-IL2Rg VHH DNA sequences

| Name | DNA Sequence | SEQ ID NO: |
|---|---|---|
| mIL2Rg_VHH1 | CAGGTGCAACTCCAGGAGTCCGGCGGGGGCTCCGT<br>GCTGGCTGGCGGATCTTTGAGGCTGTCTTGCGTGG<br>CTTCTGGCTATGGCTATAATTACATCGGCTGGTTCC<br>GTCAGACACCCGGCAAGGAGCGCGAAGGGGTGGC<br>GGTCATTTACACAGGGGGTGGGGACACTTATTACG<br>CCGACTCCGTCAAGGGTAGGTTTACCGCTAGTCGC<br>GATAATGCCAAAAGTACGCTGTACCTGCAAATGAA<br>CAGCTTGGAGCCAGAGGACACCGCCATGTATTACG<br>GAGTGGCTCGCTACTGTGTGGGCAGTGTGTACGCT<br>TGCCTGCGCGGAGGCCACGACGAGTACGCACACTG<br>GGGCCAGGGAACCCAGGTGACAGTGTCTAGC | 290 |
| mIL2Rg_VHH2 | CAGGTGCAGCTCCAGGAGTCTGGGGGTGGCAGCGT<br>CCAGCCAGGTGGCTCATTGAGACTGTCTTGTGCTG<br>CATCTGGCTCCACCTACGCTAATTACCTGATGGGA<br>TGGTTCAGGCAGGCCCCTGGTAAGGAGCGTGAGG<br>GCGTGGCCGCTATCTATTCTGGCGGTGGGTCCACC<br>TACTATGCTGACTCCGTCAAGGGACGCTTCACTAT<br>TTCTCAAGACAATGCCAAGAACACTTTGTACTTGC<br>AAATGAACTCACTCAAACCTGAGGACACCGCGATG<br>TACTATTGCGCAGCGGCATCCGCAGTGAAGGGAGA<br>CAAAGGGGATATCGTGGTAGTTGTGACCGGCACCC<br>AGCGTATGGAGTACGACTACTGGGGACATGGCACC<br>CAGGTGACAGTTAGCTCC | 291 |
| mIL2Rg_VHH3 | CAGGTACAGTTGCAGGAGAGTGGTGGGGGTTCCGT<br>CCAGGCCGGTGCCTCTCTTCGCCTCAGTTGTAGCGT | 292 |

TABLE 10-continued

| murine anti-IL2Rg VHH DNA sequences | | |
|---|---|---|
| Name | DNA Sequence | SEQ ID NO: |
| | GAGCGGTTTCACGTTCGACGAGTCAGTGATGTCCT GGTTGCGCCAGGGTCCCGGCAATGAGTGCGACGCG GTCGCTATTATCAGCTCCGATGACAACACCTATTA CGACGATAGCGTGAAAGGCCGCTTTACCATCTCCG AGGACAACGCCAAAAACATGGTGTATCTGCAAAT GAACTCACTGAAGCCGGAAGACACCGCAGTGTACT ATTGCGCCGCGCGTCGGCGCAGACCTGTGTACGAT TCCGATTATGAACTCCGGCCACGTCCGCTGTGTGG CGATTTCGGCGTGTGGGGCCAGGGGACCCAGGTGA CGGTCTCCTCC | |
| mIL2Rg_VHH4 | CAGGTGCAGCTCCAGGAATCTGGCGGGGGCTCTGT GCAGGCTGGTGGCTCCCTTCGCCTGTCCTGTATTGG CTCCGGTCTTCCTTTCGACGAGGATGACATGGGCT GGTATCGCCAGGCCCCTGGGAATGAGTGTGAATTG GTCAGCTCAATCTCCAGTGACGGCACCGCCTATTA CGCCGATTCCGTCAAGGGACGCTTCACTATCTCCA GAGACAACGCCAAGAACACTGTGCTGTTGCAGATG AACTCCCTGAAGCCCGAGGATACCGCTGTCTATTA CTGCGCAGCCGGGGTCCACAGACAGTTCGGCGGTT CCAGTTCCTGCGGCGACGCCTTCTACGGCATGGAT TACTGGGGCAAGGGAACTCAGGTCACAGTGTCTTC C | 293 |
| mIL2Rg_VHH5 | CAGGTTCAGCTTCAGGAGTCCGGCGGGGGCTCCGT ACAGGCAGGGGGCTCACTGCGTCTTTCCTGTGTGG CGAGTGGCGACGTGTATGGCCGTAACAGCATGGCT TGGTTCCGGCAGGCACCTGGAAAGGAACGCGAGG GCGTTGCAGTTGGGTATTCCGTAGTGACAACCACT TACTATGCCGACAGTGTGAAGGGCCGGTTTACGAT CTCAGAGGACAACGATAAAAACACAGTGTACCTG GAGATGAACTCCCTGAAGCCGGAAGACACTGCTAT GTATTACTGCGCTGCCGATGGCAACCTGTGGCGCG GACTCAGGCCCTCCGAGTACACTTATTGGGGTCAG GGCACCCAGGTGACCGTTTCAAGT | 294 |
| mIL2Rg_VHH6 | CAGGTCCAGCTTCAGGAGTCAGGTGGCGGTAGTGT CCAGGCAGGCGGTAGCCTGCGCCTTAGCTGTGCTA CATCCGGCTTCCCTTACTCACGCTATTGTATGGGCT GGTTCAGGCAAGCTCCCGGTAAAGAGCGCGAGGG AGTGGCAGCCATCGAGCCTGACGGGAGCACATCTT ATGCTGACTCTGTAAAGGGGCGTTTCACCATCTCT CAGGACAACGCCGTTAATACACTGTACTTGCAAAT GAATAACCTGAAGCCCGAGGACACAGCTATGTATT ACTGCGCAGCCGACGAGCGTTGCTTCTATTTGAAG GACTATGACCTCAGAAGGCCAGCCCAGTACCGCTA CTGGGGGCAGGGCACCCAGGTTACCGTGTCATCT | 295 |
| mIL2Rg_VHH7 | CAGGTGCAGTTGCAGGAGAGTGGCGGTGGCCTCGT GCAGCCTGGCGGAAGCCTCCGTCTGAGCTGCACTG TGTCCGGCTTCACTTTCGACGAGAGCGACATGGGC TGGCTGAGGCAGAACCCTGGTAACGAGTGCGGCGT TGTGAGTGTCATCACGTCTGATGACAACCCATACT ATGATGACAGCGTCAAGGGCCGCTTTACTATCTCC GAGGATAACGCCAAGAACATGGTGTACCTCCAGAT GAACTCACTGAAGCCCGAGGATACCGGCGTTTATT ACTGTGCAACCAGGAGCCGTCAGCCTGTGTACTCA CGCGATTACGAGCTGCGGCCCCGCCCCCTCTGTGG AGACTTTGGTGTGTGGGGCCAGGGCACCCAGGTGA CTGTTTCCAGC | 296 |
| mIL2Rg_VHH8 | CAGGTGCAGTTGCAGGAGAGTGGAGGGGGCTCAG TGCAGGCTGGCGGGTCCTTGCGTCTGTCTTGCACC GCCTCTGGCTTCACCTTCGATGACTTCGATATGGGT TGGTATCGCCAGGCTCCAGGGAACGAGTGCGAATT GGTCAGCACTATCAGCGACGATGGCTCAACATATT ACGCCGACTCTGTGAAGGGACGGTCTAGCATTAGC CGGGACAACGCAAAGAACACCGTCTATCTCCAGAT GAACCGCTTGAAGCCTGAGGATACCGGAGTCTATT ACTGCGCCGCTGAGGGCGCGTTGGGCTCCAAGACT AATTGTGGCTGGGTGGGCAACTTCGGATATTGGGG CCAGGGAACACAGGTTACCGTTTCCAGC | 297 |
| mIL2Rg_VHH9 | CAGGTGCAGTTGCAGGAGTCTGGAGGCGGTTCCGT TCAGGCCGGGGGCTCTCTGCGCCTGTCCTGCGCTG CCTCCGGGTTTACATTTGACGATTTCGATATGGGCT | 298 |

TABLE 10-continued

| murine anti-IL2Rg VHH DNA sequences | | |
|---|---|---|
| Name | DNA Sequence | SEQ ID NO: |
| | GGTATCGCCAGGCCCCTGGCAACGAGTGCGAACTG GTGTCTACTATCTCCGATGACGGCTCAACCTACTAT GCAGACTCCGTAAAGGGCAGATCCAGCATCTCCCG CGACAATGCCAAAAACACTGTGTACCTCCAGATGA ACTCCCTCAAGCCTGAGGATACGGCGGTGTACTAT TGTGCTGCCGAGGGTGCGCTCGGTAGCAAGACTAA TTGCGGCTGGGTGGGCAACTTCGGGTACTGGGGTC AGGGGACCCAGGTAACCGTGTCTTCT | |
| mIL2Rg_VHH10 | CAGGTGCAGTTGCAGGAAAGCGGTGGGGGCCTGG TGCAGCCCGGAGGCAGCCTGCGCTTGAGCTGCGCT GCCTCTGGCTTCACATTCGATGACTTCGATATGGG CTGGTATCGTCAAGCACCCGGAAACGAGTGCGAGC TGGTGAGTACAATCAGTGATGACGGATCTACCTAC TATGCCGACAGCGTCAAGGGAAGATCCAGCATCA GTCGCGACAACGCCAAGAGCACCGTTTACCTCCAG ATGAACCGCCTCAAGCCTGAGGACACAGGAGTCTA TTACTGTGCTGCGGAGGGGGCCTTGGGCAGCAAGA CTAACTGTGGATGGGTGGGAAACTTCGGGTATTGG GGTCAGGGTACACAGGTCACAGTGTCTTCA | 299 |
| mIL2Rg_VHH11 | CAAGTTCAGCTTCAGGAAAGTGGGGGCGGGCTGGT GCAGCCAGGGGGTTCCCTGAAGCTGAGCTGCGCTG CCTCTGGGTTTACATTCTCTGATCGCGACATGGGCT GGTATCGCCAAGCGCCGGGCAATGAATGCGAAAG AGTGAGTACTATTTCTGACGATGGTTCTACTTACTA TGCTGACTCCGTGAAGGGCCGTAGCTCCATTTCCA GGGACAACGCGAAGAACACCGTATACCTCCAGAT GAACTCTCTGAAGCCCGAGGACACCGCTGTGTATT ACTGCGCTGCCGAGGGGGCTCTCGGCTCAAAGACC AACTGCGGATGGGTCGGTAACTTCGGCTACTGGGG CCAGGGCACCCAAGTGACAGTCTCCTCC | 300 |
| mIL2Rg_VHH12 | CAGGTCCAGTTGCAGGAGAGCGGGGGTGGAAGCG TCCTCGCCGGAGGGAGCCTCCGTTTGAGCTGCGTC GCCTCAGGCTACGGCTACAATTACATCGGATGGTT CAGACAGACGCCTGGTAAAGAGCGGGAAGGCGTC GCCGTGATTTATATCGGTGGCGGAGACACCTATTA CGCTGACTCAGTGAAGGGGCGTTTCACCGCAAGCC GGGACAACGCTAAGAGCACCCTGTACCTCCAGATG AACTCTCTCGAACCTGAGGACACTGCAATGTATTA CTGCGTGGCTCGTTACTGCGTCGGGAGTGTCTACG CCTGCCTGAGGGGCGGGCATGATGAGTATGCCCAC TGGGGACAAGGAACACAGGTGACTGTCTCCAGT | 301 |
| mIL2Rg_VHH13 | CAGGTTCAGCTCCAGGAGTCTGGTGGCGGTTCCGT GCTGGCCGGGGGCTCTCTGCGCCTGTCTTGTGTCG CCTCAGGGTACGGCTATAACTACATTGGCTGGTTC AGACAGACCCCTGGGAAAGAGCGGGAGGGTGTGG CTGTCATTTACACCGGCGGAGGCGACACCTACTAT GCCGATTCAGTTAAGGGCAGGTTTACCGCGAGCCG TGACAACGCGAAGTCTACTCTGTACCTGCAAATGA ACAGCCTGGAACCTGAGGATACTGCGATGTACTAT TGTGTGGCCCGGTACTGCGTAGGCTCAGTGTATGC CTGCCTGCGCGGGGGTCACGACGAGTACGCACACT GGGGACAGGGAACTCAGGTCACCGTGTCTAGC | 302 |
| mIL2Rg_VHH14 | CAGGTGCAACTCCAGGAGTCCGGCGGGGGCTCCGT CCAAGCTGGTGGCTCACTGAGGCTTAGCTGTGCTG CCTCCGGCTTTACTTTCGACGATTTCGACATGGGTT GGTATCGCCAGGCTCCGGGCAATGAGTGCGAGCTG GTCTCTACCATTTCCGATGACGGCTCTACCTACTAT GCCAACAGTGTTAAGGGTAGGTCTTCCATCTCCCG CGACAACGCTAAGAATATGGTGTACTTGCAGATGA ACTCTCTGAAGCCTGAGGACACTGCTGTCTACTAT TGCGCTGCCGAAGGTGCCCTGGGCTCAAAGACTAA TTGCGGCTGGGTCGGTAACTTTGGCTACTGGGGTC AGGGGACTCAGGTGACCGTCAGCTCC | 303 |
| mIL2Rg_VHH15 | CAGGTCCAGTTGCAGGAAAGCGGCGGGGGCTCTGT TCAGGCAGGCGGAAGCCTTCGTCTGTCCTGTACTG CCAGTGGTTTCACCTTTGATGACTTTGACATGGGCT GGTATCGGCAAGCCCCCGGAAACGAGTGCGAGCT GGTATCCACCATTTCCGATGACGGGTCCACGTACT ATGCTGATAGCGTGAAGGGCAGGTCTTCCATCAGC CGGGACAACGCCAAGAACACAGTGTATTTGCAGAT | 304 |

TABLE 10-continued

| murine anti-IL2Rg VHH DNA sequences | | |
|---|---|---|
| Name | DNA Sequence | SEQ ID NO: |
| | GAACCGCCTCAAGCCAGAAGACACCGGGGTATATT ACTGTGCAGCGGAAGGTGCCCTGGGTAGCAAGAT GAACTGCGGATGGGTGGGTAATTTTGGATACTGGG GCCAGGGCACGCAGGTTACAGTGTCCAGC | |

TABLE 11

| FDA Antineoplastic Disease Antibodies and Indications | | | |
|---|---|---|---|
| Name | Tradename(s) | Target; format | Indication |
| [fam]-trastuzumab deruxtecan | Enhertu | HER2; Humanized IgG1 ADC | HER2$^+$ breast cancer |
| Enfortumab vedotin | Padcev | Nectin-4; Human IgG1 ADC | Urothelial cancer |
| Polatuzumab vedotin | Polivy | CD79b; Humanized IgG1 ADC | Diffuse large B-cell lymphoma |
| Cemiplimab | Libtayo | PD-1; Human mAb | Cutaneous squamous cell carcinoma |
| Moxetumomab pasudotox | Lumoxiti | CD22; Murine IgG1 dsFv immunotoxin | Hairy cell leukemia |
| Mogamuizumab | Poteligeo | CCR4; Humanized IgG1 | Cutaneous T cell lymphoma |
| Tildrakizumab | Ilumya | IL23p19; Humanized IgG1 | Plaque psoriasis |
| Ibalizumab | Trogarzo | CD4; Humanized IgG4 | HIV infection |
| Durvalumab | IMFINZI | PD-L1; Human IgG1 | Bladder cancer |
| Inotuzumab ozogamicin | BESPONSA | CD22; Humanized IgG4, ADC | Hematological malignancy |
| Avelumab | Bavencio | PD-L1; Human IgG1 | Merkel cell carcinoma |
| Atezolizumab | Tecentriq | PD-L1; Humanized IgG1 | Bladder cancer |
| Olaratumab | Lartruvo | PDGRFα; Human IgGl | Soft tissue sarcoma |
| Ixekizumab | Taltz | IL17a; Humanized IgG4 | Psoriasis |
| Daratumumab | Darzalex | CD38; Human IgG1 | Multiple myeloma |
| Elotuzumab | Empliciti | SLAMF7; Humanized IgG1 | Multiple myeloma |
| Necitumumab | Portrazza | EGFR; Human IgG1 | Non-small cell lung cancer |
| Dinutuximab | Unituxin | GD2; Chimeric IgG1 | Neuroblastoma |
| Nivolumab | Opdivo | PD1; Human IgG4 | Melanoma, non-small cell lung cancer |
| Blinatumomab | Blincyto | CD19, CD3; Murine bispecific tandem scFv | Acute lymphoblastic leukemia |
| Pembrolizumab | Keytruda | PD1; Humanized IgG4 | Melanoma |
| Ramucirumab | Cyramza | VEGFR2; Human IgG1 | Gastric cancer |
| Siltuximab | Sylvant | IL6; Chimeric IgG1 | Castleman disease |
| Obinutuzumab | Gazyva | CD20; Humanized IgG1; Glycoengineered | Chronic lymphocytic leukemia |
| Ado-trastuzumab emtansine | Kadcyla | HER2; Humanized IgG1, ADC | Breast cancer |
| Pertuzumab | Perjeta | HER2; Humanized IgG1 | Breast Cancer |
| Brentuximab vedotin | Adcetris | CD30; Chimeric IgG1, ADC | Hodgkin lymphoma, systemic anaplastic large cell lymphoma |
| Ipilimumab | Yervoy | CTLA-4; Human IgG1 | Metastatic melanoma |
| Ofatumumab | Arzerra | CD20; Human IgG1 | Chronic lymphocytic leukemia |
| Certolizumab pegol | Cimzia | TNF; Humanized Fab, pegylated | Crohn disease |
| Catumaxomab | Removab | EPCAM/CD3;Rat/mouse bispecific mAb | Malignant ascites |
| Panitumumab | Vectibix | EGFR; Human IgG2 | Colorectal cancer |
| Bevacizumab | Avastin | VEGF; Humanized IgG1 | Colorectal cancer |
| Cetuximab | Erbitux | EGFR; Chimeric IgG1 | Colorectal cancer |
| Tositumomab-I131 | Bexxar | CD20; Murine IgG2a | Non-Hodgkin lymphoma |
| Ibritumomab tiuxetan | Zevalin | CD20; Murine IgG1 | Non-Hodgkin lymphoma |
| Gemtuzumab ozogamicin | Mylotarg | CD33; Humanized IgG4, ADC | Acute myeloid leukemia |
| Trastuzumab | Herceptin | HER2; Humanized IgG1 | Breast cancer |
| Infliximab | Remicade | TNF; Chimeric IgG1 | Crohn disease |
| Rituximab | MabThera, Rituxan | CD20; Chimeric IgG1 | Non-Hodgkin lymphoma |
| Edrecolomab | Panorex | EpCAM; Murine IgG2a | Colorectal cancer |

TABLE 12

| FDA Immune Disease Antibodies and Indications | | |
|---|---|---|
| Name | Target | Indication |
| belimumab | BLyS | Systemic lupus ery thematosus |
| efalizumab | CD11a | Psoriasis |
| ocrelizumab | CD20 | Multiple sclerosis |
| rituximab | CD20 | Multiple sclerosis |
| basiliximab | CD25 | Transplantation rejection |
| daclizumab | CD25 | Transplantation rejection |
| muromonab | CD3 | Transplantation rejection |
| alemtuzumab | CD52 | Multiple sclerosis |
| omalizumab | IgE | Asthma |
| ustekinumab | IL12/IL23 | Plaque psoriasis |
| brodalumab | IL17a | Psoriasis, psoriatic arthritis, ankylosing spondylitis |
| secukinumab | IL17a | Psoriasis, psoriatic arthritis, ankylosing spondylitis |
| ixekizumab | IL17a | Psoriasis, psoriatic arthritis, ankylosing spondylitis |
| canakinumab | IL1β | Cryopyrin-associated periodic syndrome, tumor necrosis factor receptor associated periodic syndrome, hyperimmunoglobulin D syndrome, mevalonate kinase deficiency, familial Mediterranean fever, rheumatoid arthritis |
| dupilumab | IL4Rα | Asthma, dermatitis |
| mepolizumab | IL5 | Asthma |
| reslizumab | IL5 | Asthma |
| tocilizumab | IL6R | Rheumatoid arthritis |
| vedolizumab | Integrin-a4β7 | Ulcerative colitis, Crohn's disease |
| denosumab | RANKL | Osteoporosis |
| certolizumab | TNFa | Chron's disease, rheumatoid arthritis |
| golimumab | TNFa | Rheumatoid arthritis, psoriatic arthritis, ankylosing spondylitis |
| adalimumab | TNFα | Rheumatoid arthritis, juvenile idiopathic arthritis, psoriatic arthritis, ankylosing spondylitis, Crohn's disease, plaque psoriasis |
| infliximab | TNFα | Crohn's disease, ulcerative colitis, rheumatoid arthritis, ankylosing spondylitis, psoriatic arthritis, plaque psoriasis |
| ranibizumab | VEGF-A | Neovascular age-related macular degeneration, macular edema |
| natalizumab | VLA-4 | Multiple sclerosis, relapsing rultiple sclerosis, Crohn's disease |

TABLE 13

Anti-hIL10Ra/hIL2Rg dual VHH binding to human and cynomolgus IL2Rg-Fc

| Analyte | Ligand | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|---|
| A2, DR359 | hIL2Rg-Fc (SinoBiological cat#10555) | 2.0E+06 | 7.8E−03 | 3.9 | 3.4 | 99 | 74 | 5% |
| | cIL2Rg-Fc (lot#P210115SV5) | 8.0E+05 | 2.6E−03 | 3.2 | 1.9 | 153 | 115 | 2% |
| A7, DR392 | hIL2Rg-Fc (SinoBiological cat#10555) | 1.7E+06 | 6.2E−03 | 3.6 | 3.2 | 99 | 74 | 4% |
| | cIL2Rg-Fc (lot#P210115SV5) | 1.6E+06 | 4.0E−03 | 2.4 | 1.5 | 161 | 120 | 1% |
| D6, DR437 | hIL2Rg-Fc (SinoBiological cat#10555) | 1.9E+05 | 5.1E−03 | 27.5 | 1.9 | 99 | 74 | 3% |
| | cIL2Rg-Fc (lot#P210115SV5) | 2.9E+05 | 2.2E−03 | 7.8 | 1.3 | 160 | 119 | 1% |
| D12, DR438 | hIL2Rg-Fc (SinoBiological cat#10555) | 3.9E+05 | 1.0E−03 | 2.7 | 3.4 | 99 | 74 | 5% |
| | cIL2Rg-Fc (lot#P210115SV5) | 5.6E+05 | 1.2E−03 | 2.2 | 1.5 | 163 | 122 | 1% |
| E8, DR444 | hIL2Rg-Fc (SinoBiological cat#10555) | 3.8E+05 | 2.6E−03 | 6.9 | 3.4 | 99 | 74 | 5% |
| | cIL2Rg-Fc (lot#P210115SV5) | 1.5E+05 | 7.7E−04 | 5.3 | 1.8 | 161 | 120 | 2% |
| F1, DR441 | hIL2Rg-Fc (SinoBiological cat#10555) | 4.7E+05 | 5.3E−03 | 11.1 | 3.1 | 99 | 74 | 4% |
| | cIL2Rg-Fc (lot#P210115SV5) | 3.4E+05 | 2.8E−03 | 8.3 | 1.6 | 162 | 121 | 1% |

TABLE 13-continued

| Anti-hIL10Ra/hIL2Rg dual VHH binding to human and cynomolgus IL2Rg-Fc | | | | | | | | |
|---|---|---|---|---|---|---|---|---|
| Analyte | Ligand | $k_{ON}$ (1/Ms) | $k_{OFF}$ (1/s) | Affinity (nM) | Rmax (RU) | Load (RU) | Calc. Rmax (RU) | Surface Activity |
| F3, DR449 | hIL2Rg-Fc (SinoBiological cat#10555) | 2.2E+05 | 6.5E−03 | 30.4 | 1.5 | 98 | 73 | 2% |
| | cIL2Rg-Fc (lot#P210115SV5) | 2.1E+05 | 4.8E−03 | 22.6 | 0.9 | 163 | 122 | 1% |
| F7, DR442 | hIL2Rg-Fc (SinoBiological cat#10555) | 2.0E+06 | 4.2E−02 | 21.5 | 3.5 | 98 | 73 | 5% |
| | cIL2Rg-Fc (lot#P210115SV5) | 7.9E+04 | 3.3E−03 | 41.3 | 7.9 | 162 | 121 | 7% |
| G3, DR471 | hIL2Rg-Fc (SinoBiological cat#10555) | 3.4E+05 | 5.7E−03 | 16.6 | 3.6 | 98 | 73 | 5% |
| | cIL2Rg-Fc (lot#P210115SV5) | 3.6E+05 | 4.8E−03 | 13.4 | 1.6 | 164 | 122 | 1% |
| G8, DR468 | hIL2Rg-Fc (SinoBiological cat#10555) | 1.7E+05 | 1.5E−03 | 8.5 | 4.2 | 98 | 73 | 6% |
| | cIL2Rg-Fc (lot#P210115SV5) | 2.4E+05 | 1.0E−03 | 4.3 | 1.8 | 164 | 122 | 1% |
| H1, DR465 | hIL2Rg-Fc (SinoBiological cat#10555) | 2.5E+05 | 3.7E−03 | 14.5 | 2.6 | 98 | 73 | 4% |
| | cIL2Rg-Fc (lot#P210115SV5) | 7.0E+05 | 2.2E−03 | 3.2 | 0.9 | 163 | 122 | 1% |
| H7, DR466 | hIL2Rg-Fc (SinoBiological cat#10555) | 1.2E+06* | 2.6E−02 | 20.8 | 4.2 | 97 | 73 | 6% |
| | cIL2Rg-Fc (lot#P210115SV5) | 7.5E+04* | 3.7E−03 | 49.9 | 11.5 | 164 | 122 | 9% |
| H9, DR474 | hIL2Rg-Fc (SinoBiological cat#10555) | 3.1E+05 | 9.9E−04 | 3.2 | 4.1 | 97 | 73 | 6% |
| | cIL2Rg-Fc (lot#P210115SV5) | 3.3E+05 | 9.3E−04 | 2.9 | 2.3 | 163 | 121 | 2% |

TABLE 14

| Effect of Linker Length IL10Ra/IL10Rg VHH dimers on pSTAT3 Induction of on CD8 T cell | | | | |
|---|---|---|---|---|
| VHH1-VHH2 ID | Linker | Tag | Concentration of molecule (μM) | pSTAT3 (MFI) |
| hIL10Ra_VHH14-hIL2Rg_VHH19 | GGGS (SEQ ID NO: 9) | Fc | 0 | 6751 |
| hIL10Ra_VHH14-hIL2Rg_VHH19 | GGGS (SEQ ID NO: 9) | Fc | 0.0001 | 7538 |
| hIL10Ra_VHH14-hIL2Rg_VHH19 | GGGS (SEQ ID NO: 9) | Fc | 0.001 | 7889 |
| hIL10Ra_VHH14-hIL2Rg_VHH19 | GGGS (SEQ ID NO: 9) | Fc | 0.01 | 7802 |
| hIL10Ra_VHH14-hIL2Rg_VHH19 | GGGS (SEQ ID NO: 9) | Fc | 0.1 | 7330 |
| hIL10Ra_VHH14-hIL2Rg_VHH19 | GGGS (SEQ ID NO: 9) | Fc | 1 | 9316 |
| hIL10Ra_VHH14-hIL2Rg_VHH19 | GGGS (SEQ ID NO: 9) | Fo | 10 | 12256 |
| hIL10Ra_VHH14-hIL2Rg_VHH19 | GGGS (SEQ ID NO: 9) | Fc | 100 | 13188 |
| hIL10Ra_VHH14-hIL2Rg_VHH19 | GGGS (SEQ ID NO: 9) | his | 0 | 6751 |

TABLE 14-continued

| Effect of Linker Length IL10Ra/IL10Rg VHH dimers on pSTAT3 Induction of on CD8 T cell | | | | |
|---|---|---|---|---|
| VHH1-VHH2 ID | Linker | Tag | Concentration of molecule (μM) | pSTAT3 (MFI) |
| hIL10Ra_VHH14-hIL2Rg_VHH19 | GGGS (SEQ ID NO: 9) | his | 0.0001 | 7207 |
| hIL10Ra_VHH14-hIL2Rg_VHH19 | GGGS (SEQ ID NO: 9) | his | 0.001 | 7461 |
| hIL10Ra_VHH14-hIL2Rg_VHH19 | GGGS (SEQ ID NO: 9) | his | 0.01 | 7195 |
| hIL10Ra_VHH14-hIL2Rg_VHH19 | GGGS (SEQ ID NO: 9) | his | 0.1 | 6584 |
| hIL10Ra_VHH14-hIL2Rg_VHH19 | GGGS (SEQ ID NO: 9) | his | 1 | 6495 |
| hIL10Ra_VHH14-hIL2Rg_VHH19 | GGGS (SEQ ID NO: 9) | his | 10 | 7934 |
| hIL10Ra_VHH14-hIL2Rg_VHH19 | GGGS (SEQ ID NO: 9) | his | 100 | 9967 |
| hIL10Ra_VHH14-hIL2Rg_VHH19 | No linker | his | 0 | 6751 |
| hIL10Ra_VHH14-hIL2Rg_VHH19 | No linker | his | 0.0001 | 7383 |
| hIL10Ra_VHH14-hIL2Rg_VHH19 | No linker | his | 0.001 | 7742 |
| hIL10Ra_VHH14-hIL2Rg_VHH19 | No linker | his | 0.01 | 7799 |
| hIL10Ra_VHH14-hIL2Rg_VHH19 | No linke | his | 0.1 | 6775 |
| hIL10Ra_VHH14-hIL2Rg_VHH19 | No linker | his | 1 | 7725 |
| hIL10Ra_VHH14-hIL2Rg_VHH19 | No linker | his | 10 | 7486 |
| hIL10Ra_VHH14-hIL2Rg_VHH19 | No linker | his | 100 | 6202 |
| hIL10Ra_VHH14-hIL2Rg_VHH19 | GS | his | 0 | 6751 |
| hIL10Ra_VHH14-hIL2Rg_VHH19 | GS | his | 0.0001 | 7402 |
| hIL10Ra_VHH14-hIL2Rg_VHH19 | GS | his | 0.001 | 8109 |
| hIL10Ra_VHH14-hIL2Rg_VHH19 | GS | his | 0.01 | 8114 |
| hIL10Ra_VHH14-hIL2Rg_VHH19 | GS | his | 0.1 | 7101 |
| hIL10Ra_VHH14-hIL2Rg_VHH19 | GS | his | 1 | 8204 |
| hIL10Ra_VHH14-hIL2Rg_VHH19 | GS | his | 10 | 8411 |
| hIL10Ra_VHH14-hIL2Rg_VHH19 | GS | his | 100 | 7905 |
| hIL10Ra_VHH14-hIL2Rg_VHH19 | GGSGGS (SEQ ID NO: 315) | his | 0 | 6751 |

TABLE 14-continued

Effect of Linker Length IL10Ra/IL10Rg VHH dimers on pSTAT3 Induction of on CD8 T cell

| VHH1-VHH2 ID | Linker | Tag | Concentration of molecule (μM) | pSTAT3 (MFI) |
|---|---|---|---|---|
| hIL10Ra_VHH14-hIL2Rg_VHH19 | GGSGGS (SEQ ID NO: 315) | his | 0.0001 | 7955 |
| hIL10Ra_VHH14-hIL2Rg_VHH19 | GGSGGS (SEQ ID NO: 315) | his | 0.001 | 8498 |
| hIL10Ra_VHH14-hIL2Rg_VHH19 | GGSGGS (SEQ ID NO: 315) | his | 0.01 | 7658 |
| hIL10Ra_VHH14-hIL2Rg_VHH19 | GGSGGS (SEQ ID NO: 315) | his | 0.1 | 8156 |
| hIL10Ra_VHH14-hIL2Rg_VHH19 | GGSGGS (SEQ ID NO: 315) | his | 1 | 7715 |
| hIL10Ra_VHH14-hIL2Rg_VHH19 | GGSGGS (SEQ ID NO: 315) | his | 10 | 8296 |
| hIL10Ra_VHH14-hIL2Rg_VHH19 | GGSGGS (SEQ ID NO: 315) | his | 100 | 7001 |
| hIL10Ra_VHH14-hIL2Rg_VHH19 | GGGSGGGS (SEQ ID NO: 317) | his | 0 | 6751 |
| hIL10Ra_VHH14-hIL2Rg_VHH19 | GGGSGGGS (SEQ ID NO: 317) | hilL10Ras | 0.0001 | 7059 |
| hIL10Ra_VHH14-hIL2Rg_VHH19 | GGGSGGGS (SEQ ID NO: 317) | his | 0.001 | 7522 |
| hIL10Ra_VHH14-hIL2Rg_VHH19 | GGGSGGGS (SEQ ID NO: 317) | his | 0.01 | 6331 |
| hIL10Ra_VHH14-hIL2Rg_VHH19 | GGGSGGGS (SEQ ID NO: 317) | his | 0.1 | 7073 |
| hIL10Ra_VHH14-hIL2Rg_VHH19 | GGGSGGGS (SEQ ID NO: 317) | his | 1 | 7872 |
| hIL10Ra_VHH14-hIL2Rg_VHH19 | GGGSGGGS (SEQ ID NO: 317) | his | 10 | 8431 |
| hIL10Ra_VHH14-hIL2Rg_VHH19 | GGGSGGGS (SEQ ID NO: 317) | his | 100 | 7974 |
| hIL10Ra_VHH14-hIL2Rg_VHH19 | GGSGGSGGSG (SEQ ID NO: 305) | his | 0 | 6751 |
| hIL10Ra_VHH14-hIL2Rg_VHH19 | GGSGGSGGSG (SEQ ID NO: 305) | his | 0.0001 | 7840 |
| hIL10Ra_VHH14-hIL2Rg_VHH19 | GGSGGSGGSG (SEQ ID NO: 305) | his | 0.001 | 7516 |
| hIL10Ra_VHH14-hIL2Rg_VHH19 | GGSGGSGGSG (SEQ ID NO: 305) | his | 0.01 | 6922 |
| hIL10Ra_VHH14-hIL2Rg_VHH19 | GGSGGSGGSG (SEQ ID NO: 305) | his | 0.1 | 6782 |
| hIL10Ra_VHH14-hIL2Rg_VHH19 | GGSGGSGGSG (SEQ ID NO: 305) | his | 1 | 6479 |
| hIL10Ra_VHH14-hIL2Rg_VHH19 | GGSGGSGGSG (SEQ ID NO: 305) | his | 10 | 7329 |
| hIL10Ra_VHH14-hIL2Rg_VHH19 | GGSGGSGGSG (SEQ ID NO: 305) | his | 100 | 6928 |

TABLE 15

Effect of Linker Length IL10Ra/IL10Rg_VHH dimers on pSTAT3 Induction of on CD4 T cells

| VHH1 - VHH2 ID | Linker | Tag | Concentration of molecule (μM) | pSTAT3 (MFI) |
|---|---|---|---|---|
| hIL10Ra_VHH14 - hIL2Rg_VHH19 | GGGS (SEQ ID NO: 9) | Fc | 0 | 10291 |
| hIL10Ra_VHH14 - hIL2Rg_VHH19 | GGGS (SEQ ID NO: 9) | Fc | 0.0001 | 12636 |
| hIL10Ra_VHH14 - hIL2Rg_VHH19 | GGGS (SEQ ID NO: 9) | Fc | 0.001 | 12627 |
| hIL10Ra_VHH14 - hIL2Rg_VHH19 | GGGS (SEQ ID NO: 9) | Fc | 0.01 | 12526 |
| hIL10Ra_VHH14 - hIL2Rg_VHH19 | GGGS (SEQ ID NO: 9) | Fc | 0.1 | 11340 |
| hIL10Ra_VHH14 - hIL2Rg_VHH19 | GGGS (SEQ ID NO: 9) | Fc | 1 | 13578 |
| hIL 10Ra_VHH14 - hIL2Rg_VHH19 | GGGS (SEQ ID NO: 9) | Fc | 10 | 14841 |
| hIL10Ra_VHH14 - hIL2Rg_VHH19 | GGGS (SEQ ID NO: 9) | Fc | 100 | 16045 |
| hIL10Ra_VHH14 - hIL2Rg_VHH19 | GGGS (SEQ ID NO: 9) | his | 0 | 10291 |
| hIL10Ra_VHH14 - hIL2Rg_VHH19 | GGGS (SEQ ID NO: 9) | his | 0.0001 | 11924 |
| hIL10Ra_VHH14 - hIL2Rg_VHH19 | GGGS (SEQ ID NO: 9) | his | 0.001 | 12086 |
| hIL10Ra_VHH14 - hIL2Rg_VHH19 | GGGS (SEQ ID NO: 9) | his | 0.01 | 11654 |
| hIL10Ra_VHH14 - hIL2Rg_VHH19 | GGGS (SEQ ID NO: 9) | his | 0.1 | 9670 |
| hIL10Ra_VHH14 - hIL2Rg_VHH19 | GGGS (SEQ ID NO: 9) | his | 1 | 9591 |
| hIL10Ra_VHH14 - hIL2Rg_VHH19 | GGGS (SEQ ID NO: 9) | his | 10 | 11382 |
| hIL10Ra_VHH14 - hIL2Rg_VHH19 | GGGS (SEQ ID NO: 9) | his | 100 | 14725 |
| hIL10Ra_VHH14 - hIL2Rg_VHH19 | No linker | his | 0 | 10291 |
| hIL10Ra_VHH14- hIL2Rg_VHH19 | No linker | his | 0.0001 | 12174 |
| hIL10Ra_VHH14 - hIL2Rg_VHH19 | No linker | his | 0.001 | 12882 |
| hIL10Ra_VHH14 - hIL2Rg_VHH19 | No linker | his | 0.01 | 12460 |
| hIL10Ra_VHH14- hIL2Rg_VHH19 | No linker | his | 0.1 | 11004 |
| hIL10Ra_VHH14 - hIL2Rg_VHH19 | No linker | his | 1 | 12144 |
| hIL10Ra_VHH14 - hIL2Rg_VHH19 | No linker | his | 10 | 11846 |
| hIL10Ra_VHH14 - hIL2Rg_VHH19 | No linker | his | 100 | 9036 |
| hIL10Ra_VHH14 - hIL2Rg_VHH19 | GS | his | 0 | 10291 |

TABLE 15-continued

Effect of Linker Length IL10Ra/IL10Rg_VHH dimers on pSTAT3 Induction of on CD4 T cells

| VHH1 - VHH2 ID | Linker | Tag | Concentration of molecule (μM) | pSTAT3 (MFI) |
|---|---|---|---|---|
| hIL10Ra_VHH14 - hIL2Rg_VHH19 | GS | his | 0.0001 | 11707 |
| hIL10Ra_VHH14 - hIL2Rg_VHH19 | GS | his | 0.001 | 12776 |
| hIL10Ra_VHH14 - hIL2Rg_VHH19 | GS | his | 0.01 | 13621 |
| hIL10Ra_VHH14 - hIL2Rg_VHH19 | GS | his | 0.1 | 10942 |
| hIL10Ra_VHH14 - hIL2Rg_VHH19 | GS | his | 1 | 12949 |
| hIL10Ra_VHH14 - hIL2Rg_VHH19 | GS | his | 10 | 12563 |
| hIL10Ra_VHH14 - hIL2Rg_VHH19 | GS | his | 100 | 11613 |
| hIL10Ra_VHH14 - hIL2Rg_VHH19 | GGSGGS (SEQ ID NO: 315) | his | 0 | 10291 |
| hIL10Ra_VHH14 - hIL2Rg_VHH19 | GGSGGS (SEQ ID NO: 315) | his | 0.0001 | 13197 |
| hIL10Ra_VHH14 - hIL2Rg_VHH19 | GGSGGS (SEQ ID NO: 315) | his | 0.001 | 13876 |
| hIL10Ra_VHH14 - hIL2Rg_VHH19 | GGSGGS (SEQ ID NO: 315) | his | 0.01 | 12787 |
| hIL10Ra_VHH14 - hIL2Rg_VHH19 | GGSGGS (SEQ ID NO: 315) | his | 0.1 | 13577 |
| hIL10Ra_VHH14 - hIL2Rg_VHH19 | GGSGGS (SEQ ID NO: 315) | his | 1 | 12991 |
| hIL10Ra_VHH14 - hIL2Rg_VHH19 | GGSGGS (SEQ ID NO: 315) | his | 10 | 11840 |
| hIL10Ra_VHH14 - hIL2Rg_VHH19 | GGSGGS (SEQ ID NO: 315) | his | 100 | 10166 |
| hIL10Ra_VHH14 - hIL2Rg_VHH19 | GGGSGGGS (SEQ ID NO: 317) | his | 0 | 10291 |
| hIL10Ra_VHH14 - hIL2Rg_VHH19 | GGGSGGGS (SEQ ID NO: 317) | his | 0.0001 | 10704 |
| hIL 10Ra_VHH14 - hIL2Rg_VHH19 | GGGSGGGS (SEQ ID NO: 317) | his | 0.0013 | 12050 |
| hIL10Ra_VHH14 - hIL2Rg_VHH19 | GGGSGGGS (SEQ ID NO: 317) | his | 0.01 | 9547 |
| hIL 10Ra_VHH14 - hIL2Rg_VHH19 | GGGSGGGS (SEQ ID NO: 317) | his | 0.1 | 11269 |
| hIL10Ra_VHH14 - hIL2Rg_VHH19 | GGGSGGGS (SEQ ID NO: 317) | his | 1 | 12658 |
| hIL10Ra_VHH14 - hIL2Rg_VHH19 | GGGSGGGS (SEQ ID NO: 317) | his | 10 | 13170 |
| hIL10Ra_VHH14 - hIL2Rg_VHH19 | GGGSGGGS (SEQ ID NO: 317) | his | 100 | 11553 |
| hIL10Ra_VHH14 - hIL2Rg_VHH19 | GGSGGSGGSG (SEQ ID NO: 305) | his | 0 | 10291 |
| hIL10Ra_VHH14 - hIL2Rg_VHH19 | GGSGGSGGSG (SEQ ID NO: 305) | his | 0.0001 | 12805 |

TABLE 15-continued

Effect of Linker Length IL10Ra/IL10Rg_VHH dimers on pSTAT3 Induction of on CD4 T cells

| VHH1 - VHH2 ID | Linker | Tag | Concentration of molecule (μM) | pSTAT3 (MFI) |
|---|---|---|---|---|
| hIL10Ra_VHH14 - hIL2Rg_VHH19 | GGSGGSGGSG (SEQ ID NO: 305) | his | 0.001 | 11826 |
| hIL10Ra_VHH14 - hIL2Rg_VHH19 | GGSGGSGGSG (SEQ ID NO: 305) | his | 0.01 | 11130 |
| hIL10Ra_VHH14 - hIL2Rg_VHH19 | GGSGGSGGSG (SEQ ID NO: 305) | his | 0.1 | 10217 |
| hIL10Ra_VHH14 - hIL2Rg_VHH19 | GGSGGSGGSG (SEQ ID NO: 305) | his | 1 | 9972 |
| hIL10Ra_VHH14 - hIL2Rg_VHH19 | GGSGGSGGSG (SEQ ID NO: 305) | his | 10 | 11400 |
| hIL10Ra_VHH14 - hIL2Rg_VHH19 | GGSGGSGGSG (SEQ ID NO: 305) | his | 100 | 10324 |

TABLE 16

Effect of Linker Length IL10Ra/IL10Rg_VHH dimers on pSTAT3 Induction of in monocytes

| VHH1 - VHH2 ID | Linker | Tag | Concentration of molecule (μM) | pSTAT3 (MFI) |
|---|---|---|---|---|
| hIL10Ra_VHH14 - hIL2Rg_VHH19 | GGGS (SEQ ID NO: 9) | Fc | 0 | 4610 |
| hIL10Ra_VHH14 - hIL2Rg_VHH19 | GGGS (SEQ ID NO: 9) | Fc | 0.0001 | 4373 |
| hIL10Ra_VHH14 - hIL2Rg_VHH19 | GGGS (SEQ ID NO: 9) | Fc | 0.001 | 4737 |
| hIL10Ra_VHH14 - hIL2Rg_VHH19 | GGGS (SEQ ID NO: 9) | Fc | 0.01 | 4417 |
| hIL10Ra_VHH14 - hIL2Rg_VHH19 | GGGS (SEQ ID NO: 9) | Fc | 0.1 | 4808 |
| hIL10Ra_VHH14 - hIL2Rg_VHH19 | GGGS (SEQ ID NO: 9) | Fc | 1 | 5687 |
| hIL10Ra_VHH14 - hIL2Rg_VHH19 | GGGS (SEQ ID NO: 9) | Fc | 10 | 6688 |
| hIL10Ra_VHH14 - hIL2Rg_VHH19 | GGGS (SEQ ID NO: 9) | Fc | 100 | 6026 |
| hIL10Ra_VHH14 - hIL2Rg_VHH19 | GGGS (SEQ ID NO: 9) | his | 0 | 4610 |
| hIL10Ra_VHH14 - hIL2Rg_VHH19 | GGGS (SEQ ID NO: 9) | his | 0.0001 | 4151 |
| hIL10Ra_VHH14 - hIL2Rg_VHH19 | GGGS (SEQ ID NO: 9) | his | 0.001 | 4510 |
| hIL10Ra_VHH14 - hIL2Rg_VHH19 | GGGS (SEQ ID NO: 9) | his | 0.01 | 4357 |
| hIL10Ra_VHH14 - hIL2Rg_VHH19 | GGGS (SEQ ID NO: 9) | his | 0.1 | 4277 |
| hIL10Ra_VHH14 - hIL2Rg_VHH19 | GGGS (SEQ ID NO: 9) | his | 1 | 4640 |
| hIL10Ra_VHH14 - hIL2Rg_VHH19 | GGGS (SEQ ID NO: 9) | his | 10 | 4842 |
| hIL10Ra_VHH14 - hIL2Rg_ VHH19 | GGGS (SEQ ID NO: 9) | his | 100 | 4877 |

TABLE 16-continued

Effect of Linker Length IL10Ra/IL10Rg_VHH dimers on pSTAT3 Induction of in monocytes

| VHH1 - VHH2 ID | Linker | Tag | Concentration of molecule (μM) | pSTAT3 (MFI) |
|---|---|---|---|---|
| hIL10Ra_VHH14 - hIL2Rg_VHH19 | No linker | his | 0 | 4610 |
| hIL10Ra_VHH14 - hIL2Rg_VHH19 | No linker | his | 0.0001 | 3969 |
| hIL10Ra_VHH14 - hIL2Rg_VHH19 | No linker | his | 0.001 | 4602 |
| hIL10Ra_VHH14 - hIL2Rg_VHH19 | No linker | his | 0.01 | 4425 |
| hIL10Ra_VHH14 - hIL2Rg_VHH19 | No linker | his | 0.1 | 4423 |
| hIL10Ra_VHH14 - hIL2Rg_VHH19 | No linker | his | 1 | 4480 |
| hIL10Ra_VHH14 - hIL2Rg_VHH19 | No linker | his | 10 | 4331 |
| hIL10Ra_VHH14 - hIL2Rg_VHH19 | No linker | his | 100 | 4139 |
| hIL10Ra_VHH14 - hIL2Rg_VHH19 | GS | his | 0 | 4610 |
| hIL10Ra_VHH14 - hIL2Rg_VHH19 | GS | his | 0.0001 | 4035 |
| hIL10Ra_VHH14 - hIL2Rg_VHH19 | GS | his | 0.001 | 4821 |
| hIL10Ra_VHH14 - hIL2Rg_VHH19 | GS | his | 0.01 | 4012 |
| hIL10Ra_VHH14 - hIL2Rg_VHH19 | GS | his | 0.1 | 4432 |
| hIL10Ra_VHH14 - hIL2Rg_VHH19 | GS | his | 1 | 4791 |
| hIL10Ra_VHH14 - hIL2Rg_VHH19 | GS | his | 10 | 4934 |
| hIL10Ra_VHH14 - hIL2Rg_VHH19 | GS | his | 100 | 4930 |
| hIL10Ra_VHH14 - hIL2Rg_VHH19 | GGSGGS (SEQ ID NO: 315) | his | 0 | 4610 |
| hIL10Ra_VHH14 - hIL2Rg_VHH19 | GGSGGS (SEQ ID NO: 315) | his | 0.0001 | 4217 |
| hIL10Ra_VHH14 - hIL 2Rg_VHH19 | GGSGGS (SEQ ID NO: 315) | his | 0.001 | 4677 |
| hIL10Ra_VHH14 - hIL2Rg_VHH19 | GGSGGS (SEQ ID NO: 315) | his | 0.01 | 4563 |
| hIL10Ra_VHH14 - hIL2Rg_VHH19 | GGSGGS (SEQ ID NO: 315) | his | 0.1 | 4468 |
| hIL10Ra_VHH14 - hIL2Rg_VHH19 | GGSGGS (SEQ ID NO: 315) | his | 1 | 4752 |
| hIL10Ra_VHH14 - hIL2Rg_VHH19 | GGSGGS (SEQ ID NO: 315) | his | 10 | 4894 |
| hIL10Ra_VHH14 - hIL2Rg_VHH19 | GGSGGS (SEQ ID NO: 315) | his | 100 | 4726 |
| hIL10Ra_VHH14 - hIL2Rg_VHH19 | GGGSGGGS (SEQ ID NO: 317) | his | 0 | 4610 |

TABLE 16-continued

Effect of Linker Length IL10Ra/IL10Rg_VHH dimers on pSTAT3 Induction of in monocytes

| VHH1 - VHH2 ID | Linker | Tag | Concentration of molecule (μM) | pSTAT3 (MFI) |
|---|---|---|---|---|
| hIL10Ra_VHH14 - hIL2Rg_VHH19 | GGGSGGGS (SEQ ID NO: 317) | his | 0.0001 | 4666 |
| hIL10Ra_VHH14 - hIL2Rg_VHH19 | GGGSGGGS (SEQ ID NO: 317) | his | 0.001 | 4821 |
| hIL10Ra_VHH14 - hIL2Rg_VHH19 | GGGSGGGS (SEQ ID NO: 317) | his | 0.01 | 4356 |
| hIL10Ra_VHH14 - hIL2Rg_VHH19 | GGGSGGGS (SEQ ID NO: 317) | his | 0.1 | 4425 |
| hIL10Ra_VHH14 - hIL2Rg_VHH19 | GGGSGGGS (SEQ ID NO: 317) | his | 1 | 4760 |
| hIL10Ra_VHH14 - hIL2Rg_VHH19 | GGGSGGGS (SEQ ID NO: 317) | his | 10 | 4879 |
| hIL10Ra_VHH14 - hIL2Rg_VHH19 | GGGSGGGS (SEQ ID NO: 317) | his | 100 | 4617 |
| hIL10Ra_VHH14- hIL2Rg_VHH19 | GGSGGSGGSG (SEQ ID NO: 305) | his | 0 | 4610 |
| hIL10Ra_VHH14 - hIL2Rg_VHH19 | GGSGGSGGSG (SEQ ID NO: 305) | his | 0.0001 | 4232 |
| hIL10Ra_VHH14 - hIL2Rg_VHH19 | GGSGGSGGSG (SEQ ID NO: 305) | his | 0.001 | 4709 |
| hIL10Ra_VHH14 - hIL2Rg_VHH19 | GGSGGSGGSG (SEQ ID NO: 305) | his | 0.01 | 4701 |
| hIL10Ra_VHH14 - hIL2Rg_VHH19 | GGSGGSGGSG (SEQ ID NO: 305) | his | 0.1 | 4694 |
| hIL10Ra_VHH14 - hIL2Rg_VHH19 | GGSGGSGGSG (SEQ ID NO: 305) | his | 1 | 4622 |
| hIL10Ra_VHH14 - hIL2Rg_VHH19 | GGSGGSGGSG (SEQ ID NO: 305) | his | 10 | 4546 |
| hIL10Ra_VHH14 - hIL2Rg_VHH19 | GGSGGSGGSG (SEQ ID NO: 305) | his | 100 | 4862 |

TABLE 17

Activity of VHH dimers on CD8 T cell IFNγ secretion.

| VHH1 - VHH2 ID | Linker | Tag | Concentration of molecule (μM) | IFNγ (pg/mL) |
|---|---|---|---|---|
| hIL10Ra_VHH14 - hIL2Rg_VHH19 | GGGS (SEQ ID NO: 9) | Fc | 0 | 122093 |
| hIL10Ra_VHH14 - hIL2Rg_VHH19 | GGGS (SEQ ID NO: 9) | Fc | 0.0001 | 103635 |
| hIL10Ra_VHH14 - hIL2Rg_VHH19 | GGGS (SEQ ID NO: 9) | Fc | 0.001 | 112903 |
| hIL10Ra_VHH14 - hIL2Rg_VHH19 | GGGS (SEQ ID NO: 9) | Fc | 0.01 | 131153 |
| hIL10Ra_VHH14 - hIL2Rg_VHH19 | GGGS (SEQ ID NO: 9) | Fc | 0.1 | 144485 |
| hIL10Ra_VHH14 - hIL2Rg_VHH19 | GGGS (SEQ ID NO: 9) | Fc | 1 | 165539 |

TABLE 17-continued

Activity of VHH dimers on CD8 T cell IFNγ secretion.

| VHH1 - VHH2 ID | Linker | Tag | Concentration of molecule (μM) | IFNγ (pg/mL) |
|---|---|---|---|---|
| hIL10Ra_VHH14 - hIL2Rg_VHH19 | GGGS (SEQ ID NO: 9) | Fc | 10 | 156982 |
| hIL10Ra_VHH14 - hIL2Rg_VHH19 | GGGS (SEQ ID NO: 9) | Fc | 100 | 147964 |
| hIL10Ra_VHH14 - hIL2Rg_VHH19 | GGGS (SEQ ID NO: 9) | his | 0 | 122093 |
| hIL10Ra_VHH14 - hIL2Rg_VHH19 | GGGS (SEQ ID NO: 9) | his | 0.0001 | 96799 |
| hIL10Ra_VHH14 - hIL 2Rg_VHH19 | GGGS (SEQ ID NO: 9) | his | 0.001 | 99579 |
| hIL10Ra_VHH14 - hIL2Rg_VHH19 | GGGS (SEQ ID NO: 9) | his | 0.01 | 106757 |
| hIL10Ra_VHH14 - hIL2Rg_VHH19 | GGGS (SEQ ID NO: 9) | his | 0.1 | 114181 |
| hIL10Ra_VHH14 - hIL2Rg_VHH19 | GGGS (SEQ ID NO: 9) | his | 1 | 130484 |
| hIL10Ra_VHH14 - hIL2Rg_VHH19 | GGGS (SEQ ID NO: 9) | his | 11 | 133684 |
| hIL10Ra_VHH14 - hIL2Rg_VHH19 | GGGS (SEQ ID NO: 9) | his | 100 | 134443 |
| hIL10Ra_VHH14 - hIL2Rg_VHH19 | No linker | his | 0 | 122093 |
| hIL10Ra_VHH14 - hIL2Rg_VHH19 | No linker | his | 0.0001 | 101945 |
| hIL10Ra_VHH14 - hIL2Rg_VHH19 | No linker | his | 0.001 | 103568 |
| hIL10Ra_VHH14 - hIL2Rg_VHH19 | No linker | his | 0.01 | 111251 |
| hIL10Ra_VHH14 - hIL2Rg_VHH19 | No linker | his | 0.1 | 111247 |
| hIL10Ra_VHH14 - hIL2Rg_VHH19 | No linker | his | 1 | 122585 |
| hIL10Ra_VHH14 - hIL2Rg_VHH19 | No linker | his | 10 | 130574 |
| hIL10Ra_VHH14 - hIL2Rg_VHH19 | No linker | his | 100 | 133923 |
| hIL10Ra_VHH14 - hIL2Rg_VHH19 | GS | his | 0 | 122093 |
| hIL10Ra_VHH14 - hIL2Rg_VHH19 | GS | his | 0.0001 | 91703 |
| hIL10Ra_VHH14 - hIL2Rg_VHH19 | GS | his | 0.001 | 105021 |
| hIL10Ra_VHH14 - hIL2Rg_VHH19 | GS | his | 0.01 | 122227 |
| hIL10Ra_VHH14 - hIL2Rg_VHH19 | GS | his | 0.1 | 128960 |
| hIL10Ra_VHH14 - hIL2Rg_VHH19 | GS | his | 1 | 133736 |
| hIL10Ra_VHH14 - hIL 2Rg_VHH19 | GS | his | 10 | 142927 |

TABLE 17-continued

Activity of VHH dimers on CD8 T cell IFNγ secretion.

| VHH1 - VHH2 ID | Linker | Tag | Concentration of molecule (μM) | IFNγ (pg/mL) |
|---|---|---|---|---|
| hIL10Ra_VHH14 - hIL2Rg_VHH19 | GS | his | 100 | 143369 |
| hIL10Ra_VHH14 - hIL2Rg_VHH19 | GGSGGS (SEQ ID NO: 315) | his | 0 | 122093 |
| hIL10Ra_VHH14 - hIL2Rg_VHH19 | GGSGGS (SEQ ID NO: 315) | his | 0.0001 | 94677 |
| hIL10Ra_VHH14 - hIL2Rg_VHH19 | GGSGGS (SEQ ID NO: 315) | his | 0.001 | 109945 |
| hIL10Ra_VHH14 - hIL2Rg_VHH19 | GGSGGS (SEQ ID NO: 315) | his | 0.01 | 116978 |
| hIL10Ra_VHH14 - hIL2Rg_VHH19 | GGSGGS (SEQ ID NO: 315) | his | 0.1 | 121735 |
| hIL10Ra_VHH14 - hIL2Rg_VHH19 | GGSGGS (SEQ ID NO: 315) | his | 1 | 143818 |
| hIL10Ra_VHH14 - hIL2Rg_VHH19 | GGSGGS (SEQ ID NO: 315) | his | 10 | 149494 |
| hIL10Ra_VHH14 - hIL2Rg_VHH19 | GGSGGS (SEQ ID NO: 315) | his | 100 | 126891 |
| hIL10Ra_VHH14 - hIL2Rg_VHH19 | GGGSGGGS (SEQ ID NO: 317) | his | 0 | 122093 |
| hIL10Ra_VHH14 - hIL2Rg_VHH19 | GGGSGGGS (SEQ ID NO: 317) | his | 0.0001 | 95530 |
| hIL10Ra_VHH14 - hIL 2Rg_VHH19 | GGGSGGGS (SEQ ID NO: 317) | his | 0.001 | 107757 |
| hIL10Ra_VHH14 - hIL2Rg_VHH19 | GGGSGGGS (SEQ ID NO: 317) | his | 0.01 | 101956 |
| hIL10Ra_VHH14 - hIL2Rg_VHH19 | GGGSGGGS (SEQ ID NO: 317) | his | 0.1 | 121526 |
| hIL10Ra_VHH14 - hIL2Rg_VHH19 | GGGSGGGS (SEQ ID NO: 317) | his | 1 | 141710 |
| hIL10Ra_VHH14- hIL2Rg_VHH19 | GGGSGGGS (SEQ ID NO: 317) | his | 10 | 143032 |
| hIL10Ra_VHH14 - hIL2Rg_VHH19 | GGGSGGGS (SEQ ID NO: 317) | his | 100 | 119598 |
| hIL10Ra_VHH14 - hIL2Rg_VHH19 | GGSGGSGGSG (SEQ ID NO: 305) | his | 0 | 122093 |
| hIL10Ra_VHH14 - hIL2Rg_VHH19 | GGSGGSGGSG (SEQ ID NO: 305) | his | 0.0001 | 90061 |
| hIL10Ra_VHH14 - hIL2Rg_VHH19 | GGSGGSGGSG (SEQ ID NO: 305) | his | 0.001 | 125238 |
| hIL10Ra_VHH14 - hIL2Rg_VHH19 | GGSGGSGGSG (SEQ ID NO: 305) | his | 0.01 | 126735 |
| hIL10Ra_VHH14 - hIL 2Rg_VHH19 | GGSGGSGGSG (SEQ ID NO: 305) | his | 0.1 | 129834 |
| hIL10Ra_VHH14 - hIL2Rg_VHH19 | GGSGGSGGSG (SEQ ID NO: 305) | his | 1 | 147457 |

TABLE 17-continued

Activity of VHH dimers on CD8 T cell IFNγ secretion.

| VHH1 - VHH2 ID | Linker | Tag | Concentration of molecule (μM) | IFNγ (pg/mL) |
|---|---|---|---|---|
| hIL10Ra_VHH14 - hIL2Rg_VHH19 | GGSGGSGGSG (SEQ ID NO: 305) | his | 10 | 154053 |
| hIL10Ra_VHH14 - hIL2Rg_VHH19 | GGSGGSGGSG (SEQ ID NO: 305) | his | 100 | 140732 |

TABLE 18

Activity of VHH dimers on CD8 T cell Granzyme A secretion.

| VHH1 - VHH2 ID | Linker | Tag | Concentration of molecule (μM) | Granzyme A (pg/ml) |
|---|---|---|---|---|
| hIL10Ra_VHH14 - hIL2Rg_VHH19 | GGGS (SEQ ID NO: 9) | Fc | 0 | 25242 |
| hIL10Ra_VHH14 - hIL2Rg_VHH19 | GGGS (SEQ ID NO: 9) | Fc | 0.0001 | 22096 |
| hIL10Ra_VHH14 - hIL2Rg_VHH19 | GGGS (SEQ ID NO: 9) | Fc | 0.001 | 25929 |
| hIL10Ra_VHH14 - hIL2Rg_VHH19 | GGGS (SEQ ID NO: 9) | Fc | 0.01 | 27649 |
| hIL10Ra_VHH14 - hIL2Rg_VHH19 | GGGS (SEQ ID NO: 9) | Fc | 0.1 | 29961 |
| hIL10Ra_VHH14 - hIL2Rg_VHH19 | GGGS (SEQ ID NO: 9) | Fc | 1 | 29754 |
| hIL10Ra_VHH14 - hIL2Rg_VHH19 | GGGS (SEQ ID NO: 9) | Fc | 10 | 28484 |
| hIL10Ra_VHH14 - hIL2Rg_VHH19 | GGGS (SEQ ID NO: 9) | Fc | 100 | 25731 |
| hIL10Ra_VHH14 - hIL2Rg_VHH19 | GGGS (SEQ ID NO: 9) | his | 0 | 25242 |
| hIL10Ra_VHH14 - hIL2Rg_VHH19 | GGGS (SEQ ID NO: 9) | his | 0.0001 | 19701 |
| hIL10Ra_VHH14 - hIL2Rg_VHH19 | GGGS (SEQ ID NO: 9) | his | 0.001 | 20912 |
| hIL10Ra_VHH14 - hIL2Rg_VHH19 | GGGS (SEQ ID NO: 9) | his | 0.01 | 22320 |
| hIL10Ra_VHH14 - hIL2Rg_VHH19 | GGGS (SEQ ID NO: 9) | his | 0.1 | 23735 |
| hIL10Ra_VHH14 - hIL2Rg_VHH19 | GGGS (SEQ ID NO: 9) | his | 1 | 26393 |
| hIL10Ra_VHH14 - hIL2Rg_VHH19 | GGGS (SEQ ID NO: 9) | his | 10 | 26515 |
| hIL10Ra_VHH14 - hIL2Rg_VHH19 | GGGS (SEQ ID NO: 9) | his | 100 | 27258 |
| hIL10Ra_VHH14 hIL2Rg_VHH19 | No linker | his | 0 | 25242 |
| hIL10Ra_VHH14 - hIL2Rg_VHH19 | No linker | his | 0.0001 | 19660 |
| hIL10Ra_VHH14 - hIL2Rg_VHH19 | No linker | his | 0.001 | 22316 |

TABLE 18-continued

Activity of VHH dimers on CD8 T cell Granzyme A secretion.

| VHH1 - VHH2 ID | Linker | Tag | Concentration of molecule (µM) | Granzyme A (pg/ml) |
|---|---|---|---|---|
| hIL10Ra_VHH14 - hIL2Rg_VHH19 | No linker | his | 0.01 | 22237 |
| hIL10Ra_VHH14 - hIL2Rg_VHH19 | No linker | his | 0.1 | 22894 |
| hIL10Ra_VHH14 - hIL2Rg_VHH19 | No linker | his | 1 | 24422 |
| hIL10Ra_VHH14- hIL2Rg_VHH19 | No linker | his | 10 | 26020 |
| hIL10Ra_VHH14 - hIL2Rg_VHH19 | No linker | his | 100 | 27507 |
| hIL10Ra_VHH14 - hIL2Rg_VHH19 | GS | his | 0 | 25242 |
| hIL10Ra_VHH14 - hIL2Rg_VHH19 | GS | his | 0.0001 | 19871 |
| hIL10Ra_VHH14 - hIL2Rg_VHH19 | GS | his | 0.001 | 22696 |
| hIL10Ra_VHH14 - hIL2Rg_VHH19 | GS | his | 0.01 | 25887 |
| hIL10Ra_VHH14 - hIL2Rg_VHH19 | GS | his | 0.1 | 26102 |
| hIL10Ra_VHH14 - hIL2Rg_VHH19 | GS | his | 1 | 27877 |
| hIL10Ra_VHH14 - hIL2Rg_VHH19 | GS | his | 10 | 28634 |
| hIL10Ra_VHH14 - hIL2Rg_VHH19 | GS | his | 100 | 28383 |
| hIL10Ra_VHH14 - hIL2Rg_VHH19 | GGSGGS (SEQ ID NO: 315) | his | 0 | 25242 |
| hIL10Ra_VHH14 - hIL2Rg_VHH19 | GGSGGS (SEQ ID NO: 315) | his | 0.0001 | 20762 |
| hIL10Ra_VHH14 - hIL2Rg_VHH19 | GGSGGS (SEQ ID NO: 315) | his | 0.001 | 22985 |
| hIL10Ra_VHH14 - hIL2Rg_VHH19 | GGSGGS (SEQ ID NO: 315) | his | 0.01 | 25327 |
| hIL10Ra_VHH14 - hIL2Rg_VHH19 | GGSGGS (SEQ ID NO: 315) | his | 0.1 | 27132 |
| hIL10Ra_VHH14 - hIL2Rg_VHH19 | GGSGGS (SEQ ID NO: 315) | his | 1 | 28702 |
| hIL10Ra_VHH14 - hIL2Rg_VHH19 | GGSGGS (SEQ ID NO: 315) | his | 10 | 29363 |
| hIL10Ra_VHH14 - hIL2Rg_VHH19 | GGSGGS (SEQ ID NO: 315) | his | 100 | 25620 |
| hIL10Ra_VHH14 - hIL2Rg_VHH19 | GGGSGGGS (SEQ ID NO: 317) | his | 0 | 25242 |
| hIL10Ra_VHH14 - hIL2Rg_VHH19 | GGGSGGGS (SEQ ID NO: 317) | his | 0.0001 | 19660 |
| hIL10Ra_VHH14 - hIL2Rg_VHH19 | GGGSGGGS (SEQ ID NO: 317) | his | 0.001 | 22300 |
| hIL10Ra_VHH14 - hIL2Rg_VHH19 | GGGSGGGS (SEQ ID NO: 317) | his | 0.01 | 22652 |

TABLE 18-continued

Activity of VHH dimers on CD8 T cell Granzyme A secretion.

| VHH1 - VHH2 ID | Linker | Tag | Concentration of molecule (μM) | Granzyme A (pg/ml) |
|---|---|---|---|---|
| hIL10Ra_VHH14 - hIL2Rg_VHH19 | GGGSGGGS (SEQ ID NO: 317) | his | 0.1 | 26036 |
| hIL10Ra_VHH14 - hIL2Rg_VHH19 | GGGSGGGS (SEQ ID NO: 317) | his | 1 | 30060 |
| hIL10Ra_VHH14 - hIL2Rg_VHH19 | GGGSGGGS (SEQ ID NO: 317) | his | 10 | 29261 |
| hIL10Ra_VHH14 - hIL2Rg_VHH19 | GGGSGGGS (SEQ ID NO: 317) | his | 100 | 24800 |
| hIL10Ra_VHH14 - hIL2Rg_VHH19 | GGSGGSGGSG (SEQ ID NO: 305) | his | 0 | 25242 |
| hIL10Ra_VHH14 - hIL2Rg_VHH19 | GGSGGSGGSG (SEQ ID NO: 305) | his | 0.0001 | 20606 |
| hIL10Ra_VHH14 - hIL2Rg_VHH19 | GGSGGSGGSG (SEQ ID NO: 305) | his | 0.001 | 25240 |
| hIL10Ra_VHH14 - hIL2Rg_VHH19 | GGSGGSGGSG (SEQ ID NO: 305) | his | 0.01 | 28085 |
| hIL10Ra_VHH14 - hIL2Rg_VHH19 | GGSGGSGGSG (SEQ ID NO: 305) | his | 0.1 | 29307 |
| hIL10Ra_VHH14 - hIL2Rg_VHH19 | GGSGGSGGSG (SEQ ID NO: 305) | his | 1 | 30958 |
| hIL10Ra_VHH14 - hIL2Rg_VHH19 | GGSGGSGGSG (SEQ ID NO: 305) | his | 10 | 31489 |
| hIL10Ra_VHH14 - hIL2Rg_VHH19 | GGSGGSGGSG (SEQ ID NO: 305) | his | 100 | 29905 |

TABLE 19

Activity of VHH dimers on CD8 T cell Granzyme B secretion.

| VHH1 - VHH2 ID | Linker | Tag | Concentration of molecule (μM) | Granzyme B (pg/ml) |
|---|---|---|---|---|
| hIL10Ra_VHH14 - hIL2Rg_VHH19 | GGGS (SEQ ID NO: 9) | Fc | 0 | 77743 |
| hIL10Ra_VHH14 - hIL2Rg_VHH19 | GGGS (SEQ ID NO: 9) | Fc | 0.0001 | 54536 |
| hIL10Ra_VHH14 - hIL2Rg_VHH19 | GGGS (SEQ ID NO: 9) | Fc | 0.001 | 60933 |
| hIL10Ra_VHH14 - hIL2Rg_VHH19 | GGGS (SEQ ID NO: 9) | Fc | 0.01 | 78976 |
| hIL10Ra_VHH14 - hIL2Rg_VHH19 | GGGS (SEQ ID NO: 9) | Fc | 0.1 | 108176 |
| hIL10Ra_VHH14 - hIL2Rg_VHH19 | GGGS (SEQ ID NO: 9) | Fc | 1 | 134135 |
| hIL10Ra_VHH14 - hIL2Rg_VHH19 | GGGS (SEQ ID NO: 9) | Fc | 10 | 151338 |
| hIL10Ra_VHH14- hIL2Rg_VHH19 | GGGS (SEQ ID NO: 9) | Fc | 100 | 93281 |
| hIL10Ra_VHH14 - hIL2Rg_VHH19 | GGGS (SEQ ID NO: 9) | his | 0 | 77743 |

TABLE 19-continued

Activity of VHH dimers on CD8 T cell Granzyme B secretion.

| VHH1 - VHH2 ID | Linker | Tag | Concentration of molecule (μM) | Granzyme B (pg/ml) |
|---|---|---|---|---|
| hIL10Ra_VHH14 - hIL2Rg_VHH19 | GGGS (SEQ ID NO: 9) | his | 0.0001 | 49291 |
| hIL10Ra_VHH14 - hIL2Rg_VHH19 | GGGS (SEQ ID NO: 9) | his | 0.001 | 45559 |
| hIL10Ra_VHH14 - hIL2Rg_VHH19 | GGGS (SEQ ID NO: 9) | his | 0.01 | 48088 |
| hIL10Ra_VHH14 - hIL2Rg_VHH19 | GGGS (SEQ ID NO: 9) | his | 0.1 | 55281 |
| hIL10Ra_VHH14 - hIL2Rg_VHH19 | GGGS (SEQ ID NO: 9) | his | 1 | 72656 |
| hIL10Ra_VHH14 - hIL2Rg_VHH19 | GGGS (SEQ ID NO: 9) | his | 10 | 84685 |
| hIL10Ra_VHH14 - hIL2Rg_VHH19 | GGGS (SEQ ID NO: 9) | his | 100 | 94573 |
| hIL10Ra_VHH14 - hIL2Rg_VHH19 | No linker | his | 0 | 77743 |
| hIL10Ra_VHH14 - hIL2Rg_VHH19 | No linker | his | 0.0001 | 49323 |
| hIL10Ra_VHH14 - hIL2Rg_VHH19 | No linker | his | 0.001 | 47261 |
| hIL10Ra_VHH14 - hIL2Rg_VHH19 | No linker | his | 0.01 | 44212 |
| hIL10Ra_VHH14 - hIL2Rg_VHH19 | No linker | his | 0.1 | 54822 |
| hIL10Ra_VHH14 - hIL2Rg_VHH19 | No linker | his | 1 | 56290 |
| hIL10Ra_VHH14 - hIL2Rg_VHH19 | No linker | his | 10 | 67061 |
| hIL10Ra_VHH14 - hIL2Rg_VHH19 | No linker | his | 100 | 74310 |
| hIL10Ra_VHH14 - hIL2Rg_VHH19 | GS | his | 0 | 77743 |
| hIL10Ra_VHH14 - hIL2Rg_VHH19 | GS | his | 0.0001 | 49205 |
| hIL10Ra_VHH14 - hIL2Rg_VHH19 | GS | his | 0.001 | 49379 |
| hIL10Ra_VHH14 - hIL2Rg_VHH19 | GS | his | 0.01 | 55456 |
| hIL10Ra_VHH14 - hIL2Rg_VHH19 | GS | his | 0.1 | 58033 |
| hIL10Ra_VHH14 - hIL2Rg_VHH19 | GS | his | 1 | 80216 |
| hIL10Ra_VHH14 - hIL2Rg_VHH19 | GS | his | 10 | 86955 |
| hIL10Ra_VHH14 - hIL2Rg_VHH19 | GS | his | 100 | 99876 |
| hIL10Ra_VHH14 - hIL2Rg_VHH19 | GGSGGS (SEQ ID NO: 315) | his | 0 | 77743 |
| hIL10Ra_VHH14 - hIL2Rg_VHH19 | GGSGGS (SEQ ID NO: 315) | his | 0.0001 | 54496 |

TABLE 19-continued

Activity of VHH dimers on CD8 T cell Granzyme B secretion.

| VHH1 - VHH2 ID | Linker | Tag | Concentration of molecule (μM) | Granzyme B (pg/ml) |
|---|---|---|---|---|
| hIL10Ra_VHH14 - hIL2Rg_VHH19 | GGSGGS (SEQ ID NO: 315) | his | 0.001 | 50920 |
| hIL10Ra_VHH14 - hIL2Rg_VHH19 | GGSGGS (SEQ ID NO: 315) | his | 0.01 | 54056 |
| hIL10Ra_VHH14 - hIL2Rg_VHH19 | GGSGGS (SEQ ID NO: 315) | his | 0.1 | 62317 |
| hIL10Ra_VHH14 - hIL2Rg_VHH19 | GGSGGS (SEQ ID NO: 315) | his | 1 | 77563 |
| hIL10Ra_VHH14 - hIL2Rg_VHH19 | GGSGGS (SEQ ID NO: 315) | his | 10 | 89980 |
| hIL10Ra_VHH14 - hIL2Rg_VHH19 | GGSGGS (SEQ ID NO: 315) | his | 100 | 77902 |
| hIL10Ra_VHH14 - hIL2Rg_VHH19 | GGGSGGGS (SEQ ID NO: 317) | his | 0 | 77743 |
| hIL10Ra_VHH14 - hIL2Rg_VHH19 | GGGSGGGS (SEQ ID NO: 317) | his | 0.0001 | 52639 |
| hIL10Ra_VHH14 - hIL2Rg_VHH19 | GGGSGGGS (SEQ ID NO: 317) | his | 0.001 | 45454 |
| hIL10Ra_VHH14 - hIL2Rg_VHH19 | GGGSGGGS (SEQ ID NO: 317) | his | 0.01 | 47256 |
| hIL10Ra_VHH14 - hIL2Rg_VHH19 | GGGSGGGS (SEQ ID NO: 317) | his | 0.1 | 62245 |
| hIL10Ra_VHH14 - hIL2Rg_VHH19 | GGGSGGGS (SEQ ID NO: 317) | his | 1 | 80475 |
| hIL10Ra_VHH14 - hIL2Rg_VHH19 | GGGSGGGS (SEQ ID NO: 317) | his | 10 | 83472 |
| hIL10Ra_VHH14 - hIL2Rg_VHH19 | GGGSGGGS (SEQ ID NO: 317) | his | 100 | 78110 |
| hIL10Ra_VHH14 - hIL2Rg_VHH19 | GGSGGSGGSG (SEQ ID NO: 305) | his | 0 | 77743 |
| hIL10Ra_VHH14- hIL2Rg_VHH19 | GGSGGSGGSG (SEQ ID NO: 305) | his | 0.0001 | 68889 |
| hIL10Ra_VHH14- hIL2Rg_VHH19 | GGSGGSGGSG (SEQ ID NO: 305) | his | 0.001 | 70609 |
| hIL10Ra_VHH14 - hIL2Rg_VHH19 | GGSGGSGGSG (SEQ ID NO: 305) | his | 0.01 | 70990 |
| hIL10Ra_VHH14 - hIL2Rg_VHH19 | GGSGGSGGSG (SEQ ID NO: 305) | his | 0.1 | 79349 |
| hIL10Ra_VHH14 - hIL2Rg_VHH19 | GGSGGSGGSG (SEQ ID NO: 305) | his | 1 | 111535 |
| hIL10Ra_VHH14 - hIL2Rg_VHH19 | GGSGGSGGSG (SEQ ID NO: 305) | his | 10 | 125459 |
| hIL10Ra_VHH14 - hIL2Rg_VHH19 | GGSGGSGGSG (SEQ ID NO: 305) | his | 100 | 106090 |

TABLE 20

Activity of VHH dimers on CD8 T cell Granzyme B secretion.

| VHH1 - VHH2 ID | Linker | Tag | Concentration of molecule (μM) | Granzyme B (pg/ml) |
|---|---|---|---|---|
| hIL10Ra_VHH14 - hIL2Rg_VHH19 | GGGS (SEQ ID NO: 9) | Fc | 0 | 77743 |
| hIL10Ra_VHH14 - hIL2Rg_VHH19 | GGGS (SEQ ID NO: 9) | Fc | 0.0001 | 54536 |
| hIL10Ra_VHH14 - hIL2Rg_VHH19 | GGGS (SEQ ID NO: 9) | Fc | 0.001 | 60933 |
| hIL10Ra_VHH14 - hIL2Rg_VHH19 | GGGS (SEQ ID NO: 9) | Fc | 0.01 | 78976 |
| hIL10Ra_VHH14 - hIL2Rg_VHH19 | GGGS (SEQ ID NO: 9) | Fc | 0.1 | 108176 |
| hIL10Ra_VHH14 - hIL2Rg_VHH19 | GGGS (SEQ ID NO: 9) | Fc | 1 | 134135 |
| hIL10Ra_VHH14 - hIL2Rg_VHH19 | GGGS (SEQ ID NO: 9) | Fc | 10 | 151338 |
| hIL10Ra_VHH14 - hIL2Rg_VHH19 | GGGS (SEQ ID NO: 9) | Fc | 100 | 93281 |
| hIL10Ra_VHH14 - hIL2Rg_VHH19 | GGGS (SEQ ID NO: 9) | his | 0 | 77743 |
| hIL10Ra_VHH14 - hIL2Rg_VHH19 | GGGS (SEQ ID NO: 9) | his | 0.0001 | 49291 |
| hIL10Ra_VHH14 - hIL2Rg_VHH19 | GGGS (SEQ ID NO: 9) | his | 0.001 | 45559 |
| hIL10Ra_VHH14 - hIL2Rg_VHH19 | GGGS (SEQ ID NO: 9) | his | 0.01 | 48088 |
| hIL10Ra_VHH14 - hIL2Rg_VHH 19 | GGGS (SEQ ID NO: 9) | his | 0.1 | 55281 |
| hIL10Ra_VHH14 - hIL2Rg_VHH19 | GGGS (SEQ ID NO: 9) | his | 1 | 72656 |
| hIL10Ra_VHH14 - hIL2Rg_VHH19 | GGGS (SEQ ID NO: 9) | his | 10 | 84685 |
| hIL10Ra_VHH14 - hIL2Rg_VHH19 | GGGS (SEQ ID NO: 9) | his | 100 | 94573 |
| hIL10Ra_VHH14 - hIL2Rg_VHH19 | No linker | his | 0 | 77743 |
| hIL10Ra_VHH14 - hIL2Rg_VHH19 | No linker | his | 0.0001 | 49323 |
| hIL10Ra_VHH14 - hIL2Rg_VHH19 | No linker | his | 0.001 | 47261 |
| hIL10Ra_VHH14 - hIL2Rg_VHH19 | No linker | his | 0.01 | 44212 |
| hIL10Ra_VHH14 - hIL2Rg_VHH19 | No linker | his | 0.1 | 54822 |
| hIL10Ra_VHH14 - hIL2Rg_VHH19 | No linker | his | 1 | 56290 |
| hIL10Ra_VHH14 - hIL2Rg_VHH19 | No linker | his | 10 | 67061 |
| hIL10Ra_VHH14 - hIL2Rg_VHH19 | No linker | his | 100 | 74310 |
| hIL10Ra_VHH14 - hIL2Rg_VHH19 | GS | his | 0 | 77743 |

TABLE 20-continued

Activity of VHH dimers on CD8 T cell Granzyme B secretion.

| VHH1 - VHH2 ID | Linker | Tag | Concentration of molecule (μM) | Granzyme B (pg/ml) |
|---|---|---|---|---|
| hIL10Ra_VHH14 - hIL2Rg_VHH19 | GS | his | 0.0001 | 49205 |
| hIL10Ra_VHH14 - hIL2Rg_VHH19 | GS | his | 0.001 | 49379 |
| hIL10Ra_VHH14 - hIL2Rg_VHH19 | GS | his | 0.01 | 55456 |
| hIL10Ra_VHH14 - hIL2Rg_VHH19 | GS | his | 0.1 | 58033 |
| hIL10Ra_VHH14 - hIL2Rg_VHH19 | GS | his | 1 | 80216 |
| hIL10Ra_VHH14 - hIL2Rg_VHH19 | GS | his | 10 | 86955 |
| hIL10Ra_VHH14 - hIL2Rg_VHH19 | GS | his | 100 | 99876 |
| hIL10Ra_VHH14 - hIL2Rg_VHH19 | GGSGGS (SEQ ID NO: 315) | his | 0 | 77743 |
| hIL10Ra_VHH14 - hIL2Rg_VHH19 | GGSGGS (SEQ ID NO: 315) | his | 0.0001 | 54496 |
| hIL10Ra_VHH14 - hIL2Rg_VHH19 | GGSGGS (SEQ ID NO: 315) | his | 0.001 | 50920 |
| hIL10Ra_VHH14 - hIL2Rg_VHH19 | GGSGGS (SEQ ID NO: 315) | his | 0.01 | 54056 |
| hIL10Ra_VHH14 - hIL2Rg_VHH19 | GGSGGS (SEQ ID NO: 315) | his | 0.1 | 62317 |
| hIL10Ra_VHH14 - hIL2Rg_VHH19 | GGSGGS (SEQ ID NO: 315) | his | 1 | 77563 |
| hIL10Ra_VHH14 - hIL2Rg_VHH19 | GGSGGS (SEQ ID NO: 315) | his | 10 | 89980 |
| hIL10Ra_VHH14 - hIL2Rg_VHH19 | GGSGGS (SEQ ID NO: 315) | his | 100 | 77902 |
| hIL10Ra_VHH14 - hIL2Rg_VHH19 | GGGSGGGS (SEQ ID NO: 317) | his | 0 | 77743 |
| hIL10Ra_VHH14 - hIL2Rg_VHH19 | GGGSGGGS (SEQ ID NO: 317) | his | 0.0001 | 52639 |
| hIL10Ra_VHH14 - hIL2Rg_VHH19 | GGGSGGGS (SEQ ID NO: 317) | his | 0.001 | 45454 |
| hIL10Ra_VHH14 - hIL2Rg_VHH19 | GGGSGGGS (SEQ ID NO: 317) | his | 0.01 | 47256 |
| hIL10Ra_VHH14 - hIL2Rg_VHH19 | GGGSGGGS (SEQ ID NO: 317) | his | 0.1 | 62245 |
| hIL10Ra_VHH14 - hIL2Rg_VHH19 | GGGSGGGS (SEQ ID NO: 317) | his | 1 | 80475 |
| hIL10Ra_VHH14 - hIL2Rg_VHH19 | GGGSGGGS (SEQ ID NO: 317) | his | 10 | 83472 |
| hIL10Ra_VHH14 - hIL2Rg_VHH19 | GGGSGGGS (SEQ ID NO: 317) | his | 100 | 78110 |
| hIL10Ra_VHH14 - hIL2Rg_VHH19 | GGSGGSGGSG (SEQ ID NO: 305) | his | 0 | 77743 |
| hIL10Ra_VHH14 - hIL2Rg_VHH19 | GGSGGSGGSG (SEQ ID NO: 305) | his | 0.0001 | 68889 |

TABLE 20-continued

Activity of VHH dimers on CD8 T cell Granzyme B secretion.

| VHH1 - VHH2 ID | Linker | Tag | Concentration of molecule (μM) | Granzyme B (pg/ml) |
|---|---|---|---|---|
| hIL10Ra_VHH14 - hIL2Rg_VHH19 | GGSGGSGGSG (SEQ ID NO: 305) | his | 0.001 | 70609 |
| hIL10Ra_VHH14 - hIL2Rg_VHH19 | GGSGGSGGSG (SEQ ID NO: 305) | his | 0.01 | 70990 |
| hIL10Ra_VHH14 - hIL2Rg_VHH19 | GGSGGSGGSG (SEQ ID NO: 305) | his | 0.1 | 79349 |
| hIL10Ra_VHH14- hIL2Rg_VHH19 | GGSGGSGGSG (SEQ ID NO: 305) | his | 1 | 111535 |
| hIL10Ra_VHH14 - hIL2Rg_VHH19 | GGSGGSGGSG (SEQ ID NO: 305) | his | 10 | 125459 |
| hIL10Ra_VHH14- hIL2Rg_VHH19 | GGSGGSGGSG (SEQ ID NO: 305) | his | 100 | 106090 |

TABLE 21

Activity of VHH dimers on CD8 T cell IL-9 secretion.

| VHH1-VHH2 ID | Linker | Tag | Concentration of molecule (μM) | IL-9 (pg/mL) |
|---|---|---|---|---|
| hIL10Ra_VHH14- hIL2Rg_VHH19 | GGGS (SEQ ID NO: 9) | FC | 0 | 1348 |
| hIL10Ra_VHH14- hIL2Rg_VHH19 | GGGS (SEQ ID NO: 9) | Fc | 0.0001 | 1055 |
| hIL10Ra_VHH14- hIL2Rg_VHH19 | GGGS (SEQ ID NO: 9) | FC | 0.001 | 1116 |
| hIL10Ra_VHH14- hIL2Rg_VHH19 | GGGS (SEQ ID NO: 9) | Fc | 0.01 | 1162 |
| hIL10Ra_VHH14- hIL2Rg_VHH19 | GGGS (SEQ ID NO: 9) | Fc | 0.1 | 1424 |
| hIL10Ra_VHH14- hIL2Rg_VHH19 | GGGS (SEQ ID NO: 9) | Fc | 1 | 1782 |
| hIL10Ra_VHH14- hIL2Rg_VHH19 | GGGS (SEQ ID NO: 9) | Fc | 10 | 2146 |
| hIL10Ra_VHH14- hIL2Rg_VHH19 | GGGS (SEQ ID NO: 9) | Fc | 100 | 1926 |
| hIL10Ra_VHH14- hIL2Rg_VHH19 | GGGS (SEQ ID NO: 9) | his | 0 | 1348 |
| hIL10Ra_VHH14- hIL2Rg_VHH19 | GGGS (SEQ ID NO: 9) | his | 0.0001 | 941 |
| hIL10Ra_VHH14- hIL2Rg_VHH19 | GGGS (SEQ ID NO: 9) | his | 0.001 | 1001 |
| hIL10Ra_VHH14- hIL2Rg_VHH19 | GGGS (SEQ ID NO: 9) | his | 0.01 | 1117 |
| hIL10Ra_VHH14- hIL2Rg_VHH19 | GGGS (SEQ ID NO: 9) | his | 0.1 | 1338 |
| hIL10Ra_VHH14- hIL2Rg_VHH19 | GGGS (SEQ ID NO: 9) | his | 1 | 1399 |
| hIL10Ra_VHH14- hIL2Rg_VHH19 | GGGS (SEQ ID NO: 9) | his | 1 | 1685 |

TABLE 21-continued

Activity of VHH dimers on CD8 T cell IL-9 secretion.

| VHH1-VHH2 ID | Linker | Tag | Concentration of molecule (μM) | IL-9 (pg/mL) |
|---|---|---|---|---|
| hIL10Ra_VHH14- hIL2Rg_VHH19 | GGGS (SEQ ID NO: 9) | his | 100 | 1707 |
| hIL10Ra_VHH14- hIL2Rg_VHH19 | No linker | his | 0 | 1348 |
| hIL10Ra_VHH14- hIL2Rg_VHH19 | No linker | his | 0.0001 | 933 |
| hIL10Ra_VHH14- hIL2Rg_VHH19 | No linker | his | 0.001 | 1125 |
| hIL10Ra_VHH14- hIL2Rg_VHH19 | No linker | his | 0.01 | 1141 |
| hIL10Ra_VHH14- hIL2Rg_VHH19 | No linker | his | 0.1 | 1066 |
| hIL10Ra_VHH14- hIL2Rg_VHH19 | No linker | his | 1 | 1216 |
| hIL10Ra_VHH14- hIL2Rg_VHH19 | No linker | his | 10 | 1438 |
| hIL10Ra_VHH14- hIL2Rg_VHH19 | No linker | his | 100 | 1666 |
| hIL10Ra_VHH14- hIL2Rg_VHH19 | GS | his | 0 | 1348 |
| hIL10Ra_VHH14- hIL2Rg_VHH19 | GS | his | 0.0001 | 918 |
| hIL10Ra_VHH14- hIL2Rg_VHH19 | GS | his | 0.001 | 998 |
| hIL10Ra_VHH14- hIL2Rg_VHH19 | GS | his | 0.01 | 1072 |
| hIL10Ra_VHH14- hIL2Rg_VHH19 | GS | his | 0.1 | 1228 |
| hIL10Ra_VHH14- hIL2Rg_VHH19 | GS | his | 1 | 1608 |

TABLE 21-continued

Activity of VHH dimers on CD8 T cell IL-9 secretion.

| VHH1-VHH2 ID | Linker | Tag | Concentration of molecule (μM) | IL-9 (pg/mL) |
|---|---|---|---|---|
| hIL10Ra_VHH14-hIL2Rg_VHH19 | GS | his | 10 | 1729 |
| hIL10Ra_VHH14-hIL2Rg_VHH19 | GS | his | 100 | 1882 |
| hIL10Ra_VHH14-hIL2Rg_VHH19 | GGSGGS (SEQ ID NO: 315) | his | 0 | 1348 |
| hIL10Ra_VHH14-hIL2Rg_VHH19 | GGSGGS (SEQ ID NO: 315) | his | 0.0001 | 951 |
| hIL10Ra_VHH14-hIL2Rg_VHH19 | GGSGGS (SEQ ID NO: 315) | his | 0.001 | 1006 |
| hIL10Ra_VHH14-hIL2Rg_VHH19 | GGSGGS (SEQ ID NO: 315) | his | 0.01 | 1144 |
| hIL10Ra_VHH14-hIL2Rg_VHH19 | GGSGGS (SEQ ID NO: 315) | his | 0.1 | 1090 |
| hIL10Ra_VHH14-hIL2Rg_VHH19 | GGSGGS (SEQ ID NO: 315) | his | 1 | 1436 |
| hIL10Ra_VHH14-hIL2Rg_VHH19 | GGSGGS (SEQ ID NO: 315) | his | 10 | 1604 |
| hIL10Ra_VHH14-hIL2Rg_VHH19 | GGSGGS (SEQ ID NO: 315) | his | 100 | 1698 |
| hIL10Ra_VHH14-hIL2Rg_VHH19 | GGGSGGGS (SEQ ID NO: 317) | his | 0 | 1348 |
| hIL10Ra_VHH14-hIL2Rg_VHH19 | GGGSGGGS (SEQ ID NO: 317) | his | 0.0001 | 988 |
| hIL10Ra_VHH14-hIL2Rg_VHH19 | GGGSGGGS (SEQ ID NO: 317) | his | 0.001 | 1053 |
| hIL10Ra_VHH14-hIL2Rg_VHH19 | GGGSGGGS (SEQ ID NO: 317) | his | 0.01 | 1007 |
| hIL10Ra_VHH14-hIL2Rg_VHH19 | GGGSGGGS (SEQ ID NO: 317) | his | 0.1 | 1305 |
| hIL10Ra_VHH14-hIL2Rg_VHH19 | GGGSGGGS (SEQ ID NO: 317) | his | 1 | 1381 |
| hIL10Ra_VHH14-hIL2Rg_VHH19 | GGGSGGGS (SEQ ID NO: 317) | his | 10 | 1885 |
| hIL10Ra_VHH14-hIL2Rg_VHH19 | GGGSGGGS (SEQ ID NO: 317) | his | 100 | 1700 |
| hIL10Ra_VHH14-hIL2Rg_VHH19 | GGSGGSGGSG (SEQ ID NO: 305) | his | 0 | 1348 |
| hIL10Ra_VHH14-hIL2Rg_VHH19 | GGSGGSGGSG (SEQ ID NO: 305) | his | 0.0001 | 1007 |
| hIL10Ra_VHH14-hIL2Rg_VHH19 | GGSGGSGGSG (SEQ ID NO: 305) | his | 0.001 | 1315 |
| hIL10Ra_VHH14-hIL2Rg_VHH19 | GGSGGSGGSG (SEQ ID NO: 305) | his | 0.01 | 1391 |
| hIL10Ra_VHH14-hIL2Rg_VHH19 | GGSGGSGGSG (SEQ ID NO: 305) | his | 0.1 | 1449 |
| hIL10Ra_VHH14-hIL2Rg_VHH19 | GGSGGSGGSG (SEQ ID NO: 305) | his | 1 | 1588 |
| hIL10Ra_VHH14-hIL2Rg_VHH19 | GGSGGSGGSG (SEQ ID NO: 305) | his | 10 | 2052 |
| hIL10Ra_VHH14-hIL2Rg_VHH19 | GGSGGSGGSG (SEQ ID NO: 305) | his | 100 | 1965 |

TABLE 22

Activity of VHH dimers on LPS treated Monocyte IL-1ß secretion.

| VHH1-VHH2 ID | Linker | Tag | Concentration of molecule (μM) | IL-1ß (pg/mL) |
|---|---|---|---|---|
| hIL10Ra_VHH14-hIL2Rg_VHH19 | GGGS (SEQ ID NO: 9) | Fc | 0 | 6244 |
| hIL10Ra_VHH14-hIL2Rg_VHH19 | GGGS (SEQ ID NO: 9) | Fc | 0 (LPS only) | 6880 |
| hIL10Ra_VHH14-hIL2Rg_VHH19 | GGGS (SEQ ID NO: 9) | Fc | 0.0001 | 6290 |
| hIL10Ra_VHH14-hIL2Rg_VHH19 | GGGS (SEQ ID NO: 9) | Fc | 0.001 | 5571 |
| hIL10Ra_VHH14-hIL2Rg_VHH19 | GGGS (SEQ ID NO: 9) | Fc | 0.01 | 5259 |
| hIL10Ra_VHH14-hIL2Rg_VHH19 | GGGS (SEQ ID NO: 9) | Fc | 0.1 | 4018 |
| hIL10Ra_VHH14-hIL2Rg_VHH19 | GGGS (SEQ ID NO: 9) | Fc | 1 | 3665 |
| hIL10Ra_VHH14-hIL2Rg_VHH19 | GGGS (SEQ ID NO: 9) | Fc | 10 | 4143 |
| hIL10Ra_VHH14-hIL2Rg_VHH19 | GGGS (SEQ ID NO: 9) | Fc | 100 | 6478 |
| hIL10Ra_VHH14-hIL2Rg_VHH19 | GGGS (SEQ ID NO: 9) | his | 0 | 6244 |
| hIL10Ra_VHH14- | GGGS (SEQ ID | his | 0 | 6880 |

TABLE 22-continued

Activity of VHH dimers on LPS treated Monocyte IL-1ß secretion.

| VHH1-VHH2 ID | Linker | Tag | Concentration of molecule (μM) | IL-1ß (pg/mL) |
|---|---|---|---|---|
| hIL2Rg_VHH19 | NO: 9) | | (LPS only) | |
| hIL10Ra_VHH14-hIL2Rg_VHH19 | GGGS (SEQ ID NO: 9) | his | 0.0001 | 6424 |
| hIL10Ra_VHH14-hIL2Rg_VHH19 | GGGS (SEQ ID NO: 9) | his | 0.001 | 6644 |
| hIL10Ra_VHH14-hIL2Rg_VHH19 | GGGS (SEQ ID NO: 9) | his | 0.01 | 5763 |
| hIL10Ra_VHH14-hIL2Rg_VHH19 | GGGS (SEQ ID NO: 9) | his | 0.1 | 6124 |
| hIL10Ra_VHH14-hIL2Rg_VHH19 | GGGS (SEQ ID NO: 9) | his | 1 | 5354 |
| hIL10Ra_VHH14-hIL2Rg_VHH19 | GGGS (SEQ ID NO: 9) | his | 10 | 5951 |
| hIL10Ra_VHH14-hIL2Rg_VHH19 | GGGS (SEQ ID NO: 9) | his | 100 | 6580 |
| hIL10Ra_VHH14-hIL2Rg_VHH19 | No linker | his | 0 | 6244 |
| hIL10Ra_VHH14-hIL2Rg_VHH19 | No linker | his | 0 (LPS only) | 6880 |
| hIL10Ra_VHH14-hIL2Rg_VHH19 | No linker | his | 0.0001 | 5541 |
| hIL10Ra_VHH14-hIL2Rg_VHH19 | No linker | his | 0.001 | 5549 |
| hIL10Ra_VHH14-hIL2Rg_VHH19 | No linker | his | 0.01 | 5373 |
| hIL10Ra_VHH14-hIL2Rg_VHH19 | No linker | his | 0.1 | 5290 |
| hIL10Ra_VHH14-hIL2Rg_VHH19 | No linker | his | 1 | 5801 |
| hIL10Ra_VHH14-hIL2Rg_VHH19 | No linker | his | | 5792 |
| hIL10Ra_VHH14-hIL2Rg_VHH19 | No linker | his | 100 | 7100 |
| hIL10Ra_VHH14-hIL2Rg_VHH19 | GS | his | 0 | 6244 |
| hIL10Ra_VHH14-hIL2Rg_VHH19 | GS | his | 0 (LPS only) | 6880 |
| hIL10Ra_VHH14-hIL2Rg_VHH19 | GS | his | 0.0001 | 5964 |
| hIL10Ra_VHH14-hIL2Rg_VHH19 | GS | his | 0.001 | 6266 |
| hIL10Ra_VHH14-hIL2Rg_VHH19 | GS | his | 0.01 | 5065 |
| hIL10Ra_VHH14-hIL2Rg_VHH19 | GS | his | 0.1 | 6592 |

TABLE 22-continued

Activity of VHH dimers on LPS treated Monocyte IL-1ß secretion.

| VHH1-VHH2 ID | Linker | Tag | Concentration of molecule (μM) | IL-1ß (pg/mL) |
|---|---|---|---|---|
| hIL10Ra_VHH14-hIL2Rg_VHH19 | GS | his | 1 | 5765 |
| hIL10Ra_VHH14-hIL2Rg_VHH19 | GS | his | 10 | 6707 |
| hIL10Ra_VHH14-hIL2Rg_VHH19 | GS | his | 100 | 8142 |
| hIL10Ra_VHH14-hIL2Rg_VHH19 | GGSGGS (SEQ ID NO: 315) | his | 0 | 6244 |
| hIL10Ra_VHH14-hIL2Rg_VHH19 | GGSGGS (SEQ ID NO: 315) | his | 0 (LPS only) | 6880 |
| hIL10Ra_VHH14-hIL2Rg_VHH19 | GGSGGS (SEQ ID NO: 315) | his | 0.0001 | 6288 |
| hIL10Ra_VHH14-hIL2Rg_VHH19 | GGSGGS (SEQ ID NO: 315) | his | 0.001 | 5849 |
| hIL10Ra_VHH14-hIL2Rg_VHH19 | GGSGGS (SEQ ID NO: 315) | his | 0.01 | 6103 |
| hIL10Ra_VHH14-hIL2Rg_VHH19 | GGSGGS (SEQ ID NO: 315) | his | 0.1 | 4955 |
| hIL10Ra_VHH14-hIL2Rg_VHH19 | GGSGGS (SEQ ID NO: 315) | his | 1 | 5780 |
| hIL10Ra_VHH14-hIL2Rg_VHH19 | GGSGGS (SEQ ID NO: 315) | his | 10 | 6425 |
| hIL10Ra_VHH14-hIL2Rg_VHH19 | GGSGGS (SEQ ID NO: 315) | his | 100 | 7844 |
| hIL10Ra_VHH14-hIL2Rg_VHH19 | GGGSGGGS (SEQ ID NO: 317) | his | 0 | 6244 |
| hIL10Ra_VHH14-hIL2Rg_VHH19 | GGGSGGGS (SEQ ID NO: 317) | his | 0 (LPS only) | 6880 |
| hIL10Ra_VHH14-hIL2Rg_VHH19 | GGGSGGGS (SEQ ID NO: 317) | his | 0.0001 | 5950 |
| hIL10Ra_VHH14-hIL2Rg_VHH19 | GGGSGGGS (SEQ ID NO: 317) | his | 0.001 | 6200 |
| hIL10Ra_VHH14-hIL2Rg_VHH19 | GGGSGGGS (SEQ ID NO: 317) | his | 0.01 | 4959 |
| hIL10Ra_VHH14-hIL2Rg_VHH19 | GGGSGGGS (SEQ ID NO: 317) | his | 0.1 | 5594 |
| hIL10Ra_VHH14-hIL2Rg_VHH19 | GGGSGGGS (SEQ ID NO: 317) | his | 1 | 5672 |
| hIL10Ra_VHH14-hIL2Rg_VHH19 | GGGSGGGS (SEQ ID NO: 317) | his | 10 | 6017 |
| hIL10Ra_VHH14-hIL2Rg_VHH19 | GGGSGGGS (SEQ ID NO: 317) | his | 100 | 6843 |

TABLE 22-continued

Activity of VHH dimers on LPS treated Monocyte IL-1ß secretion.

| VHH1-VHH2 ID | Linker | Tag | Concentration of molecule (μM) | IL-1ß (pg/mL) |
|---|---|---|---|---|
| hIL10Ra_VHH14-hIL2Rg_VHH19 | GGSGGSGGSG (SEQ ID NO: 305) | his | 0 | 6244 |
| hIL10Ra_VHH14-hIL2Rg_VHH19 | GGSGGSGGSG (SEQ ID NO: 305) | his | 0 (LPS only) | 6880 |
| hIL10Ra_VHH14-hIL2Rg_VHH19 | GGSGGSGGSG (SEQ ID NO: 305) | his | 0.0001 | 5894 |
| hIL10Ra_VHH14-hIL2Rg_VHH19 | GGSGGSGGSG (SEQ ID NO: 305) | his | 0.001 | 5389 |
| hIL10Ra_VHH14-hIL2Rg_VHH19 | GGSGGSGGSG (SEQ ID NO: 305) | his | 0.01 | 6018 |
| hIL10Ra_VHH14-hIL2Rg_VHH19 | GGSGGSGGSG (SEQ ID NO: 305) | his | 0.1 | 5241 |
| hIL10Ra_VHH14-hIL2Rg_VHH19 | GGSGGSGGSG (SEQ ID NO: 305) | his | 1 | 5680 |
| hIL10Ra_VHH14-hIL2Rg_VHH19 | GGSGGSGGSG (SEQ ID NO: 305) | his | 10 | 7124 |
| hIL10Ra_VHH14-hIL2Rg_VHH19 | GGSGGSGGSG (SEQ ID NO: 305) | his | 100 | 8781 |

TABLE 23

Activity of VHH dimers on LPS treated Monocyte IL-6 secretion.

| VHH1-VHH2 ID | Linker | Tag | Concentration of molecule (μM) | IL-6 (pg/mL |
|---|---|---|---|---|
| hIL10Ra_VHH14-hIL2Rg_VHH19 | GGGS (SEQ ID NO: 9) | Fc | 0 | 31269 |
| hIL10Ra_VHH14-hIL2Rg_VHH19 | GGGS (SEQ ID NO: 9) | Fo | 0 (LPS only) | 45404 |
| hIL10Ra_VHH14-hIL2Rg_VHH19 | GGGS (SEQ ID NO: 9) | Fc | 0.0001 | 36196 |
| hIL10Ra_VHH14-hIL2Rg_VHH19 | GGGS (SEQ ID NO: 9) | Fc | 0.001 | 30932 |
| hIL10Ra_VHH14-hIL2Rg_VHH19 | GGGS (SEQ ID NO: 9 | Fc | 0.01 | 27747 |
| hIL10Ra_VHH14-hIL2Rg_VHH19 | GGGS (SEQ ID NO: 9) | Fc | 0.1 | 24512 |
| hIL10Ra_VHH14-hIL2Rg_VHH19 | GGGS (SEQ ID NO: 9 | Fc | 1 | 21794 |

TABLE 23-continued

Activity of VHH dimers on LPS treated Monocyte IL-6 secretion.

| VHH1-VHH2 ID | Linker | Tag | Concentration of molecule (μM) | IL-6 (pg/mL |
|---|---|---|---|---|
| hIL10Ra_VHH14-hIL2Rg_VHH19 | GGGS (SEQ ID NO: 9) | Fc | 10 | 31465 |
| hIL10Ra_VHH14-hIL2Rg_VHH19 | GGGS (SEQ ID NO: 9) | Fc | 100 | 44297 |
| hIL10Ra_VHH14-hIL2Rg_VHH19 | GGGS (SEQ ID NO: 9) | his | 0 | 31269 |
| hIL10Ra_VHH14-hIL2Rg_VHH19 | GGGS (SEQ ID NO: 9) | his | 0 (LPS only) | 45404 |
| hIL10Ra_VHH14-hIL2Rg_VHH19 | GGGS (SEQ ID NO: 9) | his | 0.0001 | 39223 |
| hIL10Ra_VHH14-hIL2Rg_VHH19 | GGGS (SEQ ID NO: 9) | his | 0.001 | 41699 |
| hIL10Ra_VHH14-hIL2Rg_VHH19 | GGGS (SEQ ID NO: 9) | his | 0.01 | 33346 |
| hIL10Ra_VHH14-hIL2Rg_VHH19 | GGGS (SEQ ID NO: 9) | his | 0.1 | 32608 |
| hIL10Ra_VHH14-hIL2Rg_VHH19 | GGGS (SEQ ID NO: 9) | his | 1 | 24493 |
| hIL10Ra_VHH14-hIL2Rg_VHH19 | GGGS (SEQ ID NO: 9) | his | 10 | 30616 |
| hIL10Ra_VHH14-hIL2Rg_VHH19 | GGGS (SEQ ID NO: 9) | his | 100 | 32878 |
| hIL10Ra_VHH14-hIL2Rg_VHH19 | No linker | his | 0 | 31269 |
| hIL10Ra_VHH14-hIL2Rg_VHH19 | No linker | his | 0 (LPS only) | 45404 |
| hIL10Ra_VHH14-hIL2Rg_VHH19 | No linker | his | 0.0001 | 30458 |
| hIL10Ra_VHH14-hIL2Rg_VHH19 | No linker | his | 0.001 | 31485 |
| hIL10Ra_VHH14-hIL2Rg_VHH19 | No linker | his | 0.01 | 30025 |
| hIL10Ra_VHH14-hIL2Rg_VHH19 | No linker | his | 0.1 | 37420 |
| hIL10Ra_VHH14-hIL2Rg_VHH19 | No linker | his | 1 | 27897 |
| hIL10Ra_VHH14-hIL2Rg_VHH19 | No linker | his | 10 | 33304 |
| hIL10Ra_VHH14-hIL2Rg_VHH19 | No linker | his | 100 | 36593 |
| hIL10Ra_VHH14-hIL2Rg_VHH19 | GS | his | 0 | 31269 |

TABLE 23-continued

Activity of VHH dimers on LPS treated Monocyte IL-6 secretion.

| VHH1-VHH2 ID | Linker | Tag | Concentration of molecule (μM) | IL-6 (pg/mL |
|---|---|---|---|---|
| hIL10Ra_VHH14-hIL2Rg_VHH19 | GS | his | 0 (LPS only) | 45404 |
| hIL10Ra_VHH14-hIL2Rg_VHH19 | GS | his | 0.0001 | 32766 |
| hIL10Ra_VHH14-hIL2Rg_VHH19 | GS | his | 0.001 | 42398 |
| hIL10Ra_VHH14-hIL2Rg_VHH19 | GS | his | 0.01 | 19882 |
| hIL10Ra_VHH14-hIL2Rg_VHH19 | GS | his | 0.1 | 41496 |
| hIL10Ra_VHH14-hIL2Rg_VHH19 | GS | his | 1 | 29074 |
| hIL10Ra_VHH14-hIL2Rg_VHH19 | GS | his | 10 | 47742 |
| hIL10Ra_VHH14-hIL2Rg_VHH19 | GS | his | 100 | 50764 |
| hIL10Ra_VHH14-hIL2Rg_VHH19 | GGSGGS (SEQ ID NO: 315) | his | 0 | 31269 |
| hIL10Ra_VHH14-hIL2Rg_VHH19 | GGSGGS (SEQ ID NO: 315) | his | 0 (LPS only) | 45404 |
| hIL10Ra_VHH14-hIL2Rg_VHH19 | GGSGGS (SEQ ID NO: 315) | his | 0.0001 | 34223 |
| hIL10Ra_VHH14-hIL2Rg_VHH19 | GGSGGS (SEQ ID NO: 315) | his | 0.001 | 33794 |
| hIL10Ra_VHH14-hIL2Rg_VHH19 | GGSGGS (SEQ ID NO: 315) | his | 0.01 | 30119 |
| hIL10Ra_VHH14-hIL2Rg_VHH19 | GGSGGS (SEQ ID NO: 315) | his | 0.1 | 27763 |
| hIL10Ra_VHH14-hIL2Rg_VHH19 | GGSGGS (SEQ ID NO: 315) | his | 1 | 26000 |
| hIL10Ra_VHH14-hIL2Rg_VHH19 | GGSGGS (SEQ ID NO: 315) | his | 10 | 38429 |
| hIL10Ra_VHH14-hIL2Rg_VHH19 | GGSGGS (SEQ ID NO: 315) | his | 100 | 48903 |
| hIL10Ra_VHH14-hIL2Rg_VHH19 | GGGSGGGS (SEQ ID NO: 317) | his | 0 | 31269 |
| hIL10Ra_VHH14-hIL2Rg_VHH19 | GGGSGGGS (SEQ ID NO: 317) | his | 0 (LPS only) | 45404 |
| hIL10Ra_VHH14-hIL2Rg_VHH19 | GGGSGGGS (SEQ ID NO: 317) | his | 0.0001 | 36784 |
| hIL10Ra_VHH14-hIL2Rg_VHH19 | GGGSGGGS (SEQ ID NO: 317) | his | 0.001 | 46305 |

TABLE 23-continued

Activity of VHH dimers on LPS treated Monocyte IL-6 secretion.

| VHH1-VHH2 ID | Linker | Tag | Concentration of molecule (μM) | IL-6 (pg/mL |
|---|---|---|---|---|
| hIL10Ra_VHH14-hIL2Rg_VHH19 | GGGSGGGS (SEQ ID NO: 317) | his | 0.01 | 21646 |
| hIL10Ra_VHH14-hIL2Rg_VHH19 | GGGSGGGS (SEQ ID NO: 317) | his | 0.1 | 35779 |
| hIL10Ra_VHH14-hIL2Rg_VHH19 | GGGSGGGS (SEQ ID NO: 317) | his | 1 | 27065 |
| hIL10Ra_VHH14-hIL2Rg_VHH19 | GGGSGGGS (SEQ ID NO: 317) | his | 10 | 29227 |
| hIL10Ra_VHH14-hIL2Rg_VHH19 | GGGSGGGS (SEQ ID NO: 317) | his | 100 | 36634 |
| hIL10Ra_VHH14-hIL2Rg_VHH19 | GGSGGSGGSG (SEQ ID NO: 305) | his | 0 | 31269 |
| hIL10Ra_VHH14-hIL2Rg_VHH19 | GGSGGSGGSG (SEQ ID NO: 305) | his | 0 (LP S only) | 45404 |
| hIL10Ra_VHH14-hIL2Rg_VHH19 | GGSGGSGGSG (SEQ ID NO: 305) | his | 0.0001 | 32788 |
| hIL10Ra_VHH14-hIL2Rg_VHH19 | GGSGGSGGSG (SEQ ID NO: 305) | his | 0.001 | 41119 |
| hIL10Ra_VHH14-hIL2Rg_VHH19 | GGSGGSGGSG (SEQ ID NO: 305) | his | 0.01 | 37396 |
| hIL10Ra_VHH14-hIL2Rg_VHH19 | GGSGGSGGSG (SEQ ID NO: 305) | his | 0.1 | 35343 |
| hIL10Ra_VHH14-hIL2Rg_VHH19 | GGSGGSGGSG (SEQ ID NO: 305) | his | 1 | 29405 |
| hIL10Ra_VHH14-hIL2Rg_VHH19 | GGSGGSGGSG (SEQ ID NO: 305) | his | 10 | 49333 |
| hIL10Ra_VHH14-hIL2Rg_VHH19 | GGSGGSGGSG (SEQ ID NO: 305) | his | 100 | 55000 |

TABLE 24

Activity of VHH dimers on LPS treated Monocyte TNF-α secretion.

| VHH1-VHH2 ID | Linker | Tag | Concentration ofmolecule (μM) | TNF-α (pg/mL) |
|---|---|---|---|---|
| hIL10Ra_VHH14-hIL2Rg_VHH19 | GGGS (SEQ ID NO: 9) | Fc | 0 | 7455 |

TABLE 24-continued

Activity of VHH dimers on LPS treated Monocyte TNF-α secretion.

| VHH1-VHH2 ID | Linker | Tag | Concentration ofmolecule (μM) | TNF-α (pg/mL) |
|---|---|---|---|---|
| hIL10Ra_VHH14 hIL2Rg_VHH19 | GGGS (SEQ ID NO: 9) | Fc | 0 (LPS only) | 10138 |
| hIL10Ra_VHH14- hIL2Rg_VHH19 | GGGS (SEQ ID NO: 9) | Fc | 0.0001 | 6234 |
| hIL10Ra_VHH14- hIL2Rg_VHH19 | GGGS (SEQ ID NO: 9) | Fc | 0.001 | 5120 |
| hIL10Ra_VHH14- hIL2Rg_VHH19 | GGGS (SEQ ID NO: 9) | Fc | 0.01 | 5443 |
| hIL10Ra_VHH14- hIL2Rg_VHH19 | GGGS (SEQ ID NO: 9) | Fc | 0.1 | 3960 |
| hIL10Ra_VHH14- hIL2Rg_VHH19 | GGGS (SEQ ID NO: 9) | Fc | 1 | 2790 |
| hIL10Ra_VHH14- hIL2Rg_VHH19 | GGGS (SEQ ID NO: 9) | FC | 10 | 3887 |
| hIL10Ra_VHH14- hIL2Rg_VHH19 | GGGS (SEQ ID NO: 9) | Fc | 100 | 6253 |
| hIL10Ra_VHH14- hIL2Rg_VHH19 | GGGS (SEQ ID NO: 9) | his | 0 | 7455 |
| hIL10Ra_VHH14- hIL2Rg_VHH19 | GGGS (SEQ ID NO: 9) | his | 0 (LPS only) | 10138 |
| hIL10Ra_VHH14- hIL2Rg_VHH19 | GGGS (SEQ ID NO: 9) | his | 0.0001 | 8435 |
| hIL10Ra_VHH14- hIL2Rg_VHH19 | GGGS (SEQ ID NO: 9) | his | 0.001 | 6253 |
| hIL10Ra_VHH14- hIL2Rg_VHH19 | GGGS (SEQ ID NO: 9) | his | 0.01 | 5501 |
| hIL10Ra_VHH14- hIL2Rg_VHH19 | GGGS (SEQ ID NO: 9) | his | 0.1 | 5631 |
| hIL10Ra_VHH14- hIL2Rg_VHH19 | GGGS (SEQ ID NO: 9) | his | 1 | 4741 |
| hIL10Ra_VHH14- hIL2Rg_VHH19 | GGGS (SEQ ID NO: 9) | his | 10 | 6068 |
| hIL10Ra_VHH14- hIL2Rg_VHH19 | GGGS (SEQ ID NO: 9) | his | 100 | 7228 |
| hIL10Ra_VHH14- hIL2Rg_VHH19 | No linker | his | 0 | 7455 |
| hIL10Ra_VHH14- hIL2Rg_VHH19 | No linker | his | 0 (LPS only) | 10138 |
| hIL10Ra_VHH14- hIL2Rg_VHH19 | No linker | his | 0.0001 | 6656 |
| hIL10Ra_VHH14- hIL2Rg_VHH19 | No linker | his | 0.001 | 5247 |
| hIL10Ra_VHH14- hIL2Rg_VHH19 | No linker | his | 0.01 | 5400 |
| hIL10Ra_VHH14- hIL2Rg_VHH19 | No linker | his | 0.1 | 7258 |
| hIL10Ra_VHH14- hIL2Rg_VHH19 | No linker | his | 1 | 5004 |
| hIL10Ra_VHH14- hIL2Rg_VHH19 | No linker | his | 10 | 6609 |
| hIL10Ra_VHH14- hIL2Rg_VHH19 | No linker | his | 100 | 7923 |
| hIL10Ra_VHH14- hIL2Rg_VHH19 | GS | his | 0 | 7455 |
| hIL10Ra_VHH14- hIL2Rg_VHH19 | GS | his | 0 (LPS only) | 10138 |
| hIL10Ra_VHH14- hIL2Rg_VHH19 | GS | his | 0.0001 | 6800 |
| hIL10Ra_VHH14- hIL2Rg_VHH19 | GS | his | 0.001 | 6768 |
| hIL10Ra_VHH14- hIL2Rg_VHH19 | GS | his | 0.01 | 4996 |
| hIL10Ra_VHH14- hIL2Rg_VHH19 | GS | his | 0.1 | 5787 |
| hIL10Ra_VHH14- hIL2Rg_VHH19 | GS | his | 1 | 5153 |
| hIL10Ra_VHH14- hIL2Rg_VHH19 | GS | his | 10 | 6176 |
| hIL10Ra_VHH14- hIL2Rg_VHH19 | GS | his | 100 | 8029 |
| hIL10Ra_VHH14- hIL2Rg_VHH19 | GGSGGS (SEQ ID NO: 315) | his | 0 | 7455 |
| hIL10Ra_VHH14- hIL2Rg_VHH19 | GGSGGS (SEQ ID NO: 315) | his | 0 (LPS only) | 10138 |
| hIL10Ra_VHH14- hIL2Rg_VHH19 | GGSGGS (SEQ ID NO: 315) | his | 0.0001 | 7239 |
| hIL10Ra_VHH14- hIL2Rg_VHH19 | GGSGGS (SEQ ID NO: 315) | his | 0.001 | 6237 |
| hIL10Ra_VHH14- hIL2Rg_VHH19 | GGSGGS (SEQ ID NO: 315) | his | 0.01 | 6102 |
| hIL10Ra_VHH14- hIL2Rg_VHH19 | GGSGGS (SEQ ID NO: 315) | his | 0.1 | 5731 |
| hIL10Ra_VHH14- hIL2Rg_VHH19 | GGSGGS (SEQ ID NO: 315) | his | 1 | 5739 |
| hIL10Ra_VHH14- hIL2Rg_VHH19 | GGSGGS (SEQ ID NO: 315) | his | 10 | 6621 |
| hIL10Ra_VHH14- hIL2Rg_VHH19 | GGSGGS (SEQ ID NO: 315) | his | 100 | 8850 |
| hIL10Ra_VHH14- hIL2Rg_VHH19 | GGGSGGGS (SEQ ID NO: 317) | his | 0 | 7455 |

TABLE 24-continued

Activity of VHH dimers on LPS treated Monocyte TNF-α secretion.

| VHH1-VHH2 ID | Linker | Tag | Concentration ofmolecule (μM) | TNF-α (pg/mL) |
|---|---|---|---|---|
| hIL10Ra_VHH14-hIL2Rg_VHH19 | GGGSGGGS (SEQ ID NO: 317) | his | 0 (LPS only) | 10138 |
| hIL10Ra_VHH14-hIL2Rg_VHH19 | GGGSGGGS (SEQ ID NO: 317) | his | 0.0001 | 6786 |
| hIL10Ra_VHH14-hIL2Rg_VHH19 | GGGSGGGS (SEQ ID NO: 317) | his | 0.001 | 7202 |
| hIL10Ra_VHH14-hIL2Rg_VHH19 | GGGSGGGS (SEQ ID NO: 317) | his | 0.01 | 4699 |
| hIL10Ra_VHH14-hIL2Rg_VHH19 | GGGSGGGS (SEQ ID NO: 317) | his | 0.1 | 6822 |
| hIL10Ra_VHH14-hIL2Rg_VHH19 | GGGSGGGS (SEQ ID NO: 317) | his | 1 | 5620 |
| hIL10Ra_VHH14-hIL2Rg_VHH19 | GGGSGGGS (SEQ ID NO: 317) | his | 10 | 6187 |
| hIL10Ra_VHH14-hIL2Rg_VHH19 | GGGSGGGS (SEQ ID NO: 317) | his | 100 | 8372 |
| hIL10Ra_VHH14-hIL2Rg_VHH19 | GGSGGSGGSG (SEQ ID NO: 305) | his | 0 | 7455 |
| hIL10Ra_VHH14-hIL2Rg_VHH19 | GGSGGSGGSG (SEQ ID NO: 305) | his | 0 (LPS only) | 10138 |
| hIL10Ra_VHH14-hIL2Rg_VHH19 | GGSGGSGGSG (SEQ ID NO: 305) | his | 0.0001 | 7366 |
| hIL10Ra_VHH14-hIL2Rg_VHH19 | GGSGGSGGSG (SEQ ID NO: 305) | his | 0.001 | 7535 |
| hIL10Ra_VHH14-hIL2Rg_VHH19 | GGSGGSGGSG (SEQ ID NO: 305) | his | 0.01 | 8008 |
| hIL10Ra_VHH14-hIL2Rg_VHH19 | GGSGGSGGSG (SEQ ID NO: 305) | his | 0.1 | 8891 |
| hIL10Ra_VHH14-hIL2Rg_VHH19 | GGSGGSGGSG (SEQ ID NO: 305) | his | 1 | 7561 |
| hIL10Ra_VHH14-hIL2Rg_VHH19 | GGSGGSGGSG (SEQ ID NO: 305) | his | 10 | 8465 |
| hIL10Ra_VHH14-hIL2Rg_VHH19 | GGSGGSGGSG (SEQ ID NO: 305) | his | 100 | 10573 |

TABLE 25

Activity of VHH dimers on LPS treated Monocyte IL-8 secretion.

| VHH1-VHH2 ID | Linker | Tag | Concentration of molecule (μM) | IL-8 (pg/mL) |
|---|---|---|---|---|
| hIL10Ra_VHH14-hIL2Rg_VHH19 | GGGS (SEQ ID NO: 9) | Fc | 0 | 68763 |
| hIL10Ra_VHH14-hIL2Rg_VHH19 | GGGS (SEQ ID NO: 9) | Fc | 0 (LPS only) | 68829 |
| hIL10Ra_VHH14-hIL2Rg_VHH19 | GGGS (SEQ ID NO: 9) | Fo | 0.0001 | 73149 |
| hIL10Ra_VHH14-hIL2Rg_VHH19 | GGGS (SEQ ID NO: 9) | Fc | 0.001 | 68963 |
| hIL10Ra_VHH14-hIL2Rg_VHH19 | GGGS (SEQ ID NO: 9) | FC | 0.01 | 72977 |
| hIL10Ra_VHH14-hIL2Rg_VHH19 | GGGS (SEQ ID NO: 9) | FC | 0.1 | 69358 |
| hIL10Ra_VHH14-hIL2Rg_VHH19 | GGGS (SEQ ID NO: 9) | FC | 1 | 72648 |
| hIL10Ra_VHH14-hIL2Rg_VHH19 | GGGS (SEQ ID NO: 9) | Fc | 10 | 68592 |
| hIL10Ra_VHH14-hIL2Rg_VHH19 | GGGS (SEQ ID NO: 9) | Fc | 100 | 71843 |
| hIL10Ra_VHH14-hIL2Rg_VHH19 | GGGS (SEQ ID NO: 9) | his | 0 | 68763 |
| hIL10Ra_VHH14-hIL2Rg_VHH19 | GGGS (SEQ ID NO: 9) | his | 0 (LPS only) | 68829 |
| hIL10Ra_VHH14-hIL2Rg_VHH19 | GGGS (SEQ ID NO: 9) | his | 0.0001 | 72537 |
| hIL10Ra_VHH14-hIL2Rg_VHH19 | GGGS (SEQ ID NO: 9) | his | 0.001 | 69567 |
| hIL10Ra_VHH14-hIL2Rg_VHH19 | GGGS (SEQ ID NO: 9) | his | 0.01 | 71836 |
| hIL10Ra_VHH14-hIL2Rg_VHH19 | GGGS (SEQ ID NO: 9) | his | 0.1 | 67444 |
| hIL10Ra_VHH14-hIL2Rg_VHH19 | GGGS (SEQ ID NO: 9) | his | 1 | 71572 |
| hIL10Ra_VHH14-hIL2Rg_VHH19 | GGGS (SEQ ID NO: 9) | his | 10 | 69052 |
| hIL10Ra_VHH14-hIL2Rg_VHH19 | GGGS (SEQ ID NO: 9) | his | 100 | 71296 |
| hIL10Ra_VHH14-hIL2Rg_VHH19 | No linker | his | 0 | 68763 |
| hIL10Ra_VHH14-hIL2Rg_VHH19 | No linker | his | 0 (LPS only) | 68829 |
| hIL10Ra_VHH14-hIL2Rg_VHH19 | No linker | his | 0.0001 | 73472 |
| hIL10Ra_VHH14-hIL2Rg_VHH19 | No linker | his | 0.001 | 69342 |
| hIL10Ra_VHH14-hIL2Rg_VHH19 | No linker | his | 0.01 | 73018 |
| hIL10Ra_VHH14-hIL2Rg_VHH19 | No linker | his | 0.1 | 69553 |

TABLE 25-continued

Activity of VHH dimers on LPS treated Monocyte IL-8 secretion.

| VHH1-VHH2 ID | Linker | Tag | Concentration of molecule (μM) | IL-8 (pg/mL) |
|---|---|---|---|---|
| hIL10Ra_VHH14-hIL2Rg_VHH19 | No linker | his | 1 | 72874 |
| hIL10Ra_VHH14-hIL2Rg_VHH19 | No linker | his | 10 | 69630 |
| hIL10Ra_VHH14-hIL2Rg_VHH19 | No linker | his | 100 | 71764 |
| hIL10Ra_VHH14-hIL2Rg_VHH19 | GS | his | 0 | 68763 |
| hIL10Ra_VHH14-hIL2Rg_VHH19 | GS | his | 0 (LPS only) | 68829 |
| hIL10Ra_VHH14-hIL2Rg_VHH19 | GS | his | 0.0001 | 73590 |
| hIL10Ra_VHH14-hIL2Rg_VHH19 | GS | his | 0.001 | 69641 |
| hIL10Ra_VHH14-hIL2Rg_VHH19 | GS | his | 0.01 | 70913 |
| hIL10Ra_VHH14-hIL2Rg_VHH19 | GS | his | 0.1 | 69034 |
| hIL10Ra_VHH14-hIL2Rg_VHH19 | GS | his | 1 | 71858 |
| hIL10Ra_VHH14-hIL2Rg_VHH19 | GS | his | 10 | 68712 |
| hIL10Ra_VHH14-hIL2Rg_VHH19 | GS | his | 100 | 72069 |
| hIL10Ra_VHH14-hIL2Rg_VHH19 | GGSGGS (SEQ ID NO: 315) | his | 0 | 68763 |
| hIL10Ra_VHH14-hIL2Rg_VHH19 | GGSGGS (SEQ ID NO: 315) | his | 0 (LPS only) | 68829 |
| hIL10Ra_VHH14-hIL2Rg_VHH19 | GGSGGS (SEQ ID NO: 315) | his | 0.0001 | 73805 |
| hIL10Ra_VHH14-hIL2Rg_VHH19 | GGSGGS (SEQ ID NO: 315) | his | 0.001 | 69583 |
| hIL10Ra_VHH14-hIL2Rg_VHH19 | GGSGGS (SEQ ID NO: 315) | his | 0.01 | 72588 |
| hIL10Ra_VHH14-hIL2Rg_VHH19 | GGSGGS (SEQ ID NO: 315) | his | 0.1 | 68146 |
| hIL10Ra_VHH14-hIL2Rg_VHH19 | GGSGGS (SEQ ID NO: 315) | his | 1 | 72922 |
| hIL10Ra_VHH14-hIL2Rg_VHH19 | GGSGGS (SEQ ID NO: 315) | his | 10 | 69402 |
| hIL10Ra_VHH14-hIL2Rg_VHH19 | GGSGGS (SEQ ID NO: 315) | his | 100 | 72996 |
| hIL10Ra_VHH14-hIL2Rg_VHH19 | GGGSGGGS (SEQ ID NO: 317) | his | 0 | 68763 |
| hIL10Ra_VHH14-hIL2Rg_VHH19 | GGGSGGGS (SEQ ID NO: 317) | his | 0 (LPS only) | 68829 |

TABLE 25-continued

Activity of VHH dimers on LPS treated Monocyte IL-8 secretion.

| VHH1-VHH2 ID | Linker | Tag | Concentration of molecule (μM) | IL-8 (pg/mL) |
|---|---|---|---|---|
| hIL10Ra_VHH14-hIL2Rg_VHH19 | GGGSGGGS (SEQ ID NO: 317) | his | 0.0001 | 72738 |
| hIL10Ra_VHH14-hIL2Rg_VHH19 | GGGSGGGS (SEQ ID NO: 317) | his | 0.001 | 69165 |
| hIL10Ra_VHH14-hIL2Rg_VHH19 | GGGSGGGS (SEQ ID NO: 317) | his | 0.01 | 70771 |
| hIL10Ra_VHH14-hIL2Rg_VHH19 | GGGSGGGS (SEQ ID NO: 317) | his | 0.1 | 67136 |
| hIL10Ra_VHH14-hIL2Rg_VHH19 | GGGSGGGS (SEQ ID NO: 317) | his | 1 | 71990 |
| hIL10Ra_VHH14-hIL2Rg_VHH19 | GGGSGGGS (SEQ ID NO: 317) | his | 10 | 68600 |
| hIL10Ra_VHH14-hIL2Rg_VHH19 | GGGSGGGS (SEQ ID NO: 317) | his | 100 | 72121 |
| hIL10Ra_VHH14-hIL2Rg_VHH19 | GGSGGSGGSG (SEQ ID NO: 305) | his | 0 | 68763 |
| hIL10Ra_VHH14-hIL2Rg_VHH19 | GGSGGSGGSG (SEQ ID NO: 305) | his | 0 (LPS only) | 68829 |
| hIL10Ra_VHH14-hIL2Rg_VHH19 | GGSGGSGGSG (SEQ ID NO: 305) | his | 0.0001 | 73256 |
| hIL10Ra_VHH14-hIL2Rg_VHH19 | GGSGGSGGSG (SEQ ID NO: 305) | his | 0.001 | 68734 |
| hIL10Ra_VHH14-hIL2Rg_VHH19 | GGSGGSGGSG (SEQ ID NO: 305) | his | 0.01 | 73317 |
| hIL10Ra_VHH14-hIL2Rg_VHH19 | GGSGGSGGSG (SEQ ID NO: 305) | his | 0.1 | 68370 |
| hIL10Ra_VHH14-hIL2Rg_VHH19 | GGSGGSGGSG (SEQ ID NO: 305) | his | 1 | 72889 |
| hIL10Ra_VHH14-hIL2Rg_VHH19 | GGSGGSGGSG (SEQ ID NO: 305) | his | 10 | 69439 |
| hIL10Ra_VHH14-hIL2Rg_VHH19 | GGSGGSGGSG (SEQ ID NO: 305) | his | 100 | 72622 |

What is claimed is:

1. An IL10Rα/IL2Rγ binding molecule that specifically binds to IL10Rα subunit (IL10Rα) and IL2Rγ subunit (IL2Rγ), wherein the binding molecule comprises a single-domain antibody (sdAb) that specifically binds to IL10Rα (an anti-IL10Rα sdAb), wherein the anti-IL10Rα sdAb comprises a CDR1 comprising SEQ ID NO: 38, a CDR2 comprising a SEQ ID NO: 56 and a CDR 3 comprising SEQ ID NO: 74 and a sdAb that specifically binds to IL2Rγ (an anti-IL2Rγ sdAb) comprising a CDR1 comprising SEQ ID NO: 97, a CDR2 comprising a SEQ ID NO: 120 and a CDR3 comprising SEQ ID NO: 143, wherein the IL10Rα sdAb and IL2Rγ sdAb are in stable association via a peptide bond, a peptide linker, or complementary knob and hole Fc domains.

2. The IL10Rα/IL2Rγ binding molecule of claim 1, wherein the anti-IL10Rα sdAb is a VHH antibody and/or the anti-IL2Rγ sdAb is a VHH antibody.

3. The IL10Rα/IL2Rγ binding molecule of claim 1, wherein the anti-IL10Rα sdAb and the anti-IL2Rγ sdAb are joined by a peptide linker.

4. The IL10Rα/IL2Rγ binding molecule of claim 3, wherein the peptide linker comprises between 1 and 50 amino acids.

5. The IL10Rα/IL2Rγ binding molecule of claim 4, wherein the peptide linker comprises a sequence of GGGS (SEQ ID NO: 9).

6. The IL10Rα/IL2Rγ binding molecule of claim 1, wherein the binding molecule comprises the anti-IL10Rα sdAb linked to the N-terminus of a linker and the anti-IL2Rγ sdAb linked to the C-terminus of the linker.

7. The IL10Rα/IL2Rγ binding molecule of claim 6, wherein the anti-IL10Rα sdAb comprises a sequence having at least 90% sequence identity to SEQ ID NO: 206.

8. The IL10Rα/IL2Rγ binding molecule of claim 6, wherein the anti-IL10Rα sdAb comprises SEQ ID NO: 206 or SEQ ID NO: 203.

9. The IL10Rα/IL2Rγ binding molecule of claim 6, wherein the anti-IL2Rγ sdAb comprises a sequence having at least 90% sequence identity to SEQ ID NO: 229.

10. The IL10Rα/IL2Rγ binding molecule of claim 6, wherein the anti-IL2Rγ sdAb comprises SEQ ID NO: 229, SEQ ID NO: 213 or SEQ ID NO: 217.

11. The IL10Rα/IL2Rγ binding molecule of claim 6, wherein the IL10Rα sdAb comprises a sequence having at least 90% sequence identity to SEQ ID NO: 206, and the anti-IL2Rγ sdAb comprises a sequence having at least 90% sequence identity to SEQ ID NO: 229.

12. The IL10Rα/IL2Rγ binding molecule of claim 6, wherein the anti-IL10Rα sdAb comprises SEQ ID NO: 206 or SEQ ID NO: 203, and the anti-IL2Rγ sdAb comprises SEQ ID NO: 229, SEQ ID NO: 213 or SEQ ID NO: 217.

13. The IL10Rα/IL2Rγ binding molecule of claim 1, wherein the binding molecule comprises the anti-IL2Rγ sdAb linked to the N-terminus of a linker and the anti-IL10Rα sdAb linked to the C-terminus of the linker.

14. A pharmaceutical composition comprising the IL10Rα/IL2Rγ binding molecule of claim 1 and a pharmaceutically acceptable carrier.

* * * * *

SEQUENCE LISTING

<160> NUMBER OF SEQ ID NOS: 317

<210> SEQ ID NO 1
<211> LENGTH: 578
<212> TYPE: PRT
<213> ORGANISM: Homo sapiens

<400> SEQUENCE: 1

Met Leu Pro Cys Leu Val Val Leu Leu Ala Ala Leu Leu Ser Leu Arg
1 5 10 15

Leu Gly Ser Asp Ala His Gly Thr Glu Leu Pro Ser Pro Pro Ser Val
20 25 30

Trp Phe Glu Ala Glu Phe Phe His His Ile Leu His Trp Thr Pro Ile
35 40 45

Pro Asn Gln Ser Glu Ser Thr Cys Tyr Glu Val Ala Leu Leu Arg Tyr
50 55 60

Gly Ile Glu Ser Trp Asn Ser Ile Ser Asn Cys Ser Gln Thr Leu Ser
65 70 75 80

Tyr Asp Leu Thr Ala Val Thr Leu Asp Leu Tyr His Ser Asn Gly Tyr
85 90 95

Arg Ala Arg Val Arg Ala Val Asp Gly Ser Arg His Ser Asn Trp Thr
100 105 110

Val Thr Asn Thr Arg Phe Ser Val Asp Glu Val Thr Leu Thr Val Gly
115 120 125

Ser Val Asn Leu Glu Ile His Asn Gly Phe Ile Leu Gly Lys Ile Gln
130 135 140

Leu Pro Arg Pro Lys Met Ala Pro Ala Asn Asp Thr Tyr Glu Ser Ile
145 150 155 160

Phe Ser His Phe Arg Glu Tyr Glu Ile Ala Ile Arg Lys Val Pro Gly
165 170 175

Asn Phe Thr Phe Thr His Lys Lys Val Lys His Glu Asn Phe Ser Leu
180 185 190

Leu Thr Ser Gly Glu Val Gly Glu Phe Cys Val Gln Val Lys Pro Ser
195 200 205

Val Ala Ser Arg Ser Asn Lys Gly Met Trp Ser Lys Glu Glu Cys Ile
210 215 220

Ser Leu Thr Arg Gln Tyr Phe Thr Val Thr Asn Val Ile Ile Phe Phe
225 230 235 240

Ala Phe Val Leu Leu Leu Ser Gly Ala Leu Ala Tyr Cys Leu Ala Leu
245 250 255

Gln Leu Tyr Val Arg Arg Arg Lys Lys Leu Pro Ser Val Leu Leu Phe
260 265 270

Lys Lys Pro Ser Pro Phe Ile Phe Ile Ser Gln Arg Pro Ser Pro Glu
275 280 285

Thr Gln Asp Thr Ile His Pro Leu Asp Glu Glu Ala Phe Leu Lys Val
290 295 300

Ser Pro Glu Leu Lys Asn Leu Asp Leu His Gly Ser Thr Asp Ser Gly
305 310 315 320

Phe Gly Ser Thr Lys Pro Ser Leu Gln Thr Glu Glu Pro Gln Phe Leu
325 330 335

Leu Pro Asp Pro His Pro Gln Ala Asp Arg Thr Leu Gly Asn Arg Glu
340 345 350

Pro Pro Val Leu Gly Asp Ser Cys Ser Ser Gly Ser Ser Asn Ser Thr
355 360 365

Asp Ser Gly Ile Cys Leu Gln Glu Pro Ser Leu Ser Pro Ser Thr Gly
    370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Pro Glu Pro Glu Val
            420                 425                 430

Pro Gly Glu Glu Asp Pro Ala Ala Val Ala Phe Gln Gly Tyr Leu Arg
        435                 440                 445

Gln Thr Arg Cys Ala Glu Glu Lys Ala Thr Lys Thr Gly Cys Leu Glu
    450                 455                 460

Glu Glu Ser Pro Leu Thr Asp Gly Leu Gly Pro Lys Phe Gly Arg Cys
465                 470                 475                 480

Leu Val Asp Glu Ala Gly Leu His Pro Pro Ala Leu Ala Lys Gly Tyr
                485                 490                 495

Leu Lys Gln Asp Pro Leu Glu Met Thr Leu Ala Ser Ser Gly Ala Pro
            500                 505                 510

Thr Gly Gln Trp Asn Gln Pro Thr Glu Glu Trp Ser Leu Leu Ala Leu
        515                 520                 525

Ser Ser Cys Ser Asp Leu Gly Ile Ser Asp Trp Ser Phe Ala His Asp
    530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu

<210> SEQ ID NO 2
<211> LENGTH: 214
<212> TYPE: PRT
<213> ORGANISM: Homo sapiens

<400> SEQUENCE: 2

His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
            20                  25                  30

Ser Thr Cys Tyr Glu Val Ala Leu Leu Arg Tyr Gly Ile Glu Ser Trp
        35                  40                  45

Asn Ser Ile Ser Asn Cys Ser Gln Thr Leu Ser Tyr Asp Leu Thr Ala
    50                  55                  60

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
                85                  90                  95

Phe Ser Val Asp Glu Val Thr Leu Thr Val Gly Ser Val Asn Leu Glu
            100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
    130                 135                 140

Glu Tyr Glu Ile Ala Ile Arg Lys Val Pro Gly Asn Phe Thr Phe Thr
145                 150                 155                 160

```
His Lys Lys Val Lys His Glu Asn Phe Ser Leu Leu Thr Ser Gly Glu
                165                 170                 175

Val Gly Glu Phe Cys Val Gln Val Lys Pro Ser Val Ala Ser Arg Ser
            180                 185                 190

Asn Lys Gly Met Trp Ser Lys Glu Glu Cys Ile Ser Leu Thr Arg Gln
        195                 200                 205

Tyr Phe Thr Val Thr Asn
    210


<210> SEQ ID NO 3
<211> LENGTH: 369
<212> TYPE: PRT
<213> ORGANISM: Homo sapiens

<400> SEQUENCE: 3

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320
```

```
Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn
            340                 345                 350

Gln His Ser Pro Tyr Trp Ala Pro Pro Cys Tyr Thr Leu Lys Pro Glu
        355                 360                 365

Thr


<210> SEQ ID NO 4
<211> LENGTH: 240
<212> TYPE: PRT
<213> ORGANISM: Homo sapiens

<400> SEQUENCE: 4

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240


<210> SEQ ID NO 5
<211> LENGTH: 369
<212> TYPE: PRT
<213> ORGANISM: Mus musculus

<400> SEQUENCE: 5

Met Leu Lys Leu Leu Leu Ser Pro Arg Ser Phe Leu Val Leu Gln Leu
1               5                   10                  15

Leu Leu Leu Arg Ala Gly Trp Ser Ser Lys Val Leu Met Ser Ser Ala
            20                  25                  30
```

```
Asn Glu Asp Ile Lys Ala Asp Leu Ile Leu Thr Ser Thr Ala Pro Glu
        35                  40                  45

His Leu Ser Ala Pro Thr Leu Pro Leu Pro Glu Val Gln Cys Phe Val
    50                  55                  60

Phe Asn Ile Glu Tyr Met Asn Cys Thr Trp Asn Ser Ser Ser Glu Pro
65                  70                  75                  80

Gln Ala Thr Asn Leu Thr Leu His Tyr Arg Tyr Lys Val Ser Asp Asn
                85                  90                  95

Asn Thr Phe Gln Glu Cys Ser His Tyr Leu Phe Ser Lys Glu Ile Thr
            100                 105                 110

Ser Gly Cys Gln Ile Gln Lys Glu Asp Ile Gln Leu Tyr Gln Thr Phe
        115                 120                 125

Val Val Gln Leu Gln Asp Pro Gln Lys Pro Gln Arg Arg Ala Val Gln
    130                 135                 140

Lys Leu Asn Leu Gln Asn Leu Val Ile Pro Arg Ala Pro Glu Asn Leu
145                 150                 155                 160

Thr Leu Ser Asn Leu Ser Glu Ser Gln Leu Glu Leu Arg Trp Lys Ser
                165                 170                 175

Arg His Ile Lys Glu Arg Cys Leu Gln Tyr Leu Val Gln Tyr Arg Ser
            180                 185                 190

Asn Arg Asp Arg Ser Trp Thr Glu Leu Ile Val Asn His Glu Pro Arg
        195                 200                 205

Phe Ser Leu Pro Ser Val Asp Glu Leu Lys Arg Tyr Thr Phe Arg Val
    210                 215                 220

Arg Ser Arg Tyr Asn Pro Ile Cys Gly Ser Ser Gln Gln Trp Ser Lys
225                 230                 235                 240

Trp Ser Gln Pro Val His Trp Gly Ser His Thr Val Glu Glu Asn Pro
                245                 250                 255

Ser Leu Phe Ala Leu Glu Ala Val Leu Ile Pro Val Gly Thr Met Gly
            260                 265                 270

Leu Ile Ile Thr Leu Ile Phe Val Tyr Cys Trp Leu Glu Arg Met Pro
        275                 280                 285

Pro Ile Pro Pro Ile Lys Asn Leu Glu Asp Leu Val Thr Glu Tyr Gln
    290                 295                 300

Gly Asn Phe Ser Ala Trp Ser Gly Val Ser Lys Gly Leu Thr Glu Ser
305                 310                 315                 320

Leu Gln Pro Asp Tyr Ser Glu Arg Phe Cys His Val Ser Glu Ile Pro
                325                 330                 335

Pro Lys Gly Gly Ala Leu Gly Glu Gly Pro Gly Gly Ser Pro Cys Ser
            340                 345                 350

Leu His Ser Pro Tyr Trp Pro Pro Pro Cys Tyr Ser Leu Lys Pro Glu
        355                 360                 365

Ala


<210> SEQ ID NO 6
<211> LENGTH: 241
<212> TYPE: PRT
<213> ORGANISM: Mus musculus

<400> SEQUENCE: 6

Trp Ser Ser Lys Val Leu Met Ser Ser Ala Asn Glu Asp Ile Lys Ala
1               5                   10                  15

Asp Leu Ile Leu Thr Ser Thr Ala Pro Glu His Leu Ser Ala Pro Thr
            20                  25                  30
```

```
Leu Pro Leu Pro Glu Val Gln Cys Phe Val Phe Asn Ile Glu Tyr Met
        35                  40                  45

Asn Cys Thr Trp Asn Ser Ser Ser Glu Pro Gln Ala Thr Asn Leu Thr
    50                  55                  60

Leu His Tyr Arg Tyr Lys Val Ser Asp Asn Asn Thr Phe Gln Glu Cys
65                  70                  75                  80

Ser His Tyr Leu Phe Ser Lys Glu Ile Thr Ser Gly Cys Gln Ile Gln
                85                  90                  95

Lys Glu Asp Ile Gln Leu Tyr Gln Thr Phe Val Val Gln Leu Gln Asp
            100                 105                 110

Pro Gln Lys Pro Gln Arg Arg Ala Val Gln Lys Leu Asn Leu Gln Asn
        115                 120                 125

Leu Val Ile Pro Arg Ala Pro Glu Asn Leu Thr Leu Ser Asn Leu Ser
    130                 135                 140

Glu Ser Gln Leu Glu Leu Arg Trp Lys Ser Arg His Ile Lys Glu Arg
145                 150                 155                 160

Cys Leu Gln Tyr Leu Val Gln Tyr Arg Ser Asn Arg Asp Arg Ser Trp
                165                 170                 175

Thr Glu Leu Ile Val Asn His Glu Pro Arg Phe Ser Leu Pro Ser Val
            180                 185                 190

Asp Glu Leu Lys Arg Tyr Thr Phe Arg Val Arg Ser Arg Tyr Asn Pro
        195                 200                 205

Ile Cys Gly Ser Ser Gln Gln Trp Ser Lys Trp Ser Gln Pro Val His
    210                 215                 220

Trp Gly Ser His Thr Val Glu Glu Asn Pro Ser Leu Phe Ala Leu Glu
225                 230                 235                 240

Ala


<210> SEQ ID NO 7
<211> LENGTH: 557
<212> TYPE: PRT
<213> ORGANISM: Homo sapiens

<400> SEQUENCE: 7

His Gly Thr Glu Leu Pro Ser Pro Pro Ser Val Trp Phe Glu Ala Glu
1               5                   10                  15

Phe Phe His His Ile Leu His Trp Thr Pro Ile Pro Asn Gln Ser Glu
            20                  25                  30

Ser Thr Cys Tyr Glu Val Ala Leu Leu Arg Tyr Gly Ile Glu Ser Trp
        35                  40                  45

Asn Ser Ile Ser Asn Cys Ser Gln Thr Leu Ser Tyr Asp Leu Thr Ala
    50                  55                  60

Val Thr Leu Asp Leu Tyr His Ser Asn Gly Tyr Arg Ala Arg Val Arg
65                  70                  75                  80

Ala Val Asp Gly Ser Arg His Ser Asn Trp Thr Val Thr Asn Thr Arg
                85                  90                  95

Phe Ser Val Asp Glu Val Thr Leu Thr Val Gly Ser Val Asn Leu Glu
            100                 105                 110

Ile His Asn Gly Phe Ile Leu Gly Lys Ile Gln Leu Pro Arg Pro Lys
        115                 120                 125

Met Ala Pro Ala Asn Asp Thr Tyr Glu Ser Ile Phe Ser His Phe Arg
    130                 135                 140

Glu Tyr Glu Ile Ala Ile Arg Lys Val Pro Gly Asn Phe Thr Phe Thr
145                 150                 155                 160
```

His Lys Lys Val Lys His Glu Asn Phe Ser Leu Leu Thr Ser Gly Glu
165 170 175

Val Gly Glu Phe Cys Val Gln Val Lys Pro Ser Val Ala Ser Arg Ser
180 185 190

Asn Lys Gly Met Trp Ser Lys Glu Glu Cys Ile Ser Leu Thr Arg Gln
195 200 205

Tyr Phe Thr Val Thr Asn Val Ile Ile Phe Phe Ala Phe Val Leu Leu
210 215 220

Leu Ser Gly Ala Leu Ala Tyr Cys Leu Ala Leu Gln Leu Tyr Val Arg
225 230 235 240

Arg Arg Lys Lys Leu Pro Ser Val Leu Leu Phe Lys Lys Pro Ser Pro
245 250 255

Phe Ile Phe Ile Ser Gln Arg Pro Ser Pro Glu Thr Gln Asp Thr Ile
260 265 270

His Pro Leu Asp Glu Glu Ala Phe Leu Lys Val Ser Pro Glu Leu Lys
275 280 285

Asn Leu Asp Leu His Gly Ser Thr Asp Ser Gly Phe Gly Ser Thr Lys
290 295 300

Pro Ser Leu Gln Thr Glu Glu Pro Gln Phe Leu Leu Pro Asp Pro His
305 310 315 320

Pro Gln Ala Asp Arg Thr Leu Gly Asn Arg Glu Pro Pro Val Leu Gly
325 330 335

Asp Ser Cys Ser Ser Gly Ser Ser Asn Ser Thr Asp Ser Gly Ile Cys
340 345 350

Leu Gln Glu Pro Ser Leu Ser Pro Ser Thr Gly Pro Thr Trp Glu Gln
355 360 365

Gln Val Gly Ser Asn Ser Arg Gly Gln Asp Asp Ser Gly Ile Asp Leu
370 375 380

Val Gln Asn Ser Glu Gly Arg Ala Gly Asp Thr Gln Gly Gly Ser Ala
385 390 395 400

Leu Gly His His Ser Pro Pro Glu Pro Glu Val Pro Gly Glu Glu Asp
405 410 415

Pro Ala Ala Val Ala Phe Gln Gly Tyr Leu Arg Gln Thr Arg Cys Ala
420 425 430

Glu Glu Lys Ala Thr Lys Thr Gly Cys Leu Glu Glu Glu Ser Pro Leu
435 440 445

Thr Asp Gly Leu Gly Pro Lys Phe Gly Arg Cys Leu Val Asp Glu Ala
450 455 460

Gly Leu His Pro Pro Ala Leu Ala Lys Gly Tyr Leu Lys Gln Asp Pro
465 470 475 480

Leu Glu Met Thr Leu Ala Ser Ser Gly Ala Pro Thr Gly Gln Trp Asn
485 490 495

Gln Pro Thr Glu Glu Trp Ser Leu Leu Ala Leu Ser Ser Cys Ser Asp
500 505 510

Leu Gly Ile Ser Asp Trp Ser Phe Ala His Asp Leu Ala Pro Leu Gly
515 520 525

Cys Val Ala Ala Pro Gly Gly Leu Leu Gly Ser Phe Asn Ser Asp Leu
530 535 540

Val Thr Leu Pro Leu Ile Ser Ser Leu Gln Ser Ser Glu
545 550 555

<210> SEQ ID NO 8
<211> LENGTH: 347
<212> TYPE: PRT

<213> ORGANISM: Homo sapiens

<400> SEQUENCE: 8

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

Ser Gly Val Ser Lys Gly Leu Ala Glu Ser Leu Gln Pro Asp Tyr Ser
    290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345
```

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Gly Gly Gly Ser
1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Gly Gly Gly Gly Ser
1 5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Gly Ser Gly
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Gly Gly Ser Gly Gly
1 5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Gly Ser Gly Ser Gly
1 5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Gly Ser Gly Gly Gly
1 5

<210> SEQ ID NO 15
<211> LENGTH: 5
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 15

Gly Gly Gly Ser Gly
1 5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gly Ser Ser Ser Gly
1 5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Gly Gly Ser Gly Gly Gly Ser Gly
1 5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Gly Gly Ser Gly Gly Gly Ser Gly Gly Gly Ser Gly
1 5 10

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Gly Gly Ser Gly Gly Gly Ser Gly Gly Gly Ser Gly Gly Gly Ser Gly
1 5 10 15

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Gly Gly Ser Gly Gly Gly Ser Gly Gly Gly Ser Gly Gly Gly Ser Gly
1 5 10 15

Gly Gly Ser Gly
20

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Ala Ser His His His His His His
1 5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Gly Ser His His His His His His His His
1 5 10

<210> SEQ ID NO 23

<400> SEQUENCE: 23

000

<210> SEQ ID NO 24

<400> SEQUENCE: 24

000

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Tyr Leu Tyr Ser Ile Asp Tyr Met Ala
1 5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Tyr Leu Tyr Ser Thr Asn Tyr Met Ala
1 5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Tyr Leu Tyr Ser Thr Asn Tyr Met Ala
1 5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Tyr Leu Tyr Ser Ile Asp Tyr Met Ala
1 5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Tyr Leu Tyr Ser Thr Asn Tyr Met Ala
1 5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Phe Thr Tyr Ser Ser Tyr Cys Met Gly
1 5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Tyr Thr Phe Asn Ser Asn Cys Met Gly
1 5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Tyr Thr Tyr Ser Met Tyr Cys Met Gly
1 5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Tyr Ala Tyr Ser Thr Tyr Cys Met Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Tyr Leu Tyr Ser Ile Asp Tyr Met Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Tyr Thr Tyr Ser Ser Tyr Cys Met Gly
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Tyr Thr Tyr Ser Ser Asn Cys Met Gly
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Tyr Ser Tyr Ser Ser Asn Cys Met Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Tyr Thr Tyr Ser Ser Tyr Cys Met Gly
1 5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Tyr Thr Tyr Ser Gly Tyr Cys Met Gly
1 5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Tyr Thr Tyr Ser Asn Tyr Cys Met Gly
1 5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Tyr Ser Asn Cys Ser Tyr Asp Met Thr
1 5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Tyr Thr Tyr Asn Ser Asn Cys Met Gly
1 5

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Val Ile Tyr Thr Ala Ser Gly Ala Thr Phe Tyr Pro Asp Ser Val Lys
1 5 10 15

Gly

<210> SEQ ID NO 44

<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Val Ile Tyr Thr Ala Ser Gly Ala Thr Leu Tyr Thr Asp Ser Val Lys
1 5 10 15

Gly

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Val Ile Tyr Thr Ala Ser Gly Ala Thr Leu Tyr Thr Asp Ser Val Lys
1 5 10 15

Gly

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Val Ile Tyr Thr Ala Ser Gly Ala Thr Phe Tyr Pro Asp Ser Val Lys
1 5 10 15

Gly

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Ala Ile Tyr Thr Ala Ser Gly Ala Thr Leu Tyr Ser Asp Ser Asn Lys
1 5 10 15

Gly

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Ser Ile Asp Ser Asp Gly Ser Thr Ser Tyr Thr Asp Ser Val Lys Gly
1 5 10 15

<210> SEQ ID NO 49
<211> LENGTH: 17

<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Thr Ile Tyr Thr Gly Val Gly Ser Thr Tyr Tyr Ala Asp Ser Val Lys
1 5 10 15

Gly

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gln Ile Asn Ser Asp Gly Ser Thr Ser Tyr Ala Asp Ser Val Lys Gly
1 5 10 15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ala Ile Asp Ser Gly Gly Ser Thr Ser Tyr Ala Asp Ser Val Lys Gly
1 5 10 15

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Val Ile Tyr Thr Ala Ser Gly Ala Thr Phe Tyr Pro Asp Ser Val Lys
1 5 10 15

Gly

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Val Ile Asp Ser Asp Gly Ser Thr Ser Tyr Ala Asp Ser Val Lys Gly
1 5 10 15

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Thr Ile Tyr Thr Gly Gly Gly Asn Thr Tyr Tyr Ala Asp Ser Val Lys
1 5 10 15

Gly

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Thr Ile His Thr Gly Gly Gly Ser Thr Tyr Tyr Ala Asp Ser Val Lys
1 5 10 15

Gly

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

Val Ile Asp Ser Asp Gly Ser Thr Ser Tyr Ala Asp Ser Val Lys Gly
1 5 10 15

<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Val Ile Asp Ser Asp Gly Ser Thr Ser Tyr Ala Asp Ser Val Lys Gly
1 5 10 15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Thr Ile Asp Ser Asp Gly Asn Thr Ser Tyr Ala Asp Ser Val Lys Gly
1 5 10 15

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Ala Ile His Ser Asp Gly Ser Thr Arg Tyr Ala Asp Ser Val Lys Gly
1 5 10 15

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Thr Ile Tyr Thr Gly Val Gly Ser Thr Tyr Tyr Ala Asp Ser Val Lys
1 5 10 15

Gly

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Val Arg Lys Thr Asp Ser Tyr Leu Phe Asp Ala Gln Ser Phe Thr Tyr
1 5 10 15

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Val Arg Lys Thr Asp Ser Tyr Leu Phe Asp Ala Gln Ser Phe Thr Tyr
1 5 10 15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Val Arg Lys Thr Asp Ser Tyr Leu Phe Asp Ala Gln Ser Phe Thr Tyr
1 5 10 15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Val Arg Lys Thr Asp Ser Tyr Leu Phe Asp Ala Gln Ser Phe Thr Tyr
1 5 10 15

<210> SEQ ID NO 65
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 65

Val Arg Lys Thr Gly Ser Tyr Leu Phe Asp Ala Gln Ser Phe Thr Tyr
1               5                   10                  15

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Leu Met Ser Thr Val Val Pro Gly Phe Cys Gly Phe Leu Leu Ser
1               5                   10                  15

Ala Gly Met Asp Tyr
            20

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Pro Leu Ser Arg Val Tyr Gly Gly Ser Cys Pro Thr Pro Thr Phe
1               5                   10                  15

Gly Tyr

<210> SEQ ID NO 68
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Ser Arg Val Tyr Gly Gly Ser Trp Tyr Glu Arg Leu Cys Gly Pro
1               5                   10                  15

Tyr Thr Tyr Glu Tyr Asn Tyr
            20

<210> SEQ ID NO 69
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Pro Pro Pro Pro Asp Gly Gly Ser Cys Leu Phe Leu Gly Pro Glu
1               5                   10                  15

Ile Lys Val Ser Lys Ala Asp Phe Arg Tyr
            20                  25

<210> SEQ ID NO 70
<211> LENGTH: 16
<212> TYPE: PRT

<213> ORGANISM: Artificial Sequence
<220> FEATURE:
<223> OTHER INFORMATION: Description of Artificial Sequence: Synthetic peptide

<400> SEQUENCE: 70

Val Arg Lys Thr Asp Ser Tyr Leu Phe Asp Ala Gln Ser Phe Thr Tyr
1 5 10 15

<210> SEQ ID NO 71
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Asp Leu Gly His Tyr Arg Pro Pro Cys Gly Val Leu Tyr Leu Gly Met
1 5 10 15

Asp Tyr

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Glu Pro Leu Ser Arg Val Tyr Gly Gly Ser Cys Pro Thr Pro Thr Phe
1 5 10 15

Asp Tyr

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Glu Pro Leu Ser Arg Leu Tyr Gly Gly Ser Cys Pro Thr Pro Thr Phe
1 5 10 15

Gly Tyr

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Asp Leu Gly His Tyr Arg Pro Pro Cys Gly Val Leu Tyr Leu Gly Met
1 5 10 15

Asp Tyr

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Asp Leu Gly His Tyr Arg Pro Pro Cys Gly Val Leu Tyr Leu Gly Met
1 5 10 15

Asp Tyr

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Asp Leu Gly His Tyr Arg Pro Pro Cys Gly Ala Tyr Tyr Tyr Gly Met
1 5 10 15

Asp Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Asp Pro Leu His Cys Arg Ala His Gly Gly Ser Trp Tyr Ser Val Arg
1 5 10 15

Ala Asn Tyr

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Glu Pro Leu Ser Arg Val Tyr Gly Gly Ser Cys Pro Thr Pro Thr Phe
1 5 10 15

Gly Tyr

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Phe Thr Phe Asp Asp Ser Asp Met Gly
1 5

<210> SEQ ID NO 80
<211> LENGTH: 9
<212> TYPE: PRT
<213> ORGANISM: Artificial Sequence
<220> FEATURE:

<223> OTHER INFORMATION: Description of Artificial Sequence: Synthetic peptide

<400> SEQUENCE: 80

Phe Ser Phe Ser Ser Tyr Pro Met Thr
1 5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Phe Thr Phe Asp Asp Arg Glu Met Asn
1 5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Phe Thr Phe Asp Asp Ser Asp Met Gly
1 5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Phe Ser Phe Ser Ser Tyr Pro Met Thr
1 5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Phe Thr Phe Ser Asn Ala His Met Ser
1 5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Phe Thr Phe Asp Asp Arg Glu Met Asn
1 5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Thr Phe Ser Ser Tyr Cys Met Gly
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Phe Thr Phe Asp Asp Ser Asp Met Gly
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Ile Tyr Ser Ser Ala Tyr Ile Gly
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Phe Thr Phe Ser Ser Ala His Met Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Thr Phe Ser Asn Ala His Met Ser
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Phe Ile Phe Asp Asp Ser Asp Met Gly
1 5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Phe Thr Ala Asp Asp Ser Asp Met Gly
1 5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Phe Thr Phe Ser Ser Ala His Met Ser
1 5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Phe Thr Phe Ser Asn Ala His Met Ser
1 5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Phe Thr Phe Ser Asn Ala His Met Ser
1 5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Phe Thr Phe Ser Ser Tyr Pro Met Thr
1 5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Phe Thr Phe Asp Asp Arg Glu Met Asn
1 5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Phe Thr Phe Asp Asp Ser Asp Met Gly
1 5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Tyr Thr Ser Cys Met Gly
1 5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Phe Ser Phe Ser Ser Tyr Pro Met Thr
1 5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Phe Ser Phe Ser Ser Tyr Pro Met Thr
1 5

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Thr Ile Ser Ser Asp Gly Ser Thr Tyr Tyr Ala Asp Ser Val Lys Gly
1 5 10 15

```
<210> SEQ ID NO 103
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Ile Ala Ser Asp Gly Gly Ser Thr Ala Tyr Ala Ala Ser Val Glu
1               5                   10                  15

Gly


<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Ile Ser Ser Asp Gly Ser Thr Tyr Tyr Ala Asp Ser Val Lys Gly
1               5                   10                  15


<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Ile Ser Ser Asp Gly Asn Thr Tyr Tyr Thr Asp Ser Val Lys Gly
1               5                   10                  15


<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Ile Ala Ser Asp Gly Gly Ser Thr Ala Tyr Ala Ala Ser Val Glu
1               5                   10                  15

Gly


<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Ile Tyr Ser Gly Gly Ser Thr Trp Tyr Ala Asp Ser Val Lys Gly
1               5                   10                  15


<210> SEQ ID NO 108
<211> LENGTH: 16
<212> TYPE: PRT
<213> ORGANISM: Artificial Sequence
```

<220> FEATURE:
<223> OTHER INFORMATION: Description of Artificial Sequence: Synthetic peptide

<400> SEQUENCE: 108

Thr Ile Ser Ser Asp Gly Ser Thr Tyr Tyr Ala Asp Ser Val Lys Gly
1 5 10 15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Ala Leu Gly Gly Gly Ser Thr Tyr Tyr Ala Asp Ser Val Lys Gly
1 5 10 15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Thr Ile Ser Ser Asp Gly Ser Thr Tyr Tyr Ala Asp Ser Val Lys Gly
1 5 10 15

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Gly Ile Tyr Thr Arg Asp Gly Ser Thr Ala Tyr Ala Asp Ser Val Lys
1 5 10 15

Gly

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Ser Ile Tyr Ser Gly Gly Gly Thr Phe Tyr Ala Asp Ser Val Lys Gly
1 5 10 15

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Ser Ile Tyr Ser Gly Gly Ser Thr Trp Tyr Ala Asp Ser Val Lys Gly 1 5 10 15

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Thr Ile Ser Ser Asp Gly Ser Thr Tyr Tyr Ala Asp Ser Val Lys Gly
1 5 10 15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Thr Ile Ser Ser Asp Gly Ser Thr Tyr Tyr Ala Asp Ser Val Lys Gly
1 5 10 15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Ser Ile Tyr Ser Gly Gly Gly Thr Phe Tyr Ala Asp Ser Val Lys Gly
1 5 10 15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Ser Ile Tyr Ser Gly Gly Ser Thr Trp Tyr Ala Asp Ser Val Lys Gly
1 5 10 15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Ser Ile Tyr Ser Gly Gly Ser Thr Trp Tyr Ala Asp Ser Val Lys Gly
1 5 10 15

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Thr Ile Ala Ser Asp Gly Gly Ser Thr Ala Tyr Ala Ala Ser Val Glu
1 5 10 15

Gly

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Thr Ile Ser Ser Asp Gly Ser Thr Tyr Tyr Ala Asp Ser Val Lys Gly
1 5 10 15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Thr Ile Ser Ser Asp Gly Ser Thr Tyr Tyr Ala Asp Ser Val Lys Gly
1 5 10 15

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Thr Ile Tyr Thr Arg Gly Arg Ser Ile Tyr Tyr Ala Asp Ser Val Lys
1 5 10 15

Gly

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Thr Ile Ala Ser Asp Gly Gly Ser Thr Ala Tyr Ala Ala Ser Val Glu
1 5 10 15

Gly

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Thr Ile Ala Ser Asp Gly Gly Ser Thr Ala Tyr Ala Ala Ser Val Glu
1 5 10 15

Gly

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Asp Phe Met Ile Ala Ile Gln Ala Pro Gly Ala Gly Cys
1 5 10

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Gly Tyr Gly Asp Gly Thr Pro Ala
1 5

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Asp Phe Met Ile Ala Ile Gln Ala Pro Gly Ala Gly Cys
1 5 10

<210> SEQ ID NO 128
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Glu Pro Arg Gly Tyr Tyr Ser Asn Tyr Gly Gly Arg Arg Glu Cys Asn
1 5 10 15

Tyr

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Gly Tyr Gly Asp Gly Thr Pro Ala
1 5

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Asn Arg Leu His Tyr Tyr Ser Asp Asp Asp Ser Leu
1 5 10

<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Asp Phe Met Ile Ala Ile Gln Ala Pro Gly Ala Gly Cys
1 5 10

<210> SEQ ID NO 132
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Ala Trp Val Ala Cys Leu Glu Phe Gly Gly Ser Trp Tyr Asp Leu Ala
1 5 10 15

Arg Tyr Lys His
20

<210> SEQ ID NO 133
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Glu Pro Arg Gly Tyr Tyr Ser Asn Tyr Gly Gly Arg Arg Glu Cys Asn
1 5 10 15

Tyr

<210> SEQ ID NO 134
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Gly Arg Arg Thr Lys Ser Tyr Val Tyr Ile Phe Arg Pro Glu Glu Tyr
1 5 10 15

Asn Tyr

<210> SEQ ID NO 135
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asn Arg Leu His Tyr Tyr Ser Asp Asp Asp Ser Leu
1               5                   10


<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Arg Leu His Tyr Tyr Ser Asp Asp Asp Ser Leu
1               5                   10


<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Glu Pro Arg Gly Tyr Tyr Ser Asn Tyr Gly Gly Arg Arg Glu Cys Asn
1               5                   10                  15

Tyr


<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Glu Pro Arg Gly Tyr Tyr Ser Asn Tyr Gly Gly Arg Arg Glu Cys Asn
1               5                   10                  15

Tyr


<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asn Arg Leu His Tyr Tyr Ser Asp Asp Asp Ser Leu
1               5                   10


<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 140

Asn Arg Leu His Tyr Tyr Ser Asp Asp Asp Ser Leu
1 5 10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Asn Arg Leu His Tyr Tyr Ser Asp Asp Asp Ser Leu
1 5 10

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Gly Tyr Gly Asp Gly Thr Pro Ala
1 5

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Asp Phe Met Ile Ala Ile Gln Ala Pro Gly Ala Gly Cys
1 5 10

<210> SEQ ID NO 144
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Glu Pro Arg Gly Tyr Tyr Ser Asn Tyr Gly Gly Arg Arg Glu Cys Asn
1 5 10 15

Tyr

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Gly Gly Tyr Ser Trp Ser Ala Gly Cys Glu Phe Asn Tyr
1 5 10

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 146

Gly Tyr Gly Asp Gly Thr Pro Ala
1               5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 147

Gly Tyr Gly Asp Gly Thr Pro Ala
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Tyr Gly Tyr Asn Tyr Ile Gly
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Ser Thr Tyr Ala Asn Tyr Leu Met Gly
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Phe Thr Phe Asp Glu Ser Val Met Ser
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Leu Pro Phe Asp Glu Asp Asp Met Gly
1 5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Asp Val Tyr Gly Arg Asn Ser Met Ala
1 5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Phe Pro Tyr Ser Arg Tyr Cys Met Gly
1 5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Phe Thr Phe Asp Glu Ser Asp Met Gly
1 5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Phe Thr Phe Asp Asp Phe Asp Met Gly
1 5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Phe Thr Phe Asp Asp Phe Asp Met Gly
1 5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Phe Thr Phe Asp Asp Phe Asp Met Gly
1 5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Phe Thr Phe Ser Asp Arg Asp Met Gly
1 5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Tyr Gly Tyr Asn Tyr Ile Gly
1 5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Tyr Gly Tyr Asn Tyr Ile Gly
1 5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 161

Phe Thr Phe Asp Asp Phe Asp Met Gly
1 5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 162

Phe Thr Phe Asp Asp Phe Asp Met Gly
1 5

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Val Ile Tyr Thr Gly Gly Gly Asp Thr Tyr Tyr Ala Asp Ser Val Lys
1 5 10 15

Gly

<210> SEQ ID NO 164
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Ala Ile Tyr Ser Gly Gly Gly Ser Thr Tyr Tyr Ala Asp Ser Val Lys
1 5 10 15

Gly

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Ile Ile Ser Ser Asp Asp Asn Thr Tyr Tyr Asp Asp Ser Val Lys Gly
1 5 10 15

<210> SEQ ID NO 166
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Ser Ile Ser Ser Asp Gly Thr Ala Tyr Tyr Ala Asp Ser Val Lys Gly
1 5 10 15

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Val Gly Tyr Ser Val Val Thr Thr Thr Tyr Tyr Ala Asp Ser Val Lys
1 5 10 15

Gly

<210> SEQ ID NO 168
<211> LENGTH: 16

<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Ala Ile Glu Pro Asp Gly Ser Thr Ser Tyr Ala Asp Ser Val Lys Gly
1 5 10 15

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Val Ile Thr Ser Asp Asp Asn Pro Tyr Tyr Asp Asp Ser Val Lys Gly
1 5 10 15

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Thr Ile Ser Asp Asp Gly Ser Thr Tyr Tyr Ala Asp Ser Val Lys Gly
1 5 10 15

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Thr Ile Ser Asp Asp Gly Ser Thr Tyr Tyr Ala Asp Ser Val Lys Gly
1 5 10 15

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Thr Ile Ser Asp Asp Gly Ser Thr Tyr Tyr Ala Asp Ser Val Lys Gly
1 5 10 15

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Thr Ile Ser Asp Asp Gly Ser Thr Tyr Tyr Ala Asp Ser Val Lys Gly 1 5 10 15

<210> SEQ ID NO 174
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Val Ile Tyr Ile Gly Gly Gly Asp Thr Tyr Tyr Ala Asp Ser Val Lys
1 5 10 15

Gly

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Val Ile Tyr Thr Gly Gly Gly Asp Thr Tyr Tyr Ala Asp Ser Val Lys
1 5 10 15

Gly

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 176

Thr Ile Ser Asp Asp Gly Ser Thr Tyr Tyr Ala Asn Ser Val Lys Gly
1 5 10 15

<210> SEQ ID NO 177
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Thr Ile Ser Asp Asp Gly Ser Thr Tyr Tyr Ala Asp Ser Val Lys Gly
1 5 10 15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Ser Val Tyr Ala Cys Leu Arg Gly Gly His Asp Glu Tyr Ala His
1 5 10 15

<210> SEQ ID NO 179
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Ser Ala Val Lys Gly Asp Lys Gly Asp Ile Val Val Val Val Thr
1               5                   10                  15

Gly Thr Gln Arg Met Glu Tyr Asp Tyr
            20                  25


<210> SEQ ID NO 180
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Arg Arg Arg Pro Val Tyr Asp Ser Asp Tyr Glu Leu Arg Pro Arg
1               5                   10                  15

Pro Leu Cys Gly Asp Phe Gly Val
            20


<210> SEQ ID NO 181
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Val His Arg Gln Phe Gly Gly Ser Ser Ser Cys Gly Asp Ala Phe
1               5                   10                  15

Tyr Gly Met Asp Tyr
            20


<210> SEQ ID NO 182
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Gly Asn Leu Trp Arg Gly Leu Arg Pro Ser Glu Tyr Thr Tyr
1               5                   10                  15


<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Asp Glu Arg Cys Phe Tyr Leu Lys Asp Tyr Asp Leu Arg Arg Pro Ala
1               5                   10                  15

Gln Tyr Arg Tyr
            20
```

<210> SEQ ID NO 184
<211> LENGTH: 24
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Arg Ser Arg Gln Pro Val Tyr Ser Arg Asp Tyr Glu Leu Arg Pro Arg
1 5 10 15

Pro Leu Cys Gly Asp Phe Gly Val
20

<210> SEQ ID NO 185
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Glu Gly Ala Leu Gly Ser Lys Thr Asn Cys Gly Trp Val Gly Asn Phe
1 5 10 15

Gly Tyr

<210> SEQ ID NO 186
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 186

Glu Gly Ala Leu Gly Ser Lys Thr Asn Cys Gly Trp Val Gly Asn Phe
1 5 10 15

Gly Tyr

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 187

Glu Gly Ala Leu Gly Ser Lys Thr Asn Cys Gly Trp Val Gly Asn Phe
1 5 10 15

Gly Tyr

<210> SEQ ID NO 188
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 188

Glu Gly Ala Leu Gly Ser Lys Thr Asn Cys Gly Trp Val Gly Asn Phe
1 5 10 15

Gly Tyr

<210> SEQ ID NO 189
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 189

Arg Tyr Cys Val Gly Ser Val Tyr Ala Cys Leu Arg Gly Gly His Asp
1 5 10 15

Glu Tyr Ala His
20

<210> SEQ ID NO 190
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Arg Tyr Cys Val Gly Ser Val Tyr Ala Cys Leu Arg Gly Gly His Asp
1 5 10 15

Glu Tyr Ala His
20

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 191

Glu Gly Ala Leu Gly Ser Lys Thr Asn Cys Gly Trp Val Gly Asn Phe
1 5 10 15

Gly Tyr

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Glu Gly Ala Leu Gly Ser Lys Met Asn Cys Gly Trp Val Gly Asn Phe
1 5 10 15

Gly Tyr

<210> SEQ ID NO 193
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 193

```
Gln Val Gln Leu Gln Glu Ser Gly Gly Gly Ser Ile Gln Ala Gly Gly
1               5                   10                  15

Ser Leu Arg Leu Ser Cys Ala Ala Ser Arg Tyr Leu Tyr Ser Ile Asp
            20                  25                  30

Tyr Met Ala Trp Phe Arg Gln Ser Pro Gly Lys Glu Arg Glu Pro Val
        35                  40                  45

Ala Val Ile Tyr Thr Ala Ser Gly Ala Thr Phe Tyr Pro Asp Ser Val
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125
```

<210> SEQ ID NO 194
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

```
Gln Val Gln Leu Gln Glu Ser Gly Gly Gly Ser Val Gln Ala Gly Gly
1               5                   10                  15

Ser Leu Arg Leu Ser Cys Val Ala Ser Arg Tyr Leu Tyr Ser Thr Asn
            20                  25                  30

Tyr Met Ala Trp Phe Arg Gln Ser Pro Gly Lys Glu Arg Glu Ala Val
        35                  40                  45

Ala Val Ile Tyr Thr Ala Ser Gly Ala Thr Leu Tyr Thr Asp Ser Val
    50                  55                  60

Lys Gly Arg Phe Thr Ile Ser Gln Asp Asn Ala Lys Met Thr Val Tyr
65                  70                  75                  80

Leu Gln Met Asn Arg Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125
```

<210> SEQ ID NO 195
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 195

```
Gln Val Gln Leu Gln Glu Ser Gly Gly Gly Ser Ile Gln Ala Gly Gly
1               5                   10                  15

Ser Leu Arg Leu Ser Cys Val Ala Ser Arg Tyr Leu Tyr Ser Thr Asn
            20                  25                  30

Tyr Met Ala Trp Phe Arg Gln Ser Pro Gly Lys Glu Arg Glu Ala Val
        35                  40                  45
```

```
Ala Val Ile Tyr Thr Ala Ser Gly Ala Thr Leu Tyr Thr Asp Ser Val
    50                  55                  60

Lys Gly Arg Phe Thr Ile Ser Gln Asp Asn Ala Lys Met Thr Val Tyr
65                  70                  75                  80

Leu Gln Met Asn Arg Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125


<210> SEQ ID NO 196
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Gln Leu Gln Glu Ser Gly Gly Gly Ser Ile Gln Ala Gly Gly
1               5                   10                  15

Ser Leu Arg Leu Ser Cys Ala Ala Ser Arg Tyr Leu Tyr Ser Ile Asp
            20                  25                  30

Tyr Met Ala Trp Phe Arg Gln Ser Pro Gly Lys Glu Arg Glu Pro Ala
        35                  40                  45

Ala Val Ile Tyr Thr Ala Ser Gly Ala Thr Phe Tyr Pro Asp Ser Val
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125


<210> SEQ ID NO 197
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gln Val Gln Leu Gln Glu Ser Gly Gly Gly Ser Ile Gln Ala Gly Gly
1               5                   10                  15

Ser Leu Arg Leu Ser Cys Val Ala Ser Lys Tyr Leu Tyr Ser Thr Asn
            20                  25                  30

Tyr Met Ala Trp Phe Arg Gln Ser Pro Gly Lys Glu Arg Glu Ala Val
        35                  40                  45

Ala Ala Ile Tyr Thr Ala Ser Gly Ala Thr Leu Tyr Ser Asp Ser Asn
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95
```

```
Ala Ala Val Arg Lys Thr Gly Ser Tyr Leu Phe Asp Ala Gln Ser Phe
            100                 105                 110

Thr Tyr Trp Gly Gln Gly Thr Gln Val Thr Val Ser Ser
        115                 120                 125


<210> SEQ ID NO 198
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Gln Glu Ser Gly Gly Gly Ser Val Gln Ala Gly Gly
1               5                   10                  15

Ser Leu Arg Leu Ser Cys Ala Ala Ser Arg Phe Thr Tyr Ser Ser Tyr
            20                  25                  30

Cys Met Gly Trp Phe Arg Gln Ala Pro Gly Lys Glu Arg Glu Gly Val
        35                  40                  45

Ala Ser Ile Asp Ser Asp Gly Ser Thr Ser Tyr Thr Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Leu Asp Leu Met Ser Thr Val Val Pro Gly Phe Cys Gly Phe Leu Leu
            100                 105                 110

Ser Ala Gly Met Asp Tyr Trp Gly Lys Gly Thr Gln Val Thr Val Ser
        115                 120                 125

Ser


<210> SEQ ID NO 199
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Phe Asn Ser Asn
            20                  25                  30

Cys Met Gly Trp Phe Arg Gln Ala Pro Gly Lys Glu Arg Glu Gly Val
        35                  40                  45

Ala Thr Ile Tyr Thr Gly Val Gly Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Glu Pro Leu Ser Arg Val Tyr Gly Gly Ser Cys Pro Thr Pro
            100                 105                 110

Thr Phe Gly Tyr Trp Gly Gln Gly Thr Gln Val Thr Val Ser Ser
        115                 120                 125
```

<210> SEQ ID NO 200
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 200

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Met Tyr
            20                  25                  30

Cys Met Gly Trp Phe Arg Gln Ala Pro Gly Lys Glu Arg Glu Gly Val
        35                  40                  45

Ala Gln Ile Asn Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Ser Arg Val Tyr Gly Gly Ser Trp Tyr Glu Arg Leu Cys Gly
            100                 105                 110

Pro Tyr Thr Tyr Glu Tyr Asn Tyr Trp Gly Gln Gly Thr Gln Val Thr
        115                 120                 125

Val Ser Ser
    130
```

<210> SEQ ID NO 201
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 201

```
Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Ala Tyr Ser Thr Tyr
            20                  25                  30

Cys Met Gly Trp Phe Arg Gln Ala Pro Gly Lys Glu Arg Glu Gly Val
        35                  40                  45

Ala Ala Ile Asp Ser Gly Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Arg Met Asn Ser Leu Lys Pro Glu Asp Thr Ala Met Tyr Tyr Cys Ala
                85                  90                  95

Ala Val Pro Pro Pro Pro Asp Gly Gly Ser Cys Leu Phe Leu Gly Pro
            100                 105                 110

Glu Ile Lys Val Ser Lys Ala Asp Phe Arg Tyr Trp Gly Gln Gly Thr
        115                 120                 125

Gln Val Thr Val Ser Ser
    130
```

<210> SEQ ID NO 202
<211> LENGTH: 125
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 202

Gln Val Gln Leu Gln Glu Ser Gly Gly Gly Ser Val Gln Ala Gly Gly
1               5                   10                  15

Ser Leu Arg Leu Ser Cys Ala Ala Ser Arg Tyr Leu Tyr Ser Ile Asp
            20                  25                  30

Tyr Met Ala Trp Phe Arg Gln Ser Pro Gly Lys Glu Arg Glu Pro Val
        35                  40                  45

Ala Val Ile Tyr Thr Ala Ser Gly Ala Thr Phe Tyr Pro Asp Ser Val
    50                  55                  60

Lys Gly Arg Phe Thr Ile Ser Gln Asp Asn Ala Lys Met Thr Val Tyr
65                  70                  75                  80

Leu Gln Met Asn Ser Leu Lys Ser Glu Asp Thr Ala Met Tyr Tyr Cys
                85                  90                  95

Ala Ala Val Arg Lys Thr Asp Ser Tyr Leu Phe Asp Ala Gln Ser Phe
            100                 105                 110

Thr Tyr Trp Gly Gln Gly Thr Gln Val Thr Val Ser Ser
        115                 120                 125


<210> SEQ ID NO 203
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Gln Val Gln Leu Gln Glu Ser Gly Gly Gly Ser Val Gln Ala Gly Gly
1               5                   10                  15

Ser Leu Arg Leu Ser Cys Gly Ala Ser Arg Tyr Thr Tyr Ser Ser Tyr
            20                  25                  30

Cys Met Gly Trp Phe Arg Gln Ala Pro Gly Lys Glu Arg Glu Gly Val
        35                  40                  45

Ala Val Ile Asp Ser Asp Gly Ser Thr Ser Tyr Ala Asp Ser Val Lys
    50                  55                  60

Gly Arg Phe Thr Ile Ser Lys Asp Asn Gly Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Leu Gly His Tyr Arg Pro Pro Cys Gly Val Leu Tyr Leu Gly
            100                 105                 110

Met Asp Tyr Trp Gly Lys Gly Thr Gln Val Thr Val Ser Ser
        115                 120                 125


<210> SEQ ID NO 204
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Gln Val Gln Leu Gln Glu Ser Gly Gly Gly Ser Val Gln Ala Gly Gly
1               5                   10                  15
```

Ser Leu Arg Leu Ser Cys Thr Val Ser Gly Tyr Thr Tyr Ser Ser Asn
20 25 30

Cys Met Gly Trp Phe Arg Gln Ala Pro Gly Lys Glu Arg Glu Gly Val
35 40 45

Ala Thr Ile Tyr Thr Gly Gly Gly Asn Thr Tyr Tyr Ala Asp Ser Val
50 55 60

Lys Gly Arg Phe Thr Ile Ser Gln Asp Asn Ala Lys Asn Thr Val Tyr
65 70 75 80

Leu Gln Met Asn Asn Leu Lys Pro Glu Asp Thr Ala Met Tyr Tyr Cys
85 90 95

Ala Ala Glu Pro Leu Ser Arg Val Tyr Gly Gly Ser Cys Pro Thr Pro
100 105 110

Thr Phe Asp Tyr Trp Gly Gln Gly Thr Gln Val Thr Val Ser Ser
115 120 125

<210> SEQ ID NO 205
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 205

Gln Val Gln Leu Gln Glu Ser Gly Gly Gly Ser Val Gln Ala Gly Gly
1 5 10 15

Ser Leu Arg Leu Ser Cys Ala Val Ser Gly Tyr Ser Tyr Ser Ser Asn
20 25 30

Cys Met Gly Trp Phe Arg Gln Ala Pro Gly Lys Glu Arg Glu Gly Val
35 40 45

Ala Thr Ile His Thr Gly Gly Gly Ser Thr Tyr Tyr Ala Asp Ser Val
50 55 60

Lys Gly Arg Phe Thr Ile Ser Gln Asp Asn Ala Lys Asn Thr Val Tyr
65 70 75 80

Leu Gln Met Asn Ser Leu Lys Pro Glu Asp Thr Ala Met Tyr Tyr Cys
85 90 95

Ala Ala Glu Pro Leu Ser Arg Leu Tyr Gly Gly Ser Cys Pro Thr Pro
100 105 110

Thr Phe Gly Tyr Trp Gly Gln Gly Thr Gln Val Thr Val Ser Ser
115 120 125

<210> SEQ ID NO 206
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Gln Val Gln Leu Gln Glu Ser Gly Gly Gly Ser Val Gln Ala Gly Gly
1 5 10 15

Ser Leu Arg Leu Ser Cys Gly Ala Ser Gly Tyr Thr Tyr Ser Ser Tyr
20 25 30

Cys Met Gly Trp Phe Arg Gln Val Pro Gly Lys Glu Arg Glu Gly Val
35 40 45

Ala Val Ile Asp Ser Asp Gly Ser Thr Ser Tyr Ala Asp Ser Val Lys
50 55 60

```
Gly Arg Phe Thr Ile Ser Lys Asp Asn Gly Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Leu Gly His Tyr Arg Pro Pro Cys Gly Val Leu Tyr Leu Gly
            100                 105                 110

Met Asp Tyr Trp Gly Lys Gly Thr Gln Val Thr Val Ser Ser
        115                 120                 125


<210> SEQ ID NO 207
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Gln Val Gln Leu Gln Glu Ser Gly Gly Gly Ser Val Gln Ala Gly Gly
1               5                   10                  15

Ser Leu Arg Leu Ser Cys Gly Ala Ser Gly Tyr Thr Tyr Ser Gly Tyr
            20                  25                  30

Cys Met Gly Trp Phe Arg Gln Ala Pro Gly Lys Glu Arg Glu Gly Val
        35                  40                  45

Ala Val Ile Asp Ser Asp Gly Ser Thr Ser Tyr Ala Asp Ser Val Lys
    50                  55                  60

Gly Arg Phe Thr Ile Ser Lys Asp Asn Gly Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Asp Leu Gly His Tyr Arg Pro Pro Cys Gly Val Leu Tyr Leu Gly
            100                 105                 110

Met Asp Tyr Trp Gly Lys Gly Thr Gln Val Thr Val Ser Ser
        115                 120                 125


<210> SEQ ID NO 208
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Gln Val Gln Leu Gln Glu Ser Gly Gly Gly Ser Val Gln Ala Gly Gly
1               5                   10                  15

Ser Leu Arg Leu Ala Cys Ala Ala Ser Arg Tyr Thr Tyr Ser Asn Tyr
            20                  25                  30

Cys Met Gly Trp Phe Arg Gln Ala Pro Gly Lys Glu Arg Glu Gly Val
        35                  40                  45

Ala Thr Ile Asp Ser Asp Gly Asn Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Gly Asp Thr Ala Met Tyr Tyr Cys Ala
                85                  90                  95

Ala Asp Leu Gly His Tyr Arg Pro Pro Cys Gly Ala Tyr Tyr Tyr Gly
            100                 105                 110
```

Met Asp Tyr Trp Gly Lys Gly Thr Gln Val Thr Val Ser Ser
115 120 125

<210> SEQ ID NO 209
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 209

Gln Val Gln Leu Gln Glu Ser Gly Gly Gly Ser Val Gln Ala Gly Gly
1 5 10 15

Ser Leu Arg Leu Ser Cys Ala Ala Ser Gly Tyr Ser Asn Cys Ser Tyr
20 25 30

Asp Met Thr Trp Tyr Arg Gln Ala Pro Gly Lys Glu Arg Glu Phe Val
35 40 45

Ser Ala Ile His Ser Asp Gly Ser Thr Arg Tyr Ala Asp Ser Val Lys
50 55 60

Gly Arg Phe Phe Ile Ser Gln Asp Asn Ala Lys Asn Thr Val Tyr Leu
65 70 75 80

Gln Met Asn Ser Leu Lys Pro Glu Asp Thr Ala Met Tyr Tyr Cys Lys
85 90 95

Thr Asp Pro Leu His Cys Arg Ala His Gly Gly Ser Trp Tyr Ser Val
100 105 110

Arg Ala Asn Tyr Trp Gly Gln Gly Thr Gln Val Thr Val Ser Ser
115 120 125

<210> SEQ ID NO 210
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 210

Gln Val Gln Leu Gln Glu Ser Gly Gly Gly Ser Val Gln Ala Gly Gly
1 5 10 15

Ser Leu Arg Leu Ser Cys Ala Val Ser Gly Tyr Thr Tyr Asn Ser Asn
20 25 30

Cys Met Gly Trp Phe Arg Gln Ala Pro Gly Lys Glu Arg Glu Gly Val
35 40 45

Ala Thr Ile Tyr Thr Gly Val Gly Ser Thr Tyr Tyr Ala Asp Ser Val
50 55 60

Lys Gly Arg Phe Thr Ile Ser Gln Asp Asn Ala Lys Asn Thr Val Tyr
65 70 75 80

Leu Gln Met Asn Ser Leu Lys Pro Glu Asp Thr Ala Met Tyr Tyr Cys
85 90 95

Ala Ala Glu Pro Leu Ser Arg Val Tyr Gly Gly Ser Cys Pro Thr Pro
100 105 110

Thr Phe Gly Tyr Trp Gly Gln Gly Thr Gln Val Thr Val Ser Ser
115 120 125

<210> SEQ ID NO 211
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 211

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Asp Asp Ser
            20                  25                  30

Asp Met Gly Trp Tyr Arg Gln Ala Pro Gly Asn Glu Cys Asp Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110

Gln Gly Thr Gln Val Thr Val Ser Ser
        115                 120

<210> SEQ ID NO 212
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 212

Gln Val Gln Leu Gln Glu Ser Gly Gly Gly Ser Val Pro Ala Gly Gly
1               5                   10                  15

Ser Leu Lys Leu Ser Cys Ala Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115

<210> SEQ ID NO 213
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 213

Gln Val Gln Leu Gln Glu Ser Gly Gly Gly Ser Val Gln Thr Gly Gly
1               5                   10                  15

```
Ser Leu Arg Leu Ser Cys Thr Ala Ser Gly Phe Thr Phe Asp Asp Arg
            20                  25                  30

Glu Met Asn Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110

Gln Gly Thr Gln Val Thr Val Ser Ser
        115                 120
```

<210> SEQ ID NO 214
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 214

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Ser
            20                  25                  30

Asp Met Gly Trp Tyr Arg Gln Ala Pro Gly Asn Glu Cys Glu Leu Val
        35                  40                  45

Ser Thr Ile Ser Ser Asp Gly Asn Thr Tyr Tyr Thr Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Gly Pro Glu Asp Thr Ala Val Tyr Tyr Cys Ala
                85                  90                  95

Ala Glu Pro Arg Gly Tyr Tyr Ser Asn Tyr Gly Gly Arg Arg Glu Cys
            100                 105                 110

Asn Tyr Trp Gly Gln Gly Thr Gln Val Thr Val Ser Ser
        115                 120                 125
```

<210> SEQ ID NO 215
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 215

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60
```

```
Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115
```

<210> SEQ ID NO 216
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

```
Gln Val Gln Leu Gln Glu Ser Gly Gly Gly Ala Val Gln Ala Gly Gly
1               5                   10                  15

Ser Leu Arg Leu Ser Cys Ala Ala Ser Gly Phe Thr Phe Ser Asn Ala
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Asp Ser Leu Arg Gly Gln
            100                 105                 110

Gly Thr Gln Val Thr Val Ser Ser
        115                 120
```

<210> SEQ ID NO 217
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 217

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Arg
            20                  25                  30

Glu Met Asn Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110
```

Gln Gly Thr Gln Val Thr Val Ser Ser
115 120

<210> SEQ ID NO 218
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

Gln Val Gln Leu Gln Glu Ser Gly Gly Gly Ser Val Gln Ala Gly Gly
1 5 10 15

Ser Leu Arg Leu Ser Cys Val Ala Ser Gly Tyr Thr Phe Ser Ser Tyr
20 25 30

Cys Met Gly Trp Phe Arg Gln Ala Pro Gly Lys Glu Arg Glu Gly Val
35 40 45

Ala Ala Leu Gly Gly Gly Ser Thr Tyr Tyr Ala Asp Ser Val Lys Gly
50 55 60

Arg Phe Thr Ile Ser Gln Asp Asn Ala Lys Asn Thr Leu Tyr Leu Gln
65 70 75 80

Met Asn Ser Leu Lys Pro Glu Asp Thr Ala Met Tyr Tyr Cys Ala Ala
85 90 95

Ala Trp Val Ala Cys Leu Glu Phe Gly Gly Ser Trp Tyr Asp Leu Ala
100 105 110

Arg Tyr Lys His Trp Gly Gln Gly Thr Gln Val Thr Val Ser Ser
115 120 125

<210> SEQ ID NO 219
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

Gln Val Gln Leu Gln Glu Ser Gly Gly Gly Ser Val Gln Ala Gly Gly
1 5 10 15

Ser Leu Arg Leu Ser Cys Thr Ala Ser Gly Phe Thr Phe Asp Asp Ser
20 25 30

Asp Met Gly Trp Tyr Arg Gln Ala Pro Gly Gly Glu Cys Glu Leu Val
35 40 45

Thr Ile Ser Ser Asp Gly Ser Thr Tyr Tyr Ala Asp Ser Val Lys Gly
50 55 60

Arg Phe Thr Ile Ser Gln Asp Asn Ala Lys Asn Thr Val Tyr Leu Gln
65 70 75 80

Met Asn Ser Leu Lys Pro Glu Asp Thr Ala Val Tyr Tyr Cys Ala Ala
85 90 95

Glu Pro Arg Gly Tyr Tyr Ser Asn Tyr Gly Gly Arg Arg Glu Cys Asn
100 105 110

Tyr Trp Gly Gln Gly Thr Gln Val Thr Val Ser Ser
115 120

<210> SEQ ID NO 220
<211> LENGTH: 127
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 220

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Tyr Ser Ser Ala
            20                  25                  30

Tyr Ile Gly Trp Phe Arg Gln Ala Pro Gly Lys Lys Arg Glu Gly Val
        35                  40                  45

Ala Gly Ile Tyr Thr Arg Asp Gly Ser Thr Ala Tyr Ala Asp Ser Val
    50                  55                  60

Lys Gly Arg Phe Thr Ile Ser Gln Asp Ser Ala Lys Lys Thr Val Tyr
65                  70                  75                  80

Leu Gln Met Asn Ser Leu Lys Pro Glu Asp Thr Ala Met Tyr Tyr Cys
                85                  90                  95

Ala Ala Gly Arg Arg Thr Lys Ser Tyr Val Tyr Ile Phe Arg Pro Glu
            100                 105                 110

Glu Tyr Asn Tyr Trp Gly Gln Gly Thr Gln Val Thr Val Ser Ser
        115                 120                 125

<210> SEQ ID NO 221
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser Ser Ala
            20                  25                  30

His Met Ser Trp Val Arg Gln Ala Pro Gly Lys Gly Arg Glu Trp Ile
        35                  40                  45

Ala Ser Ile Tyr Ser Gly Gly Gly Thr Phe Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Thr Asn Arg Leu His Tyr Tyr Ser Asp Asp Asp Ser Leu Arg Gly Gln
            100                 105                 110

Gly Thr Gln Val Thr Val Ser Ser
        115                 120

<210> SEQ ID NO 222
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser Asn Ala

```
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Asp Ser Leu Arg Gly Gln
            100                 105                 110

Gly Thr Gln Val Thr Val Ser Ser
        115                 120


<210> SEQ ID NO 223
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Gln Glu Ser Gly Gly Gly Ser Val Gln Ala Gly Gly
1               5                   10                  15

Ser Leu Arg Leu Ser Cys Thr Ala Ser Arg Phe Ile Phe Asp Asp Ser
            20                  25                  30

Asp Met Gly Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Pro Arg Gly Tyr Tyr Ser Asn Tyr Gly Gly Arg Arg Glu Cys
            100                 105                 110

Asn Tyr Trp Gly Gln Gly Thr Gln Val Thr Val Ser Ser
        115                 120                 125


<210> SEQ ID NO 224
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gln Val Gln Leu Gln Glu Ser Gly Gly Gly Ser Val Gln Ala Gly Gly
1               5                   10                  15

Ser Leu Lys Leu Ser Cys Thr Val Ser Gly Phe Thr Ala Asp Asp Ser
            20                  25                  30

Asp Met Gly Trp Tyr Arg Gln Gly Pro Gly Asn Glu Cys Glu Leu Val
        35                  40                  45

Thr Ile Ser Ser Asp Gly Ser Thr Tyr Tyr Ala Asp Ser Val Lys Gly
    50                  55                  60

Arg Phe Thr Ile Ser Gln Asp Asn Ala Lys Asn Thr Val Tyr Leu Gln
```

```
65                  70                  75                  80

Met Asn Ser Leu Lys Pro Glu Asp Thr Ala Val Tyr Tyr Cys Ala Ala
                85                  90                  95

Glu Pro Arg Gly Tyr Tyr Ser Asn Tyr Gly Gly Arg Arg Glu Cys Asn
            100                 105                 110

Tyr Trp Gly Gln Gly Thr Gln Val Thr Val Ser Ser
        115                 120


<210> SEQ ID NO 225
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

His Met Ser Trp Val Arg Gln Ala Pro Gly Lys Gly Arg Glu Trp Ile
        35                  40                  45

Ala Ser Ile Tyr Ser Gly Gly Gly Thr Phe Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Lys Ala Glu Asp Thr Ala Met Tyr Tyr Cys Ala
                85                  90                  95

Thr Asn Arg Leu His Tyr Tyr Ser Asp Asp Asp Ser Leu Arg Gly Gln
            100                 105                 110

Gly Thr Gln Val Thr Val Ser Ser
        115                 120


<210> SEQ ID NO 226
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Asn Ala
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Asp Ser Leu Arg Gly Gln
            100                 105                 110

Gly Thr Gln Val Thr Val Ser Ser
```

115 120

<210> SEQ ID NO 227
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 227

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Thr Phe Ser Asn Ala
20 25 30

His Met Ser Trp Val Arg Gln Ala Pro Gly Lys Gly Arg Glu Trp Ile
35 40 45

Ser Ser Ile Tyr Ser Gly Gly Ser Thr Trp Tyr Ala Asp Ser Val Lys
50 55 60

Gly Arg Phe Thr Ile Ser Arg Asp Asn Ser Lys Asn Thr Leu Tyr Leu
65 70 75 80

Gln Leu Asn Ser Leu Lys Thr Glu Asp Thr Ala Met Tyr Tyr Cys Ala
85 90 95

Glu Asn Arg Leu His Tyr Tyr Ser Asp Asp Asp Ser Leu Arg Gly Gln
100 105 110

Gly Thr Gln Val Thr Val Ser Ser
115 120

<210> SEQ ID NO 228
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

Gln Val Gln Leu Gln Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Pro Met Thr Trp Ala Arg Gln Ala Pro Gly Lys Gly Leu Glu Trp Val
35 40 45

Ser Thr Ile Ala Ser Asp Gly Gly Ser Thr Ala Tyr Ala Ala Ser Val
50 55 60

Glu Gly Arg Phe Thr Ile Ser Arg Asp Asn Ala Lys Ser Thr Leu Tyr
65 70 75 80

Leu Gln Leu Asn Ser Leu Lys Thr Glu Asp Thr Ala Met Tyr Tyr Cys
85 90 95

Thr Lys Gly Tyr Gly Asp Gly Thr Pro Ala Pro Gly Gln Gly Thr Gln
100 105 110

Val Thr Val Ser Ser
115

<210> SEQ ID NO 229
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

Gln Val Gln Leu Gln Glu Ser Gly Gly Gly Ser Val Gln Ala Gly Gly
1 5 10 15

Ser Leu Arg Leu Ser Cys Thr Ala Ser Gly Phe Thr Phe Asp Asp Arg
20 25 30

Glu Met Asn Trp Tyr Arg Gln Ala Pro Gly Asn Glu Cys Glu Leu Val
35 40 45

Ser Thr Ile Ser Ser Asp Gly Ser Thr Tyr Tyr Ala Asp Ser Val Lys
50 55 60

Gly Arg Phe Thr Ile Ser Gln Asp Asn Ala Lys Asn Thr Val Tyr Leu
65 70 75 80

Gln Met Asp Ser Val Lys Pro Glu Asp Thr Ala Val Tyr Tyr Cys Ala
85 90 95

Ala Asp Phe Met Ile Ala Ile Gln Ala Pro Gly Ala Gly Cys Trp Gly
100 105 110

Gln Gly Thr Gln Val Thr Val Ser Ser
115 120

<210> SEQ ID NO 230
<211> LENGTH: 125
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 230

Gln Val Gln Leu Gln Glu Ser Gly Gly Gly Ser Val Gln Ala Gly Gly
1 5 10 15

Ser Leu Arg Leu Ser Cys Thr Ala Ser Gly Phe Thr Phe Asp Asp Ser
20 25 30

Asp Met Gly Trp Tyr Arg Gln Ala Pro Gly Asn Glu Cys Glu Leu Val
35 40 45

Ser Thr Ile Ser Ser Asp Gly Ser Thr Tyr Tyr Ala Asp Ser Val Lys
50 55 60

Gly Arg Phe Thr Ile Ser Gln Asp Asn Ala Lys Asn Thr Val Tyr Leu
65 70 75 80

Gln Met Asn Ser Leu Lys Pro Glu Asp Thr Ala Val Tyr Tyr Cys Ala
85 90 95

Ala Glu Pro Arg Gly Tyr Tyr Ser Asn Tyr Gly Gly Arg Arg Glu Cys
100 105 110

Asn Tyr Trp Gly Gln Gly Thr Gln Val Thr Val Ser Ser
115 120 125

<210> SEQ ID NO 231
<211> LENGTH: 119
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 231

Gln Val Gln Leu Gln Glu Ser Gly Gly Gly Ser Val Gln Ala Gly Gly
1 5 10 15

Ser Leu Arg Leu Ser Cys Val Ala Ser Gly Tyr Thr Ser Cys Met Gly
20 25 30

```
Trp Phe Arg Gln Ala Pro Gly Lys Glu Arg Glu Ala Val Ala Thr Ile
        35                  40                  45

Tyr Thr Arg Gly Arg Ser Ile Tyr Tyr Ala Asp Ser Val Lys Gly Arg
    50                  55                  60

Phe Thr Ile Ser Gln Asp Asn Ala Lys Asn Thr Leu Tyr Leu Gln Met
65                  70                  75                  80

Asn Ser Leu Lys Pro Glu Asp Ile Ala Met Tyr Ser Cys Ala Ala Gly
                85                  90                  95

Gly Tyr Ser Trp Ser Ala Gly Cys Glu Phe Asn Tyr Trp Gly Gln Gly
            100                 105                 110

Thr Gln Val Thr Val Ser Ser
        115
```

<210> SEQ ID NO 232
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 232

```
Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115
```

<210> SEQ ID NO 233
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80
```

```
Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115


<210> SEQ ID NO 234
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Gln Glu Ser Gly Gly Gly Ser Val Leu Ala Gly Gly
1               5                   10                  15

Ser Leu Arg Leu Ser Cys Val Ala Ser Gly Tyr Gly Tyr Asn Tyr Ile
            20                  25                  30

Gly Trp Phe Arg Gln Thr Pro Gly Lys Glu Arg Glu Gly Val Ala Val
        35                  40                  45

Ile Tyr Thr Gly Gly Gly Asp Thr Tyr Tyr Ala Asp Ser Val Lys Gly
    50                  55                  60

Arg Phe Thr Ala Ser Arg Asp Asn Ala Lys Ser Thr Leu Tyr Leu Gln
65                  70                  75                  80

Met Asn Ser Leu Glu Pro Glu Asp Thr Ala Met Tyr Tyr Gly Val Ala
                85                  90                  95

Arg Tyr Cys Val Gly Ser Val Tyr Ala Cys Leu Arg Gly Gly His Asp
            100                 105                 110

Glu Tyr Ala His Trp Gly Gln Gly Thr Gln Val Thr Val Ser Ser
        115                 120                 125


<210> SEQ ID NO 235
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Gln Glu Ser Gly Gly Gly Ser Val Gln Pro Gly Gly
1               5                   10                  15

Ser Leu Arg Leu Ser Cys Ala Ala Ser Gly Ser Thr Tyr Ala Asn Tyr
            20                  25                  30

Leu Met Gly Trp Phe Arg Gln Ala Pro Gly Lys Glu Arg Glu Gly Val
        35                  40                  45

Ala Ala Ile Tyr Ser Gly Gly Gly Ser Thr Tyr Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Ala Ser Ala Val Lys Gly Asp Lys Gly Asp Ile Val Val Val
            100                 105                 110

Val Thr Gly Thr Gln Arg Met Glu Tyr Asp Tyr Trp Gly His Gly Thr
        115                 120                 125
```

Gln Val Thr Val Ser Ser
    130

<210> SEQ ID NO 236
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Gln Glu Ser Gly Gly Gly Ser Val Gln Ala Gly Ala
1               5                   10                  15

Ser Leu Arg Leu Ser Cys Ser Val Ser Gly Phe Thr Phe Asp Glu Ser
            20                  25                  30

Val Met Ser Trp Leu Arg Gln Gly Pro Gly Asn Glu Cys Asp Ala Val
        35                  40                  45

Ala Ile Ile Ser Ser Asp Asp Asn Thr Tyr Tyr Asp Asp Ser Val Lys
    50                  55                  60

Gly Arg Phe Thr Ile Ser Glu Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Ala Arg Arg Arg Arg Pro Val Tyr Asp Ser Asp Tyr Glu Leu Arg Pro
            100                 105                 110

Arg Pro Leu Cys Gly Asp Phe Gly Val Trp Gly Gln Gly Thr Gln Val
        115                 120                 125

Thr Val Ser Ser
    130

<210> SEQ ID NO 237
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Gln Glu Ser Gly Gly Gly Ser Val Gln Ala Gly Gly
1               5                   10                  15

Ser Leu Arg Leu Ser Cys Ile Gly Ser Gly Leu Pro Phe Asp Glu Asp
            20                  25                  30

Asp Met Gly Trp Tyr Arg Gln Ala Pro Gly Asn Glu Cys Glu Leu Val
        35                  40                  45

Ser Ser Ile Ser Ser Asp Gly Thr Ala Tyr Tyr Ala Asp Ser Val Lys
    50                  55                  60

Gly Arg Phe Thr Ile Ser Arg Asp Asn Ala Lys Asn Thr Val Leu Leu
65                  70                  75                  80

Gln Met Asn Ser Leu Lys Pro Glu Asp Thr Ala Val Tyr Tyr Cys Ala
                85                  90                  95

Ala Gly Val His Arg Gln Phe Gly Gly Ser Ser Ser Cys Gly Asp Ala
            100                 105                 110

Phe Tyr Gly Met Asp Tyr Trp Gly Lys Gly Thr Gln Val Thr Val Ser
        115                 120                 125

Ser

<210> SEQ ID NO 238
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 238

```
Gln Val Gln Leu Gln Glu Ser Gly Gly Gly Ser Val Gln Ala Gly Gly
1               5                   10                  15

Ser Leu Arg Leu Ser Cys Val Ala Ser Gly Asp Val Tyr Gly Arg Asn
            20                  25                  30

Ser Met Ala Trp Phe Arg Gln Ala Pro Gly Lys Glu Arg Glu Gly Val
        35                  40                  45

Ala Val Gly Tyr Ser Val Val Thr Thr Thr Tyr Tyr Ala Asp Ser Val
    50                  55                  60

Lys Gly Arg Phe Thr Ile Ser Glu Asp Asn Asp Lys Asn Thr Val Tyr
65                  70                  75                  80

Leu Glu Met Asn Ser Leu Lys Pro Glu Asp Thr Ala Met Tyr Tyr Cys
                85                  90                  95

Ala Ala Asp Gly Asn Leu Trp Arg Gly Leu Arg Pro Ser Glu Tyr Thr
            100                 105                 110

Tyr Trp Gly Gln Gly Thr Gln Val Thr Val Ser Ser
        115                 120
```

<210> SEQ ID NO 239
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 239

```
Gln Val Gln Leu Gln Glu Ser Gly Gly Gly Ser Val Gln Ala Gly Gly
1               5                   10                  15

Ser Leu Arg Leu Ser Cys Ala Thr Ser Gly Phe Pro Tyr Ser Arg Tyr
            20                  25                  30

Cys Met Gly Trp Phe Arg Gln Ala Pro Gly Lys Glu Arg Glu Gly Val
        35                  40                  45

Ala Ala Ile Glu Pro Asp Gly Ser Thr Ser Tyr Ala Asp Ser Val Lys
    50                  55                  60

Gly Arg Phe Thr Ile Ser Gln Asp Asn Ala Val Asn Thr Leu Tyr Leu
65                  70                  75                  80

Gln Met Asn Asn Leu Lys Pro Glu Asp Thr Ala Met Tyr Tyr Cys Ala
                85                  90                  95

Ala Asp Glu Arg Cys Phe Tyr Leu Lys Asp Tyr Asp Leu Arg Arg Pro
            100                 105                 110

Ala Gln Tyr Arg Tyr Trp Gly Gln Gly Thr Gln Val Thr Val Ser Ser
        115                 120                 125
```

<210> SEQ ID NO 240
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 240

```
Gln Val Gln Leu Gln Glu Ser Gly Gly Gly Leu Val Gln Pro Gly Gly
1               5                   10                  15

Ser Leu Arg Leu Ser Cys Thr Val Ser Gly Phe Thr Phe Asp Glu Ser
            20                  25                  30

Asp Met Gly Trp Leu Arg Gln Asn Pro Gly Asn Glu Cys Gly Val Val
        35                  40                  45

Ser Val Ile Thr Ser Asp Asp Asn Pro Tyr Tyr Asp Asp Ser Val Lys
    50                  55                  60

Gly Arg Phe Thr Ile Ser Glu Asp Asn Ala Lys Asn Met Val Tyr Leu
65                  70                  75                  80

Gln Met Asn Ser Leu Lys Pro Glu Asp Thr Gly Val Tyr Tyr Cys Ala
                85                  90                  95

Thr Arg Ser Arg Gln Pro Val Tyr Ser Arg Asp Tyr Glu Leu Arg Pro
            100                 105                 110

Arg Pro Leu Cys Gly Asp Phe Gly Val Trp Gly Gln Gly Thr Gln Val
        115                 120                 125

Thr Val Ser Ser
    130
```

<210> SEQ ID NO 241
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Arg Leu Lys Pro Glu Asp Thr Gly Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125
```

<210> SEQ ID NO 242
<211> LENGTH: 126
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Asp Asp Phe
```

```
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125


<210> SEQ ID NO 243
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Ser Thr Val Tyr Leu
65                  70                  75                  80

Gln Met Asn Arg Leu Lys Pro Glu Asp Thr Gly Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125


<210> SEQ ID NO 244
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Asp Arg
            20                  25                  30

Asp Met Gly Trp Tyr Arg Gln Ala Pro Gly Asn Glu Cys Glu Arg Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
```

```
65                  70                  75                  80

Gln Met Asn Ser Leu Lys Pro Glu Asp Thr Ala Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125


<210> SEQ ID NO 245
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Val Gln Leu Gln Glu Ser Gly Gly Gly Ser Val Leu Ala Gly Gly
1               5                   10                  15

Ser Leu Arg Leu Ser Cys Val Ala Ser Gly Tyr Gly Tyr Asn Tyr Ile
            20                  25                  30

Gly Trp Phe Arg Gln Thr Pro Gly Lys Glu Arg Glu Gly Val Ala Val
        35                  40                  45

Ile Tyr Ile Gly Gly Gly Asp Thr Tyr Tyr Ala Asp Ser Val Lys Gly
    50                  55                  60

Arg Phe Thr Ala Ser Arg Asp Asn Ala Lys Ser Thr Leu Tyr Leu Gln
65                  70                  75                  80

Met Asn Ser Leu Glu Pro Glu Asp Thr Ala Met Tyr Tyr Cys Val Ala
                85                  90                  95

Arg Tyr Cys Val Gly Ser Val Tyr Ala Cys Leu Arg Gly Gly His Asp
            100                 105                 110

Glu Tyr Ala His Trp Gly Gln Gly Thr Gln Val Thr Val Ser Ser
        115                 120                 125


<210> SEQ ID NO 246
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Val Gln Leu Gln Glu Ser Gly Gly Gly Ser Val Leu Ala Gly Gly
1               5                   10                  15

Ser Leu Arg Leu Ser Cys Val Ala Ser Gly Tyr Gly Tyr Asn Tyr Ile
            20                  25                  30

Gly Trp Phe Arg Gln Thr Pro Gly Lys Glu Arg Glu Gly Val Ala Val
        35                  40                  45

Ile Tyr Thr Gly Gly Gly Asp Thr Tyr Tyr Ala Asp Ser Val Lys Gly
    50                  55                  60

Arg Phe Thr Ala Ser Arg Asp Asn Ala Lys Ser Thr Leu Tyr Leu Gln
65                  70                  75                  80

Met Asn Ser Leu Glu Pro Glu Asp Thr Ala Met Tyr Tyr Cys Val Ala
                85                  90                  95

Arg Tyr Cys Val Gly Ser Val Tyr Ala Cys Leu Arg Gly Gly His Asp
            100                 105                 110

Glu Tyr Ala His Trp Gly Gln Gly Thr Gln Val Thr Val Ser Ser
```

```
        115                 120                 125


<210> SEQ ID NO 247
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asn Ser Val Lys
    50                  55                  60

Gly Arg Ser Ser Ile Ser Arg Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125


<210> SEQ ID NO 248
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Arg Leu Lys Pro Glu Asp Thr Gly Val Tyr Tyr Cys Ala
                85                  90                  95

Ala Glu Gly Ala Leu Gly Ser Lys Met Asn Cys Gly Trp Val Gly Asn
            100                 105                 110

Phe Gly Tyr Trp Gly Gln Gly Thr Gln Val Thr Val Ser Ser
        115                 120                 125


<210> SEQ ID NO 249
<211> LENGTH: 375
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 249
caggttcagc ttcaggagtc cggtggaggc tccatccagg ccgggggctc tctccgcctg 60
tcttgcgccg cttccagata cctctacagt atcgactaca tggcttggtt tcgtcagagc 120
ccaggaaaag agcgggaacc cgtggcagta atctacactg cctcaggtgc cacattttac 180
cccgactctg tcaagggcag gttcaccatc tctcaggata atgccaagat gacagtgtac 240
ttgcagatga actccctgaa atctgaggat accgctatgt attactgtgc cgcagtgcgc 300
aagaccgatt cttacctgtt cgacgctcag agttttacct actggggcca gggcactcag 360
gtcaccgtca gcagc 375

<210> SEQ ID NO 250
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 250
caggtgcagt tgcaggagtc cggcgggggt tccgtgcaag caggcggatc tctgcgcctg 60
tcctgcgtgg cctctcgtta tttgtatagc accaactaca tggcttggtt ccgtcagtcc 120
ccaggcaaag agcgcgaagc cgtagccgta atctatacgg cctctggggc aacactctat 180
accgactcag tgaagggacg cttcacgatt tcccaagaca atgcaaagat gaccgtgtac 240
ttgcagatga accgcctgaa gagcgaggac acggctatgt attactgcgc agccgtgcgc 300
aagaccgact cctacttgtt tgacgctcag tccttcactt attggggcca gggtacacag 360
gtcaccgtga gcagt 375

<210> SEQ ID NO 251
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 251
caagtacagc tccaggagag cggcggtgga tctatccaag caggggggtag ccttaggttg 60 tcctgtgtgg cgtccagata cctgtatagc acgaactaca tggcatggtt cagacagtcc 120
ccaggcaagg aacgcgaggc agtcgccgtt atttacactg catctggggc caccctctat 180
acggacagcg tgaagggaag gtttacaatc tcccaggaca acgcgaagat gaccgtgtac 240
cttcagatga accgcctgaa gtccgaggac accgccatgt attactgtgc agcggtgcgc 300
aagaccgaca gctatctgtt cgacgcgcag tcattcactt attggggcca aggaacccaa 360
gtgaccgtca gctca 375

<210> SEQ ID NO 252
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 252
caggtgcagc tccaagagtc cgggggaggc tctatccagg cgggaggcag tctgcgcttg 60
tcctgcgccg caagtcgtta tctgtactcc attgattaca tggcatggtt ccgccagtcc 120
ccaggtaagg aacgtgaacc tgccgctgtg atctacaccg cttctggagc aacctttttat 180 cctgatagcg ttaagggtcg cttcaccatc tctcaggata acgccaaaat gacagtgtac 240
ctccagatga acagcctgaa gtctgaggac actgccatgt actattgtgc ggctgtgcgc 300
aagaccgact cctatctgtt tgatgcacag agctttacct attggggtca gggcacccag 360
gtgactgtgt ctagc 375

<210> SEQ ID NO 253
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 253
caggtccagt tgcaggagtc cggtggaggt tccatccagg cgggtgggtc ccttcgtctc 60
tcctgcgtgg cctctaagta cctgtattca accaactaca tggcatggtt cagacagtct 120
cccggcaaag agcgtgaggc agtggccgcg atctatacag cttctggggc caccctgtac 180
tctgattcca ataagggaag gttcactatc tcacaggata acgccaaaat gaccgtctac 240
cttcagatga acagcctcaa gtctgaagac acggcaatgt attactgtgc agccgtgcgc 300
aaaactggga gctacctgtt tgacgctcag tctttcactt attggggcca gggtacgcag 360
gtgacagtct cttct 375

<210> SEQ ID NO 254
<211> LENGTH: 387
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 254
caggtgcaac tccaggagag cggaggcggt tctgttcagg caggaggttc cctgagactg 60
tcctgtgccg cgtctcgctt tacgtattca tcctactgca tgggatggtt cagacaagcg 120
ccggggaaag aaagggaagg cgtggcctcc attgactccg acggctcaac ttcatacact 180
gatagcgtga aaggccggtt caccatctct aaggacaacg cgaagaacac cctgtatctc 240
cagatgaaca gcctcaagcc tgaggatact gccatgtact attgcgcact cgacctgatg 300
tctactgtgg tcccaggctt ctgcgggttc ctgctctctg ctggcatgga ctactggggg 360
aagggcactc aggtaacggt tagctcc 387

<210> SEQ ID NO 255
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 255
caggtgcagc ttcaggaatc tggcgggggc tccgtgcagg ccgggggctc cctcagactt 60
tcctgtgccg tctccggtta cacatttaac agtaactgta tgggctggtt ccgccaggca 120

```
ccaggcaagg agagggaagg tgtggccaca atctatactg gtgttgggag tacgtactat    180

gctgattccg tgaaaggtcg cttcacaatt tcccaggaca acgcgaagaa cactgtgtac    240

ttgcagatga atagcctgaa gcctgaagat accgcaatgt attactgcgc tgccgagcca    300

ctctcccgcg tatatggtgg aagttgcccc accccccactt tcggttactg gggccagggc    360

actcaagtga ccgtgtcctc t                                              381
```

```
<210> SEQ ID NO 256
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256

caggttcagc ttcaggagtc tgggggcggt tcagtgcagg ctggcggttc tctccgcctg     60

tcctgcgctg ccagcggcta tacttacagc atgtactgca tgggctggtt ccggcaagcc    120

cccggcaaag agcgtgaggg cgtcgctcaa atcaacagcg acgggtcaac cagctacgcc    180

gattctgtca agggcagatt tactatcagc aaggacaacg ccaaaaacac actgtacctc    240

cagatgaact ctttgaagcc tgaggacacc gcgatgtatt actgcgccgc tgacagccgc    300

gtgtacggtg gcagctggta tgagaggctg tgcggcccgt acacctacga gtacaactat    360

tggggacagg gcacgcaggt gacagttagc tcc                                 393
```

```
<210> SEQ ID NO 257
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257

caggtgcaac tgcaagagag tggcggaggc tccgtccagg ctggaggttc cctgcggctg     60

tcttgcgccg tcagcggcta cgcatattcc acttactgta tgggttggtt ccgccaggcc    120

cctggaaagg aacgcgaggg tgttgccgct attgatagcg gaggctccac atcctatgcg    180

gactccgtga aaggtcgttt caccatctcc aaggataacg ccaagaacac tctgtacctg    240

cgcatgaact ctctgaagcc tgaggacact gccatgtatt actgcgccgc tgtgcccccct    300

ccacccgacg ggggctcttg tctgtttctt ggcccggaga tcaaggtgtc caaggctgat    360

ttccgttatt ggggccaggg aactcaagtc accgtgtctt cc                       402
```

```
<210> SEQ ID NO 258
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258

caggtccagc tccaggagtc cggtggaggc tccgttcagg ccggtggcag cttgcgtctg     60

agctgcgcgg cttcaagata cctgtactcc attgattaca tggcatggtt ccgtcagtct    120

cctggcaagg agcgcgagcc cgtcgctgtg atctataccg ccagcggagc cacgttctac    180

cctgattccg tcaagggccg cttcaccatt agccaagaca acgctaagat gacggtgtac    240
```

```
ctccaaatga atagcctgaa aagcgaggac acagcgatgt attactgcgc cgctgttagg    300

aaaactgata gttacctgtt cgatgcacag tctttcactt actgggggca gggcacccaa    360

gttaccgtct cctct                                                     375


<210> SEQ ID NO 259
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259

caggtgcagc tccaggaatc tggagggggc agtgtgcagg ccgggggctc cctgcgcttg     60

agctgtggag ccagccgcta cacgtattcc agttactgta tgggctggtt cagacaagct    120

ccgggtaagg agagagaggg agttgccgta attgattctg acgggtccac tagctatgcg    180

gattcagtca agggccggtt caccatcagc aaggacaatg gtaagaacac actgtacctg    240

caaatgaaca gcctgaagcc cgaggacacc gccatgtact attgtgccgc tgatctcgga    300

cattaccgcc ctccctgcgg tgtgctctat ctcgggatgg actattgggg taagggcacc    360

caggtgaccg tgtcctct                                                  378


<210> SEQ ID NO 260
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260

caggtgcagc tccaggaaag cggcgggggt agcgttcaag caggtgggtc cctgcgcttg     60

agctgtactg tgtccggcta cacctactca agcaactgca tgggatggtt ccgtcaggcc    120

cctggcaagg aacgcgaagg cgtggctact atctacaccg gcggtggcaa cacttattac    180

gccgactccg ttaaggggcg tttcactatc agccaagaca acgccaagaa caccgtgtat    240

ctgcaaatga ataacctgaa gcctgaagac accgccatgt attactgtgc tgccgagccc    300

ctttcccgcg tttacggcgg ttcttgtcct acccctacct ttgactactg gggtcaggga    360

acacaggtga cagtgtccag t                                              381


<210> SEQ ID NO 261
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 261

caagtccaac tccaggaatc tgggggaggc tccgtacagg ctggcggttc ccttcgtctg     60

tcctgtgctg tgtcagggta ctcctactcc agtaactgta tgggctggtt ccggcaagcc    120

cccggaaagg agcgcgaggg cgtggctacc atccacacag gggcggttc cacatattac    180

gccgatagtg tcaagggccg cttcaccatt agtcaggaca acgccaagaa taccgtttac    240

cttcaaatga actctttgaa acctgaggac actgcgatgt attactgtgc ggcagagcct    300

ttgtcccgcc tgtacggggg atcttgtccg accccgactt tcgggtactg gggacagggc    360
```

acccaggtga cagtgtcctc c 381

<210> SEQ ID NO 262
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 262
caggtgcagt tgcaggaaag cgggggtggc agcgtccaag ccggtggcag cctgcgtctg 60
tcctgcggtg cctccggcta tacttactcc agctattgca tgggttggtt ccgccaagtg 120
ccaggaaagg agcgtgaggg ggtggctgta attgattcag atgggtcaac aagctacgct 180
gacagcgtta aaggtcgctt caccatcagt aaggacaacg gcaagaacac cctctacctg 240
caaatgaact ccctgaagcc ggaggatacc gcaatgtatt actgtgccgc tgacttggga 300
cactaccgcc ctccgtgcgg tgtgctttat ctgggcatgg attactgggg taagggaacc 360
caagtgacgg tgtcttct 378

<210> SEQ ID NO 263
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 263
caggtacaac tccaggagtc tggcggtggg tccgtgcagg caggtggcag ccttcgcctc 60
tcctgcgggg cctccgggta cacctatagt ggctactgca tggggtggtt caggcaagcc 120
cccggtaagg aacgtgaggg agttgctgtg attgattcag atgggtccac gagttacgct 180
gactccgtga aaggtaggtt cacaatctcc aaagataatg gcaagaacac cctctacctt 240
cagatgaata gcctgaagcc agaagacacc gccatgtatt actgtgctgc cgacctggga 300
cactatcgcc ctccgtgcgg ggtcctgtac ttgggcatgg actattgggg caaggggacc 360
caggtgactg tgtcctct 378

<210> SEQ ID NO 264
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 264
caggtgcagt tgcaggaatc cggtggaggc tctgttcagg ccgggggctc tctccgcctg 60
gcctgcgcag cctccaggta tacttacagc aactactgca tggggtggtt tcgccaggct 120
ccgggcaaag agcgtgaggg agtggctact attgattccg atggaaacac cagctacgcc 180
gatagcgtga agggcagatt tactatcagc agagataacg ctaaaaacac gttgtacctc 240
cagatgaact cactcaagcc gggggacaca gctatgtatt actgcgcagc cgatctgggt 300
cactaccgcc cgccctgcgg cgcatattac tatggcatgg actactgggg caagggcacc 360
caggtgaccg tgtccagt 378

<210> SEQ ID NO 265

<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 265
caggtgcagc tccaagagtc tggcgggggt tccgtgcaag ccggtggctc actcaggttg 60
agttgcgcag ccagcggcta tagcaactgt tcctatgaca tgacttggta tcgccaggcc 120
cctggcaaag agcgtgagtt cgtgtcagct attcactccg acggctccac tcgttatgcg 180
gactctgtga agggccggtt tttcatctcc caggacaacg ctaaaaacac tgtctatttg 240
cagatgaact ctctgaaacc cgaagatacc gccatgtact attgcaaaac cgatcctctg 300
cattgtcgcg cccacggcgg gagttggtac tctgtgcggg ccaactattg gggccagggc 360
acccaggtca ccgtgtcctc a 381

<210> SEQ ID NO 266
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 266
caggtacaac tccaggagtc tggcggtggc agcgtgcagg caggcggaag cctgaggctg 60
tcctgcgctg tatctggcta cacttataat tccaactgca tgggttggtt tcggcaggct 120
ccaggtaagg agcgcgaggg cgtcgccacc atttatacag gtgttggcag cacatattac 180
gccgacagcg tgaagggaag gttcaccatc tcccaagaca atgcgaaaaa cacagtgtat 240
ctccagatga atagcctgaa gcccgaggac acggctatgt attactgcgc tgccgagcca 300
ctgagcagag tgtatggggg cagctgtcct acacccactt tcggctattg gggtcaaggc 360
acccaggtta cagtcagctc c 381

<210> SEQ ID NO 267
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 267
caggtccagc tccaggagag cgggggcggt tctgtgcaag ccggaggctc attgagactc 60
tcatgcgctg caagtggttt taccttcgat gacagcgata tgggatggta tcgtcaggct 120
ccgggcaatg agtgtgatct ggtctccact atctcctctg atggttccac atactatgct 180
gactctgtca aggggcgctt taccatctcc caagataatg ccaagaacac cgtgtacctt 240
cagatggatt cagttaagcc cgaggacaca gccgtctatt actgcgctgc ggattttatg 300
attgccatcc aagctcccgg agcgggatgc tggggccagg gaacccaggt cactgtgagc 360
agt 363

<210> SEQ ID NO 268
<211> LENGTH: 351
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 268
caggtgcagt tgcaggagtc cggcgggggt tctgtgccag cgggtgggag cctcaagctc 60
tcctgtgccg cttccggctt ctcattctcc tcttacccta tgacctgggc acgccaagcg 120
cccggcaagg gactggaatg ggtgtccacc attgcttccg atggcggtag tacagcctac 180
gccgcgtcag tggagggtcg gttcacgatc agccgggaca acgcgaagag cacactctac 240
ctccagctga actctctgaa gaccgaggac accgccatgt actattgcac aaagggctac 300
ggcgacggca ccccggcacc cggccagggc acccaggtga cagtctcttc c 351

<210> SEQ ID NO 269
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 269
caggtgcagt tgcaggaaag tggtggaggg agtgtgcaga ctgggggctc tctccgcctc 60
agctgcacag cctctggatt taccttcgat gatcgcgaga tgaactggta tcgccaggct 120
ccgggaaacg agtgcgaact ggtgtctaca atcagttctg acgggtccac ctattacgct 180
gatagtgtca agggccgctt cactatctct caggacaacg cgaagaacac cgtttacttg 240
cagatggata gcgtgaagcc tgaagataca gcggtgtatt actgcgctgc cgactttatg 300
attgccatcc aggcaccggg ggcggggtgt tggggacagg gaactcaggt gactgtgtcc 360
tcc 363

<210> SEQ ID NO 270
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 270
caggttcaac tccaagagag tggtggcgga agcgtgcagg cgggcggttc tctgcgtctg 60
agttgcactg ccagcggatt taccttcgac gattccgaca tgggatggta cagacaggcc 120
cctggtaacg agtgcgaact cgtgagtact atcagctccg acggcaacac ctattacacc 180
gattctgtga agggcaggtt caccatctcc caggacaacg ctaagaacac tgtgtacctg 240
caaatgaata gcctgggacc cgaggacaca gcggtctatt actgcgcggc agagccgcgc 300
ggctattaca gcaactacgg cggtagacgc gagtgcaact actgggggca ggggacgcaa 360
gtgactgtct cctcc 375

<210> SEQ ID NO 271
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 271
caagtgcagc ttcaggagtc cgggggtggc agcgtccagg ctgggggcag cttgcgcctg 60
tcttgcgctg cgtctgggtt cagctttagc tcctacccta tgacctgggc tagacaggcc 120
cccggcaagg ggctggagtg ggtgagtaca atcgcctccg acggaggtag tacggcctac 180
gcagcgtccg tcgagggtcg cttcaccatc agccgggata acgctaagtc caccctgtac 240
cttcagctca attctctcaa aacggaggat accgccatgt actattgcac caagggatat 300
ggcgacggca ccccagctcc tggacagggc acacaggtca ccgttagctc c 351

<210> SEQ ID NO 272
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 272
caggtccagc ttcaggagtc tggcgggggc gcagtacagg caggggggttc tctgcgtctg 60 tcctgcgccg cgtccggctt tactttcagc aacgcacaca tgagttgggt gcgccaagcg 120
cccggcaagg gccgggaatg gatcagtagc atctacagtg gaggcagcac atggtacgcc 180
gactctgtta agggtcgttt tacgatctct cgtgacaact ccaagaacac tttgtacctc 240
cagctcaatt ctctcaagac cgaggacacc gcgatgtact attgtgccga gaacaggctg 300
cactactatt ccgacgatga ctctctcagg ggccagggaa ctcaagttac cgtgtccagc 360

<210> SEQ ID NO 273
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 273
caagtgcagc tccaagagag tggtggcggg ctggttcagc cagggggcag cttgagactc 60
tcctgcgcag cttcaggctt taccttcgat gaccgtgaga tgaactggta tcgtcaggcc 120
ccaggcaacg agtgtgagct ggttagcacg atttcttccg acggttccac ctattacgcc 180
gactctgtga agggacgttt cactatctcc caggacaatg ccaagaacac cgtgtacctc 240
cagatggaca gcgtgaagcc ggaggatact gctgtgtatt actgcgctgc cgactttatg 300
atcgccatcc aggcccctgg cgcgggttgc tggggccagg gcactcaggt gaccgtgtct 360
tcc 363

<210> SEQ ID NO 274
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 274
caagtgcaac tgcaagagtc cggcggtgga tctgtgcagg ccggaggcag cctgcggctg 60
agctgtgtag cttccgggta tacctttagc tcatactgta tgggctggtt tcgtcaggcc 120
cccggtaagg agcgcgaggg cgtggccgct cttggtggag gctccaccta ttacgccgat 180
tccgtgaagg gcaggtttac tatctcccag gacaacgcga agaatacgct ctatctccag 240
atgaatagcc tgaagcccga ggatacagct atgtattact gtgctgccgc ttgggtagcc 300
tgcctggagt tcggtggctc ctggtacgat ctggcacggt acaaacattg ggggcagggc 360
acccaggtca ccgtgtctag c 381

<210> SEQ ID NO 275
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 275
caggtccagt tgcaggaatc tgggggcggt tccgtacaag caggtggctc ccttcggttg 60
agctgtaccg catccggctt tactttcgac gatagcgata tgggctggta tcgtcaggcc 120
ccagggggcg agtgcgagct ggttacaatc tcctctgacg gcagtaccta ttacgcagac 180
tccgtcaagg gcaggttcac tatcagtcag gacaatgcaa agaacactgt gtatctccag 240
atgaactctc tgaagccaga agatactgcc gtgtattact gcgctgcgga accgagaggc 300
tattactcta attatggcgg gcgtcgggag tgtaattatt ggggacaggg aacccaggtg 360
accgtgtcct cc 372

<210> SEQ ID NO 276
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 276
caggtgcagc tccaggagag tggcggaggc tccgtgcagg ctgggggctc tctgcgtctg 60
agctgtgccg caagcggtag catttacagc tctgcctaca tcgggtggtt tcgtcaagcg 120
ccgggcaaaa agcgcgaagg cgtggccgga atctacacgc gcgatggctc caccgcttat 180
gctgacagcg ttaagggacg ttttacgatc agccaggact ctgccaaaaa gactgtgtat 240
ctccagatga actccctgaa acctgaggac acagccatgt attactgcgc cgctggccgc 300
cgtacaaaga gctatgttta catctttcgc cccgaagagt acaactactg ggccagggga 360
acccaagtga ctgtgtccag t 381

<210> SEQ ID NO 277
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 277
caggttcagt tgcaggagtc cggcggaggc agcgtgcagg ccggaggctc cttgcgcttg 60
tcctgtgcgg cttctggctt caccttctca tctgctcaca tgagttgggt gcgtcaggcc 120
ccagggaaag gtcgcgagtg gattgcctcc atctacagcg gtgggggcac tttttatgcg 180
gacagcgtga agggccgctt taccatcagc cgtgacaacg ctaagaacac cctgtatctc 240
caactcaatt ccctcaagac cgaggataca gcgatgtact attgtgcaac caaccgcctt 300
cactattact ccgacgatga cagcctgcgc ggacagggga cccaggtgac ggtgtccagc 360

<210> SEQ ID NO 278
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 278
caggtgcaac tccaggaaag tggcggaggc tcagtgcagg caggtggctc tctccgcctt 60
tcctgcgctg ccagcggatt caccttctct aacgctcaca tgagctgggt tcgtcaggct 120
cccggcaaag gccgtgaatg gattagctcc atctatagtg gcggaagtac ttggtacgca 180
gatagcgtca agggccgctt cactattagt cgggataact ccaagaacac tctgtacctc 240
cagctgaact cattgaaaac cgaggacacg gctatgtact attgtgctga gaacaggctg 300
cactattact ccgacgatga ctctctgagg ggtcagggca cccaggtgac cgtcagctcc 360

<210> SEQ ID NO 279
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 279
caggtccaac tccaggagtc cggcggaggc agcgtgcagg ctggaggctc tctccgcctg 60
agctgcacag cttccagatt catcttcgat gactccgaca tgggctggta tcgccaggct 120
ccagggaacg agtgcgaact ggtgagcacc atctcttcag acggtagcac ctattacgcc 180
gacagtgtga aggggcgctt caccatctcc cgcgacaatg ctaaaaatac ggtgtatctc 240
cagatgaact ccctcaaacc ggaggacaca gctgtatatt actgtgctgc ggaaccacgg 300
ggctactata gcaactatgg tggaaggcgc gagtgcaact actggggtca gggcacacag 360
gtgacggttt cctcc 375

<210> SEQ ID NO 280
<211> LENGTH: 372
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 280
caggtgcagc tccaggagag cggcggtggc tccgtgcagg ctggtggcag cctgaagctg 60
tcctgcaccg tgagtggctt cacagccgac gattctgata tgggctggta tcgccaaggc 120
cccggcaatg agtgcgagct ggtaaccatt agctcagacg gctctacata ctatgccgat 180
tctgttaagg gccgctttac tatctcacag gataatgcca agaacacagt gtacttgcag 240
atgaactctc tgaaaccgga agacacagct gtgtattact gtgctgcgga gcctagaggg 300
tattacagca attacggggg ccggagagag tgtaactatt gggggcaggg cacccaagtg 360
accgtttcct cc 372

<210> SEQ ID NO 281
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 281
caggtccagc ttcaggaatc tgggggcggt ctcgtgcagc ccggcgggtc cctgcgtctg 60
tcttgtgctg cgagcggctt cacgttctca agtgcccaca tgagctgggt aaggcaggca 120
ccgggcaagg ggcgcgagtg gattgcaagc atctattcag gcgggggcac attctacgcc 180
gacagcgtga agggacgttt tacaatctcc agagataacg caaagaacac tctctacctc 240
caactcaact ccttgaaggc ggaagatact gcaatgtatt actgtgctac taaccgtctt 300
cattattact ctgacgatga ctccctgcgg gggcagggta cacaggtgac agtgagttcc 360

<210> SEQ ID NO 282
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 282
caggtgcagc tgcaagaatc tggtggaggg ctggtccagc ctgggggctc cctgcgcctc 60
tcatgtgtcg catctggctt caccttcagc aacgcccaca tgagctgggt tcgccaagcc 120
cctgggaagg gccgggagtg gatctccagt atctattccg gcggaagcac ttggtatgca 180
gacagcgtca aaggacggtt cactatttct cgtgataatt ctaagaacac cctgtacctt 240
cagctgaaca gcctgaagac cgaggacact gctatgtact attgtgctga gaatcgcctg 300
cattactata gcgacgatga cagtctgcgc ggacagggga cccaggtcac cgtgtcctct 360

<210> SEQ ID NO 283
<211> LENGTH: 360
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 283
caggttcagt tgcaggaatc aggaggcggt ctggtgcagc ctgggggctc tctgcgtctc 60
tcctgcgccg cttccggctt cacattctcc aacgcccaca tgagctgggt ccgccaggcc 120
cctgggaagg gccgcgagtg gatctccagt atctacagcg ggggctccac ttggtacgca 180
gacagcgtca aagggaggtt taccattagc cgtgacaatt ctaagaacac attgtatttg 240
cagctgaact ctcttaaaac cgaggacacc gccatgtact attgtgctga gaacaggctc 300
cactattact cagacgatga ctcacttcgc gggcagggaa cccaggtcac cgtctcctct 360

<210> SEQ ID NO 284
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 284
caagtccagc tccaggaaag cggcggtggc ctggtgcaac ctggcgggtc tctgcgcttg 60
tcatgcgctg cctccggctt caccttctca tcttacccta tgacctgggc gcgtcaggct 120
cccggcaagg gattggagtg ggtgtctact attgcctccg acggtggcag cacggcctac 180

```
gcagcgtctg tagaaggacg cttcacaatt agcagagaca acgcaaaatc tactttgtac    240

cttcagctca acagcctgaa gaccgaagac acagctatgt attactgcac aaaaggctac    300

ggggacggca cgccagcgcc tggacagggg acacaggtga ccgtatcttc t             351
```

<210> SEQ ID NO 285
<211> LENGTH: 363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 285

```
caggtgcagt tgcaggaatc aggggggtggc tctgtgcagg ccgggggctc cctgcgtctg     60

tcctgtactg cgagcggctt cacctttgat gaccgcgaga tgaactggta tcgccaggct    120

ccggggaacg agtgcgaact cgtgtctaca attagctccg atggttcaac atactatgct    180

gattctgtca aaggtcgctt taccatctca caggacaacg ccaagaacac cgtctacctc    240

cagatggact ctgtgaagcc tgaagatacc gccgtatact attgcgccgc tgactttatg    300

attgccattc aggctccggg tgctggatgc tggggtcagg ggactcaggt gaccgtgtct    360

tca                                                                  363
```

<210> SEQ ID NO 286
<211> LENGTH: 375
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 286

```
caagtgcagt tgcaggaaag cggcggtggg tccgtgcaag ccggaggttc tctccgcctg     60

tcttgcactg cctcaggttt taccttcgac gattccgata tgggctggta caggcaggct    120

cccggcaatg agtgcgagct ggtgtctacg atctcaagtg atggctccac ctactatgcc    180

gatagcgtaa aaggaaggtt tactattagc caggataacg cgaagaacac ggtgtacctc    240

cagatgaaca gtctcaagcc ggaggatact gccgtgtatt actgtgctgc cgagccgcgt    300

ggctattact ccaactacgg tggcagacgt gaatgcaatt actggggaca gggtactcag    360

gttaccgtgt cctct                                                     375
```

<210> SEQ ID NO 287
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 287

```
caggttcaac ttcaggaatc cgggggcggt tccgtgcaag ccgggggtag cctgcgtctg     60

tcttgcgtgg ccagcggcta tacctcctgt atgggttggt ttcggcaggc tcctgggaag    120

gagcgcgaag ccgtggcgac catctacaca cggggccgca gcatctatta cgctgacagt    180

gtgaagggcc gcttcaccat ctcccaggat aacgccaaga ataccctgta tctgcaaatg    240

aactccctga agcctgagga catcgccatg tattcctgcg cagctggagg gtactcatgg    300

tccgctgggt gcgagtttaa ttattggggc caaggaaccc aggtgaccgt ctcctca       357
```

<210> SEQ ID NO 288
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 288
caagtgcagc tccaggagtc tggcgggggc ctggttcagc ctggtgggtc cctgcgcctg 60
tcttgcacgg cttccggctt tagcttctcc tcatatccaa tgacctgggc acgccaggct 120
cctggtaagg gcctggagtg ggtctccacc atcgcctctg atggtgggtc aactgcctat 180
gctgcctccg tcgagggtag attcacaatc agcagagaca acgccaaatc cacgctgtac 240
ctgcaactca actccttgaa gaccgaggac acagctatgt attactgtac caaaggctac 300
ggcgacggca ctcctgctcc cggacagggg acccaggtga ctgtgtctag c 351

<210> SEQ ID NO 289
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 289
caggtccaac ttcaggaaag cgggggtgga ctggtacagc cagggggcag tctgcgcctg 60
tcctgtgccg caagcgggtt ttctttctcc agttacccca tgacctgggc tcgccaagca 120
cctggaaagg gactggagtg ggtgtctact attgcgtcag atggtgggag tacggcttac 180
gccgcgagcg tggagggtcg ttttacgatc agtagggaca acgccaaaag cactctgtac 240
ctccagctta acagcctgaa gaccgaggac accgccatgt attactgtac caagggctac 300
ggagacggca cccctgcgcc ggggcaaggc acccaggtga ccgtaagttc a 351

<210> SEQ ID NO 290
<211> LENGTH: 381
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 290
caggtgcaac tccaggagtc cggcgggggc tccgtgctgg ctggcggatc tttgaggctg 60
tcttgcgtgg cttctggcta tggctataat tacatcggct ggttccgtca gacacccggc 120
aaggagcgcg aaggggtggc ggtcatttac acagggggtg gggacactta ttacgccgac 180
tccgtcaagg gtaggtttac cgctagtcgc gataatgcca aaagtacgct gtacctgcaa 240
atgaacagct tggagccaga ggacaccgcc atgtattacg gagtggctcg ctactgtgtg 300
ggcagtgtgt acgcttgcct gcgcggaggc cacgacgagt acgcacactg gggccaggga 360
acccaggtga cagtgtctag c 381

<210> SEQ ID NO 291
<211> LENGTH: 402
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 291
caggtgcagc tccaggagtc tgggggtggc agcgtccagc caggtggctc attgagactg 60
tcttgtgctg catctggctc cacctacgct aattacctga tgggatggtt caggcaggcc 120
cctggtaagg agcgtgaggg cgtggccgct atctattctg gcggtgggtc cacctactat 180
gctgactccg tcaagggacg cttcactatt tctcaagaca atgccaagaa cactttgtac 240
ttgcaaatga actcactcaa acctgaggac accgcgatgt actattgcgc agcggcatcc 300
gcagtgaagg gagacaaagg ggatatcgtg gtagttgtga ccggcaccca gcgtatggag 360
tacgactact ggggacatgg cacccaggtg acagttagct cc 402

<210> SEQ ID NO 292
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 292
caggtacagt tgcaggagag tggtgggggt tccgtccagg ccggtgcctc tcttcgcctc 60
agttgtagcg tgagcggttt cacgttcgac gagtcagtga tgtcctggtt gcgccagggt 120
cccggcaatg agtgcgacgc ggtcgctatt atcagctccg atgacaacac ctattacgac 180
gatagcgtga aaggccgctt taccatctcc gaggacaacg ccaaaaacat ggtgtatctg 240
caaatgaact cactgaagcc ggaagacacc gcagtgtact attgcgccgc gcgtcggcgc 300
agacctgtgt acgattccga ttatgaactc cggccacgtc cgctgtgtgg cgatttcggc 360
gtgtggggcc aggggaccca ggtgacggtc tcctcc 396

<210> SEQ ID NO 293
<211> LENGTH: 387
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 293
caggtgcagc tccaggaatc tggcgggggc tctgtgcagg ctggtggctc ccttcgcctg 60
tcctgtattg gctccggtct tcctttcgac gaggatgaca tgggctggta tcgccaggcc 120
cctgggaatg agtgtgaatt ggtcagctca atctccagtg acggcaccgc ctattacgcc 180
gattccgtca agggacgctt cactatctcc agagacaacg ccaagaacac tgtgctgttg 240
cagatgaact ccctgaagcc cgaggatacc gctgtctatt actgcgcagc cggggtccac 300
agacagttcg gcggttccag ttcctgcggc gacgccttct acggcatgga ttactggggc 360
aagggaactc aggtcacagt gtcttcc 387

<210> SEQ ID NO 294
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 294
caggttcagc ttcaggagtc cggcgggggc tccgtacagg cagggggctc actgcgtctt 60
tcctgtgtgg cgagtggcga cgtgtatggc cgtaacagca tggcttggtt ccggcaggca 120
cctggaaagg aacgcgaggg cgttgcagtt gggtattccg tagtgacaac cacttactat 180
gccgacagtg tgaagggccg gtttacgatc tcagaggaca acgataaaaa cacagtgtac 240
ctggagatga actccctgaa gccggaagac actgctatgt attactgcgc tgccgatggc 300
aacctgtggc gcggactcag gccctccgag tacacttatt ggggtcaggg cacccaggtg 360
accgtttcaa gt 372

<210> SEQ ID NO 295
<211> LENGTH: 384
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 295
caggtccagc ttcaggagtc aggtggcggt agtgtccagg caggcggtag cctgcgcctt 60
agctgtgcta catccggctt cccttactca cgctattgta tgggctggtt caggcaagct 120
cccggtaaag agcgcgaggg agtggcagcc atcgagcctg acgggagcac atcttatgct 180
gactctgtaa aggggcgttt caccatctct caggacaacg ccgttaatac actgtacttg 240
caaatgaata acctgaagcc cgaggacaca gctatgtatt actgcgcagc cgacgagcgt 300
tgcttctatt tgaaggacta tgacctcaga aggccagccc agtaccgcta ctgggggcag 360
ggcacccagg ttaccgtgtc atct 384

<210> SEQ ID NO 296
<211> LENGTH: 396
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 296
caggtgcagt tgcaggagag tggcggtggc ctcgtgcagc ctggcggaag cctccgtctg 60
agctgcactg tgtccggctt cactttcgac gagagcgaca tgggctggct gaggcagaac 120
cctggtaacg agtgcggcgt tgtgagtgtc atcacgtctg atgacaaccc atactatgat 180
gacagcgtca agggccgctt tactatctcc gaggataacg ccaagaacat ggtgtacctc 240
cagatgaact cactgaagcc cgaggatacc ggcgtttatt actgtgcaac caggagccgt 300
cagcctgtgt actcacgcga ttacgagctg cggccccgcc ccctctgtgg agactttggt 360
gtgtggggcc agggcaccca ggtgactgtt tccagc 396

<210> SEQ ID NO 297
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 297
caggtgcagt tgcaggagag tggagggggc tcagtgcagg ctggcgggtc cttgcgtctg 60
tcttgcaccg cctctggctt caccttcgat gacttcgata tgggttggta tcgccaggct 120
ccagggaacg agtgcgaatt ggtcagcact atcagcgacg atggctcaac atattacgcc 180

```
gactctgtga agggacggtc tagcattagc cgggacaacg caaagaacac cgtctatctc    240

cagatgaacc gcttgaagcc tgaggatacc ggagtctatt actgcgccgc tgagggcgcg    300

ttgggctcca agactaattg tggctgggtg ggcaacttcg gatattgggg ccagggaaca    360

caggttaccg tttccagc                                                  378
```

<210> SEQ ID NO 298
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 298

```
caggtgcagt tgcaggagtc tggaggcggt tccgttcagg ccgggggctc tctgcgcctg     60

tcctgcgctg cctccgggtt tacatttgac gatttcgata tgggctggta tcgccaggcc    120

cctggcaacg agtgcgaact ggtgtctact atctccgatg acggctcaac ctactatgca    180

gactccgtaa agggcagatc cagcatctcc cgcgacaatg ccaaaaacac tgtgtacctc    240

cagatgaact ccctcaagcc tgaggatacg gcggtgtact attgtgctgc cgagggtgcg    300

ctcggtagca agactaattg cggctgggtg ggcaacttcg ggtactgggg tcaggggacc    360

caggtaaccg tgtcttct                                                  378
```

<210> SEQ ID NO 299
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 299

```
caggtgcagt tgcaggaaag cggtgggggc ctggtgcagc ccggaggcag cctgcgcttg     60

agctgcgctg cctctggctt cacattcgat gacttcgata tgggctggta tcgtcaagca    120

cccggaaacg agtgcgagct ggtgagtaca atcagtgatg acggatctac ctactatgcc    180

gacagcgtca agggaagatc cagcatcagt cgcgacaacg ccaagagcac cgtttacctc    240

cagatgaacc gcctcaagcc tgaggacaca ggagtctatt actgtgctgc ggagggggcc    300

ttgggcagca agactaactg tggatgggtg ggaaacttcg ggtattgggg tcagggtaca    360

caggtcacag tgtcttca                                                  378
```

<210> SEQ ID NO 300
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 300

```
caagttcagc ttcaggaaag tgggggcggg ctggtgcagc cagggggttc cctgaagctg     60

agctgcgctg cctctgggtt tacattctct gatcgcgaca tgggctggta tcgccaagcg    120

ccgggcaatg aatgcgaaag agtgagtact atttctgacg atggttctac ttactatgct    180

gactccgtga agggccgtag ctccatttcc agggacaacg cgaagaacac cgtatacctc    240

cagatgaact ctctgaagcc cgaggacacc gctgtgtatt actgcgctgc cgagggggct    300
```

ctcggctcaa agaccaactg cggatgggtc ggtaacttcg gctactgggg ccagggcacc 360
caagtgacag tctcctcc 378

<210> SEQ ID NO 301
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 301
caggtccagt tgcaggagag cgggggtgga agcgtcctcg ccggagggag cctccgtttg 60
agctgcgtcg cctcaggcta cggctacaat tacatcggat ggttcagaca gacgcctggt 120
aaagagcggg aaggcgtcgc cgtgatttat atcggtggcg gagacaccta ttacgctgac 180
tcagtgaagg ggcgtttcac cgcaagccgg gacaacgcta agagcaccct gtacctccag 240
atgaactctc tcgaacctga ggacactgca atgtattact gcgtggctcg ttactgcgtc 300
gggagtgtct acgcctgcct gaggggcggg catgatgagt atgcccactg gggacaagga 360
acacaggtga ctgtctccag t 381

<210> SEQ ID NO 302
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302
caggttcagc tccaggagtc tggtggcggt tccgtgctgg ccgggggctc tctgcgcctg 60
tcttgtgtcg cctcagggta cggctataac tacattggct ggttcagaca gacccctggg 120
aaagagcggg agggtgtggc tgtcatttac accggcggag gcgacaccta ctatgccgat 180
tcagttaagg gcaggtttac cgcgagccgt gacaacgcga agtctactct gtacctgcaa 240
atgaacagcc tggaacctga ggatactgcg atgtactatt gtgtggcccg gtactgcgta 300
ggctcagtgt atgcctgcct gcgcgggggt cacgacgagt acgcacactg gggacaggga 360
actcaggtca ccgtgtctag c 381

<210> SEQ ID NO 303
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 303
caggtgcaac tccaggagtc cggcgggggc tccgtccaag ctggtggctc actgaggctt 60
agctgtgctg cctccggctt tactttcgac gatttcgaca tgggttggta tcgccaggct 120
ccgggcaatg agtgcgagct ggtctctacc atttccgatg acggctctac ctactatgcc 180
aacagtgtta agggtaggtc ttccatctcc cgcgacaacg ctaagaatat ggtgtacttg 240
cagatgaact ctctgaagcc tgaggacact gctgtctact attgcgctgc cgaaggtgcc 300
ctgggctcaa agactaattg cggctgggtc ggtaactttg gctactgggg tcaggggact 360
caggtgaccg tcagctcc 378

<210> SEQ ID NO 304
<211> LENGTH: 378
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 304
caggtccagt tgcaggaaag cggcgggggc tctgttcagg caggcggaag ccttcgtctg 60
tcctgtactg ccagtggttt cacctttgat gactttgaca tgggctggta tcggcaagcc 120
cccggaaacg agtgcgagct ggtatccacc atttccgatg acgggtccac gtactatgct 180
gatagcgtga agggcaggtc ttccatcagc cgggacaacg ccaagaacac agtgtatttg 240
cagatgaacc gcctcaagcc agaagacacc ggggtatatt actgtgcagc ggaaggtgcc 300
ctgggtagca agatgaactg cggatgggtg ggtaattttg gatactgggg ccagggcacg 360
caggttacag tgtccagc 378

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 305

Gly Gly Ser Gly Gly Ser Gly Gly Ser Gly
1 5 10

<210> SEQ ID NO 306
<211> LENGTH: 800
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)

<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (1)..(800)
<223> OTHER INFORMATION: This sequence may encompass 1-20
"(Gly)m(Ser)o" repeating units, wherein m = 1 to 20, o = 1 to 20
<220> FEATURE:
<223> OTHER INFORMATION: See specification as filed for detailed
description of substitutions and preferred embodiments

<400> SEQUENCE: 306

```
Gly Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser Ser
            20                  25                  30

Ser Ser Ser Ser Ser Ser Ser Ser Gly Gly Gly Gly Gly Gly Gly Gly
        35                  40                  45

Gly Gly Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly Gly
                85                  90                  95
```

-continued

Gly Gly Gly Gly Ser Ser Ser Ser Ser Ser Ser Ser Ser Ser Ser Ser
            100                 105                 110

Ser Ser Ser Ser Ser Ser Ser Ser Gly Gly Gly Gly Gly Gly Gly Gly
        115                 120                 125

Gly Gly Gly Gly Gly Gly Gly Gly Gly Gly Gly Gly Ser Ser Ser Ser
    130                 135                 140

Ser Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly Gly
                165                 170                 175

Gly Gly Gly Gly Ser Ser Ser Ser Ser Ser Ser Ser Ser Ser Ser Ser
            180                 185                 190

Ser Ser Ser Ser Ser Ser Ser Ser Gly Gly Gly Gly Gly Gly Gly Gly
        195                 200                 205

Gly Gly Gly Gly Gly Gly Gly Gly Gly Gly Gly Gly Ser Ser Ser Ser
    210                 215                 220

Ser Ser Ser Ser Ser Ser Ser Ser Ser Ser Ser Ser Ser Ser Ser Ser
225                 230                 235                 240

Gly Gly Gly Gly Gly Gly Gly Gly Gly Gly Gly Gly Gly Gly Gly Gly
                245                 250                 255

Gly Gly Gly Gly Ser Ser Ser Ser Ser Ser Ser Ser Ser Ser Ser Ser
            260                 265                 270

Ser Ser Ser Ser Ser Ser Ser Ser Gly Gly Gly Gly Gly Gly Gly Gly
        275                 280                 285

Gly Gly Gly Gly Gly Gly Gly Gly Gly Gly Gly Gly Ser Ser Ser Ser
    290                 295                 300

Ser Ser Ser Ser Ser Ser Ser Ser Ser Ser Ser Ser Ser Ser Ser Ser
305                 310                 315                 320

Gly Gly Gly Gly Gly Gly Gly Gly Gly Gly Gly Gly Gly Gly Gly Gly
                325                 330                 335

Gly Gly Gly Gly Ser Ser Ser Ser Ser Ser Ser Ser Ser Ser Ser Ser
            340                 345                 350

Ser Ser Ser Ser Ser Ser Ser Ser Gly Gly Gly Gly Gly Gly Gly Gly
        355                 360                 365

Gly Gly Gly Gly Gly Gly Gly Gly Gly Gly Gly Gly Ser Ser Ser Ser
    370                 375                 380

Ser Ser Ser Ser Ser Ser Ser Ser Ser Ser Ser Ser Ser Ser Ser Ser
385                 390                 395                 400

Gly Gly Gly Gly Gly Gly Gly Gly Gly Gly Gly Gly Gly Gly Gly Gly
                405                 410                 415

Gly Gly Gly Gly Ser Ser Ser Ser Ser Ser Ser Ser Ser Ser Ser Ser
            420                 425                 430

Ser Ser Ser Ser Ser Ser Ser Ser Gly Gly Gly Gly Gly Gly Gly Gly
        435                 440                 445

Gly Gly Gly Gly Gly Gly Gly Gly Gly Gly Gly Gly Ser Ser Ser Ser
    450                 455                 460

Ser Ser Ser Ser Ser Ser Ser Ser Ser Ser Ser Ser Ser Ser Ser Ser
465                 470                 475                 480

Gly Gly Gly Gly Gly Gly Gly Gly Gly Gly Gly Gly Gly Gly Gly Gly
                485                 490                 495

Gly Gly Gly Gly Ser Ser Ser Ser Ser Ser Ser Ser Ser Ser Ser Ser
            500                 505                 510

Ser Ser Ser Ser Ser Ser Ser Ser Gly Gly Gly Gly Gly Gly Gly Gly

```
        515                 520                 525

Gly Gly Gly Gly Gly Gly Gly Gly Gly Gly Gly Gly Ser Ser Ser Ser
    530                 535                 540

Ser Ser Ser Ser Ser Ser Ser Ser Ser Ser Ser Ser Ser Ser Ser Ser
545                 550                 555                 560

Gly Gly Gly Gly Gly Gly Gly Gly Gly Gly Gly Gly Gly Gly Gly Gly
                565                 570                 575

Gly Gly Gly Gly Ser Ser Ser Ser Ser Ser Ser Ser Ser Ser Ser Ser
            580                 585                 590

Ser Ser Ser Ser Ser Ser Ser Ser Gly Gly Gly Gly Gly Gly Gly Gly
        595                 600                 605

Gly Gly Gly Gly Gly Gly Gly Gly Gly Gly Gly Gly Ser Ser Ser Ser
    610                 615                 620

Ser Ser Ser Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly Gly Gly
                645                 650                 655

Gly Gly Gly Gly Ser Ser Ser Ser Ser Ser Ser Ser Ser Ser Ser Ser
            660                 665                 670

Ser Ser Ser Ser Ser Ser Ser Ser Gly Gly Gly Gly Gly Gly Gly Gly
        675                 680                 685

Gly Gly Gly Gly Gly Gly Gly Gly Gly Gly Gly Gly Ser Ser Ser Ser
    690                 695                 700

Ser Ser Ser Ser Ser Ser Ser Ser Ser Ser Ser Ser Ser Ser Ser Ser
705                 710                 715                 720

Gly Gly Gly Gly Gly Gly Gly Gly Gly Gly Gly Gly Gly Gly Gly Gly
                725                 730                 735

Gly Gly Gly Gly Ser Ser Ser Ser Ser Ser Ser Ser Ser Ser Ser Ser
            740                 745                 750

Ser Ser Ser Ser Ser Ser Ser Ser Gly Gly Gly Gly Gly Gly Gly Gly
        755                 760                 765

Gly Gly Gly Gly Gly Gly Gly Gly Gly Gly Gly Gly Ser Ser Ser Ser
    770                 775                 780

Ser Ser Ser Ser Ser Ser Ser Ser Ser Ser Ser Ser Ser Ser Ser Ser
785                 790                 795                 800


<210> SEQ ID NO 307
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(100)
<223> OTHER INFORMATION: This sequence may encompass 1-20
      "Gly Ser Gly Gly Ser" repeating units
<220> FEATURE:
<223> OTHER INFORMATION: See specification as filed for detailed
      description of substitutions and preferred embodiments

<400> SEQUENCE: 307

Gly Ser Gly Gly Ser Gly Ser Gly Gly Ser Gly Ser Gly Gly Ser Gly
1               5                   10                  15

Ser Gly Gly Ser Gly Ser Gly Gly Ser Gly Ser Gly Gly Ser Gly Ser
            20                  25                  30

Gly Gly Ser Gly Ser Gly Gly Ser Gly Ser Gly Gly Ser Gly Ser Gly
```

```
        35                  40                  45

Gly Ser Gly Ser Gly Gly Ser Gly Ser Gly Gly Ser Gly Ser Gly Gly
    50                  55                  60

Ser Gly Ser Gly Gly Ser Gly Ser Gly Gly Ser Gly Ser Gly Gly Ser
65                  70                  75                  80

Gly Ser Gly Gly Ser Gly Ser Gly Gly Ser Gly Ser Gly Gly Ser Gly
                85                  90                  95

Ser Gly Gly Ser
            100


<210> SEQ ID NO 308
<211> LENGTH: 1200
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
```

<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:
<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)

```
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1)..(1200)
<223> OTHER INFORMATION: This sequence may encompass 1-20
      "(Gly)m(Ser)o(Gly)m" repeating units, wherein m = 1 to 20, o =
      1 to 20
<220> FEATURE:
<223> OTHER INFORMATION: See specification as filed for detailed
      description of substitutions and preferred embodiments

<400> SEQUENCE: 308

Gly Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser Ser
            20                  25                  30

Ser Ser Ser Ser Ser Ser Ser Ser Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Ser Ser Ser Ser Ser Ser Ser Ser Ser Ser Ser Ser Ser Ser Ser Ser
                85                  90                  95

Ser Ser Ser Ser Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Ser Ser Ser Ser
    130                 135                 140

Ser Ser Ser Ser Ser Ser Ser Ser Ser Ser Ser Ser Ser Ser Ser Ser
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly Ser Ser Ser Ser Ser Ser Ser Ser
        195                 200                 205

Ser Ser Ser Ser Ser Ser Ser Ser Ser Ser Ser Ser Gly Gly Gly Gly
    210                 215                 220
```

-continued

```
Gly Gly Gly Gly Gly Gly Gly Gly Gly Gly Gly Gly Gly Gly Gly Gly
225                 230                 235                 240

Gly Gly Gly Gly Gly Gly Gly Gly Gly Gly Gly Gly Gly Gly Gly Gly
                245                 250                 255

Gly Gly Gly Gly Ser Ser Ser Ser Ser Ser Ser Ser Ser Ser Ser Ser
            260                 265                 270

Ser Ser Ser Ser Ser Ser Ser Ser Gly Gly Gly Gly Gly Gly Gly Gly
        275                 280                 285

Gly Gly Gly Gly Gly Gly Gly Gly Gly Gly Gly Gly Gly Gly Gly Gly
    290                 295                 300

Gly Gly Gly Gly Gly Gly Gly Gly Gly Gly Gly Gly Gly Gly Gly Gly
305                 310                 315                 320

Ser Ser Ser Ser Ser Ser Ser Ser Ser Ser Ser Ser Ser Ser Ser Ser
                325                 330                 335

Ser Ser Ser Ser Gly Gly Gly Gly Gly Gly Gly Gly Gly Gly Gly Gly
            340                 345                 350

Gly Gly Gly Gly Gly Gly Gly Gly Gly Gly Gly Gly Gly Gly Gly Gly
        355                 360                 365

Gly Gly Gly Gly Gly Gly Gly Gly Gly Gly Gly Gly Ser Ser Ser Ser
    370                 375                 380

Ser Ser Ser Ser Ser Ser Ser Ser Ser Ser Ser Ser Ser Ser Ser Ser
385                 390                 395                 400

Gly Gly Gly Gly Gly Gly Gly Gly Gly Gly Gly Gly Gly Gly Gly Gly
                405                 410                 415

Gly Gly Gly Gly Gly Gly Gly Gly Gly Gly Gly Gly Gly Gly Gly Gly
            420                 425                 430

Gly Gly Gly Gly Gly Gly Gly Gly Ser Ser Ser Ser Ser Ser Ser Ser
        435                 440                 445

Ser Ser Ser Ser Ser Ser Ser Ser Ser Ser Ser Ser Gly Gly Gly Gly
    450                 455                 460

Gly Gly Gly Gly Gly Gly Gly Gly Gly Gly Gly Gly Gly Gly Gly Gly
465                 470                 475                 480

Gly Gly Gly Gly Gly Gly Gly Gly Gly Gly Gly Gly Gly Gly Gly Gly
                485                 490                 495

Gly Gly Gly Gly Ser Ser Ser Ser Ser Ser Ser Ser Ser Ser Ser Ser
            500                 505                 510

Ser Ser Ser Ser Ser Ser Ser Ser Gly Gly Gly Gly Gly Gly Gly Gly
        515                 520                 525

Gly Gly Gly Gly Gly Gly Gly Gly Gly Gly Gly Gly Gly Gly Gly Gly
    530                 535                 540

Gly Gly Gly Gly Gly Gly Gly Gly Gly Gly Gly Gly Gly Gly Gly Gly
545                 550                 555                 560

Ser Ser Ser Ser Ser Ser Ser Ser Ser Ser Ser Ser Ser Ser Ser Ser
                565                 570                 575

Ser Ser Ser Ser Gly Gly Gly Gly Gly Gly Gly Gly Gly Gly Gly Gly
            580                 585                 590

Gly Gly Gly Gly Gly Gly Gly Gly Gly Gly Gly Gly Gly Gly Gly Gly
        595                 600                 605

Gly Gly Gly Gly Gly Gly Gly Gly Gly Gly Gly Gly Ser Ser Ser Ser
    610                 615                 620

Ser Ser Ser Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly Gly Gly
```

-continued

```
                645                 650                 655

Gly Gly Gly Gly Gly Gly Gly Gly Gly Gly Gly Gly Gly Gly Gly Gly
            660                 665                 670

Gly Gly Gly Gly Gly Gly Gly Gly Ser Ser Ser Ser Ser Ser Ser Ser
        675                 680                 685

Ser Ser Ser Ser Ser Ser Ser Ser Ser Ser Ser Ser Gly Gly Gly Gly
    690                 695                 700

Gly Gly Gly Gly Gly Gly Gly Gly Gly Gly Gly Gly Gly Gly Gly Gly
705                 710                 715                 720

Gly Gly Gly Gly Gly Gly Gly Gly Gly Gly Gly Gly Gly Gly Gly Gly
                725                 730                 735

Gly Gly Gly Gly Ser Ser Ser Ser Ser Ser Ser Ser Ser Ser Ser Ser
            740                 745                 750

Ser Ser Ser Ser Ser Ser Ser Ser Gly Gly Gly Gly Gly Gly Gly Gly
        755                 760                 765

Gly Gly Gly Gly Gly Gly Gly Gly Gly Gly Gly Gly Gly Gly Gly Gly
    770                 775                 780

Gly Gly Gly Gly Gly Gly Gly Gly Gly Gly Gly Gly Gly Gly Gly Gly
785                 790                 795                 800

Ser Ser Ser Ser Ser Ser Ser Ser Ser Ser Ser Ser Ser Ser Ser Ser
                805                 810                 815

Ser Ser Ser Ser Gly Gly Gly Gly Gly Gly Gly Gly Gly Gly Gly Gly
            820                 825                 830

Gly Gly Gly Gly Gly Gly Gly Gly Gly Gly Gly Gly Gly Gly Gly Gly
        835                 840                 845

Gly Gly Gly Gly Gly Gly Gly Gly Gly Gly Gly Gly Ser Ser Ser Ser
    850                 855                 860

Ser Ser Ser Ser Ser Ser Ser Ser Ser Ser Ser Ser Ser Ser Ser Ser
865                 870                 875                 880

Gly Gly Gly Gly Gly Gly Gly Gly Gly Gly Gly Gly Gly Gly Gly Gly
                885                 890                 895

Gly Gly Gly Gly Gly Gly Gly Gly Gly Gly Gly Gly Gly Gly Gly Gly
            900                 905                 910

Gly Gly Gly Gly Gly Gly Gly Gly Ser Ser Ser Ser Ser Ser Ser Ser
        915                 920                 925

Ser Ser Ser Ser Ser Ser Ser Ser Ser Ser Ser Ser Gly Gly Gly Gly
    930                 935                 940

Gly Gly Gly Gly Gly Gly Gly Gly Gly Gly Gly Gly Gly Gly Gly Gly
945                 950                 955                 960

Gly Gly Gly Gly Gly Gly Gly Gly Gly Gly Gly Gly Gly Gly Gly Gly
                965                 970                 975

Gly Gly Gly Gly Ser Ser Ser Ser Ser Ser Ser Ser Ser Ser Ser Ser
            980                 985                 990

Ser Ser Ser Ser Ser Ser Ser Ser  Gly Gly Gly Gly Gly  Gly Gly Gly
        995                 1000                1005

Gly Gly  Gly Gly Gly Gly Gly  Gly Gly Gly Gly Gly  Gly Gly Gly
    1010                1015                1020

Gly Gly  Gly Gly Gly Gly Gly  Gly Gly Gly Gly Gly  Gly Gly Gly
    1025                1030                1035

Gly Gly  Ser Ser Ser Ser Ser  Ser Ser Ser Ser Ser  Ser Ser Ser
    1040                1045                1050

Ser Ser  Ser Ser Ser Ser Ser  Gly Gly Gly Gly Gly  Gly Gly Gly
    1055                1060                1065
```

```
Gly Gly  Gly Gly Gly Gly Gly  Gly Gly Gly Gly Gly  Gly Gly Gly
    1070                 1075                 1080

Gly Gly  Gly Gly Gly Gly Gly  Gly Gly Gly Gly Gly  Gly Gly Gly
    1085                 1090                 1095

Gly Gly  Ser Ser Ser Ser Ser  Ser Ser Ser Ser Ser  Ser Ser Ser
    1100                 1105                 1110

Ser Ser  Ser Ser Ser Ser Ser  Gly Gly Gly Gly Gly  Gly Gly Gly
    1115                 1120                 1125

Gly Gly  Gly Gly Gly Gly Gly  Gly Gly Gly Gly Gly  Gly Gly Gly
    1130                 1135                 1140

Gly Gly  Gly Gly Gly Gly Gly  Gly Gly Gly Gly Gly  Gly Gly Gly
    1145                 1150                 1155

Gly Gly  Ser Ser Ser Ser Ser  Ser Ser Ser Ser Ser  Ser Ser Ser
    1160                 1165                 1170

Ser Ser  Ser Ser Ser Ser Ser  Gly Gly Gly Gly Gly  Gly Gly Gly
    1175                 1180                 1185

Gly Gly  Gly Gly Gly Gly Gly  Gly Gly Gly Gly Gly
    1190                 1195                 1200
```

<210> SEQ ID NO 309
<211> LENGTH: 2000
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(20)
<223> OTHER INFORMATION: This region may encompass 1-20 residues
<220> FEATURE:
<221> NAME/KEY: SITE
<222> LOCATION: (21)..(40)
<223> OTHER INFORMATION: This region may encompass 1-20 residues
<220> FEATURE:
<221> NAME/KEY: SITE
<222> LOCATION: (41)..(60)
<223> OTHER INFORMATION: This region may encompass 1-20 residues
<220> FEATURE:
<221> NAME/KEY: SITE
<222> LOCATION: (61)..(80)
<223> OTHER INFORMATION: This region may encompass 1-20 residues
<220> FEATURE:
<221> NAME/KEY: SITE
<222> LOCATION: (81)..(100)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (121)..(140)
<223> OTHER INFORMATION: This region may encompass 1-20 residues
<220> FEATURE:
<221> NAME/KEY: SITE
<222> LOCATION: (141)..(160)
<223> OTHER INFORMATION: This region may encompass 1-20 residues
<220> FEATURE:
<221> NAME/KEY: SITE
<222> LOCATION: (161)..(180)
<223> OTHER INFORMATION: This region may encompass 1-20 residues
<220> FEATURE:
<221> NAME/KEY: SITE
<222> LOCATION: (181)..(200)
<223> OTHER INFORMATION: This region may encompass 1-20 residues
<220> FEATURE:
<221> NAME/KEY: SITE
<222> LOCATION: (201)..(220)

<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (241)..(260)
<223> OTHER INFORMATION: This region may encompass 1-20 residues
<220> FEATURE:
<221> NAME/KEY: SITE
<222> LOCATION: (261)..(280)
<223> OTHER INFORMATION: This region may encompass 1-20 residues
<220> FEATURE:
<221> NAME/KEY: SITE
<222> LOCATION: (281)..(300)
<223> OTHER INFORMATION: This region may encompass 1-20 residues
<220> FEATURE:
<221> NAME/KEY: SITE
<222> LOCATION: (301)..(320)
<223> OTHER INFORMATION: This region may encompass 1-20 residues
<220> FEATURE:
<221> NAME/KEY: SITE
<222> LOCATION: (321)..(340)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (361)..(380)
<223> OTHER INFORMATION: This region may encompass 1-20 residues
<220> FEATURE:
<221> NAME/KEY: SITE
<222> LOCATION: (381)..(400)
<223> OTHER INFORMATION: This region may encompass 1-20 residues
<220> FEATURE:
<221> NAME/KEY: SITE
<222> LOCATION: (401)..(420)
<223> OTHER INFORMATION: This region may encompass 1-20 residues
<220> FEATURE:
<221> NAME/KEY: SITE
<222> LOCATION: (421)..(440)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (481)..(500)
<223> OTHER INFORMATION: This region may encompass 1-20 residues
<220> FEATURE:
<221> NAME/KEY: SITE
<222> LOCATION: (501)..(520)
<223> OTHER INFORMATION: This region may encompass 1-20 residues
<220> FEATURE:
<221> NAME/KEY: SITE
<222> LOCATION: (521)..(540)
<223> OTHER INFORMATION: This region may encompass 1-20 residues
<220> FEATURE:
<221> NAME/KEY: SITE
<222> LOCATION: (541)..(560)
<223> OTHER INFORMATION: This region may encompass 1-20 residues
<220> FEATURE:
<221> NAME/KEY: SITE
<222> LOCATION: (561)..(580)
<223> OTHER INFORMATION: This region may encompass 1-20 residues
<220> FEATURE:
<221> NAME/KEY: SITE
<222> LOCATION: (581)..(600)
<223> OTHER INFORMATION: This region may encompass 1-20 residues
<220> FEATURE:
<221> NAME/KEY: SITE
<222> LOCATION: (601)..(620)
<223> OTHER INFORMATION: This region may encompass 1-20 residues
<220> FEATURE:
<221> NAME/KEY: SITE
<222> LOCATION: (621)..(640)
<223> OTHER INFORMATION: This region may encompass 1-20 residues
<220> FEATURE:
<221> NAME/KEY: SITE
<222> LOCATION: (641)..(660)
<223> OTHER INFORMATION: This region may encompass 1-20 residues
<220> FEATURE:
<221> NAME/KEY: SITE
<222> LOCATION: (661)..(680)
<223> OTHER INFORMATION: This region may encompass 1-20 residues
<220> FEATURE:
<221> NAME/KEY: SITE
<222> LOCATION: (681)..(700)
<223> OTHER INFORMATION: This region may encompass 1-20 residues
<220> FEATURE:
<221> NAME/KEY: SITE
<222> LOCATION: (701)..(720)
<223> OTHER INFORMATION: This region may encompass 1-20 residues
<220> FEATURE:
<221> NAME/KEY: SITE
<222> LOCATION: (721)..(740)
<223> OTHER INFORMATION: This region may encompass 1-20 residues
<220> FEATURE:
<221> NAME/KEY: SITE
<222> LOCATION: (741)..(760)
<223> OTHER INFORMATION: This region may encompass 1-20 residues
<220> FEATURE:
<221> NAME/KEY: SITE
<222> LOCATION: (761)..(780)
<223> OTHER INFORMATION: This region may encompass 1-20 residues
<220> FEATURE:
<221> NAME/KEY: SITE
<222> LOCATION: (781)..(800)
<223> OTHER INFORMATION: This region may encompass 1-20 residues
<220> FEATURE:
<221> NAME/KEY: SITE
<222> LOCATION: (801)..(820)
<223> OTHER INFORMATION: This region may encompass 1-20 residues
<220> FEATURE:
<221> NAME/KEY: SITE
<222> LOCATION: (821)..(840)
<223> OTHER INFORMATION: This region may encompass 1-20 residues
<220> FEATURE:
<221> NAME/KEY: SITE
<222> LOCATION: (841)..(860)
<223> OTHER INFORMATION: This region may encompass 1-20 residues
<220> FEATURE:
<221> NAME/KEY: SITE
<222> LOCATION: (861)..(880)
<223> OTHER INFORMATION: This region may encompass 1-20 residues
<220> FEATURE:
<221> NAME/KEY: SITE
<222> LOCATION: (881)..(900)
<223> OTHER INFORMATION: This region may encompass 1-20 residues
<220> FEATURE:
<221> NAME/KEY: SITE
<222> LOCATION: (901)..(920)
<223> OTHER INFORMATION: This region may encompass 1-20 residues
<220> FEATURE:
<221> NAME/KEY: SITE
<222> LOCATION: (921)..(940)
<223> OTHER INFORMATION: This region may encompass 1-20 residues
<220> FEATURE:
<221> NAME/KEY: SITE
<222> LOCATION: (941)..(960)
<223> OTHER INFORMATION: This region may encompass 1-20 residues
<220> FEATURE:
<221> NAME/KEY: SITE
<222> LOCATION: (961)..(980)
<223> OTHER INFORMATION: This region may encompass 1-20 residues
<220> FEATURE:
<221> NAME/KEY: SITE
<222> LOCATION: (981)..(1000)
<223> OTHER INFORMATION: This region may encompass 1-20 residues
<220> FEATURE:

<221> NAME/KEY: SITE
<222> LOCATION: (1001)..(1020)
<223> OTHER INFORMATION: This region may encompass 1-20 residues
<220> FEATURE:
<221> NAME/KEY: SITE
<222> LOCATION: (1021)..(1040)
<223> OTHER INFORMATION: This region may encompass 1-20 residues
<220> FEATURE:
<221> NAME/KEY: SITE
<222> LOCATION: (1041)..(1060)
<223> OTHER INFORMATION: This region may encompass 1-20 residues
<220> FEATURE:
<221> NAME/KEY: SITE
<222> LOCATION: (1061)..(1080)
<223> OTHER INFORMATION: This region may encompass 1-20 residues
<220> FEATURE:
<221> NAME/KEY: SITE
<222> LOCATION: (1081)..(1100)
<223> OTHER INFORMATION: This region may encompass 1-20 residues
<220> FEATURE:
<221> NAME/KEY: SITE
<222> LOCATION: (1101)..(1120)
<223> OTHER INFORMATION: This region may encompass 1-20 residues
<220> FEATURE:
<221> NAME/KEY: SITE
<222> LOCATION: (1121)..(1140)
<223> OTHER INFORMATION: This region may encompass 1-20 residues
<220> FEATURE:
<221> NAME/KEY: SITE
<222> LOCATION: (1141)..(1160)
<223> OTHER INFORMATION: This region may encompass 1-20 residues
<220> FEATURE:
<221> NAME/KEY: SITE
<222> LOCATION: (1161)..(1180)
<223> OTHER INFORMATION: This region may encompass 1-20 residues
<220> FEATURE:
<221> NAME/KEY: SITE
<222> LOCATION: (1181)..(1200)
<223> OTHER INFORMATION: This region may encompass 1-20 residues
<220> FEATURE:
<221> NAME/KEY: SITE
<222> LOCATION: (1201)..(1220)
<223> OTHER INFORMATION: This region may encompass 1-20 residues
<220> FEATURE:
<221> NAME/KEY: SITE
<222> LOCATION: (1221)..(1240)
<223> OTHER INFORMATION: This region may encompass 1-20 residues
<220> FEATURE:
<221> NAME/KEY: SITE
<222> LOCATION: (1241)..(1260)
<223> OTHER INFORMATION: This region may encompass 1-20 residues
<220> FEATURE:
<221> NAME/KEY: SITE
<222> LOCATION: (1261)..(1280)
<223> OTHER INFORMATION: This region may encompass 1-20 residues
<220> FEATURE:
<221> NAME/KEY: SITE
<222> LOCATION: (1281)..(1300)
<223> OTHER INFORMATION: This region may encompass 1-20 residues
<220> FEATURE:
<221> NAME/KEY: SITE
<222> LOCATION: (1301)..(1320)
<223> OTHER INFORMATION: This region may encompass 1-20 residues
<220> FEATURE:
<221> NAME/KEY: SITE
<222> LOCATION: (1321)..(1340)
<223> OTHER INFORMATION: This region may encompass 1-20 residues
<220> FEATURE:
<221> NAME/KEY: SITE
<222> LOCATION: (1341)..(1360)
<223> OTHER INFORMATION: This region may encompass 1-20 residues
<220> FEATURE:
<221> NAME/KEY: SITE
<222> LOCATION: (1361)..(1380)
<223> OTHER INFORMATION: This region may encompass 1-20 residues
<220> FEATURE:
<221> NAME/KEY: SITE
<222> LOCATION: (1381)..(1400)
<223> OTHER INFORMATION: This region may encompass 1-20 residues
<220> FEATURE:
<221> NAME/KEY: SITE
<222> LOCATION: (1401)..(1420)
<223> OTHER INFORMATION: This region may encompass 1-20 residues
<220> FEATURE:
<221> NAME/KEY: SITE
<222> LOCATION: (1421)..(1440)
<223> OTHER INFORMATION: This region may encompass 1-20 residues
<220> FEATURE:
<221> NAME/KEY: SITE
<222> LOCATION: (1441)..(1460)
<223> OTHER INFORMATION: This region may encompass 1-20 residues
<220> FEATURE:
<221> NAME/KEY: SITE
<222> LOCATION: (1461)..(1480)
<223> OTHER INFORMATION: This region may encompass 1-20 residues
<220> FEATURE:
<221> NAME/KEY: SITE
<222> LOCATION: (1481)..(1500)
<223> OTHER INFORMATION: This region may encompass 1-20 residues
<220> FEATURE:
<221> NAME/KEY: SITE
<222> LOCATION: (1501)..(1520)
<223> OTHER INFORMATION: This region may encompass 1-20 residues
<220> FEATURE:
<221> NAME/KEY: SITE
<222> LOCATION: (1521)..(1540)
<223> OTHER INFORMATION: This region may encompass 1-20 residues
<220> FEATURE:
<221> NAME/KEY: SITE
<222> LOCATION: (1541)..(1560)
<223> OTHER INFORMATION: This region may encompass 1-20 residues
<220> FEATURE:
<221> NAME/KEY: SITE
<222> LOCATION: (1561)..(1580)
<223> OTHER INFORMATION: This region may encompass 1-20 residues
<220> FEATURE:
<221> NAME/KEY: SITE
<222> LOCATION: (1581)..(1600)
<223> OTHER INFORMATION: This region may encompass 1-20 residues
<220> FEATURE:
<221> NAME/KEY: SITE
<222> LOCATION: (1601)..(1620)
<223> OTHER INFORMATION: This region may encompass 1-20 residues
<220> FEATURE:
<221> NAME/KEY: SITE
<222> LOCATION: (1621)..(1640)
<223> OTHER INFORMATION: This region may encompass 1-20 residues
<220> FEATURE:
<221> NAME/KEY: SITE
<222> LOCATION: (1641)..(1660)
<223> OTHER INFORMATION: This region may encompass 1-20 residues
<220> FEATURE:
<221> NAME/KEY: SITE
<222> LOCATION: (1661)..(1680)
<223> OTHER INFORMATION: This region may encompass 1-20 residues
<220> FEATURE:
<221> NAME/KEY: SITE
<222> LOCATION: (1681)..(1700)
<223> OTHER INFORMATION: This region may encompass 1-20 residues
<220> FEATURE:
<221> NAME/KEY: SITE
<222> LOCATION: (1701)..(1720)
<223> OTHER INFORMATION: This region may encompass 1-20 residues
<220> FEATURE:
<221> NAME/KEY: SITE
<222> LOCATION: (1721)..(1740)
<223> OTHER INFORMATION: This region may encompass 1-20 residues
<220> FEATURE:
<221> NAME/KEY: SITE
<222> LOCATION: (1741)..(1760)
<223> OTHER INFORMATION: This region may encompass 1-20 residues
<220> FEATURE:
<221> NAME/KEY: SITE
<222> LOCATION: (1761)..(1780)
<223> OTHER INFORMATION: This region may encompass 1-20 residues
<220> FEATURE:
<221> NAME/KEY: SITE
<222> LOCATION: (1781)..(1800)

<223> OTHER INFORMATION: This region may encompass 1-20 residues
<220> FEATURE:
<221> NAME/KEY: SITE
<222> LOCATION: (1801)..(1820)
<223> OTHER INFORMATION: This region may encompass 1-20 residues
<220> FEATURE:
<221> NAME/KEY: SITE
<222> LOCATION: (1821)..(1840)
<223> OTHER INFORMATION: This region may encompass 1-20 residues
<220> FEATURE:
<221> NAME/KEY: SITE
<222> LOCATION: (1841)..(1860)
<223> OTHER INFORMATION: This region may encompass 1-20 residues
<220> FEATURE:
<221> NAME/KEY: SITE
<222> LOCATION: (1861)..(1880)
<223> OTHER INFORMATION: This region may encompass 1-20 residues
<220> FEATURE:
<221> NAME/KEY: SITE
<222> LOCATION: (1881)..(1900)
<223> OTHER INFORMATION: This region may encompass 1-20 residues
<220> FEATURE:
<221> NAME/KEY: SITE
<222> LOCATION: (1901)..(1920)
<223> OTHER INFORMATION: This region may encompass 1-20 residues
<220> FEATURE:
<221> NAME/KEY: SITE
<222> LOCATION: (1921)..(1940)
<223> OTHER INFORMATION: This region may encompass 1-20 residues
<220> FEATURE:
<221> NAME/KEY: SITE
<222> LOCATION: (1941)..(1960)
<223> OTHER INFORMATION: This region may encompass 1-20 residues
<220> FEATURE:
<221> NAME/KEY: SITE
<222> LOCATION: (1961)..(1980)
<223> OTHER INFORMATION: This region may encompass 1-20 residues
<220> FEATURE:
<221> NAME/KEY: SITE
<222> LOCATION: (1981)..(2000)
<223> OTHER INFORMATION: This region may encompass 1-20 residues
<220> FEATURE:
<221> NAME/KEY: SITE
<222> LOCATION: (1)..(2000)
<223> OTHER INFORMATION: This sequence may encompass 1-20
"(Gly)m(Ser)o(Gly)m(Ser)o(Gly)m" repeating units, wherein m = 1 to
20, o = 1 to 20
<220> FEATURE:
<223> OTHER INFORMATION: See specification as filed for detailed
description of substitutions and preferred embodiments

<400> SEQUENCE: 309

```
Gly Gly Gly Gly Gly Gly Gly Gly Gly Gly Gly Gly Gly Gly Gly Gly
1               5                   10                  15

Gly Gly Gly Gly Ser Ser Ser Ser Ser Ser Ser Ser Ser Ser Ser Ser
            20                  25                  30

Ser Ser Ser Ser Ser Ser Ser Ser Gly Gly Gly Gly Gly Gly Gly Gly
        35                  40                  45

Gly Gly Gly Gly Gly Gly Gly Gly Gly Gly Gly Gly Ser Ser Ser Ser
    50                  55                  60

Ser Ser Ser Ser Ser Ser Ser Ser Ser Ser Ser Ser Ser Ser Ser Ser
65                  70                  75                  80

Gly Gly Gly Gly Gly Gly Gly Gly Gly Gly Gly Gly Gly Gly Gly Gly
                85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Ser Ser Ser Ser Ser Ser Ser Ser
        115                 120                 125

Ser Ser Ser Ser Ser Ser Ser Ser Ser Ser Ser Ser Gly Gly Gly Gly
    130                 135                 140
```

-continued

Gly Gly Gly Gly Gly Gly Gly Gly Gly Gly Gly Gly Gly Gly Gly Gly
145 150 155 160

Ser Ser Ser Ser Ser Ser Ser Ser Ser Ser Ser Ser Ser Ser Ser Ser
165 170 175

Ser Ser Ser Ser Gly Gly Gly Gly Gly Gly Gly Gly Gly Gly Gly Gly
180 185 190

Gly Gly Gly Gly Gly Gly Gly Gly Gly Gly Gly Gly Gly Gly Gly Gly
195 200 205

Gly Gly Gly Gly Gly Gly Gly Gly Gly Gly Gly Gly Ser Ser Ser Ser
210 215 220

Ser Ser Ser Ser Ser Ser Ser Ser Ser Ser Ser Ser Ser Ser Ser Ser
225 230 235 240

Gly Gly Gly Gly Gly Gly Gly Gly Gly Gly Gly Gly Gly Gly Gly Gly
245 250 255

Gly Gly Gly Gly Ser Ser Ser Ser Ser Ser Ser Ser Ser Ser Ser Ser
260 265 270

Ser Ser Ser Ser Ser Ser Ser Ser Gly Gly Gly Gly Gly Gly Gly Gly
275 280 285

Gly Gly Gly Gly Gly Gly Gly Gly Gly Gly Gly Gly Gly Gly Gly Gly
290 295 300

Gly Gly Gly Gly Gly Gly Gly Gly Gly Gly Gly Gly Gly Gly Gly Gly
305 310 315 320

Ser Ser Ser Ser Ser Ser Ser Ser Ser Ser Ser Ser Ser Ser Ser Ser
325 330 335

Ser Ser Ser Ser Gly Gly Gly Gly Gly Gly Gly Gly Gly Gly Gly Gly
340 345 350

Gly Gly Gly Gly Gly Gly Gly Gly Ser Ser Ser Ser Ser Ser Ser Ser
355 360 365

Ser Ser Ser Ser Ser Ser Ser Ser Ser Ser Ser Ser Gly Gly Gly Gly
370 375 380

Gly Gly Gly Gly Gly Gly Gly Gly Gly Gly Gly Gly Gly Gly Gly Gly
385 390 395 400

Gly Gly Gly Gly Gly Gly Gly Gly Gly Gly Gly Gly Gly Gly Gly Gly
405 410 415

Gly Gly Gly Gly Ser Ser Ser Ser Ser Ser Ser Ser Ser Ser Ser Ser
420 425 430

Ser Ser Ser Ser Ser Ser Ser Ser Gly Gly Gly Gly Gly Gly Gly Gly
435 440 445

Gly Gly Gly Gly Gly Gly Gly Gly Gly Gly Gly Gly Ser Ser Ser Ser
450 455 460

Ser Ser Ser Ser Ser Ser Ser Ser Ser Ser Ser Ser Ser Ser Ser Ser
465 470 475 480

Gly Gly Gly Gly Gly Gly Gly Gly Gly Gly Gly Gly Gly Gly Gly Gly
485 490 495

Gly Gly Gly Gly Gly Gly Gly Gly Gly Gly Gly Gly Gly Gly Gly Gly
500 505 510

Gly Gly Gly Gly Gly Gly Gly Gly Ser Ser Ser Ser Ser Ser Ser Ser
515 520 525

Ser Ser Ser Ser Ser Ser Ser Ser Ser Ser Ser Ser Gly Gly Gly Gly
530 535 540

Gly Gly Gly Gly Gly Gly Gly Gly Gly Gly Gly Gly Gly Gly Gly Gly
545 550 555 560

```
Ser Ser Ser Ser Ser Ser Ser Ser Ser Ser Ser Ser Ser Ser Ser Ser
                565                 570                 575

Ser Ser Ser Ser Gly Gly Gly Gly Gly Gly Gly Gly Gly Gly Gly Gly
            580                 585                 590

Gly Gly Gly Gly Gly Gly Gly Gly Gly Gly Gly Gly Gly Gly Gly Gly
        595                 600                 605

Gly Gly Gly Gly Gly Gly Gly Gly Gly Gly Gly Gly Ser Ser Ser Ser
    610                 615                 620

Ser Ser Ser Ser Ser Ser Ser Ser Ser Ser Ser Ser Ser Ser Ser Ser
625                 630                 635                 640

Gly Gly Gly Gly Gly Gly Gly Gly Gly Gly Gly Gly Gly Gly Gly Gly
                645                 650                 655

Gly Gly Gly Gly Ser Ser Ser Ser Ser Ser Ser Ser Ser Ser Ser Ser
            660                 665                 670

Ser Ser Ser Ser Ser Ser Ser Ser Gly Gly Gly Gly Gly Gly Gly Gly
        675                 680                 685

Gly Gly Gly Gly Gly Gly Gly Gly Gly Gly Gly Gly Gly Gly Gly Gly
    690                 695                 700

Gly Gly Gly Gly Gly Gly Gly Gly Gly Gly Gly Gly Gly Gly Gly Gly
705                 710                 715                 720

Ser Ser Ser Ser Ser Ser Ser Ser Ser Ser Ser Ser Ser Ser Ser Ser
                725                 730                 735

Ser Ser Ser Ser Gly Gly Gly Gly Gly Gly Gly Gly Gly Gly Gly Gly
            740                 745                 750

Gly Gly Gly Gly Gly Gly Gly Gly Ser Ser Ser Ser Ser Ser Ser Ser
        755                 760                 765

Ser Ser Ser Ser Ser Ser Ser Ser Ser Ser Ser Ser Gly Gly Gly Gly
    770                 775                 780

Gly Gly Gly Gly Gly Gly Gly Gly Gly Gly Gly Gly Gly Gly Gly Gly
785                 790                 795                 800

Gly Gly Gly Gly Gly Gly Gly Gly Gly Gly Gly Gly Gly Gly Gly Gly
                805                 810                 815

Gly Gly Gly Gly Ser Ser Ser Ser Ser Ser Ser Ser Ser Ser Ser Ser
            820                 825                 830

Ser Ser Ser Ser Ser Ser Ser Ser Gly Gly Gly Gly Gly Gly Gly Gly
        835                 840                 845

Gly Gly Gly Gly Gly Gly Gly Gly Gly Gly Gly Gly Ser Ser Ser Ser
    850                 855                 860

Ser Ser Ser Ser Ser Ser Ser Ser Ser Ser Ser Ser Ser Ser Ser Ser
865                 870                 875                 880

Gly Gly Gly Gly Gly Gly Gly Gly Gly Gly Gly Gly Gly Gly Gly Gly
                885                 890                 895

Gly Gly Gly Gly Gly Gly Gly Gly Gly Gly Gly Gly Gly Gly Gly Gly
            900                 905                 910

Gly Gly Gly Gly Gly Gly Gly Gly Ser Ser Ser Ser Ser Ser Ser Ser
        915                 920                 925

Ser Ser Ser Ser Ser Ser Ser Ser Ser Ser Ser Ser Gly Gly Gly Gly
    930                 935                 940

Gly Gly Gly Gly Gly Gly Gly Gly Gly Gly Gly Gly Gly Gly Gly Gly
945                 950                 955                 960

Ser Ser Ser Ser Ser Ser Ser Ser Ser Ser Ser Ser Ser Ser Ser Ser
                965                 970                 975

Ser Ser Ser Ser Gly Gly Gly Gly Gly Gly Gly Gly Gly Gly Gly Gly
```

-continued

```
            980                 985                 990

Gly Gly Gly Gly Gly Gly Gly Gly  Gly Gly Gly Gly Gly  Gly Gly Gly
        995                 1000                1005

Gly Gly  Gly Gly Gly Gly Gly  Gly Gly Gly Gly Gly  Ser Ser Ser
    1010                1015                1020

Ser Ser  Ser Ser Ser Ser Ser  Ser Ser Ser Ser Ser  Ser Ser Ser
    1025                1030                1035

Ser Ser  Gly Gly Gly Gly Gly  Gly Gly Gly Gly Gly  Gly Gly Gly
    1040                1045                1050

Gly Gly  Gly Gly Gly Gly Gly  Ser Ser Ser Ser Ser  Ser Ser Ser
    1055                1060                1065

Ser Ser  Ser Ser Ser Ser Ser  Ser Ser Ser Ser Ser  Gly Gly Gly
    1070                1075                1080

Gly Gly  Gly Gly Gly Gly Gly  Gly Gly Gly Gly Gly  Gly Gly Gly
    1085                1090                1095

Gly Gly  Gly Gly Gly Gly Gly  Gly Gly Gly Gly Gly  Gly Gly Gly
    1100                1105                1110

Gly Gly  Gly Gly Gly Gly Gly  Ser Ser Ser Ser Ser  Ser Ser Ser
    1115                1120                1125

Ser Ser  Ser Ser Ser Ser Ser  Ser Ser Ser Ser Ser  Gly Gly Gly
    1130                1135                1140

Gly Gly  Gly Gly Gly Gly Gly  Gly Gly Gly Gly Gly  Gly Gly Gly
    1145                1150                1155

Gly Gly  Ser Ser Ser Ser Ser  Ser Ser Ser Ser Ser  Ser Ser Ser
    1160                1165                1170

Ser Ser  Ser Ser Ser Ser Ser  Gly Gly Gly Gly Gly  Gly Gly Gly
    1175                1180                1185

Gly Gly  Gly Gly Gly Gly Gly  Gly Gly Gly Gly Gly  Gly Gly Gly
    1190                1195                1200

Gly Gly  Gly Gly Gly Gly Gly  Gly Gly Gly Gly Gly  Gly Gly Gly
    1205                1210                1215

Gly Gly  Ser Ser Ser Ser Ser  Ser Ser Ser Ser Ser  Ser Ser Ser
    1220                1225                1230

Ser Ser  Ser Ser Ser Ser Ser  Gly Gly Gly Gly Gly  Gly Gly Gly
    1235                1240                1245

Gly Gly  Gly Gly Gly Gly Gly  Gly Gly Gly Gly Gly  Ser Ser Ser
    1250                1255                1260

Ser Ser  Ser Ser Ser Ser Ser  Ser Ser Ser Ser Ser  Ser Ser Ser
    1265                1270                1275

Ser Ser  Gly Gly Gly Gly Gly  Gly Gly Gly Gly Gly  Gly Gly Gly
    1280                1285                1290

Gly Gly  Gly Gly Gly Gly Gly  Gly Gly Gly Gly Gly  Gly Gly Gly
    1295                1300                1305

Gly Gly  Gly Gly Gly Gly Gly  Gly Gly Gly Gly Gly  Ser Ser Ser
    1310                1315                1320

Ser Ser  Ser Ser Ser Ser Ser  Ser Ser Ser Ser Ser  Ser Ser Ser
    1325                1330                1335

Ser Ser  Gly Gly Gly Gly Gly  Gly Gly Gly Gly Gly  Gly Gly Gly
    1340                1345                1350

Gly Gly  Gly Gly Gly Gly Gly  Ser Ser Ser Ser Ser  Ser Ser Ser
    1355                1360                1365

Ser Ser  Ser Ser Ser Ser Ser  Ser Ser Ser Ser Ser  Gly Gly Gly
    1370                1375                1380
```

```
Gly Gly  Gly Gly Gly Gly Gly  Gly Gly Gly Gly Gly  Gly Gly Gly
    1385                1390                1395

Gly Gly  Gly Gly Gly Gly Gly  Gly Gly Gly Gly Gly  Gly Gly Gly
    1400                1405                1410

Gly Gly  Gly Gly Gly Gly Gly  Ser Ser Ser Ser Ser  Ser Ser Ser
    1415                1420                1425

Ser Ser  Ser Ser Ser Ser Ser  Ser Ser Ser Ser Ser  Gly Gly Gly
    1430                1435                1440

Gly Gly  Gly Gly Gly Gly Gly  Gly Gly Gly Gly Gly  Gly Gly Gly
    1445                1450                1455

Gly Gly  Ser Ser Ser Ser Ser  Ser Ser Ser Ser Ser  Ser Ser Ser
    1460                1465                1470

Ser Ser  Ser Ser Ser Ser Ser  Gly Gly Gly Gly Gly  Gly Gly Gly
    1475                1480                1485

Gly Gly  Gly Gly Gly Gly Gly  Gly Gly Gly Gly Gly  Gly Gly Gly
    1490                1495                1500

Gly Gly  Gly Gly Gly Gly Gly  Gly Gly Gly Gly Gly  Gly Gly Gly
    1505                1510                1515

Gly Gly  Ser Ser Ser Ser Ser  Ser Ser Ser Ser Ser  Ser Ser Ser
    1520                1525                1530

Ser Ser  Ser Ser Ser Ser Ser  Gly Gly Gly Gly Gly  Gly Gly Gly
    1535                1540                1545

Gly Gly  Gly Gly Gly Gly Gly  Gly Gly Gly Gly Gly  Ser Ser Ser
    1550                1555                1560

Ser Ser  Ser Ser Ser Ser Ser  Ser Ser Ser Ser Ser  Ser Ser Ser
    1565                1570                1575

Ser Ser  Gly Gly Gly Gly Gly  Gly Gly Gly Gly Gly  Gly Gly Gly
    1580                1585                1590

Gly Gly  Gly Gly Gly Gly Gly  Gly Gly Gly Gly Gly  Gly Gly Gly
    1595                1600                1605

Gly Gly  Gly Gly Gly Gly Gly  Gly Gly Gly Gly Gly  Ser Ser Ser
    1610                1615                1620

Ser Ser  Ser Ser Ser Ser Ser  Ser Ser Ser Ser Ser  Ser Ser Ser
    1625                1630                1635

Ser Ser  Gly Gly Gly Gly Gly  Gly Gly Gly Gly Gly  Gly Gly Gly
    1640                1645                1650

Gly Gly  Gly Gly Gly Gly Gly  Ser Ser Ser Ser Ser  Ser Ser Ser
    1655                1660                1665

Ser Ser  Ser Ser Ser Ser Ser  Ser Ser Ser Ser Ser  Gly Gly Gly
    1670                1675                1680

Gly Gly  Gly Gly Gly Gly Gly  Gly Gly Gly Gly Gly  Gly Gly Gly
    1685                1690                1695

Gly Gly  Gly Gly Gly Gly Gly  Gly Gly Gly Gly Gly  Gly Gly Gly
    1700                1705                1710

Gly Gly  Gly Gly Gly Gly Gly  Ser Ser Ser Ser Ser  Ser Ser Ser
    1715                1720                1725

Ser Ser  Ser Ser Ser Ser Ser  Ser Ser Ser Ser Ser  Gly Gly Gly
    1730                1735                1740

Gly Gly  Gly Gly Gly Gly Gly  Gly Gly Gly Gly Gly  Gly Gly Gly
    1745                1750                1755

Gly Gly  Ser Ser Ser Ser Ser  Ser Ser Ser Ser Ser  Ser Ser Ser
    1760                1765                1770
```

```
Ser Ser  Ser Ser Ser Ser Ser  Gly Gly Gly Gly Gly  Gly Gly Gly
    1775                 1780                 1785

Gly Gly  Gly Gly Gly Gly Gly  Gly Gly Gly Gly Gly  Gly Gly Gly
    1790                 1795                 1800

Gly Gly  Gly Gly Gly Gly Gly  Gly Gly Gly Gly Gly  Gly Gly Gly
    1805                 1810                 1815

Gly Gly  Ser Ser Ser Ser Ser  Ser Ser Ser Ser Ser  Ser Ser Ser
    1820                 1825                 1830

Ser Ser  Ser Ser Ser Ser Ser  Gly Gly Gly Gly Gly  Gly Gly Gly
    1835                 1840                 1845

Gly Gly  Gly Gly Gly Gly Gly  Gly Gly Gly Gly Gly  Ser Ser Ser
    1850                 1855                 1860

Ser Ser  Ser Ser Ser Ser Ser  Ser Ser Ser Ser Ser  Ser Ser Ser
    1865                 1870                 1875

Ser Ser  Gly Gly Gly Gly Gly  Gly Gly Gly Gly Gly  Gly Gly Gly
    1880                 1885                 1890

Gly Gly  Gly Gly Gly Gly Gly  Gly Gly Gly Gly Gly  Gly Gly Gly
    1895                 1900                 1905

Gly Gly  Gly Gly Gly Gly Gly  Gly Gly Gly Gly Gly  Ser Ser Ser
    1910                 1915                 1920

Ser Ser  Ser Ser Ser Ser Ser  Ser Ser Ser Ser Ser  Ser Ser Ser
    1925                 1930                 1935

Ser Ser  Gly Gly Gly Gly Gly  Gly Gly Gly Gly Gly  Gly Gly Gly
    1940                 1945                 1950

Gly Gly  Gly Gly Gly Gly Gly  Ser Ser Ser Ser Ser  Ser Ser Ser
    1955                 1960                 1965

Ser Ser  Ser Ser Ser Ser Ser  Ser Ser Ser Ser Ser  Gly Gly Gly
    1970                 1975                 1980

Gly Gly  Gly Gly Gly Gly Gly  Gly Gly Gly Gly Gly  Gly Gly Gly
    1985                 1990                 1995

Gly Gly
    2000
```

<210> SEQ ID NO 310
<211> LENGTH: 480
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: SITE
<222> LOCATION: (5)..(24)
<223> OTHER INFORMATION: This region may encompass 1-20 residues
<220> FEATURE:
<221> NAME/KEY: SITE
<222> LOCATION: (29)..(48)
<223> OTHER INFORMATION: This region may encompass 1-20 residues
<220> FEATURE:
<221> NAME/KEY: SITE
<222> LOCATION: (53)..(72)
<223> OTHER INFORMATION: This region may encompass 1-20 residues
<220> FEATURE:
<221> NAME/KEY: SITE
<222> LOCATION: (77)..(96)
<223> OTHER INFORMATION: This region may encompass 1-20 residues
<220> FEATURE:
<221> NAME/KEY: SITE
<222> LOCATION: (101)..(120)
<223> OTHER INFORMATION: This region may encompass 1-20 residues
<220> FEATURE:
<221> NAME/KEY: SITE
<222> LOCATION: (125)..(144)

<223> OTHER INFORMATION: This region may encompass 1-20 residues
<220> FEATURE:
<221> NAME/KEY: SITE
<222> LOCATION: (149)..(168)
<223> OTHER INFORMATION: This region may encompass 1-20 residues
<220> FEATURE:
<221> NAME/KEY: SITE
<222> LOCATION: (173)..(192)
<223> OTHER INFORMATION: This region may encompass 1-20 residues
<220> FEATURE:
<221> NAME/KEY: SITE
<222> LOCATION: (197)..(216)
<223> OTHER INFORMATION: This region may encompass 1-20 residues
<220> FEATURE:
<221> NAME/KEY: SITE
<222> LOCATION: (221)..(240)
<223> OTHER INFORMATION: This region may encompass 1-20 residues
<220> FEATURE:
<221> NAME/KEY: SITE
<222> LOCATION: (245)..(264)
<223> OTHER INFORMATION: This region may encompass 1-20 residues
<220> FEATURE:
<221> NAME/KEY: SITE
<222> LOCATION: (269)..(288)
<223> OTHER INFORMATION: This region may encompass 1-20 residues
<220> FEATURE:
<221> NAME/KEY: SITE
<222> LOCATION: (293)..(312)
<223> OTHER INFORMATION: This region may encompass 1-20 residues
<220> FEATURE:
<221> NAME/KEY: SITE
<222> LOCATION: (317)..(336)
<223> OTHER INFORMATION: This region may encompass 1-20 residues
<220> FEATURE:
<221> NAME/KEY: SITE
<222> LOCATION: (341)..(360)
<223> OTHER INFORMATION: This region may encompass 1-20 residues
<220> FEATURE:
<221> NAME/KEY: SITE
<222> LOCATION: (365)..(384)
<223> OTHER INFORMATION: This region may encompass 1-20 residues
<220> FEATURE:
<221> NAME/KEY: SITE
<222> LOCATION: (389)..(408)
<223> OTHER INFORMATION: This region may encompass 1-20 residues
<220> FEATURE:
<221> NAME/KEY: SITE
<222> LOCATION: (413)..(432)
<223> OTHER INFORMATION: This region may encompass 1-20 residues
<220> FEATURE:
<221> NAME/KEY: SITE
<222> LOCATION: (437)..(456)
<223> OTHER INFORMATION: This region may encompass 1-20 residues
<220> FEATURE:
<221> NAME/KEY: SITE
<222> LOCATION: (461)..(480)
<223> OTHER INFORMATION: This region may encompass 1-20 residues
<220> FEATURE:
<221> NAME/KEY: SITE
<222> LOCATION: (1)..(480)
<223> OTHER INFORMATION: This sequence may encompass 1-20
"(Gly)(Ser)(Gly)(Gly)(Ser)m" repeating units, wherein m = 1 to 20
<220> FEATURE:
<223> OTHER INFORMATION: See specification as filed for detailed
description of substitutions and preferred embodiments

<400> SEQUENCE: 310

```
Gly Ser Gly Gly Ser Ser Ser Ser Ser Ser Ser Ser Ser Ser Ser Ser
1               5                   10                  15

Ser Ser Ser Ser Ser Ser Ser Ser Gly Ser Gly Gly Ser Ser Ser Ser
            20                  25                  30

Ser Ser Ser Ser Ser Ser Ser Ser Ser Ser Ser Ser Ser Ser Ser Ser
        35                  40                  45

Gly Ser Gly Gly Ser Ser Ser Ser Ser Ser Ser Ser Ser Ser Ser Ser
    50                  55                  60
```

```
Ser Ser Ser Ser Ser Ser Ser Ser Gly Ser Gly Gly Ser Ser Ser Ser
65                  70                  75                  80

Ser Ser Ser Ser Ser Ser Ser Ser Ser Ser Ser Ser Ser Ser Ser Ser
                85                  90                  95

Gly Ser Gly Gly Ser Ser Ser Ser Ser Ser Ser Ser Ser Ser Ser Ser
            100                 105                 110

Ser Ser Ser Ser Ser Ser Ser Ser Gly Ser Gly Gly Ser Ser Ser Ser
        115                 120                 125

Ser Ser Ser Ser Ser Ser Ser Ser Ser Ser Ser Ser Ser Ser Ser Ser
    130                 135                 140

Gly Ser Gly Gly Ser Ser Ser Ser Ser Ser Ser Ser Ser Ser Ser Ser
145                 150                 155                 160

Ser Ser Ser Ser Ser Ser Ser Ser Gly Ser Gly Gly Ser Ser Ser Ser
                165                 170                 175

Ser Ser Ser Ser Ser Ser Ser Ser Ser Ser Ser Ser Ser Ser Ser Ser
            180                 185                 190

Gly Ser Gly Gly Ser Ser Ser Ser Ser Ser Ser Ser Ser Ser Ser Ser
        195                 200                 205

Ser Ser Ser Ser Ser Ser Ser Ser Gly Ser Gly Gly Ser Ser Ser Ser
    210                 215                 220

Ser Ser Ser Ser Ser Ser Ser Ser Ser Ser Ser Ser Ser Ser Ser Ser
225                 230                 235                 240

Gly Ser Gly Gly Ser Ser Ser Ser Ser Ser Ser Ser Ser Ser Ser Ser
                245                 250                 255

Ser Ser Ser Ser Ser Ser Ser Ser Gly Ser Gly Gly Ser Ser Ser Ser
            260                 265                 270

Ser Ser Ser Ser Ser Ser Ser Ser Ser Ser Ser Ser Ser Ser Ser Ser
        275                 280                 285

Gly Ser Gly Gly Ser Ser Ser Ser Ser Ser Ser Ser Ser Ser Ser Ser
    290                 295                 300

Ser Ser Ser Ser Ser Ser Ser Ser Gly Ser Gly Gly Ser Ser Ser Ser
305                 310                 315                 320

Ser Ser Ser Ser Ser Ser Ser Ser Ser Ser Ser Ser Ser Ser Ser Ser
                325                 330                 335

Gly Ser Gly Gly Ser Ser Ser Ser Ser Ser Ser Ser Ser Ser Ser Ser
            340                 345                 350

Ser Ser Ser Ser Ser Ser Ser Ser Gly Ser Gly Gly Ser Ser Ser Ser
        355                 360                 365

Ser Ser Ser Ser Ser Ser Ser Ser Ser Ser Ser Ser Ser Ser Ser Ser
    370                 375                 380

Gly Ser Gly Gly Ser Ser Ser Ser Ser Ser Ser Ser Ser Ser Ser Ser
385                 390                 395                 400

Ser Ser Ser Ser Ser Ser Ser Ser Gly Ser Gly Gly Ser Ser Ser Ser
                405                 410                 415

Ser Ser Ser Ser Ser Ser Ser Ser Ser Ser Ser Ser Ser Ser Ser Ser
            420                 425                 430

Gly Ser Gly Gly Ser Ser Ser Ser Ser Ser Ser Ser Ser Ser Ser Ser
        435                 440                 445

Ser Ser Ser Ser Ser Ser Ser Ser Gly Ser Gly Gly Ser Ser Ser Ser
    450                 455                 460

Ser Ser Ser Ser Ser Ser Ser Ser Ser Ser Ser Ser Ser Ser Ser Ser
465                 470                 475                 480
```

<210> SEQ ID NO 311
<211> LENGTH: 480
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: SITE
<222> LOCATION: (4)..(23)
<223> OTHER INFORMATION: This region may encompass 1-20 residues
<220> FEATURE:
<221> NAME/KEY: SITE
<222> LOCATION: (28)..(47)
<223> OTHER INFORMATION: This region may encompass 1-20 residues
<220> FEATURE:
<221> NAME/KEY: SITE
<222> LOCATION: (52)..(71)
<223> OTHER INFORMATION: This region may encompass 1-20 residues
<220> FEATURE:
<221> NAME/KEY: SITE
<222> LOCATION: (76)..(95)
<223> OTHER INFORMATION: This region may encompass 1-20 residues
<220> FEATURE:
<221> NAME/KEY: SITE
<222> LOCATION: (100)..(119)
<223> OTHER INFORMATION: This region may encompass 1-20 residues
<220> FEATURE:
<221> NAME/KEY: SITE
<222> LOCATION: (124)..(143)
<223> OTHER INFORMATION: This region may encompass 1-20 residues
<220> FEATURE:
<221> NAME/KEY: SITE
<222> LOCATION: (148)..(167)
<223> OTHER INFORMATION: This region may encompass 1-20 residues
<220> FEATURE:
<221> NAME/KEY: SITE
<222> LOCATION: (172)..(191)
<223> OTHER INFORMATION: This region may encompass 1-20 residues
<220> FEATURE:
<221> NAME/KEY: SITE
<222> LOCATION: (196)..(215)
<223> OTHER INFORMATION: This region may encompass 1-20 residues
<220> FEATURE:
<221> NAME/KEY: SITE
<222> LOCATION: (220)..(239)
<223> OTHER INFORMATION: This region may encompass 1-20 residues
<220> FEATURE:
<221> NAME/KEY: SITE
<222> LOCATION: (244)..(263)
<223> OTHER INFORMATION: This region may encompass 1-20 residues
<220> FEATURE:
<221> NAME/KEY: SITE
<222> LOCATION: (268)..(287)
<223> OTHER INFORMATION: This region may encompass 1-20 residues
<220> FEATURE:
<221> NAME/KEY: SITE
<222> LOCATION: (292)..(311)
<223> OTHER INFORMATION: This region may encompass 1-20 residues
<220> FEATURE:
<221> NAME/KEY: SITE
<222> LOCATION: (316)..(335)
<223> OTHER INFORMATION: This region may encompass 1-20 residues
<220> FEATURE:
<221> NAME/KEY: SITE
<222> LOCATION: (340)..(359)
<223> OTHER INFORMATION: This region may encompass 1-20 residues
<220> FEATURE:
<221> NAME/KEY: SITE
<222> LOCATION: (364)..(383)
<223> OTHER INFORMATION: This region may encompass 1-20 residues
<220> FEATURE:
<221> NAME/KEY: SITE
<222> LOCATION: (388)..(407)
<223> OTHER INFORMATION: This region may encompass 1-20 residues
<220> FEATURE:
<221> NAME/KEY: SITE
<222> LOCATION: (412)..(431)

```
<223> OTHER INFORMATION: This region may encompass 1-20 residues
<220> FEATURE:
<221> NAME/KEY: SITE
<222> LOCATION: (436)..(455)
<223> OTHER INFORMATION: This region may encompass 1-20 residues
<220> FEATURE:
<221> NAME/KEY: SITE
<222> LOCATION: (460)..(479)
<223> OTHER INFORMATION: This region may encompass 1-20 residues
<220> FEATURE:
<221> NAME/KEY: SITE
<222> LOCATION: (1)..(480)
<223> OTHER INFORMATION: This sequence may encompass 1-20
      "(Gly)(Ser)(Gly)(Ser)m(Gly)" repeating units, wherein m = 1 to 20
<220> FEATURE:
<223> OTHER INFORMATION: See specification as filed for detailed
      description of substitutions and preferred embodiments

<400> SEQUENCE: 311

Gly Ser Gly Ser Ser Ser Ser Ser Ser Ser Ser Ser Ser Ser Ser Ser
1               5                   10                  15

Ser Ser Ser Ser Ser Ser Ser Gly Gly Ser Gly Ser Ser Ser Ser Ser
            20                  25                  30

Ser Ser Ser Ser Ser Ser Ser Ser Ser Ser Ser Ser Ser Ser Ser Gly
        35                  40                  45

Gly Ser Gly Ser Ser Ser Ser Ser Ser Ser Ser Ser Ser Ser Ser Ser
    50                  55                  60

Ser Ser Ser Ser Ser Ser Ser Gly Gly Ser Gly Ser Ser Ser Ser Ser
65                  70                  75                  80

Ser Ser Ser Ser Ser Ser Ser Ser Ser Ser Ser Ser Ser Ser Ser Gly
                85                  90                  95

Gly Ser Gly Ser Ser Ser Ser Ser Ser Ser Ser Ser Ser Ser Ser Ser
            100                 105                 110

Ser Ser Ser Ser Ser Ser Ser Gly Gly Ser Gly Ser Ser Ser Ser Ser
        115                 120                 125

Ser Ser Ser Ser Ser Ser Ser Ser Ser Ser Ser Ser Ser Ser Ser Gly
    130                 135                 140

Gly Ser Gly Ser Ser Ser Ser Ser Ser Ser Ser Ser Ser Ser Ser Ser
145                 150                 155                 160

Ser Ser Ser Ser Ser Ser Ser Gly Gly Ser Gly Ser Ser Ser Ser Ser
                165                 170                 175

Ser Ser Ser Ser Ser Ser Ser Ser Ser Ser Ser Ser Ser Ser Ser Gly
            180                 185                 190

Gly Ser Gly Ser Ser Ser Ser Ser Ser Ser Ser Ser Ser Ser Ser Ser
        195                 200                 205

Ser Ser Ser Ser Ser Ser Ser Gly Gly Ser Gly Ser Ser Ser Ser Ser
    210                 215                 220

Ser Ser Ser Ser Ser Ser Ser Ser Ser Ser Ser Ser Ser Ser Ser Gly
225                 230                 235                 240

Gly Ser Gly Ser Ser Ser Ser Ser Ser Ser Ser Ser Ser Ser Ser Ser
                245                 250                 255

Ser Ser Ser Ser Ser Ser Ser Gly Gly Ser Gly Ser Ser Ser Ser Ser
            260                 265                 270

Ser Ser Ser Ser Ser Ser Ser Ser Ser Ser Ser Ser Ser Ser Ser Gly
        275                 280                 285

Gly Ser Gly Ser Ser Ser Ser Ser Ser Ser Ser Ser Ser Ser Ser Ser
    290                 295                 300

Ser Ser Ser Ser Ser Ser Ser Gly Gly Ser Gly Ser Ser Ser Ser Ser
305                 310                 315                 320
```

```
Ser Ser Ser Ser Ser Ser Ser Ser Ser Ser Ser Ser Ser Ser Ser Gly
                325                 330                 335

Gly Ser Gly Ser Ser Ser Ser Ser Ser Ser Ser Ser Ser Ser Ser Ser
            340                 345                 350

Ser Ser Ser Ser Ser Ser Ser Gly Gly Ser Gly Ser Ser Ser Ser Ser
        355                 360                 365

Ser Ser Ser Ser Ser Ser Ser Ser Ser Ser Ser Ser Ser Ser Ser Gly
    370                 375                 380

Gly Ser Gly Ser Ser Ser Ser Ser Ser Ser Ser Ser Ser Ser Ser Ser
385                 390                 395                 400

Ser Ser Ser Ser Ser Ser Ser Gly Gly Ser Gly Ser Ser Ser Ser Ser
                405                 410                 415

Ser Ser Ser Ser Ser Ser Ser Ser Ser Ser Ser Ser Ser Ser Ser Gly
            420                 425                 430

Gly Ser Gly Ser Ser Ser Ser Ser Ser Ser Ser Ser Ser Ser Ser Ser
        435                 440                 445

Ser Ser Ser Ser Ser Ser Ser Gly Gly Ser Gly Ser Ser Ser Ser Ser
    450                 455                 460

Ser Ser Ser Ser Ser Ser Ser Ser Ser Ser Ser Ser Ser Ser Ser Gly
465                 470                 475                 480
```

<210> SEQ ID NO 312
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (4)..(23)
<223> OTHER INFORMATION: This region may encompass 1-20 residues
<220> FEATURE:
<221> NAME/KEY: SITE
<222> LOCATION: (27)..(46)
<223> OTHER INFORMATION: This region may encompass 1-20 residues
<220> FEATURE:
<221> NAME/KEY: SITE
<222> LOCATION: (50)..(69)
<223> OTHER INFORMATION: This region may encompass 1-20 residues
<220> FEATURE:
<221> NAME/KEY: SITE
<222> LOCATION: (73)..(92)
<223> OTHER INFORMATION: This region may encompass 1-20 residues
<220> FEATURE:
<221> NAME/KEY: SITE
<222> LOCATION: (96)..(115)
<223> OTHER INFORMATION: This region may encompass 1-20 residues
<220> FEATURE:
<221> NAME/KEY: SITE
<222> LOCATION: (119)..(138)
<223> OTHER INFORMATION: This region may encompass 1-20 residues
<220> FEATURE:
<221> NAME/KEY: SITE
<222> LOCATION: (142)..(161)
<223> OTHER INFORMATION: This region may encompass 1-20 residues
<220> FEATURE:
<221> NAME/KEY: SITE
<222> LOCATION: (165)..(184)
<223> OTHER INFORMATION: This region may encompass 1-20 residues
<220> FEATURE:
<221> NAME/KEY: SITE
<222> LOCATION: (188)..(207)
<223> OTHER INFORMATION: This region may encompass 1-20 residues
<220> FEATURE:
<221> NAME/KEY: SITE
<222> LOCATION: (211)..(230)
<223> OTHER INFORMATION: This region may encompass 1-20 residues
<220> FEATURE:
<221> NAME/KEY: SITE
<222> LOCATION: (234)..(253)
<223> OTHER INFORMATION: This region may encompass 1-20 residues
<220> FEATURE:
<221> NAME/KEY: SITE
<222> LOCATION: (257)..(276)
<223> OTHER INFORMATION: This region may encompass 1-20 residues
<220> FEATURE:
<221> NAME/KEY: SITE
<222> LOCATION: (280)..(299)
<223> OTHER INFORMATION: This region may encompass 1-20 residues
<220> FEATURE:
<221> NAME/KEY: SITE
<222> LOCATION: (303)..(322)
<223> OTHER INFORMATION: This region may encompass 1-20 residues
<220> FEATURE:
<221> NAME/KEY: SITE
<222> LOCATION: (326)..(345)
<223> OTHER INFORMATION: This region may encompass 1-20 residues
<220> FEATURE:
<221> NAME/KEY: SITE
<222> LOCATION: (349)..(368)
<223> OTHER INFORMATION: This region may encompass 1-20 residues
<220> FEATURE:
<221> NAME/KEY: SITE
<222> LOCATION: (372)..(391)
<223> OTHER INFORMATION: This region may encompass 1-20 residues
<220> FEATURE:
<221> NAME/KEY: SITE
<222> LOCATION: (395)..(414)
<223> OTHER INFORMATION: This region may encompass 1-20 residues
<220> FEATURE:
<221> NAME/KEY: SITE
<222> LOCATION: (418)..(437)
<223> OTHER INFORMATION: This region may encompass 1-20 residues
<220> FEATURE:
<221> NAME/KEY: SITE
<222> LOCATION: (441)..(460)
<223> OTHER INFORMATION: This region may encompass 1-20 residues
<220> FEATURE:
<221> NAME/KEY: SITE
<222> LOCATION: (1)..(460)
<223> OTHER INFORMATION: This sequence may encompass 1-20 "(Gly)(Gly)(Gly)(Ser)m" repeating units, wherein m = 1 to 20
<220> FEATURE:
<223> OTHER INFORMATION: See specification as filed for detailed description of substitutions and preferred embodiments

<400> SEQUENCE: 312

Gly Gly Gly Ser Ser Ser Ser Ser Ser Ser Ser Ser Ser Ser Ser Ser
1 5 10 15

Ser Ser Ser Ser Ser Ser Ser Gly Gly Gly Ser Ser Ser Ser Ser Ser
20 25 30

Ser Ser Ser Ser Ser Ser Ser Ser Ser Ser Ser Ser Ser Ser Gly Gly
35 40 45

Gly Ser Ser Ser Ser Ser Ser Ser Ser Ser Ser Ser Ser Ser Ser Ser
50 55 60

Ser Ser Ser Ser Ser Gly Gly Gly Ser Ser Ser Ser Ser Ser Ser Ser
65 70 75 80

Ser Ser Ser Ser Ser Ser Ser Ser Ser Ser Ser Ser Gly Gly Gly Ser
85 90 95

Ser Ser Ser Ser Ser Ser Ser Ser Ser Ser Ser Ser Ser Ser Ser Ser
100 105 110

Ser Ser Ser Gly Gly Gly Ser Ser Ser Ser Ser Ser Ser Ser Ser Ser
115 120 125

Ser Ser Ser Ser Ser Ser Ser Ser Ser Ser Gly Gly Gly Ser Ser Ser
130 135 140

Ser Ser Ser Ser Ser Ser Ser Ser Ser Ser Ser Ser Ser Ser Ser Ser

```
145                 150                 155                 160

Ser Gly Gly Gly Ser Ser Ser Ser Ser Ser Ser Ser Ser Ser Ser Ser
                165                 170                 175

Ser Ser Ser Ser Ser Ser Ser Ser Gly Gly Gly Ser Ser Ser Ser Ser
            180                 185                 190

Ser Ser Ser Ser Ser Ser Ser Ser Ser Ser Ser Ser Ser Ser Ser Gly
        195                 200                 205

Gly Gly Ser Ser Ser Ser Ser Ser Ser Ser Ser Ser Ser Ser Ser Ser
    210                 215                 220

Ser Ser Ser Ser Ser Ser Gly Gly Gly Ser Ser Ser Ser Ser Ser Ser
225                 230                 235                 240

Ser Ser Ser Ser Ser Ser Ser Ser Ser Ser Ser Ser Ser Gly Gly Gly
                245                 250                 255

Ser Ser Ser Ser Ser Ser Ser Ser Ser Ser Ser Ser Ser Ser Ser Ser
            260                 265                 270

Ser Ser Ser Ser Gly Gly Gly Ser Ser Ser Ser Ser Ser Ser Ser Ser
        275                 280                 285

Ser Ser Ser Ser Ser Ser Ser Ser Ser Ser Ser Gly Gly Gly Ser Ser
    290                 295                 300

Ser Ser Ser Ser Ser Ser Ser Ser Ser Ser Ser Ser Ser Ser Ser Ser
305                 310                 315                 320

Ser Ser Gly Gly Gly Ser Ser Ser Ser Ser Ser Ser Ser Ser Ser Ser
                325                 330                 335

Ser Ser Ser Ser Ser Ser Ser Ser Ser Gly Gly Gly Ser Ser Ser Ser
            340                 345                 350

Ser Ser Ser Ser Ser Ser Ser Ser Ser Ser Ser Ser Ser Ser Ser Ser
        355                 360                 365

Gly Gly Gly Ser Ser Ser Ser Ser Ser Ser Ser Ser Ser Ser Ser Ser
    370                 375                 380

Ser Ser Ser Ser Ser Ser Ser Gly Gly Gly Ser Ser Ser Ser Ser Ser
385                 390                 395                 400

Ser Ser Ser Ser Ser Ser Ser Ser Ser Ser Ser Ser Ser Ser Gly Gly
                405                 410                 415

Gly Ser Ser Ser Ser Ser Ser Ser Ser Ser Ser Ser Ser Ser Ser Ser
            420                 425                 430

Ser Ser Ser Ser Ser Gly Gly Gly Ser Ser Ser Ser Ser Ser Ser Ser
        435                 440                 445

Ser Ser Ser Ser Ser Ser Ser Ser Ser Ser Ser Ser
    450                 455                 460
```

```
<210> SEQ ID NO 313
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 313

His His His His His His
1               5


<210> SEQ ID NO 314
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      8xHis tag

<400> SEQUENCE: 314

His His His His His His His His
1               5


<210> SEQ ID NO 315
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Gly Gly Ser
1


<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Gly Ser Gly Gly Ser
1               5


<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
<222> LOCATION: (1)..(6)
<223> OTHER INFORMATION: This sequence may encompass 3-6 residues

<400> SEQUENCE: 317

His His His His His His
1               5
```